United States Patent
Jones et al.

(10) Patent No.: US 11,840,536 B2
(45) Date of Patent: *Dec. 12, 2023

(54) HETEROCYCLIC INHIBITORS OF PTPN11

(71) Applicant: BOARD OF REGENTS, THE UNIVERSITY OF TEXAS SYSTEM, Austin, TX (US)

(72) Inventors: Philip Jones, Houston, TX (US); Barbara Czako, Bellaire, TX (US); Jason Cross, Pearland, TX (US); Paul Leonard, Houston, TX (US); Faika Mseeh, Shenandoah, TX (US); Connor Parker, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/876,958

(22) Filed: Jul. 29, 2022

(65) Prior Publication Data

US 2023/0109858 A1 Apr. 13, 2023

Related U.S. Application Data

(63) Continuation of application No. 16/989,211, filed on Aug. 10, 2020, now Pat. No. 11,466,017, which is a continuation of application No. 16/270,333, filed on Feb. 7, 2019, now Pat. No. 10,851,110, which is a continuation of application No. 15/607,174, filed on May 26, 2017, now Pat. No. 10,280,171.

(60) Provisional application No. 62/451,432, filed on Jan. 27, 2017, provisional application No. 62/343,455, filed on May 31, 2016.

(51) Int. Cl.
| | |
|---|---|
| C07D 487/04 | (2006.01) |
| A61P 35/00 | (2006.01) |
| A61K 31/4985 | (2006.01) |
| A61K 31/501 | (2006.01) |
| C07D 519/00 | (2006.01) |

(52) U.S. Cl.
CPC ........ *C07D 487/04* (2013.01); *A61K 31/4985* (2013.01); *A61K 31/501* (2013.01); *A61P 35/00* (2018.01); *C07D 519/00* (2013.01)

(58) Field of Classification Search
None
See application file for complete search history.

(56) References Cited

U.S. PATENT DOCUMENTS

| | | | |
|---|---|---|---|
| 7,897,607 B2 | 3/2011 | Gyorkos | |
| 9,522,881 B2 | 12/2016 | Zhang et al. | |
| 10,280,171 B2 | 5/2019 | Jones et al. | |
| 10,851,110 B2 | 12/2020 | Jones et al. | |
| 10,954,243 B2 | 3/2021 | Jones et al. | |
| 11,104,675 B2 | 8/2021 | Jones et al. | |
| 2005/0203091 A1 | 9/2005 | Arora | |
| 2011/0152242 A1 | 6/2011 | Bayliss et al. | |
| 2017/0015680 A1 | 1/2017 | Chen et al. | |
| 2017/0342078 A1 | 11/2017 | Jones et al. | |
| 2019/0270746 A1 | 9/2019 | Jones et al. | |
| 2019/0389867 A1 | 12/2019 | Jones et al. | |
| 2020/0048249 A1 | 2/2020 | Jones et al. | |
| 2021/0317122 A1 | 10/2021 | Jones et al. | |

FOREIGN PATENT DOCUMENTS

| | | |
|---|---|---|
| CN | 107286150 A | 10/2017 |
| CN | 110143949 A | 8/2019 |
| JP | 2010111624 A | 5/2010 |
| JP | 2011246389 A | 12/2011 |
| WO | WO-2005028480 A2 | 3/2005 |
| WO | WO-2005028480 A3 | 3/2005 |
| WO | WO-2005085248 A1 | 9/2005 |
| WO | WO-2006058074 A1 | 6/2006 |
| WO | WO-2006063820 A1 | 6/2006 |
| WO | WO-2008061109 A2 | 5/2008 |
| WO | WO-2008061109 A3 | 5/2008 |
| WO | WO-2010039789 A1 | 4/2010 |
| WO | WO-2011055911 A1 | 5/2011 |
| WO | WO-2012106343 A2 | 8/2012 |
| WO | WO-2012106343 A3 | 8/2012 |
| WO | WO-2013040527 A1 | 3/2013 |
| WO | WO-2013052263 A2 | 4/2013 |
| WO | WO-2013052263 A3 | 4/2013 |
| WO | WO-2014047662 A2 | 3/2014 |
| WO | WO-2014047662 A3 | 3/2014 |
| WO | WO-2014200682 A1 | 12/2014 |
| WO | WO-2015099481 A1 | 7/2015 |
| WO | WO-2015107493 A1 | 7/2015 |
| WO | WO-2015107494 A1 | 7/2015 |
| WO | WO-2015107495 A1 | 7/2015 |
| WO | WO-2015190718 A1 | 12/2015 |
| WO | WO-2016064102 A1 | 4/2016 |

(Continued)

OTHER PUBLICATIONS

U.S. Appl. No. 62/307,103, Czako et al.
Amarnath, S. et al., The PDL1-PD1 axis converts human TH1 cells into regulatory T cells, Sci Transl Med, Nov. 30, 2011, 3(111):111ra120.
Anderson, J.N. et al., Structural and evolutionary relationships among protein tyrosine phosphatase domains, Mol Cell Biol, Nov. 2001, 21(21):7117-7136.
Banker et al., Prodrugs, Modern Pharmaceuticals, 1997, 3$^{rd}$ Edition, p. 596, 451.
Barr, A.J. et al., Large-scale structural analysis of the classical human protein tyrosine phosphatome, Cell, Jan. 23, 2009, 136(2):352-363.

(Continued)

*Primary Examiner* — Samantha L Shterengarts
(74) *Attorney, Agent, or Firm* — Mintz, Levin, Cohn, Ferris, Glovsky & Popeo, P.C.

(57) ABSTRACT

The present invention relates to compounds which may be useful as inhibitors of PTPN11 for the treatment or prevention of cancer and other PTP-mediated diseases. Disclosed herein are new compounds and compounds based on pyrazolopyrazines and their application as pharmaceuticals for the treatment of disease.

18 Claims, 2 Drawing Sheets

(56) References Cited

FOREIGN PATENT DOCUMENTS

| WO | WO-2016151501 A1 | 9/2016 |
| WO | WO-2016203404 A1 | 12/2016 |
| WO | WO-2016203405 A1 | 12/2016 |
| WO | WO-2016203406 A1 | 12/2016 |
| WO | WO-2017156397 A1 | 9/2017 |
| WO | WO-2017210134 A1 | 12/2017 |
| WO | WO-2017211303 A1 | 12/2017 |
| WO | WO-2017216706 A1 | 12/2017 |
| WO | WO-2018013597 A1 | 1/2018 |
| WO | WO-2018013597 A4 | 1/2018 |
| WO | WO-2018057884 A1 | 3/2018 |
| WO | WO-2018081091 A1 | 5/2018 |
| WO | WO-2018130928 A1 | 7/2018 |
| WO | WO-2018136264 A1 | 7/2018 |
| WO | WO-2018136265 A1 | 7/2018 |
| WO | WO-2018172984 A1 | 9/2018 |
| WO | WO-2018218133 A1 | 11/2018 |
| WO | WO-2019051084 A1 | 3/2019 |
| WO | WO-2019051469 A1 | 3/2019 |
| WO | WO-2019067843 A1 | 4/2019 |
| WO | WO-2019075265 A1 | 4/2019 |
| WO | WO-2019118909 A1 | 6/2019 |
| WO | WO-2019152454 A1 | 8/2019 |
| WO | WO-2019158019 A1 | 8/2019 |
| WO | WO-2019165073 A1 | 8/2019 |
| WO | WO-2019167000 A1 | 9/2019 |
| WO | WO-2019182960 A1 | 9/2019 |
| WO | WO-2019183364 A1 | 9/2019 |
| WO | WO-2019183367 A1 | 9/2019 |
| WO | WO-2019199792 A1 | 10/2019 |
| WO | WO-2019213318 A1 | 11/2019 |
| WO | WO-2019233810 A1 | 12/2019 |
| WO | WO-2020022323 A1 | 1/2020 |
| WO | WO-2020033784 A1 | 2/2020 |
| WO | WO-2020033828 A1 | 2/2020 |
| WO | WO-2020109509 A1 | 6/2020 |
| WO | WO-2020109511 A1 | 6/2020 |
| WO | WO-2020110056 A1 | 6/2020 |
| WO | WO-2020112700 A1 | 6/2020 |
| WO | WO-2020113209 A1 | 6/2020 |
| WO | WO-2020113213 A2 | 6/2020 |

OTHER PUBLICATIONS

Ciapetti et al., Chapter 15—Molecular Variations Based on Isosteric Replacements, The Practice of Medicinal Chemistry, Jan. 1, 2008, 3$^{rd}$ Edition, pp. 290-342.

Chan, G. et al., The tyrosine phosphatase Shp2 (PTPN11) in cancer, Cancer Metastasis Rev, Jun. 2008, 27(2):179-192.

Chen et al., Allosteric inhibition of SHP2 phosphatase inhibits cancers driven by receptor tyrosine kinases, Nature, Jul. 7, 2016, Vo. 535, pp. 148-152.

Darian, E. et al., Structural mechanism associated with domain opening in gain-of-function mutations in SHP2 phosphatase, Proteins, May 2011, e-published Mar. 1, 2011, 79(5):1573-1588.

European Patent Office, Extended European Search Report for European Application No. 19796849.8, dated Nov. 2, 2021, 9 pages.

Grossmann, K.S. et al., The tyrosine phosphatase Shp2 in development and cancer, Adv Cancer Res, 2010, 106:53-89.

Huang, W.Q. et al., Structure, function, and pathogenesis of SHP2 in developmental disorders and tumorigenesis, Curr Cancer Drug Targets, 2014, 14(6):567-588.

International Search Report for International Application No. PCT/US2017/021784, dated Jul. 7, 2017, 4 pages.

International Search Report for International Application No. PCT/US2017/034806, dated Sep. 6, 2017, 2 pages.

International Search Report for International Application No. PCT/US2017/030277, dated Jul. 26, 2019, 3 pages.

International Search Report for International Application No. PCT/US2019/045903 dated Oct. 28, 2019, 5 pages.

Li, J. et al., PD-1/SHP-2 inhibits Tc1/Th1 phenotypic responses and the activation of T cells in the tumor microenvironment, Cancer Res, Feb. 1, 2015, e-published Dec. 5, 2014, 75(3):508-518.

McMahon et al., VEGF Receptor Signaling in Tumor Angiogenesis, The Oncologist, 2000, 5(suppl 1):3-10.

Mohi, M.G. et al., The role of Shp2 (PTPN11) in cancer, Curr Opin Genet Dev, Feb. 2007, e-published Jan. 16, 2007, 17(1):23-30.

Okazaki, T. et al. (Nov. 20, 2001, e-published Nov. 6, 2001). "PD-1 immunoreceptor inhibits B cell receptor-mediated signaling by recruiting src homology 2-domain-containing tyrosine phosphatase 2 to phosphotyrosine," PNAS USA 98(24):13866-13871.

Pinedo et al., Translational Research: The Role of VEGF in Tumor Angiogenesis, the Oncologist, 2000, 5(suppl 1):1-2.

Prahallad, A. et al., PTPN11 Is a Central Node in Intrinsic and Acquired Resistance to Targeted Cancer Drugs, Cell Rep, Sep. 29, 2015, e-published Sep. 10, 2015, 12(12):1978-1985.

PubChem CID 57384833: Create Date: Jul. 23, 2012; Date accessed: Jun. 19, 2017; p. 3.

Qiu, W. et al., Structural insights into Noonan/LEOPARD syndrome-related mutants of protein-tyrosine phosphatase SHP2 (PTPN11), BMC Struct Biol, Mar. 14, 2014, 14:10.

Revesz et al., Novel p38a MAP kinase inhibiting scaffolds with oral activity Bioorganic & Medicinal Chemistry Letters, 2006, 16(2), 262-266.

Tajan, M. et al., SHP2 sails from physiology to pathology, Eur J Med Genet, Oct. 2015, e-published May 28, 2012, 58(10):509-525.

Vippagunta et al., Crystalline solids, Advance Drug Delivery Reviews, 2001, vol. 49, pp. 3-26.

Wolff, M. E., Some Considerations for Prodrug Design, Burger's Medicinal Chemistry and Drug Discovery, 1997, pp. 975-977.

Wong et al., Targeting wild-type KRAS-amplified gastroesophageal cancer through combined MEK and SHP2 inhibition, Nature Medicine, 2018, vol. 24, pp. 968-977.

Yokosuka, T. et al., Programmed cell death 1 forms negative costimulatory microclusters that directly inhibit T cell receptor signaling by recruiting phosphatase SHP2, J Exp Med, Jun. 4, 2012, e-published May 28, 2012, 209(6):1201-1217.

Yu, Z-H. et al., Structural and mechanistic insights into LEOPARD syndrome-associated SHP2 mutations, J Biol Chem, Apr. 12, 2013, e-published Mar. 1, 2013, 288(15):10472-10482.

Written Opinion for International Application No. PCT/US2017/021784, dated Jul. 7, 2017, 6 pages.

Written Opinion for International Application No. PCT/US2017/034806, dated Sep. 6, 2017, 5 pages.

Written Opinion for International Application No. PCT/US2019/030277, dated Jul. 26, 2019, 5 pages.

Written Opinion for International Application No. PCT/US2019/045903, dated Oct. 28, 2019, 6 pages.

HETEROCYCLIC INHIBITORS OF PTPN11

This application is a continuation of U.S. application Ser. No. 16/989,211, filed Aug. 10, 2020, which is a continuation of U.S. application Ser. No. 16/270,333, filed Feb. 7, 2019, now U.S. Pat. No. 10,851,110, which is a continuation of U.S. application Ser. No. 15/607,174, filed May 26, 2017, now U.S. Pat. No. 10,280,171, which claims the benefit of priority of U.S. Provisional Application No. 62/343,455, filed May 31, 2016 and U.S. Provisional Application No. 62/451,432, filed Jan. 27, 2017, the disclosures of which are hereby incorporated by reference as if written herein in their entirety.

Disclosed herein are new compounds and compounds based on pyrazolopyrazines and their application as pharmaceuticals for the treatment of disease. Methods of inhibition of PTPN11 (SHP2) activity in a human or animal subject are also provided for the treatment diseases such as cancer, including leukemia and melanoma, and cancers of the breast, lung, and colon.

Figure 1:
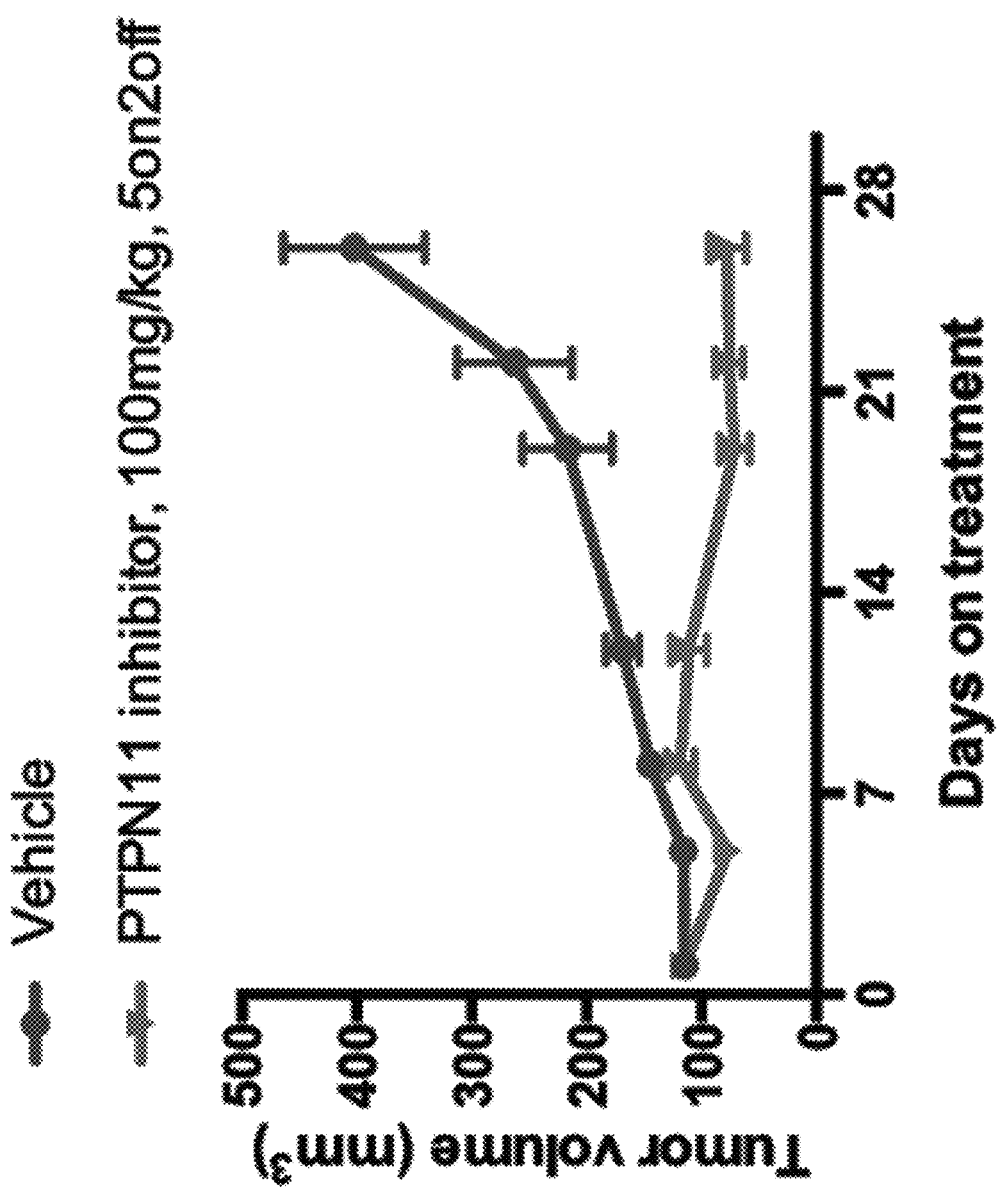
FIG. 1 shows the effect of the compound Example 1 on tumor volume, as compared to carrier alone.

Tyrosyl phosphorylation regulates human cellular processes from cell differentiation to growth and apoptosis, and others. Tyrosyl phosphorylation is regulated by protein-tyrosine kinases (PTK) and protein-tyrosine phosphatases (PTP). The breakdown of regulation governed by PTK and PTP activity is thought to lead to cancer. PTK inhibitors have been developed as potential cancer therapeutic agents. Recent studies disclose a possible role for PTPs in cellular regulation as well. (A J Barr et al. Cell 2009, 136, 352-363. J N Andersen et al Mol. Cell. Biol. 2001, 21, 7117-7136).

Protein-tyrosine phosphatase non-receptor type 11 (PTPN11, also known as Src Homology-2 phosphatase (SHP2)) is a non-receptor protein tyrosine phosphatase encoded by the PTPN11 gene. This PTP contains two tandem Src homology-2 (SH2) domains, which function as phospho-tyrosine binding domains, a catalytic domain, and a C-terminal tail. In the basal state the protein typically exists in an inactive, self-inhibited conformation with the N-terminal SH2 domain blocking the active site. When stimulated by signal transduction mediated by cytokines and growth factor binding of phosphorylated proteins to the SH2 domains the auto-inhibition is relieved, this makes the active site available for dephosphorylation of PTPN11 substrates (M G Mohl, B G Neel, Curr. Opin. Genetics Dev. 2007, 17, 23-30. KS Grossmann, Adv. Cancer Res. 2010, 106, 53-89. W. Q. Huang et. al. Curr. Cancer Drug Targets 2014, 14, 567-588. C. Gordon et. al. Cancer Metastasis Rev. 2008, 27, 179-192).

Germ-line and somatic mutations in PTPN11 have been reported in several human disease resulting in gain-of-function in the catalytic activity, including Noonan Syndrome and Leopard Syndrome; as well as multiple cancers such as juvenile myelomonocytic leukemia, neuroblastoma, myelodysplastic syndrome, B cell acute lymphoblastic leukemia/lymphoma, melanoma, acute myeloid leukemia and cancers of the breast, lung and colon (MG Mohl, B G Neel, Curr. Opin. Genetics Dev. 2007, 17, 23-30). Recent studies have demonstrated that single PTPN11 mutations are able to induce Noonan syndrome, JMML-like myeloproliferative disease and acute leukemia in mice. These mutations disrupt the auto-inhibition between the N—SH2 domains and the catalytic site allowing constitutive access of substrates to the catalytic site of the enzyme (E. Darian et al, Proteins, 2011, 79, 1573-1588. Z-H Yu et al, JBC, 2013, 288, 10472, W Qiu et al BMC Struct. Biol. 2014, 14, 10).

PTPN11 is widely expressed in most tissues and plays a regulatory role in various cell signaling events that are important for a diversity of cell functions that includes proliferation, differentiation, cell cycle maintenance, EMT transition, mitogenic activation, metabolic control, transcription regulation, and cell migration, through multiple signaling pathways including the Ras-MAPK, the JAK-STAT or the PI3K-AKT pathways (Tajan, M. et. al. Eur. J. Medical Genetics, 2015, 58, 509-525. Prahallad, A. et. al. Cell Reports, 2015, 12, 1978-1985).

Additionally there is growing evidence that PTPN11/SHP2 may be implicated in immune evasion during tumorigenesis, and hence a SHP2 inhibitor could stimulate the immune response in cancer patients (Cancer Res. 2015 Feb. 1; 75(3):508-18. T Yokosuka T, J Exp Med. 2012, 209(6), 1201. S Amamath Sci Transl Med. 2011, 3, 111ra120. T Okazaki, PNAS 2001, 98:24, 13866-71).

Novel compounds and pharmaceutical compositions, certain of which have been found to inhibit PTPN11 (SHP2) have been discovered, together with methods of synthesizing and using the compounds including methods for the treatment of PTP-mediated diseases in a patient by administering the compounds.

In certain embodiments of the present invention, compounds have structural Formula I:

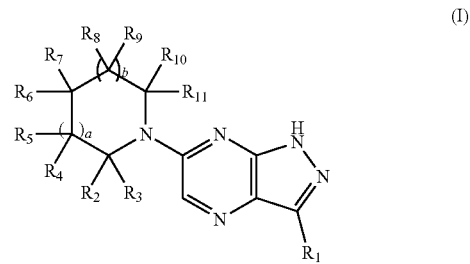

or a salt or tautomer thereof, wherein:

a is selected from 0 and 1;

b is selected from 0 and 1;

$R_1$ is selected from halo, $C_{6-10}$aryl, $C_{3-8}$cycloalkyl, $C_{3-8}$cycloalkenyl, and a 5-9 membered heteroaryl group containing 1 to 4 heteroatoms or groups independently selected from N, C(O), O, and S;

said aryl or heteroaryl of $R_1$ is optionally substituted with 1 to 5 $R_{12}$ groups independently selected from halo, hydroxy, amino, $C_{1-4}$alkylamino, $C_{1-4}$dialkylamino, cyano, $C_{1-4}$alkyl, $C_{1-4}$alkoxy, $C_{1-4}$hydroxyalkyl, $C_{1-4}$haloalkyl, $C_{1-4}$aminoalkyl, $C_{3-8}$cycloalkyl, $C_{3-8}$cycloalkenyl, $NR_{15}C(O)R_{13}$, $NR_{15}C(O)OR_{13}$, $NR_{13}C(O)NR_{15}R_{16}$, $NR_{15}S(O)R_{13}$, $NR_{15}S(O)_2R_{13}$, $C(O)NR_{15}R_{16}$, $S(O)NR_{15}R_{16}$, $S(O)_2NR_{15}R_{16}$, $C(O)R_{13}$, $C(O)OR_{13}$, $SR_{13}$, $S(O)R_{13}$, and $S(O)_2R_{13}$;

$R_2$, $R_3$, $R_{10}$, and $R_{11}$ are independently selected from hydrogen, $C_{1-4}$alkyl, and $C_{3-8}$cycloalkyl;

$R_4$, $R_5$, $R_8$, and $R_9$ are independently selected from hydrogen, cyano, $C_{1-4}$alkyl, $C_{1-4}$alkoxy, amino, hydroxy, $C_{3-8}$cycloalkyl, halo, and $C_{1-4}$alkylamino;

$R_6$ is selected from amino, $C_{1-4}$aminoalkyl, and $C_{1-4}$alkylamino;

$R_7$ is selected from hydrogen, cyano, amido, halo, and hydroxy, or is selected from $C_{1-4}$alkyl, $C_{1-4}$hydroxyalkyl, $C_{3-6}$cycloalkyl, phenyl, and 5- or 6-membered heteroaryl, any of which is optionally substituted with one or more $R_{17}$ groups;

or $R_6$ and $R_7$ together with the carbon atom to which they are both attached form a 3-to 7-membered saturated or unsaturated ring that can contain 1 to 3 heteroatoms or groups independently selected from N, C(O), O, and $S(O)_m$, and that is optionally substituted with one $R_{17}$ group, and that is optionally substituted with one or more $R_{18}$ groups;

m is selected from 0, 1, and 2;

any two groups selected from $R_2$, $R_3$, $R_4$, $R_5$, $R_7$, $R_8$, $R_9$, $R_{10}$ and $R^{11}$ can form a 5- to 6-membered ring, optionally containing a N, O or S heteroatom;

any two groups selected from $R_2$, $R_4$, $R_6$, $R_8$ and $R_{10}$ can form a direct bond, or a 1 or 2 atom carbon bridge;

$R_{13}$, $R_{15}$, and $R_{16}$ are independently selected from hydrogen, $C_{1-4}$alkyl, and $C_{3-8}$cycloakyl, wherein said alkyl or cycloalkyl is optionally substituted by one or more substituents selected from hydroxy, cyano and halo; and each $R_{17}$ and $R_{18}$ is independently selected from amino, halo, hydroxy, cyano, trifluoromethyl, trifluoromethoxy, $C_{1-4}$alkyl, and $C_{1-4}$alkoxy.

Certain compounds disclosed herein may possess useful PTPN11 inhibiting activity, and may be used in the treatment or prophylaxis of a disease or condition in which PTPN11 plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for inhibiting PTPN11. Other embodiments provide methods for treating a PTPN11-mediated disorder in a patient in need of such treatment, comprising administering to said patient a therapeutically effective amount of a compound or composition according to the present invention. Also provided is the use of certain compounds disclosed herein for use in the manufacture of a medicament for the treatment of a disease or condition ameliorated by the inhibition of PTPN11.

In certain embodiments, $R_6$ is selected from amino, $C_{1-4}$aminoalkyl, and methylamino.

In certain embodiments, each $R_{17}$ is independently selected from amino, halo, hydroxy, and cyano.

In certain embodiments, each $R_{17}$ is independently selected from amino, hydroxy, and cyano.

In certain embodiments, $R_{17}$ is amino.

In certain embodiments, each $R_{18}$ is independently selected from halo, hydroxy, and cyano.

In certain embodiments, $R_{18}$ is halo.

In certain embodiments, $R_1$ is selected from $C_{6-10}$aryl and a 5- to 9-membered heteroaryl group containing 1 to 4 heteroatoms or groups independently selected from N, C(O), O, and S;

said aryl or heteroaryl of $R_1$ is optionally substituted with 1 to 5 $R_{12}$ groups independently selected from halo, hydroxy, alkoxy, amino, $C_{1-4}$alkylamino, $C_{1-4}$dialkylamino, cyano, $C_{1-4}$alkyl, $C_{1-4}$hydroxyalkyl, $C_{1-4}$haloalkyl, $C_{1-4}$aminoalkyl, $C_{3-8}$cycloalkyl, $C_{3-8}$cycloalkenyl, $NR_{15}C(O)R_{13}$, $NR_{15}C(O)OR_{13}$, $NR_{13}C(O)NR_{15}R_{16}$, $NR_{15}S(O)R_{13}$, $NR_{15}S(O)_2R_{13}$, $C(O)NR_{15}R_{16}$, $S(O)NR_{15}R_{16}$, $S(O)_2NR_{15}R_{16}$, $C(O)R_{13}$, $C(O)OR_{13}$, $SR_{13}$, $S(O)R_{13}$, and $S(O)_2R_{13}$; and $R_{13}$, $R_{15}$, and $R_{16}$ are independently selected from hydrogen, $C_{1-4}$alkyl, and $C_{3-8}$cycloakyl, wherein said alkyl or cycloalkyl is optionally substituted by one or more substituents selected from hydroxy, cyano and halo.

In certain embodiments, $R_1$ is selected from $C_{6-10}$aryl and a 5- to 9-membered heteroaryl group containing 1 to 4 heteroatoms or groups independently selected from N, C(O), O, and S;

said aryl or heteroaryl of $R_1$ is optionally substituted with 1 to 5 $R_{12}$ groups independently selected from halo, hydroxy, alkoxy, amino, $C_{1-4}$alkyl, $C_{1-4}$haloalkyl, and $C_{1-4}$aminoalkyl; and $R_{17}$ is selected from amino, halo, and hydroxy.

In certain embodiments, $R_1$ is selected from $C_{6-10}$aryl and a 5- to 9-membered heteroaryl group containing 1 to 4 heteroatoms or groups independently selected from N, C(O), O, and S;

said aryl or heteroaryl of $R_1$ is optionally substituted with 1 to 5 $R_{12}$ groups independently selected from halo, hydroxy, alkoxy, amino, $C_{1-4}$alkyl, $C_{1-4}$haloalkyl, and $C_{1-4}$aminoalkyl;

$R_6$ is selected from amino, $C_{1-4}$aminoalkyl, and $C_{1-4}$alkylamino;

$R_7$ is selected from hydrogen, halo, and hydroxy, or is selected from $C_{1-4}$alkyl, $C_{1-4}$hydroxyalkyl, $C_{3-6}$cycloalkyl, phenyl, and 5- or 6-membered heteroaryl, any of which is optionally substituted with one or more $R_{17}$ groups.

In certain embodiments, $R_1$ is selected from $C_{6-10}$aryl and a 5- to 9-membered heteroaryl group containing 1 to 4 heteroatoms or groups independently selected from N, C(O), O, and S;

said aryl or heteroaryl of $R_1$ is optionally substituted with 1 to 5 $R_{12}$ groups independently selected from halo, hydroxy, alkoxy, amino, $C_{1-4}$alkyl, $C_{1-4}$haloalkyl, and $C_{1-4}$aminoalkyl; and $R_4$, $R_5$, $R_8$, and $R_9$ are independently selected from hydrogen, $C_{1-4}$alkyl, $C_{1-4}$alkoxy, amino, hydroxy, $C_{3-8}$cycloalkyl, and $C_{1-4}$alkylamino.

In certain embodiments, $R_2$, $R_3$, $R_4$, $R_5$, $R_8$, $R_9$, $R_{10}$ and $R_{11}$ are hydrogen.

In certain embodiments, $R_6$ and $R_7$ together with the carbon atom to which they are both attached form a 3- to 7-membered cycloalkyl ring that is optionally substituted with one $R_{17}$ group, and that is optionally substituted with one or more $R_{18}$ groups.

In certain embodiments, $R_1$ is selected from $C_{6-10}$aryl and a 5- to 9-membered heteroaryl group containing 1 to 4 heteroatoms or groups independently selected from N, C(O), O, and S;

said aryl or heteroaryl of $R_1$ is optionally substituted with 1 to 5 $R_{12}$ groups independently selected from halo, hydroxy, amino, $C_{1-4}$alkylamino, $C_{1-4}$dialkylamino, $C_{1-4}$alkyl, $C_{1-4}$alkoxy, $C_{1-4}$haloalkyl, and $C_{1-4}$aminoalkyl; and $R_{17}$ is selected from amino, halo, and hydroxy.

In certain embodiments, $R_1$ is selected from $C_{6-10}$aryl and a 5- to 9-membered heteroaryl group containing 1 to 4 heteroatoms or groups independently selected from N, C(O), O, and S;

said aryl or heteroaryl of $R_1$ is optionally substituted with 1 to 5 $R_{12}$ groups independently selected from halo, hydroxy, amino, $C_{1-4}$alkylamino, $C_{1-4}$dialkylamino, $C_{1-4}$alkyl, $C_{1-4}$alkoxy, $C_{1-4}$haloalkyl, and $C_{1-4}$aminoalkyl;

$R_6$ is selected from amino, $C_{1-4}$aminoalkyl, and $C_{1-4}$alkylamino; and $R_7$ is selected from hydrogen, cyano, amido, halo, and hydroxy, or is selected from $C_{1-4}$alkyl, $C_{1-4}$hydroxyalkyl, $C_{3-6}$cycloalkyl, phenyl, and 5- or 6-membered heteroaryl, any of which is optionally substituted with one or more $R_{17}$ groups.

In certain embodiments,

R_6 and R_7 together with the carbon atom to which they are both attached form a 3- to 7-membered saturated or unsaturated ring that can contain 1 to 3 heteroatoms or groups independently selected from N, C(O), O, and S(O)_m, and that is optionally substituted with one R_17 group, and that is optionally substituted with one or more R_18 groups.

In certain embodiments,

R_6 and R_7 together with the carbon atom to which they are both attached forms a 3- to 7-membered cycloalkyl ring that is optionally substituted with one R_17 group, and that is optionally substituted with one or more R_18 groups.

In certain embodiments,

R_6 and R_7 together with the carbon atom to which they are both attached forms a 3- to 7-membered heterocycloalkyl ring that is optionally substituted with one R_17 group, and that is optionally substituted with one or more R_18 groups.

In certain embodiments,

R_6 and R_7 together with the carbon atom to which they are both attached forms a 3- to 7-membered heterocycloalkyl ring that is optionally substituted with one R_17 group.

In certain embodiments,

R_6 and R_7 together with the carbon atom to which they are both attached form a 3- to 6-membered heterocycloalkyl ring that is optionally substituted with one R_17 group, and that is optionally substituted with one or more R_18 groups.

In certain embodiments,

R_6 and R_7 together with the carbon atom to which they are both attached form a 3- to 6-membered heterocycloalkyl ring that is optionally substituted with one R_17 group.

In certain embodiments,

R_6 is C_{1-4}aminoalkyl; and

R_7 is selected from hydroxy, or is selected from C_{1-4}alkyl, C_{1-4}hydroxyalkyl, C_{3-6}cycloalkyl, phenyl, and 5- or 6-membered heteroaryl, any of which is optionally substituted with one or more R_17 groups.

In certain embodiments,

R_6 is aminomethyl; and

R_7 is selected from hydroxy, C_{1-4}alkyl, C_{1-4}hydroxyalkyl, C_{3-6}cycloalkyl, phenyl, and 5- or 6-membered heteroaryl.

In certain embodiments,

R_6 is amino; and

R_7 is selected from amido, C_{1-4}alkyl, C_{1-4}hydroxyalkyl, C_{3-6}cycloalkyl, phenyl, and 5- or 6-membered heteroaryl, any of which is optionally substituted with one or more R_17 groups.

In certain embodiments,

R_6 is amino; and

R_7 is C_{1-4}hydroxyalkyl.

In any of the above embodiments, the amido of R_7 may specifically be —C(O)NH_2.

In certain embodiments,

R_1 is selected from C_{6-10}aryl and a 5-9 membered heteroaryl group containing 1 to 4 heteroatoms or groups independently selected from N, C(O), O, and S; and said aryl or heteroaryl of R_1 is optionally substituted with 1 to 5 R_12 groups independently selected from halo, hydroxy, alkoxy, amino, C_{1-4}alkylamino, C_{1-4}dialkylamino, cyano, and C_{1-4}alkyl.

In certain embodiments, R_1 is selected from:

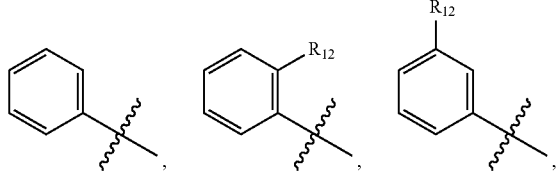

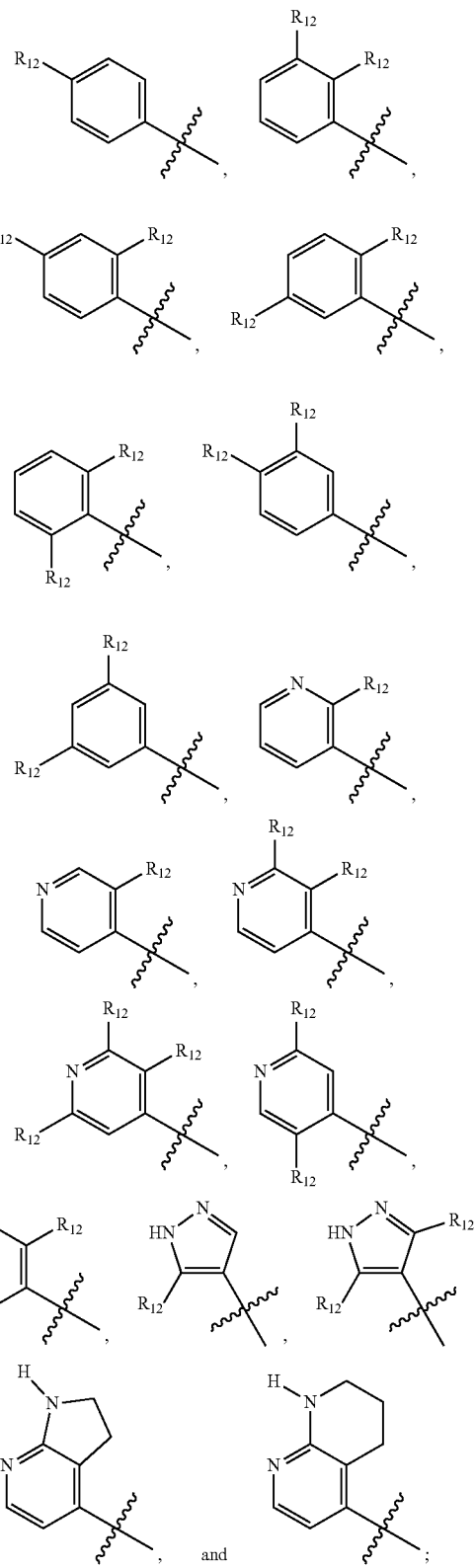

and each R_12 is independently selected from halo, hydroxy, amino, methylamino, dimethylamino, cyano, C_{1-4}alkyl, and C_{1-4}alkoxy.

In certain embodiments, $R_1$ is selected from:

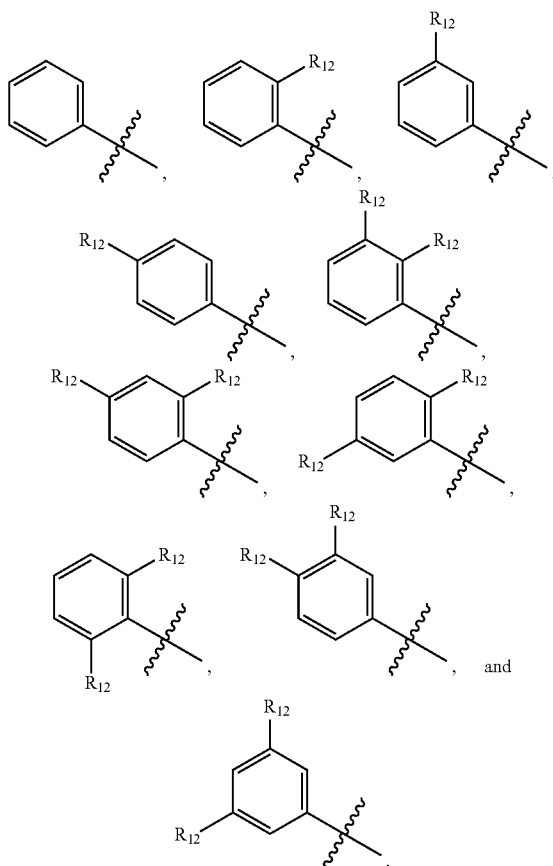

In certain embodiments, $R_1$ is selected as above, wherein each $R_{12}$ is independently selected from halo, hydroxy, $C_{1-4}$alkyl, and $C_{1-4}$alkoxy.

In certain embodiments, $R_1$ is selected from pyridyl, piperazinyl, pyrimidinyl, pyrazolyl, and pyridazinyl.

In certain embodiments, $R_1$ is phenyl.

In certain embodiments, compounds have structural Formula II:

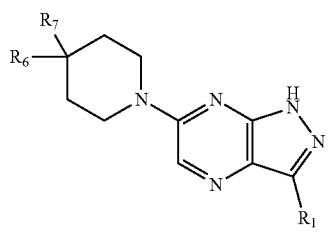

(II)

or a salt or tautomer thereof, wherein:

$R_1$ is selected from halo, $C_{6-10}$aryl, $C_{3-8}$cycloalkyl, $C_{3-8}$cycloalkenyl, and a 5-9 membered heteroaryl group containing 1 to 4 heteroatoms or groups independently selected from N, C(O), O, and S;

said aryl or heteroaryl of $R_1$ is optionally substituted with 1 to 5 $R_{12}$ groups independently selected from halo, hydroxy, amino, $C_{1-4}$alkylamino, $C_{1-4}$dialkylamino, cyano, $C_{1-4}$alkyl, $C_{1-4}$alkoxy, $C_{1-4}$hydroxyalkyl, $C_{1-4}$haloalkyl, $C_{1-4}$aminoalkyl, $C_{3-8}$cycloalkyl, $C_{3-8}$cycloalkenyl, $NR_{15}C(O)R_{13}$, $NR_{15}C(O)OR_{13}$, $NR_{13}C(O)NR_{15}R_{16}$, $NR_{15}S(O)R_{13}$, $NR_{15}S(O)_2R_{13}$, $C(O)NR_{15}R_{16}$, $S(O)NR_{15}R_{16}$, $S(O)_2NR_{15}R_{16}$, $C(O)R_{13}$, $C(O)OR_{13}$, $SR_{13}$, $S(O)R_{13}$, and $S(O)_2R_{13}$;

$R_6$ is selected from amino, $C_{1-4}$aminoalkyl, and $C_{1-4}$alkylamino;

$R_7$ is selected from hydrogen, cyano, amido, halo, and hydroxy, or is selected from $C_{1-4}$alkyl, $C_{1-4}$hydroxyalkyl, $C_{3-6}$cycloalkyl, phenyl, and 5- or 6-membered heteroaryl, any of which is optionally substituted with one or more $R_{17}$ groups;

$R_{13}$, $R_{15}$, and $R_{16}$ are independently selected from hydrogen, $C_{1-4}$alkyl, and $C_{3-8}$cycloakyl, wherein said alkyl or cycloalkyl is optionally substituted by one or more substituents selected from hydroxy, cyano and halo; and each $R_{17}$ is independently selected from amino, halo, hydroxy, cyano, trifluoromethyl, trifluoromethoxy, $C_{1-4}$alkyl, and $C_{1-4}$alkoxy.

In certain embodiments, compounds have structural Formula III:

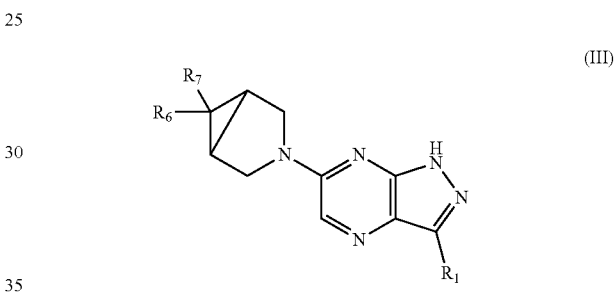

(III)

or a salt or tautomer thereof, wherein:

$R_1$ is selected from halo, $C_{6-10}$aryl, $C_{3-8}$cycloalkyl, $C_{3-8}$cycloalkenyl, and a 5-9 membered heteroaryl group containing 1 to 4 heteroatoms or groups independently selected from N, C(O), O, and S;

said aryl or heteroaryl of $R_1$ is optionally substituted with 1 to 5 $R_{12}$ groups independently selected from halo, hydroxy, amino, $C_{1-4}$alkylamino, $C_{1-4}$dialkylamino, cyano, $C_{1-4}$alkyl, $C_{1-4}$alkoxy, $C_{1-4}$hydroxyalkyl, $C_{1-4}$haloalkyl, $C_{1-4}$aminoalkyl, $C_{3-8}$cycloalkyl, $C_{3-8}$cycloalkenyl, $NR_{15}C(O)R_{13}$, $NR_{15}C(O)OR_{13}$, $NR_{13}C(O)NR_{15}R_{16}$, $NR_{15}S(O)R_{13}$, $NR_{15}S(O)_2R_{13}$, $C(O)NR_{15}R_{16}$, $S(O)NR_{15}R_{16}$, $S(O)_2NR_{15}R_{16}$, $C(O)R_{13}$, $C(O)OR_{13}$, $SR_{13}$, $S(O)R_{13}$, and $S(O)_2R_{13}$;

$R_6$ is selected from amino, $C_{1-4}$aminoalkyl, and $C_{1-4}$alkylamino;

$R_7$ is selected from hydrogen, cyano, amido, halo, and hydroxy, or is selected from $C_{1-4}$alkyl, $C_{1-4}$hydroxyalkyl, $C_{3-6}$cycloalkyl, phenyl, and 5- or 6-membered heteroaryl, any of which is optionally substituted with one or more $R_{17}$ groups;

$R_{13}$, $R_{15}$, and $R_{16}$ are independently selected from hydrogen, $C_{1-4}$alkyl, and $C_{3-8}$cycloakyl, wherein said alkyl or cycloalkyl is optionally substituted by one or more substituents selected from hydroxy, cyano and halo; and each $R_{17}$ is independently selected from amino, halo, hydroxy, cyano, trifluoromethyl, trifluoromethoxy, $C_{1-4}$alkyl, and $C_{1-4}$alkoxy.

In certain embodiments, compounds have structural Formula IV:

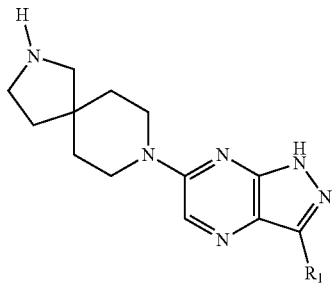

(IV)

or a salt or tautomer thereof, wherein:

$R_1$ is selected from halo, $C_{6-10}$aryl, $C_{3-8}$cycloalkyl, $C_{3-8}$cycloalkenyl, and a 5-9 membered heteroaryl group containing 1 to 4 heteroatoms or groups independently selected from N, C(O), O, and S;

said aryl or heteroaryl of $R_1$ is optionally substituted with 1 to 5 $R_{12}$ groups independently selected from halo, hydroxy, amino, $C_{1-4}$alkylamino, $C_{1-4}$dialkylamino, cyano, $C_{1-4}$alkyl, $C_{1-4}$alkoxy, $C_{1-4}$hydroxyalkyl, $C_{1-4}$haloalkyl, $C_{1-4}$aminoalkyl, $C_{3-8}$cycloalkyl, $C_{3-8}$cycloalkenyl, $NR_{15}C(O)R_{13}$, $NR_{15}C(O)OR_{13}$, $NR_{13}C(O)NR_{15}R_{16}$, $NR_{15}S(O)R_{13}$, $NR_{15}S(O)_2R_{13}$, $C(O)NR_{15}R_{16}$, $S(O)NR_{15}R_{16}$, $S(O)_2NR_{15}R_{16}$, $C(O)R_{13}$, $C(O)OR_{13}$, $SR_{13}$, $S(O)R_{13}$, and $S(O)_2R_{13}$; and $R_{13}$, $R_{15}$, and $R_{16}$ are independently selected from hydrogen, $C_{1-4}$alkyl, and $C_{3-8}$cycloakyl, wherein said alkyl or cycloalkyl is optionally substituted by one or more substituents selected from hydroxy, cyano and halo.

In certain embodiments, compounds have structural Formula V:

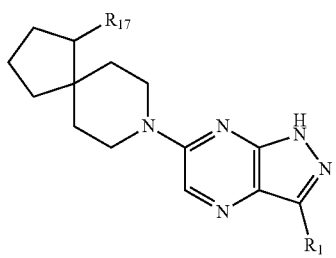

(V)

or a salt or tautomer thereof, wherein:

$R_1$ is selected from halo, $C_{6-10}$aryl, $C_{3-8}$cycloalkyl, $C_{3-8}$cycloalkenyl, and a 5-9 membered heteroaryl group containing 1 to 4 heteroatoms or groups independently selected from N, C(O), O, and S;

said aryl or heteroaryl of $R_1$ is optionally substituted with 1 to 5 $R_{12}$ groups independently selected from halo, hydroxy, amino, $C_{1-4}$alkylamino, $C_{1-4}$dialkylamino, cyano, $C_{1-4}$alkyl, $C_{1-4}$alkoxy, $C_{1-4}$hydroxyalkyl, $C_{1-4}$haloalkyl, $C_{1-4}$aminoalkyl, $C_{3-8}$cycloalkyl, $C_{3-8}$cycloalkenyl, $NR_{15}C(O)R_{13}$, $NR_{15}C(O)OR_{13}$, $NR_{13}C(O)NR_{15}R_{16}$, $NR_{15}S(O)R_{13}$, $NR_{15}S(O)_2R_{13}$, $C(O)NR_{15}R_{16}$, $S(O)NR_{15}R_{16}$, $S(O)_2NR_{15}R_{16}$, $C(O)R_{13}$, $C(O)OR_{13}$, $SR_{13}$, $S(O)R_{13}$, and $S(O)_2R_{13}$;

$R_{13}$, $R_{15}$, and $R_{16}$ are independently selected from hydrogen, $C_{1-4}$alkyl, and $C_{3-8}$cycloakyl, wherein said alkyl or cycloalkyl is optionally substituted by one or more substituents selected from hydroxy, cyano and halo; and $R_{17}$ is selected from amino, halo, hydroxy, cyano, trifluoromethyl, trifluoromethoxy, $C_{1-4}$alkyl, and $C_{1-4}$alkoxy.

In certain embodiments, compounds have structural Formula VI:

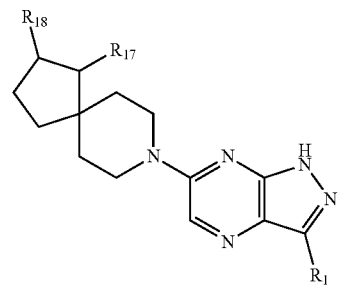

(VI)

or a salt or tautomer thereof, wherein:

$R_1$ is selected from halo, $C_{6-10}$aryl, $C_{3-8}$cycloalkyl, $C_{3-8}$cycloalkenyl, and a 5-9 membered heteroaryl group containing 1 to 4 heteroatoms or groups independently selected from N, C(O), O, and S;

said aryl or heteroaryl of $R_1$ is optionally substituted with 1 to 5 $R_{12}$ groups independently selected from halo, hydroxy, amino, $C_{1-4}$alkylamino, $C_{1-4}$dialkylamino, cyano, $C_{1-4}$alkyl, $C_{1-4}$alkoxy, $C_{1-4}$hydroxyalkyl, $C_{1-4}$haloalkyl, $C_{1-4}$aminoalkyl, $C_{3-8}$cycloalkyl, $C_{3-8}$cycloalkenyl, $NR_{15}C(O)R_{13}$, $NR_{15}C(O)OR_{13}$, $NR_{13}C(O)NR_{15}R_{16}$, $NR_{15}S(O)R_{13}$, $NR_{15}S(O)_2R_{13}$, $C(O)NR_{15}R_{16}$, $S(O)NR_{15}R_{16}$, $S(O)_2NR_{15}R_{16}$, $C(O)R_{13}$, $C(O)OR_{13}$, $SR_{13}$, $S(O)R_{13}$, and $S(O)_2R_{13}$;

$R_{13}$, $R_{15}$, and $R_{16}$ are independently selected from hydrogen, $C_{1-4}$alkyl, and $C_{3-8}$cycloakyl, wherein said alkyl or cycloalkyl is optionally substituted by one or more substituents selected from hydroxy, cyano and halo;

$R_{17}$ is selected from amino, halo, hydroxy, cyano, trifluoromethyl, trifluoromethoxy, $C_{1-4}$alkyl, and $C_{1-4}$alkoxy; and $R_{18}$ is selected from halo, hydroxy, and cyano.

In certain embodiments, compounds have structural Formula VII:

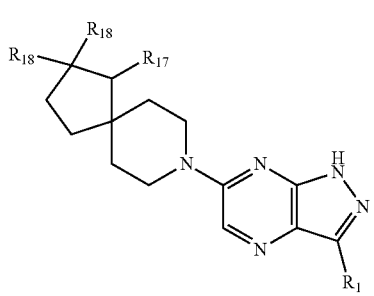

(VII)

or a salt or tautomer thereof, wherein:

$R_1$ is selected from halo, $C_{6-10}$aryl, $C_{3-8}$cycloalkyl, $C_{3-8}$cycloalkenyl, and a 5-9 membered heteroaryl group containing 1 to 4 heteroatoms or groups independently selected from N, C(O), O, and S;

said aryl or heteroaryl of $R_1$ is optionally substituted with 1 to 5 $R_{12}$ groups independently selected from halo, hydroxy, amino, $C_{1-4}$alkylamino, $C_{1-4}$dialkylamino, cyano, $C_{1-4}$alkyl, $C_{1-4}$alkoxy, $C_{1-4}$hydroxyalkyl, $C_{1-4}$haloalkyl, $C_{1-4}$aminoalkyl, $C_{3-8}$cycloalkyl, $C_{3-8}$cycloalkenyl, $NR_{15}C(O)R_{13}$, $NR_{15}C(O)OR_{13}$, $NR_{13}C(O)NR_{15}R_{16}$, $NR_{15}S(O)R_{13}$, $NR_{15}S(O)_2R_{13}$, $C(O)NR_{15}R_{16}$, $S(O)NR_{15}R_{16}$, $S(O)_2NR_{15}R_{16}$, $C(O)R_{13}$, $C(O)OR_{13}$, $SR_{13}$, $S(O)R_{13}$, and $S(O)_2R_{13}$;

$R_{13}$, $R_{15}$, and $R_{16}$ are independently selected from hydrogen, $C_{1-4}$alkyl, and $C_{3-8}$cycloakyl, wherein said alkyl or cycloalkyl is optionally substituted by one or more substituents selected from hydroxy, cyano and halo;

$R_{17}$ is selected from amino, halo, hydroxy, cyano, trifluoromethyl, trifluoromethoxy, $C_{1-4}$alkyl, and $C_{1-4}$alkoxy; and each $R_{18}$ is independently selected from halo, hydroxy, and cyano.

In certain embodiments, compounds have structural Formula VIII:

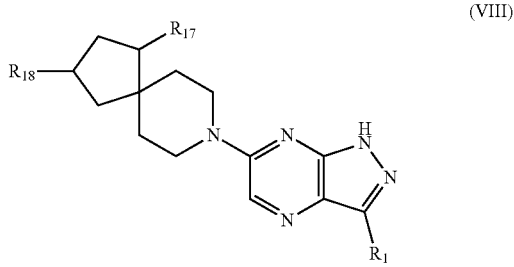

(VIII)

or a salt or tautomer thereof, wherein:

$R_1$ is selected from halo, $C_{6-10}$aryl, $C_{3-8}$cycloalkyl, $C_{3-8}$cycloalkenyl, and a 5-9 membered heteroaryl group containing 1 to 4 heteroatoms or groups independently selected from N, C(O), O, and S;

said aryl or heteroaryl of $R_1$ is optionally substituted with 1 to 5 $R_{12}$ groups independently selected from halo, hydroxy, amino, $C_{1-4}$alkylamino, $C_{1-4}$dialkylamino, cyano, $C_{1-4}$alkyl, $C_{1-4}$alkoxy, $C_{1-4}$hydroxyalkyl, $C_{1-4}$haloalkyl, $C_{1-4}$aminoalkyl, $C_{3-8}$cycloalkyl, $C_{3-8}$cycloalkenyl, $NR_{15}C(O)R_{13}$, $NR_{15}C(O)OR_{13}$, $NR_{13}C(O)NR_{15}R_{16}$, $NR_{15}S(O)R_{13}$, $NR_{15}S(O)_2R_{13}$, $C(O)NR_{15}R_{16}$, $S(O)NR_{15}R_{16}$, $S(O)_2NR_{15}R_{16}$, $C(O)R_{13}$, $C(O)OR_{13}$, $SR_{13}$, $S(O)R_{13}$, and $S(O)_2R_{13}$;

$R_{13}$, $R_{15}$, and $R_{16}$ are independently selected from hydrogen, $C_{1-4}$alkyl, and $C_{3-8}$cycloakyl, wherein said alkyl or cycloalkyl is optionally substituted by one or more substituents selected from hydroxy, cyano and halo;

$R_{17}$ is selected from amino, halo, hydroxy, cyano, trifluoromethyl, trifluoromethoxy, $C_{1-4}$alkyl, and $C_{1-4}$alkoxy; and $R_{18}$ is selected from halo, hydroxy, and cyano.

In certain embodiments, compounds have structural Formula IX:

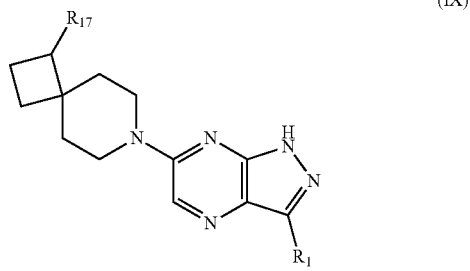

(IX)

or a salt or tautomer thereof, wherein:

$R_1$ is selected from halo, $C_{6-10}$aryl, $C_{3-8}$cycloalkyl, $C_{3-8}$cycloalkenyl, and a 5-9 membered heteroaryl group containing 1 to 4 heteroatoms or groups independently selected from N, C(O), O, and S;

said aryl or heteroaryl of $R_1$ is optionally substituted with 1 to 5 $R_{12}$ groups independently selected from halo, hydroxy, amino, $C_{1-4}$alkylamino, $C_{1-4}$dialkylamino, cyano, $C_{1-4}$alkyl, $C_{1-4}$alkoxy, $C_{1-4}$hydroxyalkyl, $C_{1-4}$haloalkyl, $C_{1-4}$aminoalkyl, $C_{3-8}$cycloalkyl, $C_{3-8}$cycloalkenyl, $NR_{15}C(O)R_{13}$, $NR_{15}C(O)OR_{13}$, $NR_{13}C(O)NR_{15}R_{16}$, $NR_{15}S(O)R_{13}$, $NR_{15}S(O)_2R_{13}$, $C(O)NR_{15}R_{16}$, $S(O)NR_{15}R_{16}$, $S(O)_2NR_{15}R_{16}$, $C(O)R_{13}$, $C(O)OR_{13}$, $SR_{13}$, $S(O)R_{13}$, and $S(O)_2R_{13}$;

$R_{13}$, $R_{15}$, and $R_{16}$ are independently selected from hydrogen, $C_{1-4}$alkyl, and $C_{3-8}$cycloakyl, wherein said alkyl or cycloalkyl is optionally substituted by one or more substituents selected from hydroxy, cyano and halo; and $R_{17}$ is selected from amino, halo, hydroxy, cyano, trifluoromethyl, trifluoromethoxy, $C_{1-4}$alkyl, and $C_{1-4}$alkoxy.

In certain embodiments, compounds have structural Formula X:

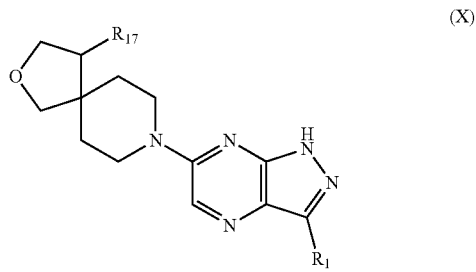

(X)

or a salt or tautomer thereof, wherein:

$R_1$ is selected from halo, $C_{6-10}$aryl, $C_{3-8}$cycloalkyl, $C_{3-8}$cycloalkenyl, and a 5-9 membered heteroaryl group containing 1 to 4 heteroatoms or groups independently selected from N, C(O), O, and S;

said aryl or heteroaryl of $R_1$ is optionally substituted with 1 to 5 $R_{12}$ groups independently selected from halo, hydroxy, amino, $C_{1-4}$alkylamino, $C_{1-4}$dialkylamino, cyano, $C_{1-4}$alkyl, $C_{1-4}$alkoxy, $C_{1-4}$hydroxyalkyl, $C_{1-4}$haloalkyl, $C_{1-4}$aminoalkyl, $C_{3-8}$cycloalkyl, $C_{3-8}$cycloalkenyl, $NR_{15}C(O)R_{13}$, $NR_{15}C(O)OR_{13}$, $NR_{13}C(O)NR_{15}R_{16}$, $NR_{15}S(O)R_{13}$, $NR_{15}S(O)_2R_{13}$, $C(O)NR_{15}R_{16}$, $S(O)NR_{15}R_{16}$, $S(O)_2NR_{15}R_{16}$, $C(O)R_{13}$, $C(O)OR_{13}$, $SR_{13}$, $S(O)R_{13}$, and $S(O)_2R_{13}$;

$R_{13}$, $R_{15}$, and $R_{16}$ are independently selected from hydrogen, $C_{1-4}$alkyl, and $C_{3-8}$cycloakyl, wherein said alkyl or cycloalkyl is optionally substituted by one or more substituents selected from hydroxy, cyano and halo; and $R_{17}$ is selected from amino, halo, hydroxy, cyano, trifluoromethyl, trifluoromethoxy, $C_{1-4}$alkyl, and $C_{1-4}$alkoxy.

In certain embodiments of any of Formulas II-X, $R_1$, $R_6$, $R_7$, $R_{17}$, and $R_{18}$ are as defined and described herein.

In certain embodiments, the compound is selected from:
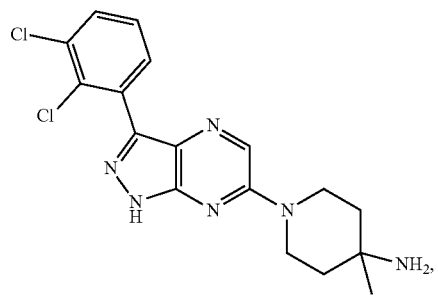
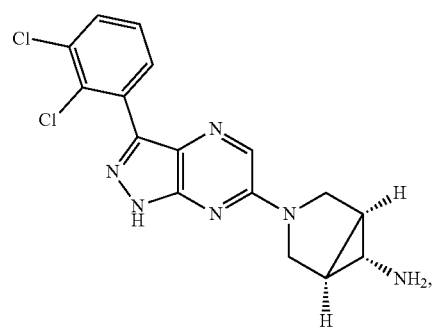
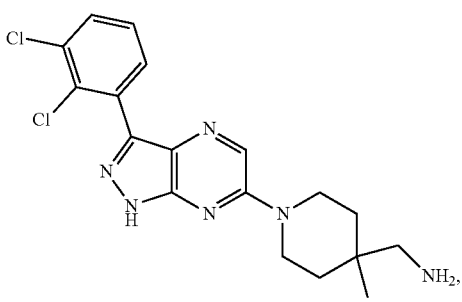
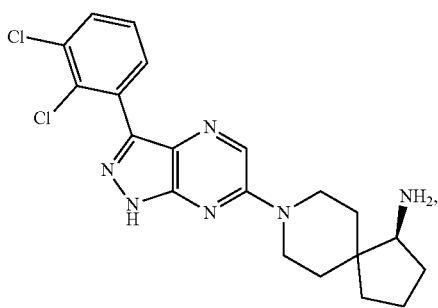
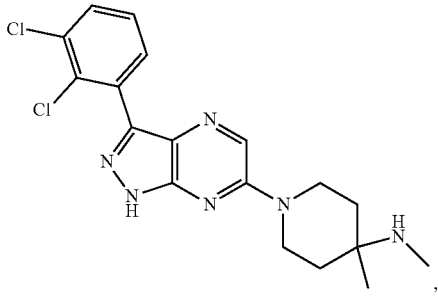
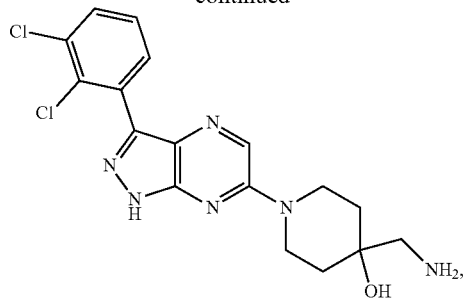
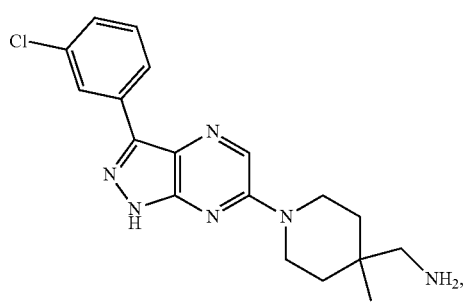
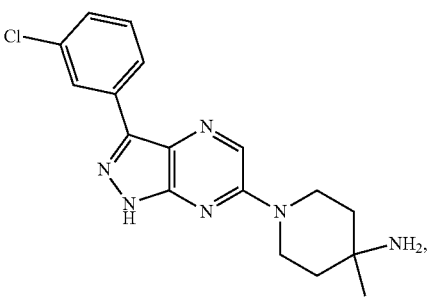
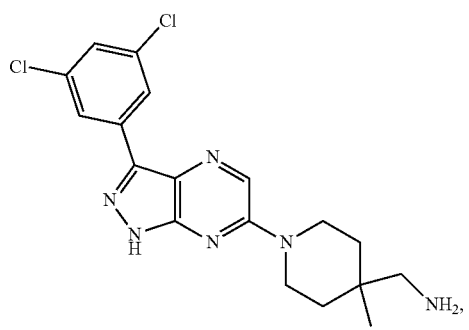
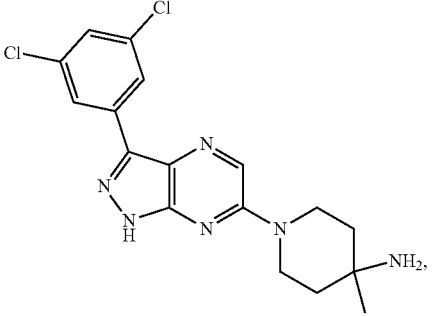

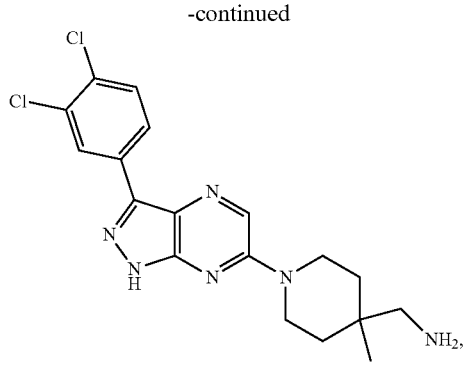
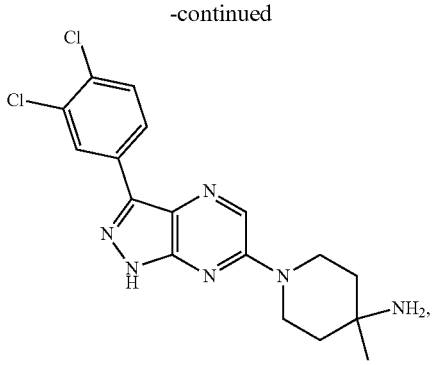
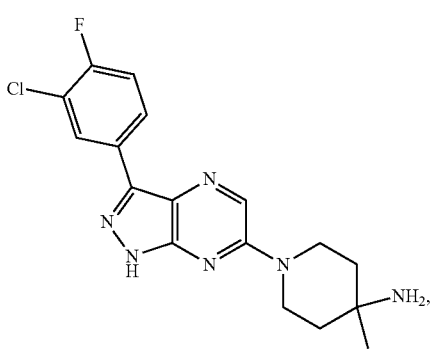
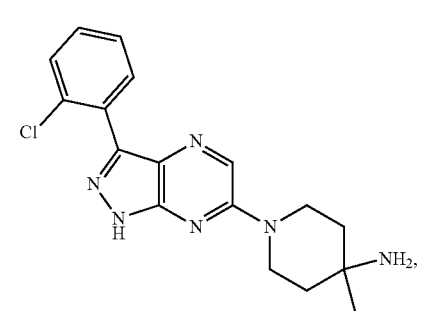
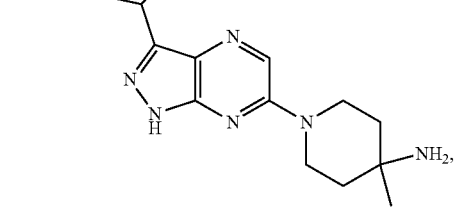
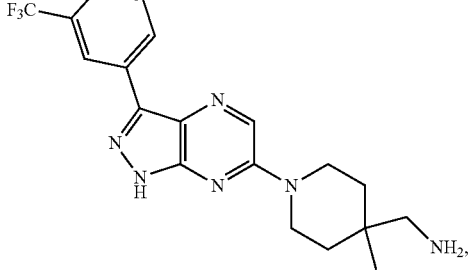

-continued
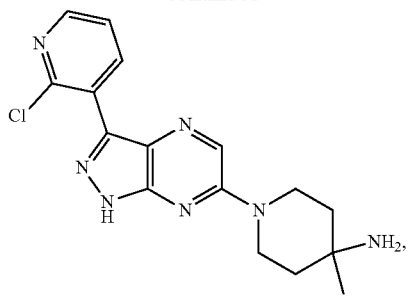
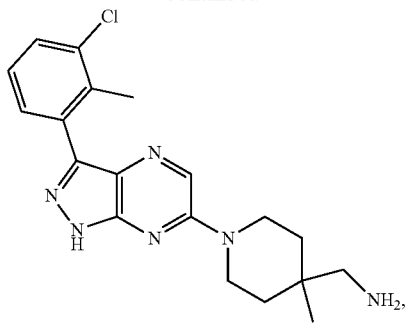
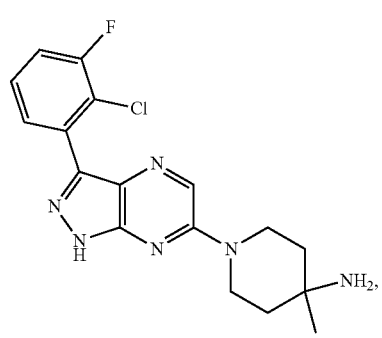
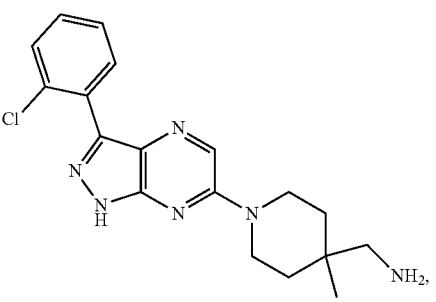
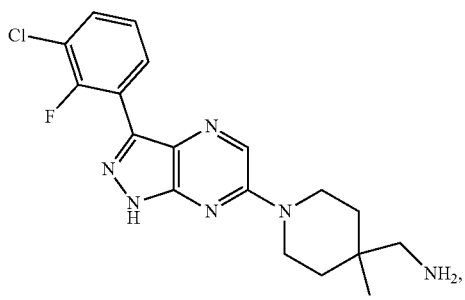
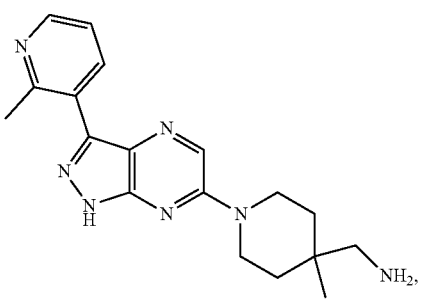
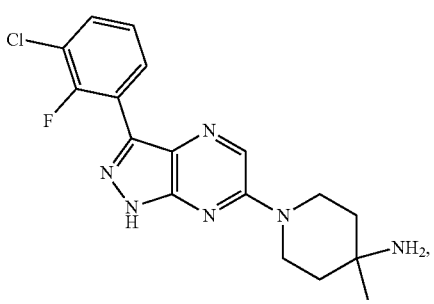
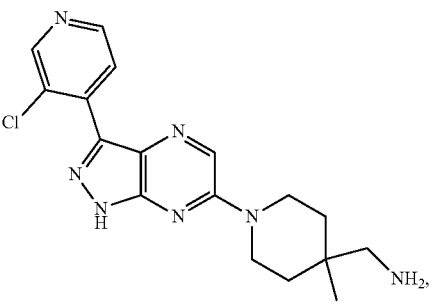
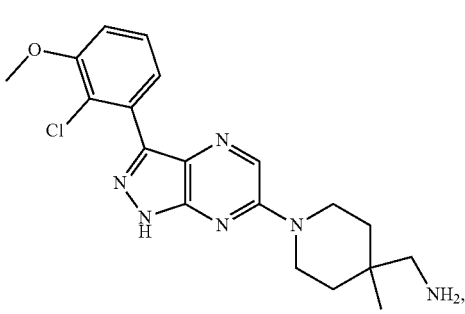
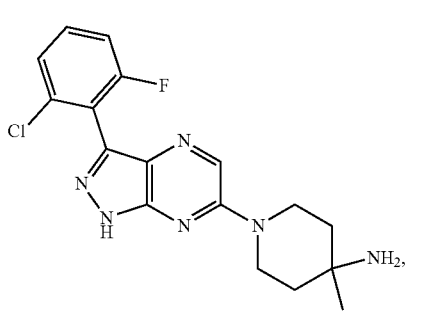

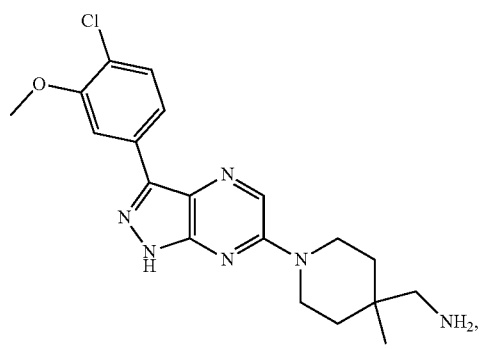
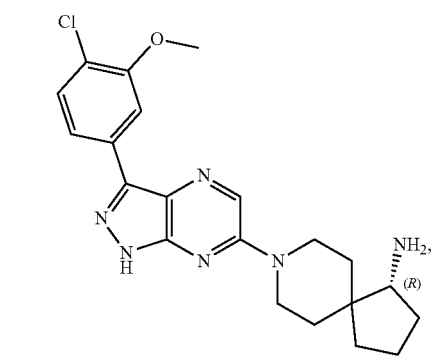
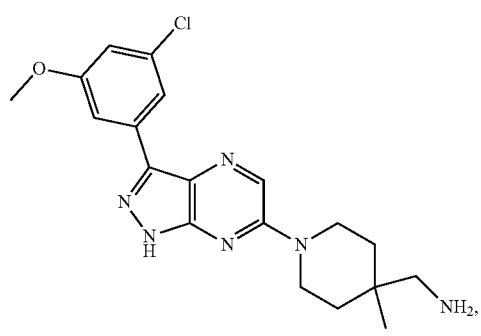
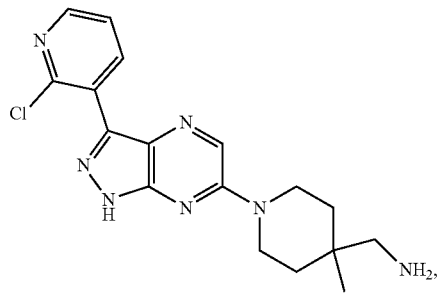
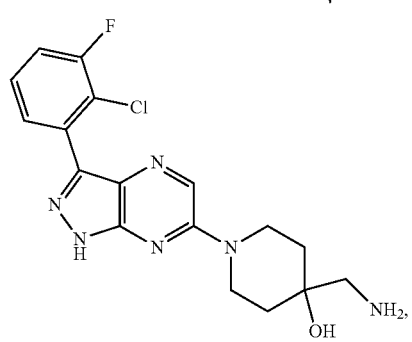
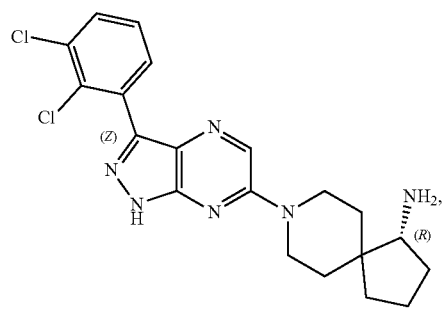
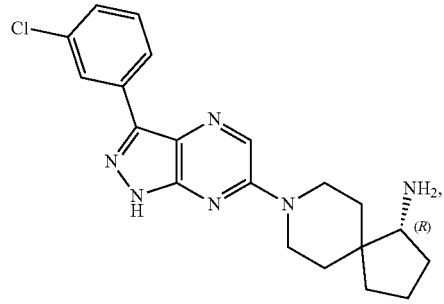
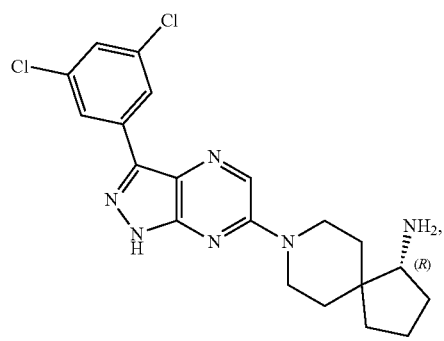
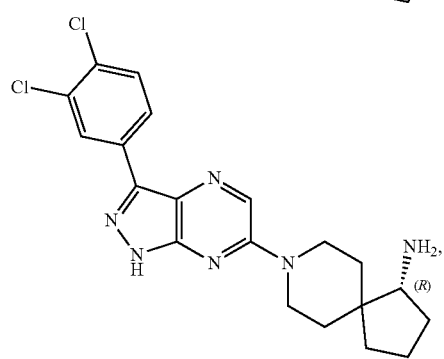
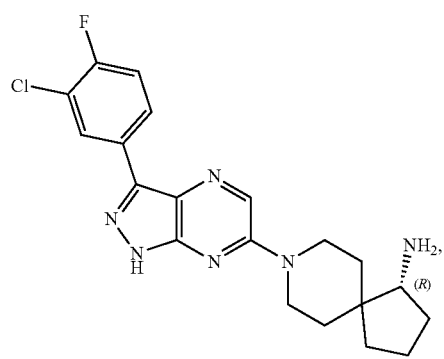

-continued
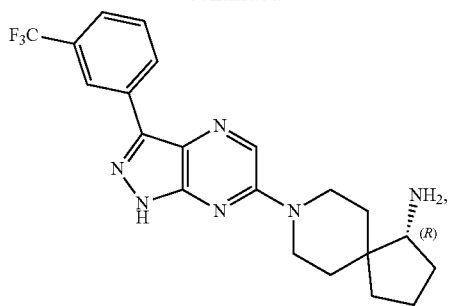
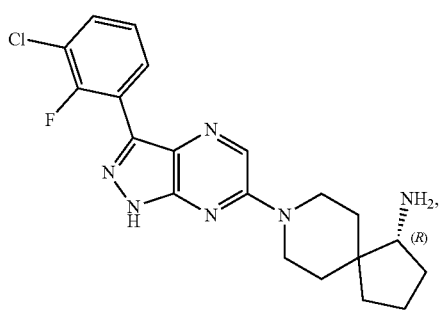
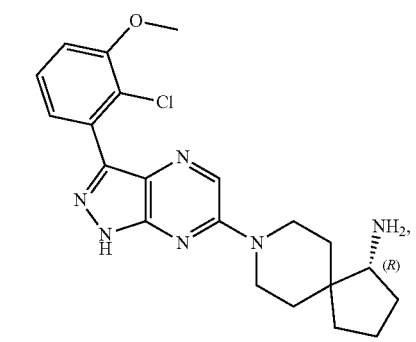
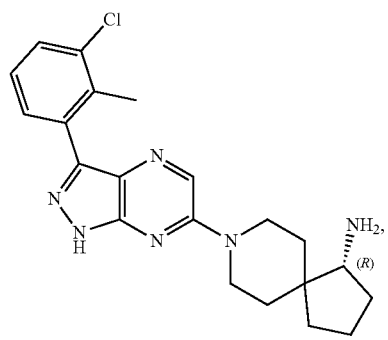
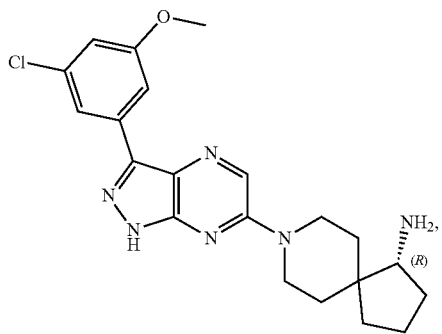
-continued
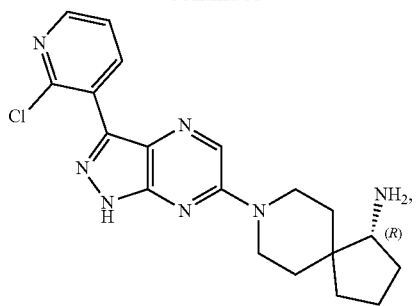
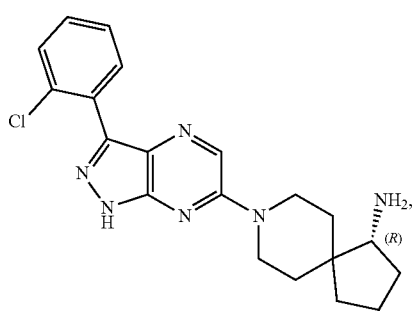
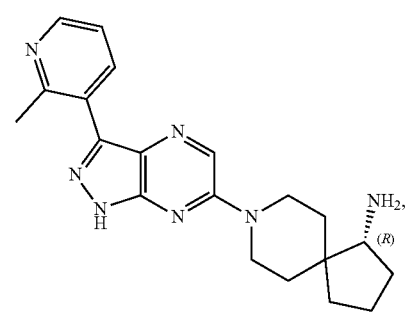
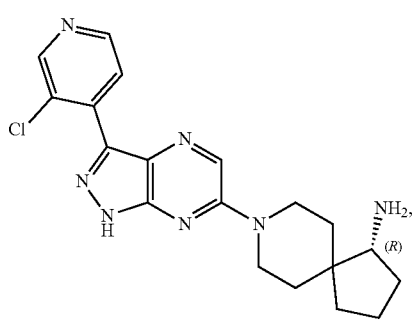
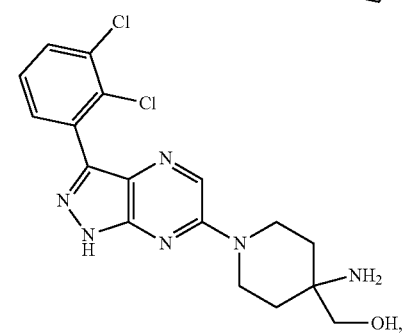

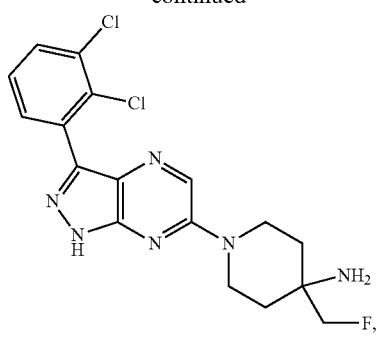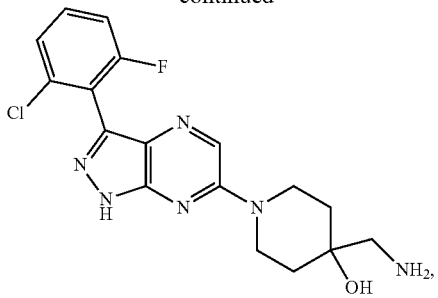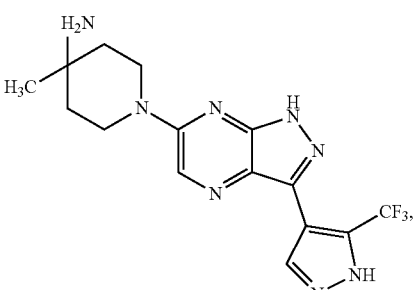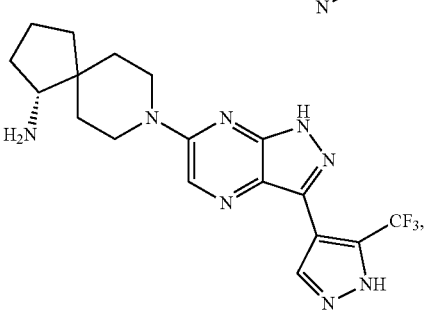

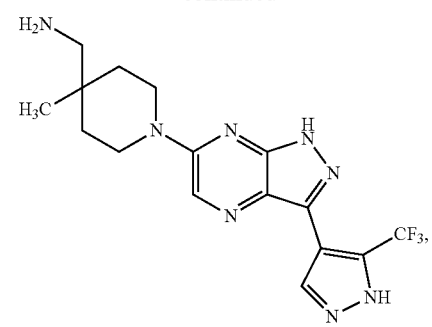
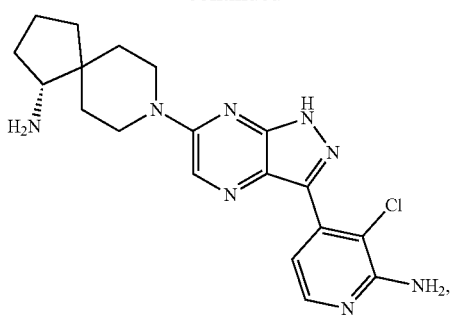
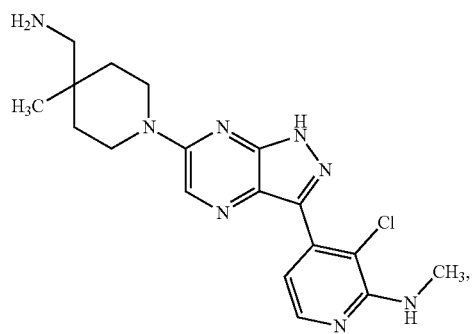
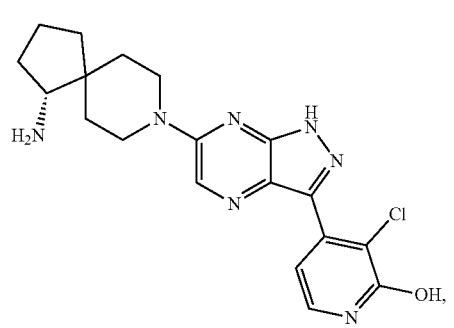
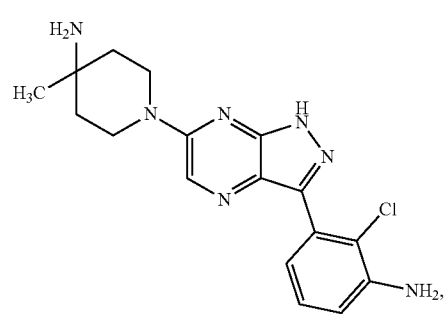
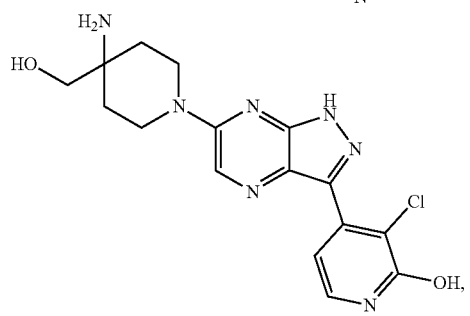
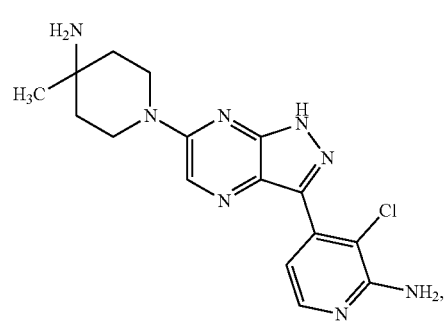
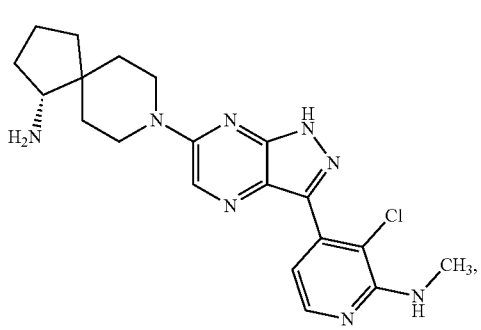
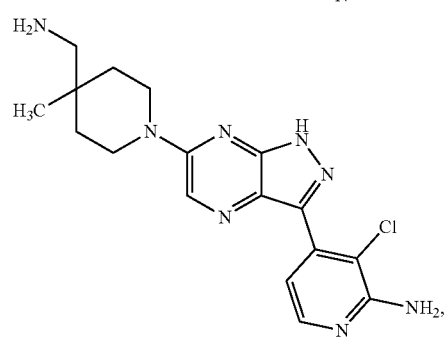
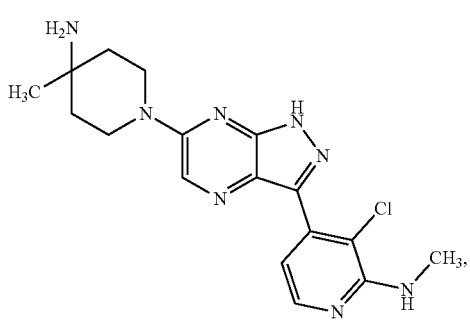

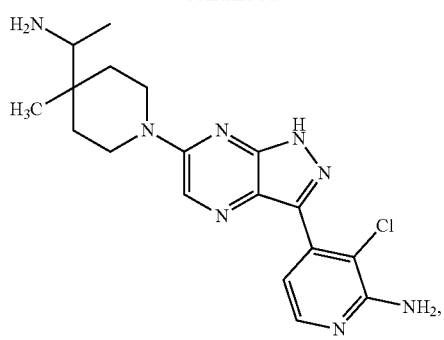 [SMILES: CC(N)C1(C)CCN(c2cnc3c(-c4ccnc(N)c4Cl)n[nH]c3n2)CC1]
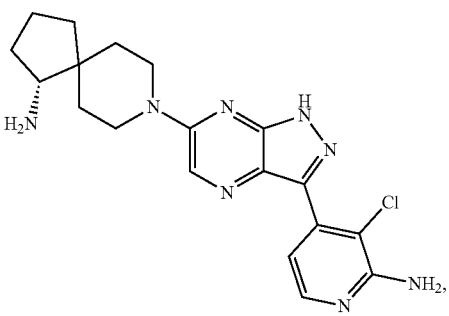
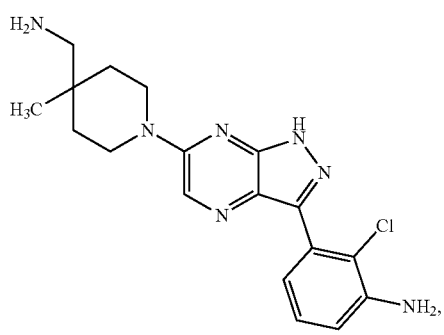
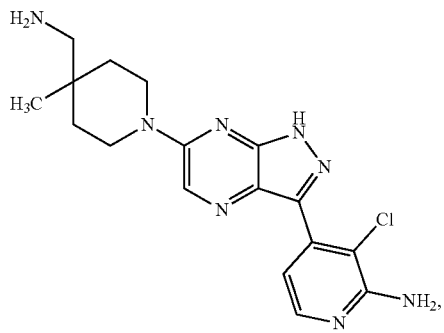
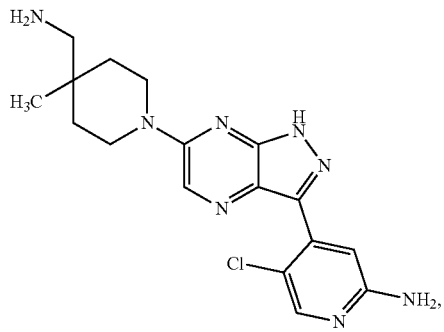
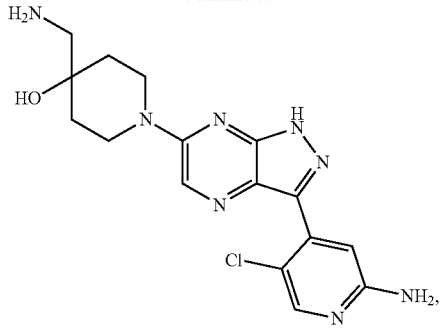
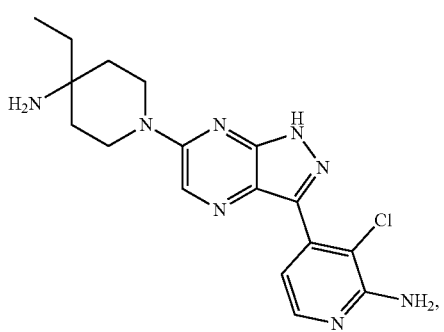
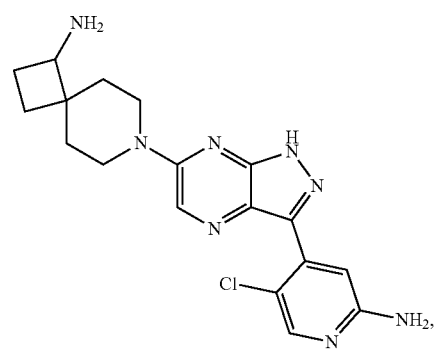
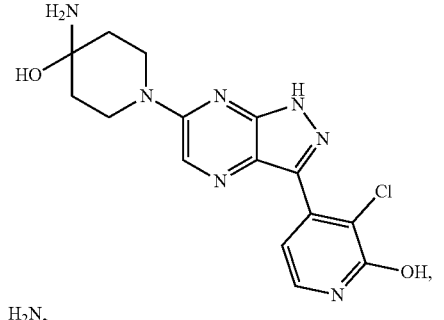
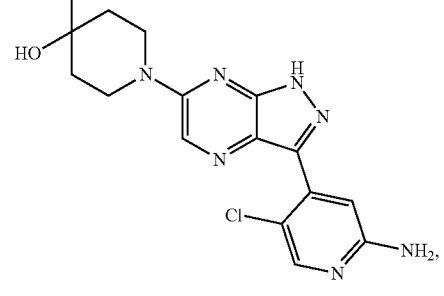

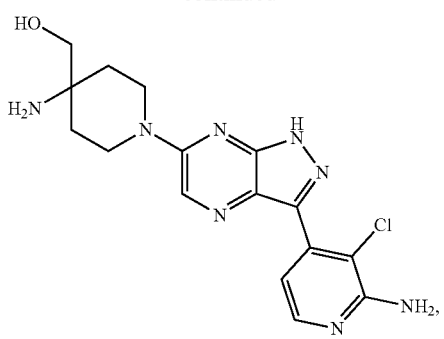
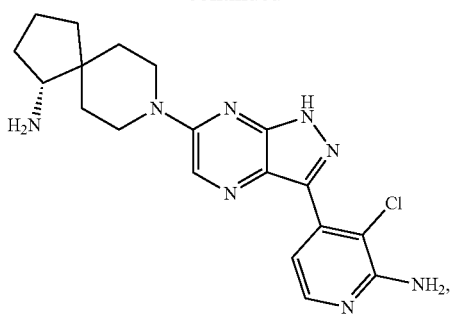
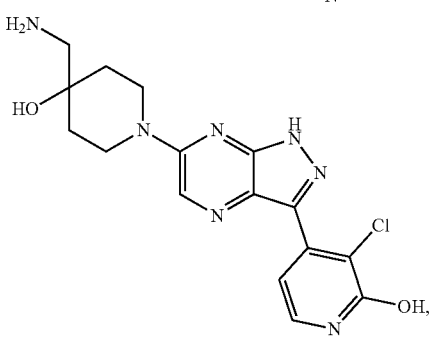
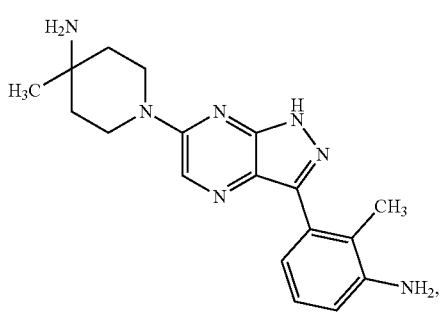
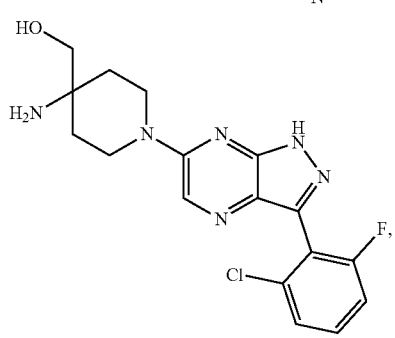
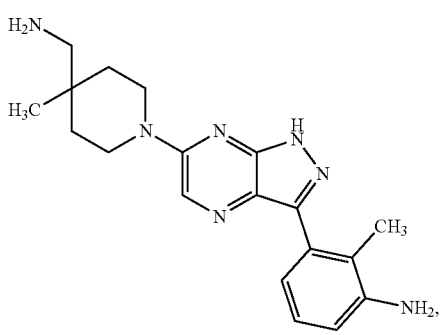
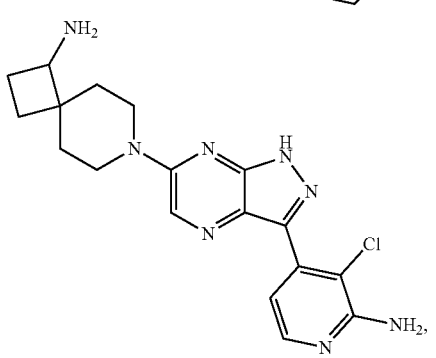
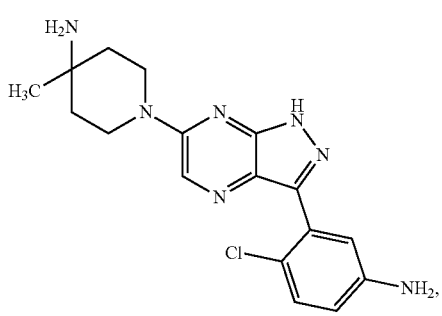
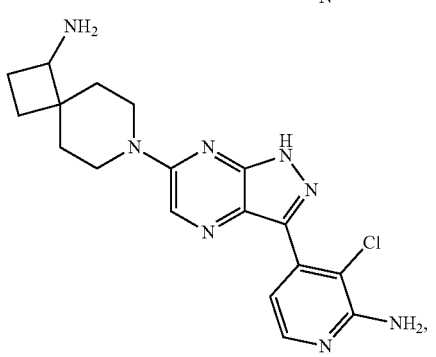
, and -continued
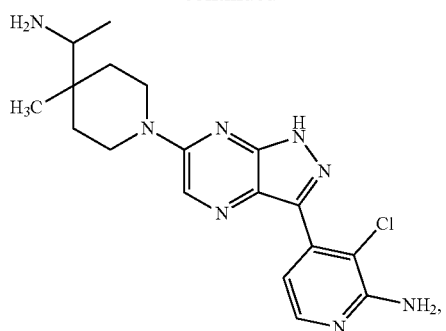
or a salt or tautomer thereof.
In certain embodiments, the compound is selected from:
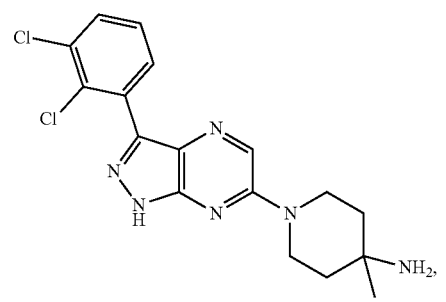
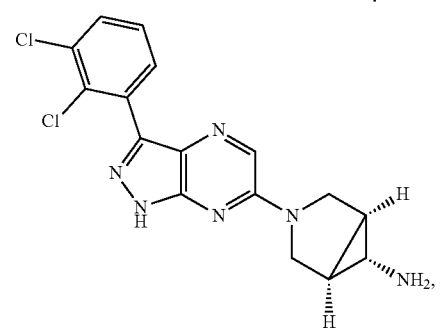
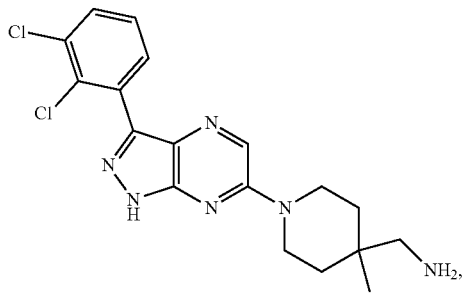
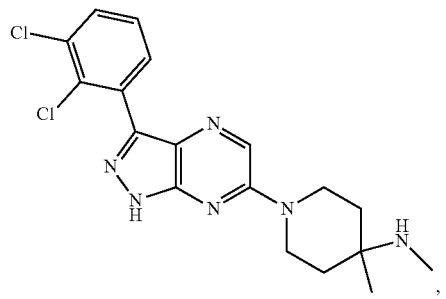
-continued
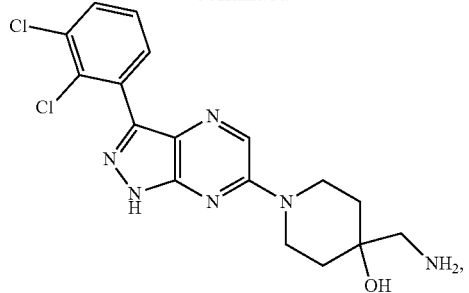
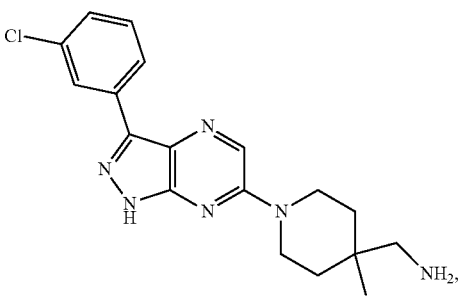
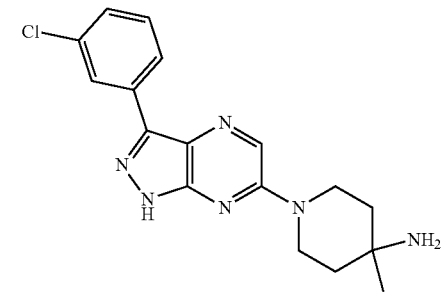
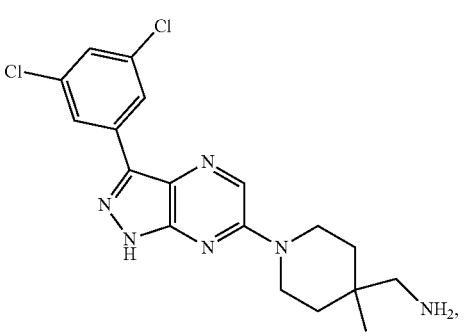
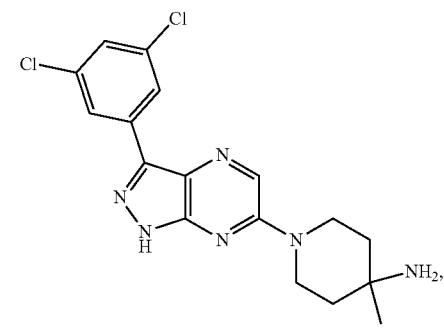

33
-continued
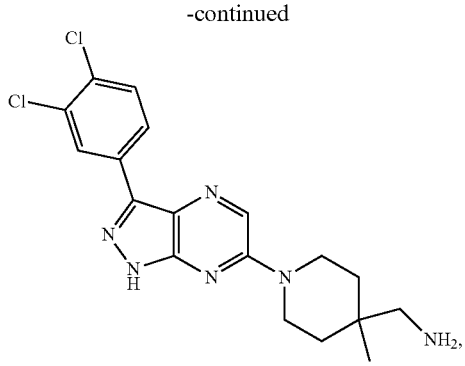
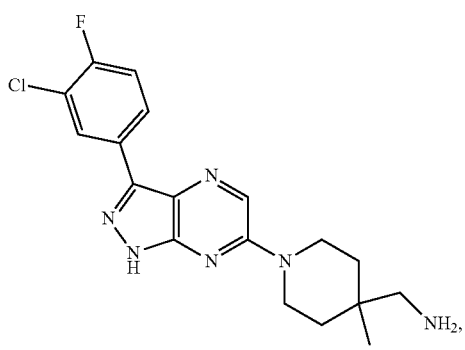
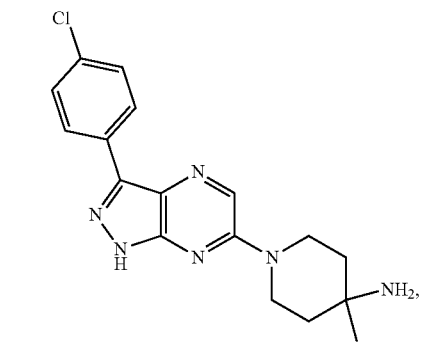
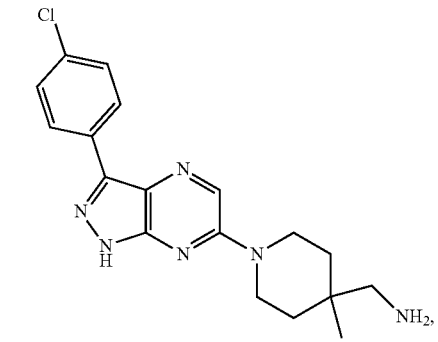
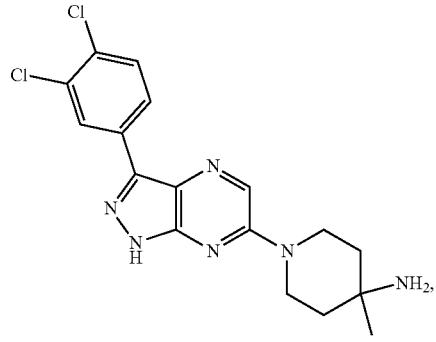
34
-continued
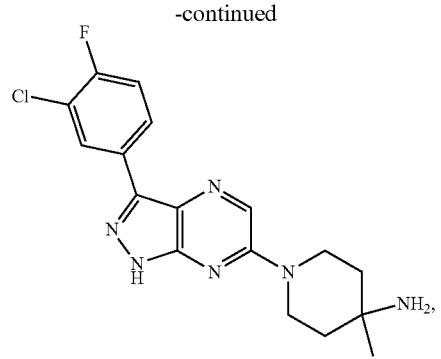
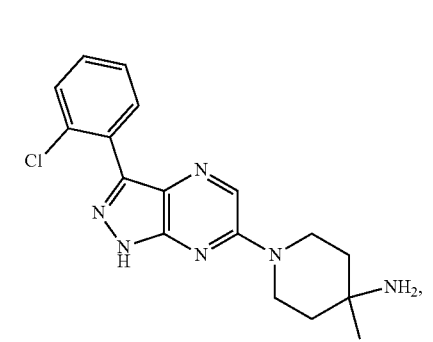
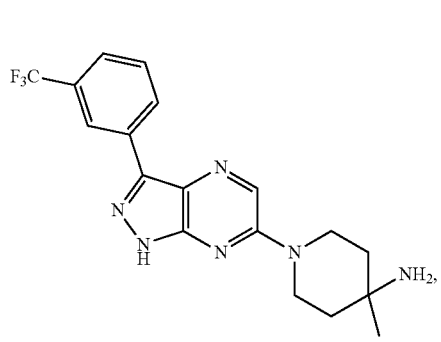
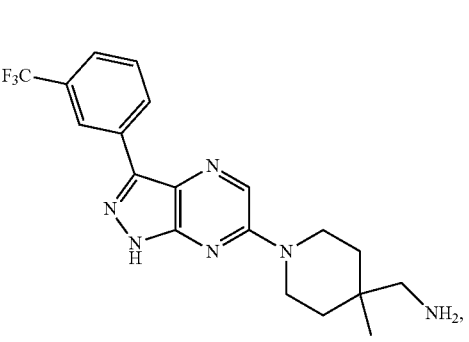
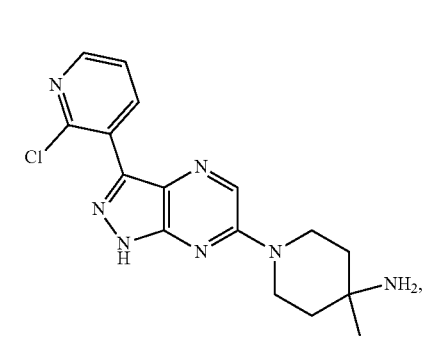

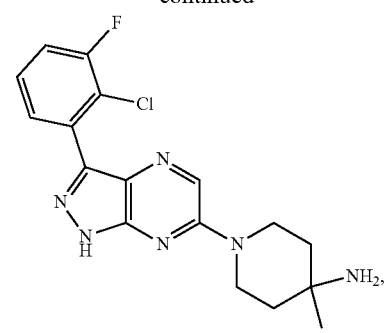
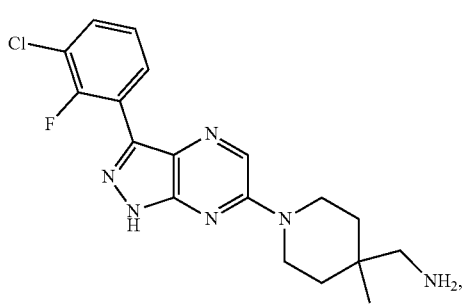
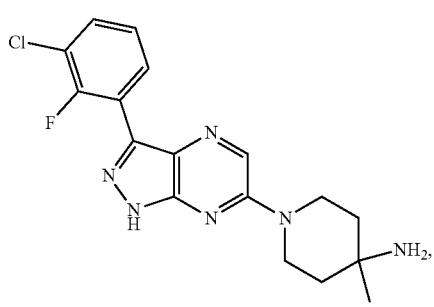
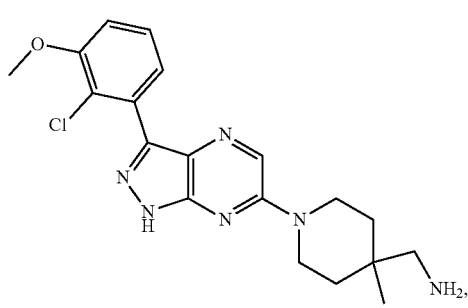
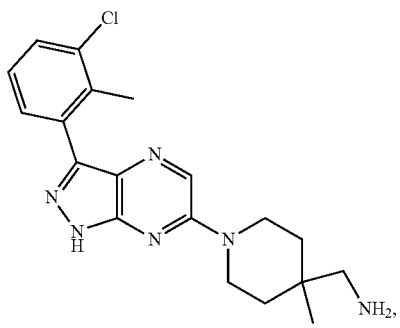
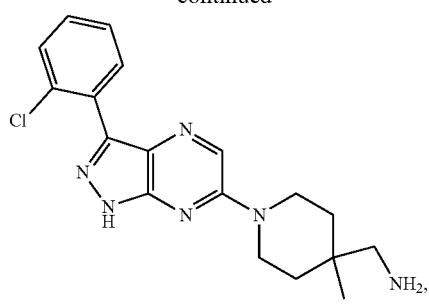
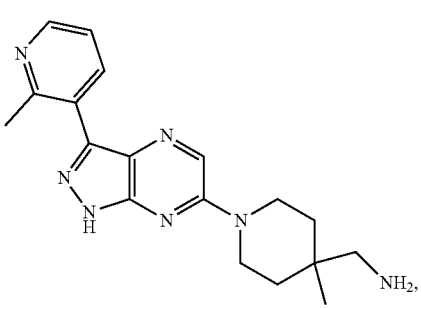
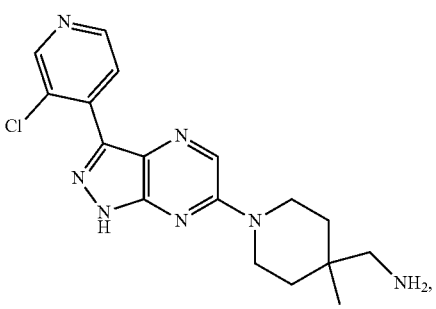
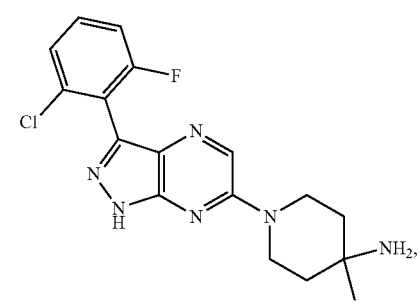
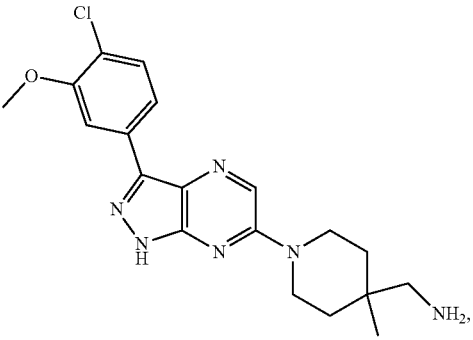

37
-continued
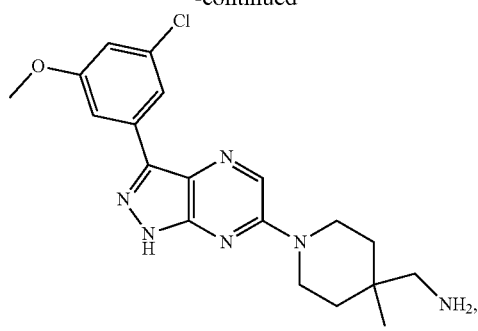
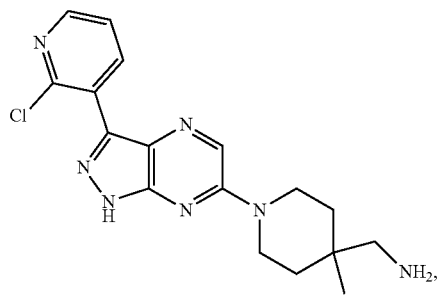
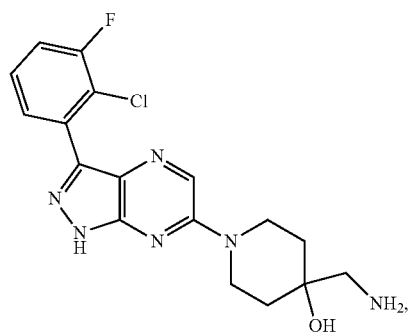
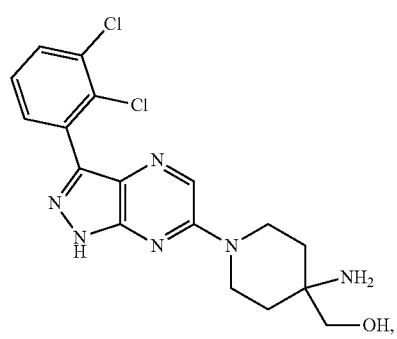
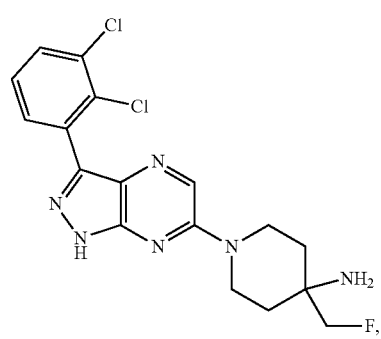
38
-continued
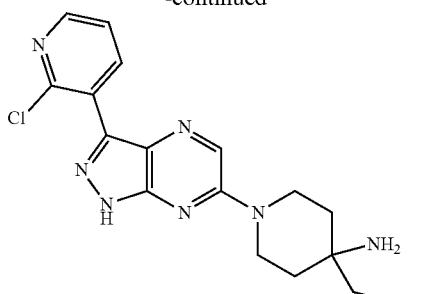
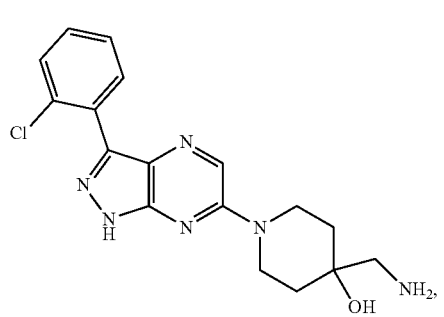
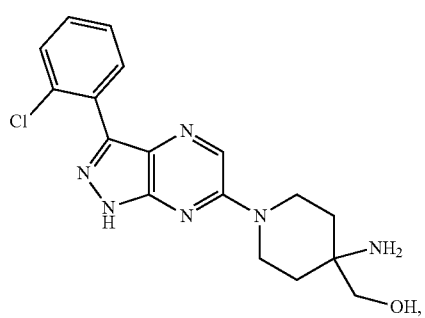
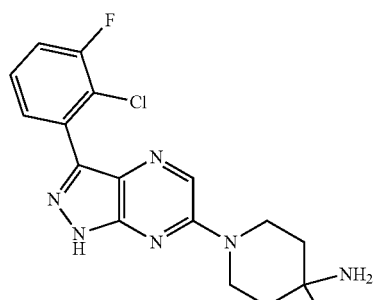
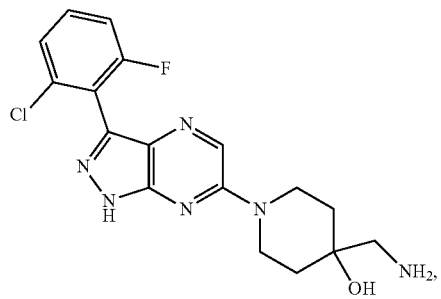

-continued
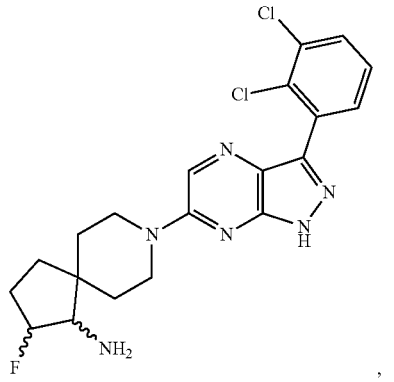
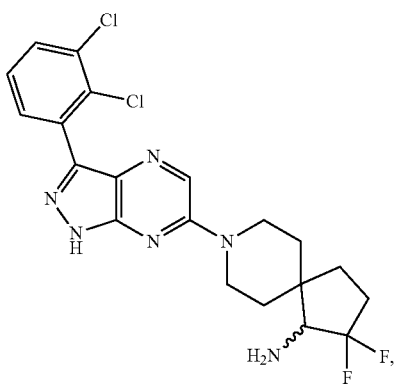
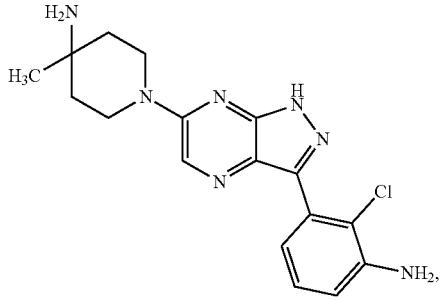
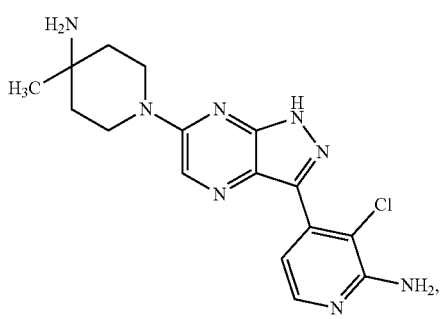
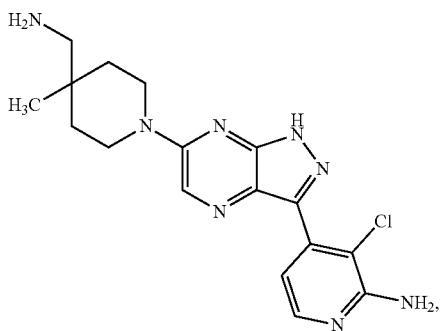
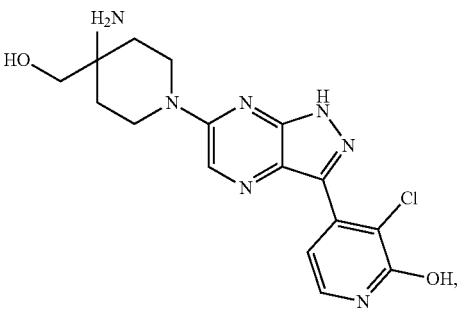
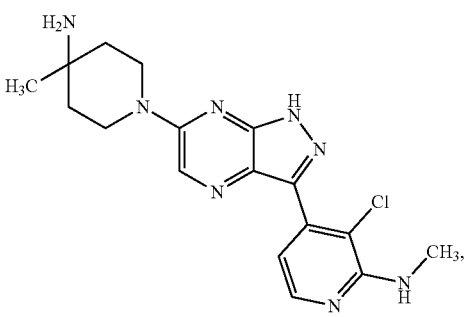

41
-continued
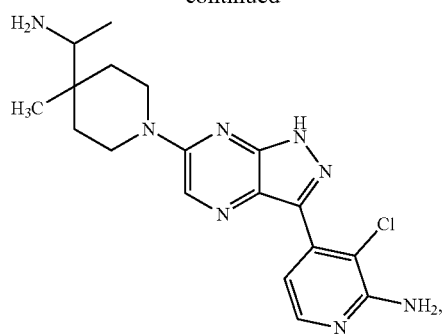
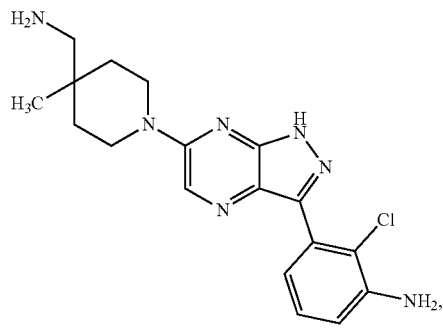
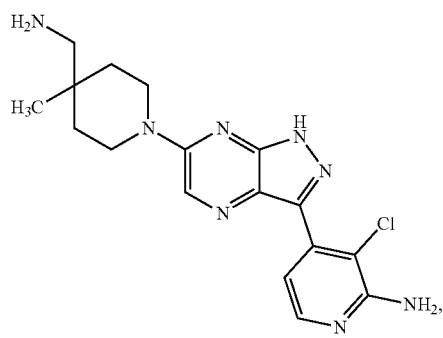
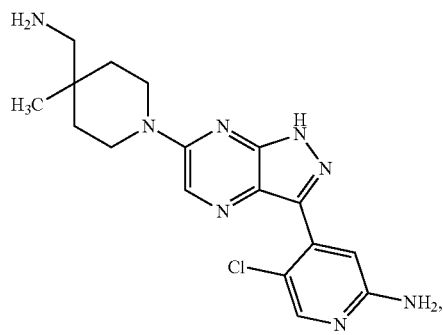
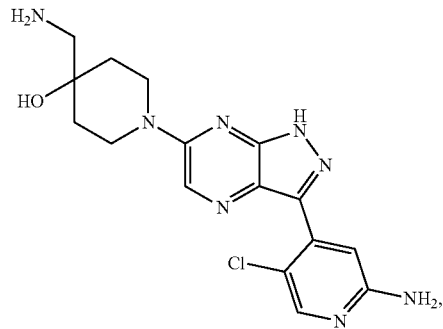
42
-continued
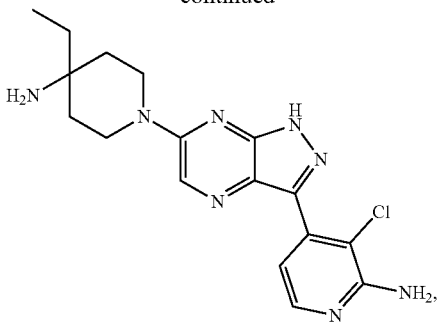
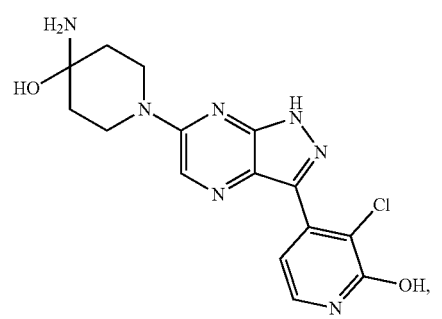
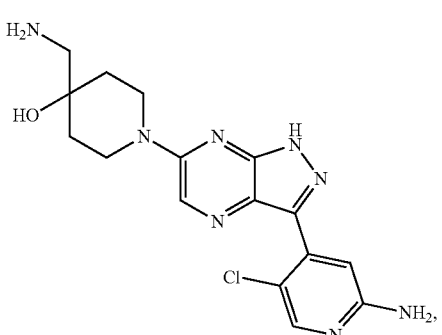
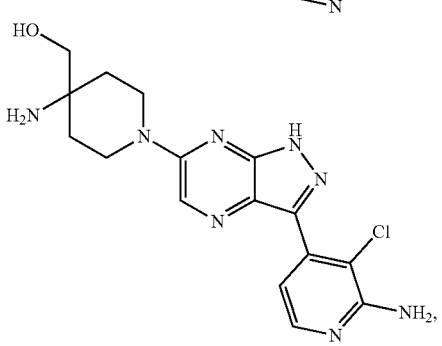
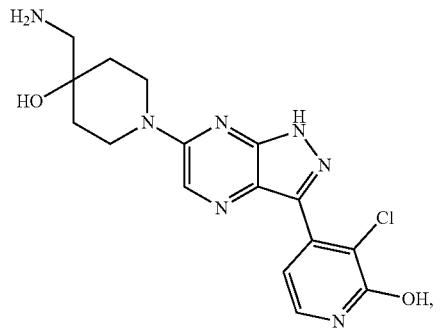

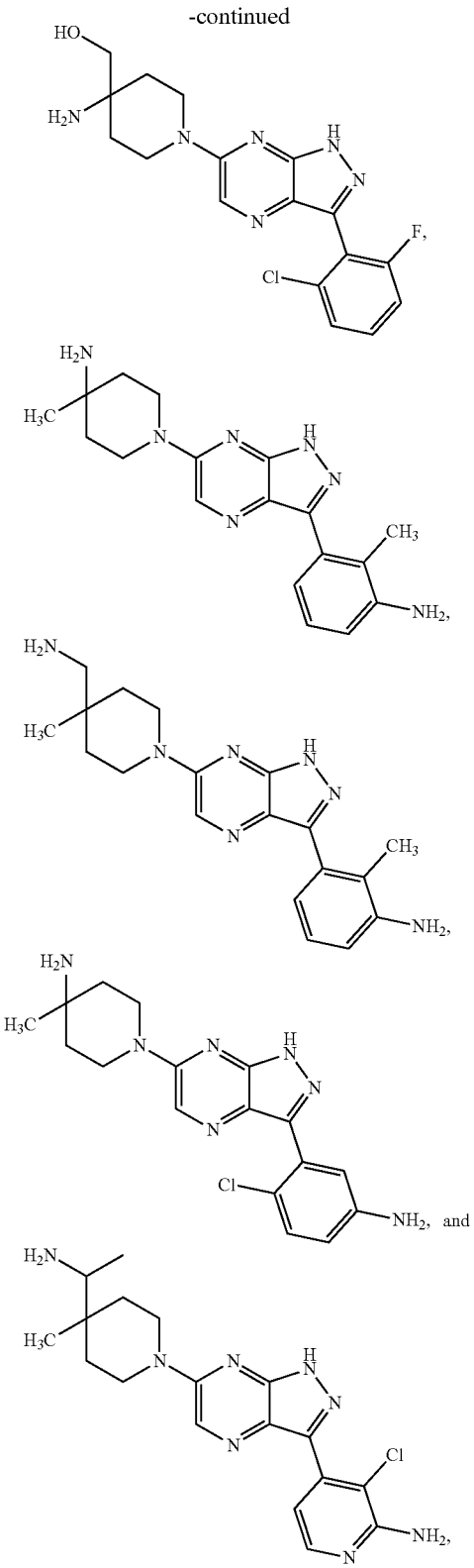

or a salt or tautomer thereof.
In certain embodiments, $R_6$ is amino.
In certain embodiments, $R_6$ is $C_{1-4}$aminoalkyl.
In certain embodiments, $R_6$ is aminomethyl.
In certain embodiments, $R_6$ is methylamino.
In certain embodiments, $R_7$ is hydroxy.

In certain embodiments, $R_7$ is $C_{1-4}$hydroxyalkyl.
In certain embodiments, $R_7$ is hydroxymethyl.
In certain embodiments, $R_7$ is selected from cyano and amido.
In certain embodiments, $R_7$ is selected from cyano and —C(O)NH$_2$.

In certain embodiments, each $R_{12}$ group is independently selected from halo, hydroxy, amino, methylamino, dimethylamino, cyano, $C_{1-4}$alkyl, $C_{1-4}$alkoxy, $C_{1-4}$hydroxyalkyl, $C_{1-4}$haloalkyl, and $C_{1-4}$aminoalkyl.

In certain embodiments, each $R_{12}$ group is independently selected from halo, hydroxy, cyano, $C_{1-4}$alkyl, $C_{1-4}$alkoxy, and $C_{1-4}$hydroxyalkyl.

Also provided are embodiments wherein any embodiment above may be combined with any one or more of these embodiments, provided the combination is not mutually exclusive.

As used herein, two embodiments are "mutually exclusive" when one is defined to be something which is different than the other. For example, an embodiment wherein two groups combine to form a cycloalkyl is mutually exclusive with an embodiment in which one group is ethyl the other group is hydrogen. Similarly, an embodiment wherein one group is $CH_2$ is mutually exclusive with an embodiment wherein the same group is NH.

Also provided is a compound selected from the Examples disclosed herein.

The present invention also relates to a method of inhibiting at least one PTPN11 function comprising the step of contacting PTPN11 with a compound as described herein. The cell phenotype, cell proliferation, activity of PTPN11, change in biochemical output produced by active PTPN11, expression of PTPN11, or binding of PTPN11 with a natural binding partner may be monitored. Such methods may be modes of treatment of disease, biological assays, cellular assays, biochemical assays, or the like.

Also provided herein is a method of treatment of a PTPN11-mediated disease comprising the administration of a therapeutically effective amount of a compound as disclosed herein, or a salt or tautomer thereof, to a patient in need thereof.

In certain embodiments, the disease is selected from Noonan Syndrome and Leopard Syndrome.
In certain embodiments, the disease is cancer.
In certain embodiments, the cancer is selected from breast cancer, colon cancer, leukemia, or melanoma.

Also provided herein is a method of treatment of a PTP-mediated disease comprising the administration of a therapeutically effective amount of a compound as disclosed herein, or a salt or tautomer thereof, to a patient in need thereof.

In certain embodiments, the disease is selected from Noonan Syndrome and Leopard Syndrome.
In certain embodiments, the disease is cancer.
In certain embodiments, the cancer is selected from breast cancer, colon cancer, leukemia, or melanoma.

Also provided herein is a compound as disclosed herein for use as a medicament.

Also provided herein is a compound as disclosed herein for use as a medicament for the treatment of a PTPN11-mediated disease.

Also provided herein is a compound as disclosed herein for use as a medicament for the treatment of a PTP-mediated disease.

Also provided is the use of a compound as disclosed herein as a medicament.

Also provided is the use of a compound as disclosed herein as a medicament for the treatment of a PTPN11-mediated disease.

Also provided is a compound as disclosed herein for use in the manufacture of a medicament for the treatment of a PTPN11-mediated disease.

Also provided is the use of a compound as disclosed herein for the treatment of a PTPN11-mediated disease.

Also provided is the use of a compound as disclosed herein for the treatment of a PTP-mediated disease.

Also provided herein is a method of inhibition of PTPN11 comprising contacting PTPN11 with a compound as disclosed herein, or a salt or tautomer thereof.

Also provided herein is a method of inhibition of PTP comprising contacting PTP with a compound as disclosed herein, or a salt or tautomer thereof.

Also provided herein is a method for achieving an effect in a patient comprising the administration of a therapeutically effective amount of a compound as disclosed herein, or a salt or tautomer thereof, to a patient, wherein the effect is selected from cognition enhancement.

In certain embodiments, the PTPN11-mediated disease is selected from Noonan Syndrome and Leopard Syndrome.

In certain embodiments, the PTPN11-mediated disease is cancer.

In certain embodiments, the PTPN11-mediated disease is selected from breast cancer, colon cancer, leukemia, or melanoma.

Also provided is a method of modulation of a PTPN11-mediated function in a subject comprising the administration of a therapeutically effective amount of a compound as disclosed herein.

Also provided is a pharmaceutical composition comprising a compound as disclosed herein, together with a pharmaceutically acceptable carrier.

In certain embodiments, the pharmaceutical composition is formulated for oral administration.

In certain embodiments, the pharmaceutical composition is formulated for parenteral administration.

In certain embodiments, the pharmaceutical composition is formulated for intravenous administration.

In certain embodiments, the pharmaceutical composition is formulated for subcutaneous administration.

In certain embodiments, the oral pharmaceutical composition is selected from a tablet and a capsule.

Terms

As used herein, the terms below have the meanings indicated.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH═CH—), (—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 8 carbon atoms. Alkyl groups are optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently selected from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which is optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term aryloxy as used herein, alone or in combination, refers to an aryl group attached to the parent molecular moiety through an oxy.

The term "carbamate," as used herein, alone or in combination, refers to an ester of carbamic acid (—NHCOO—) which may be attached to the parent molecular moiety from either the nitrogen or acid end, and which is optionally substituted as defined herein.

The term "O-carbamyl" as used herein, alone or in combination, refers to a —OC(O)NRR', group — with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro, or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or combinations thereof, fully saturated or containing from 1 to 3 degrees of unsaturation, consisting of the stated number of carbon atoms and from one to three heteroatoms selected from N, O, and S, and wherein the N and S atoms may optionally be oxidized and the N heteroatom may optionally be quaternized. The heteroatom(s) may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom selected from N, O, and S. In certain embodiments, said heteroaryl will comprise from 1 to 4 heteroatoms as ring members. In further embodiments, said heteroaryl will comprise from 1 to 2 heteroatoms as ring members. In certain embodiments, said heteroaryl will comprise from 5 to 7 atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated (but nonaromatic) monocyclic, bicyclic, or tricyclic heterocyclic group containing at least one heteroatom as a ring member, wherein each said heteroatom may be independently selected from nitrogen, oxygen, and sulfur. In certain embodiments, said heterocycloalkyl will comprise from 1 to 4 heteroatoms as ring members. In further embodiments, said heterocycloalkyl will comprise from 1 to 2 heteroatoms as ring members. In certain embodiments, said heterocycloalkyl will comprise from 3 to 8 ring members in each ring. In further embodiments, said heterocycloalkyl will comprise from 3 to 7 ring members in each ring. In yet further embodiments, said heterocycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups are optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "iminohydroxy," as used herein, alone or in combination, refers to —N(OH) and —N—O—.

The term "lower amino," as used herein, alone or in combination, refers to —NRR', wherein R and R' are independently selected from hydrogen and lower alkyl, either of which is optionally substituted.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The term "ring," or equivalently, "cycle," as used herein, in reference to a chemical structure or portion thereof, means a group in which every atom is a member of a common cyclic structure. A ring can be saturated or unsaturated, including aromatic, unless otherwise provided, and may have between 3 and 9 members. If the ring is a heterocycle, it may contain between 1 and 4 heteroatoms or heteroatom-comprising groups selected from B, N, O, S, C(O), S(O)m. Unless specifically prohibited, a ring is optionally substituted.

The terms "sulfonate," "sulfonic acid," and "sulfonic," as used herein, alone or in combination, refer to the —SO$_3$H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The term "tautomer", as use herein, alone or in combination, refers to one of two or more isomers that rapidly interconvert. Generally, this interconversion is sufficiently fast so that an individual tautomer is not isolated in the absence of another tautomer. The ratio of the amount of tautomers can be dependent on solvent composition, ionic strength, and pH, as well as other solution parameters. The ratio of the amount of tautomers can be different in a particular solution and in the microenvironment of a biomolecular binding site in said solution. Examples of tautomers that are well known in the art include keto/enol, enamine/imine, and lactam/lactim tautomers. Examples of tautomers that are well known in the art also include 2-hydroxypyridine/2(1H)-pyridone and 2-aminopyridine/2(1H)-iminopyridone tautomers.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination:

lower alkyl, lower alkenyl, lower alkynyl, lower alkanoyl, lower heteroalkyl, lower haloalkyl, lower haloalkenyl, lower haloalkynyl, lower perhaloalkyl, lower perhaloalkoxy, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Where structurally feasible, two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety selected from hydrogen, alkyl, cycloalkyl, heteroalkyl, aryl, heteroaryl and heterocycloalkyl, any of which is optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. For example, an unsymmetrical group such as —C(O)N (R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and 1-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"PTPN11 inhibitor" is used herein to refer to a compound that exhibits an $IC_{50}$ with respect to PTPN11 activity of no more than about 100 µM and more typically not more than about 50 µM, as measured in the PTPN11 assay described generally herein. "$IC_{50}$" is that concentration of inhibitor which reduces the activity of an enzyme (e.g., PTPN11) to half-maximal level. Certain compounds disclosed herein have been discovered to exhibit inhibition against PTPN11. In certain embodiments, compounds will exhibit an ICs with respect to PTPN11 of no more than about 50 µM; in further embodiments, compounds will exhibit an $IC_{50}$ with respect to PTPN11 of no more than about 10 µM; in yet further embodiments, compounds will exhibit an $IC_{50}$ with respect to PTPN11 of not more than about 1 µM; in yet further embodiments, compounds will exhibit an $IC_{50}$ with respect to PTPN11 of not more than about 200 nM, as measured in the PTPN11 assay described herein.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs. Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable.

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N-dibenzylethylenediamine. Other representative organic amines useful for the formation of base addition salts include ethylenediamine, ethanolamine, diethanolamine, piperidine, and piperazine.

A salt of a compound can be made by reacting the appropriate compound in the form of the free base with the appropriate acid.

While it may be possible for the compounds of the subject invention to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration selected. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, tautomer, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of certain compounds of the invention with anti-cancer (chemotherapeutic) drugs. Classes of anti-cancer drugs include, but are not limited to: alkylating agents, anti-metabolites, antimitotics, checkpoint inhibitors, plant alkaloids and terpenoids, topoisomerase inhibitors, cytotoxic antibiotics, aromatase inhibitors, angiogenesis inhibitors, anti-steroids and anti-androgens, mTOR inhibitors, tyrosine kinase inhibitors, and others.

For use in cancer and neoplastic diseases a PTPN11 (SHP2) inhibitor may be optimally used together with one or more of the following non-limiting examples of anti-cancer agents:

(1) alkylating agents, including but not limited to carmustine, chlorambucil (LEUKERAN), cisplatin (PLATIN), carboplatin (PARAPLATIN), oxaliplatin (ELOXATIN), streptozocin (ZANOSAR), busulfan (MYLERAN), dacarbazine, ifosfamide, lomustine (CCNU), melphalan (ALKERAN), procarbazine (MATULAN), temozolomide (TEMODAR), thiotepa, and cyclophosphamide (ENDOXAN);

(2) anti-metabolites, including but not limited to cladribine (LEUSTATIN), mercaptopurine (PURINETHOL), thioguanine, pentostatin (NIPENT), cytosine arabinoside (cytarabine, ARA-C), gemcitabine (GEMZAR), fluorouracil (5-FU, CARAC), capecitabine (XELODA), leucovorin (FUSILEV), methotrexate (RHEUMATREX), raltitrexed;

(3) antimitotics, which are often plant alkaloids and terpenoids, or derivatives thereof, including but not limited to taxanes such as docetaxel (TAXITERE) and paclitaxel (ABRAXANE, TAXOL); vinca alkaloids such as vincristine (ONCOVIN), vinblastine, vindesine, and vinorelbine (NAVELBINE);

(4) checkpoint inhibitors, such as anti-PD-1 or PD-L1 antibodies pembrolizumab (KEYTRUDA), nivolumab (OPDIVO), MEDI4736, and MPDL3280A; anti-CTLA-4 antibody ipilimumab (YERVOY); and those that target LAG3 (lymphocyte activation gene 3 protein), KIR (killer cell immunoglobulin-like receptor), 4-1BB (tumour necrosis factor receptor superfamily member 9), TIM3 (T-cell immunoglobulin and mucin-domain containing-3) and OX40 (tumour necrosis factor receptor superfamily member 4);

(5) topoisomerase inhibitors, including but not limited to camptothecin (CTP), irinotecan (CAMPTOSAR), topotecan (HYCAMTIN), teniposide (VUMON), and etoposide (EPOSIN);

(6) cytotoxic antibiotics, including but not limited to actinomycin D (dactinomycin, COSMEGEN), bleomycin (BLENOXANE) doxorubicin (ADRIAMYCIN), daunorubicin (CERUBIDINE), epirubicin (ELLENCE), fludarabine (FLUDARA), idarubicin, mitomycin (MITOSOL), mitoxantrone (NOVANTRONE), plicamycin;

(7) aromatase inhibitors, including but not limited to aminoglutethimide, anastrozole (ARIMIDEX), letrozole (FEMARA), vorozole (RIVIZOR), exemestane (AROMASIN);

(8) angiogenesis inhibitors, including but not limited to genistein, sunitinib (SUTENT) and bevacizumab (AVASTIN);

(9) anti-steroids and anti-androgens such as aminoglutethimide (CYTADREN), bicalutamide (CASODEX), cyproterone, flutamide (EULEXIN), nilutamide (NILANDRON);

(10) tyrosine kinase inhibitors, including but not limited to imatinib (GLEEVEC), erlotinib (TARCEVA), lapatinib (TYKERB), sorafenib (NEXAVAR), and axitinib (INLYTA);

(11) mTOR inhibitors such as everolimus, temsirolimus (TORISEL), and sirolimus;

(12) monoclonal antibodies such as trastuzumab (HERCEPTIN) and rituximab (RITUXAN);

(13) other agents, such as amsacrine; Bacillus Calmette-Guérin (B-C-G) vaccine; buserelin (ETILAMIDE); chloroquine (ARALEN); clodronate, pamidronate, and other bisphosphonates; colchicine; demethoxyviridin; dichloroacetate; estramustine; filgrastim (NEUPOGEN); fludrocortisone (FLORINEF); goserelin (ZOLADEX); interteron; leucovorin; leuprolide (LUPRON); levamisole; lonidamine; mesna; metformin; mitotane (o,p'-DDD, LYSODREN); nocodazole; octreotide (SANDOSTATIN); perifosine; porfimer (particularly in combination with photo- and radiotherapy); suramin; tamoxifen; titanocene dichloride; tretinoin; anabolic steroids such as fluoxymesterone (HALOTESTIN); estrogens such as estradiol, diethylstilbestrol (DES), and dienestrol; progestins such as medroxyprogesterone acetate (MPA) and megestrol; and testosterone.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating PTPN11-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of PTPN11-mediated disorders.

In some embodiments, methods described herein are used to treat a disease condition comprising administering to a subject in need thereof a therapeutically effective amount of a compound of Formula I or pharmaceutically acceptable salt thereof, wherein the condition is cancer which has developed resistance to chemotherapeutic drugs and/or ionizing radiation.

In some embodiments, methods described herein are used to treat a disease condition comprising administering to a subject in need thereof a therapeutically effective amount of a compound of Formula I or pharmaceutically acceptable salt thereof, wherein the condition is cancer which has developed resistance to chemotherapeutic drugs and/or ionizing radiation.

The compounds, compositions, and methods disclosed herein are useful for the treatment of disease. In certain embodiments, the disease is one of dysregulated cellular proliferation, including cancer. The cancer may be hormone-dependent or hormone-resistant, such as in the case of breast cancers. In certain embodiments, the cancer is a solid tumor. In other embodiments, the cancer is a lymphoma or leukemia. In certain embodiments, the cancer is and a drug resistant phenotype of a cancer disclosed herein or known in the art. Tumor invasion, tumor growth, tumor metastasis, and angiogenesis may also be treated using the compositions and methods disclosed herein. Precancerous neoplasias are also treated using the compositions and methods disclosed herein.

Cancers to be treated by the methods disclosed herein include colon cancer, breast cancer, ovarian cancer, lung cancer and prostate cancer; cancers of the oral cavity and pharynx (lip, tongue, mouth, larynx, pharynx), esophagus, stomach, small intestine, large intestine, colon, rectum, liver and biliary passages; pancreas, bone, connective tissue, skin, cervix, uterus, corpus endometrium, testis, bladder, kidney and other urinary tissues, including renal cell carcinoma (RCC); cancers of the eye, brain, spinal cord, and other components of the central and peripheral nervous systems, as well as associated structures such as the meninges; and thyroid and other endocrine glands. The term "cancer" also encompasses cancers that do not necessarily form solid tumors, including Hodgkin's disease, non-Hodgkin's lymphomas, multiple myeloma and hematopoietic malignancies including leukemias (Chronic Lymphocytic Leukemia (CLL), Acute Lymphocytic Leukemia (ALL), Chronic Myelogenous Leukemia (CML), Acute Myelogenous Leukemia (AML)) and lymphomas including lymphocytic, granulocytic and monocytic. Additional types of cancers which may be treated using the compounds and methods of the invention include, but are not limited to, adenocarcinoma, angiosarcoma, astrocytoma, acoustic neuroma, anaplastic astrocytoma, basal cell carcinoma, blastoglioma, chondrosarcoma, choriocarcinoma, chordoma, craniopharyngioma, cutaneous melanoma, cystadenocarcinoma, endotheliosarcoma, embryonal carcinoma, ependymoma, Ewing's tumor, epithelial carcinoma, fibrosarcoma, gastric cancer, genitourinary tract cancers, glioblastoma multiforme, head and neck cancer, hemangioblastoma, hepatocellular carcinoma, hepatoma, Kaposi's sarcoma, large cell carcinoma, leiomyosarcoma, leukemias, liposarcoma, lymphatic system cancer, lymphomas, lymphangiosarcoma, lymphangioendotheliosarcoma, medullary thyroid carcinoma, medulloblastoma, meningioma mesothelioma, myelomas, myxosarcoma neuroblastoma, neurofibrosarcoma, oligodendroglioma, osteogenic sarcoma, epithelial ovarian cancer, papillary carcinoma, papillary adenocarcinomas, paraganglioma, parathyroid tumours, pheochromocytoma, pinealoma, plasmacytomas, retinoblastoma, rhabdomyosarcoma, sebaceous gland carcinoma, seminoma, skin cancers, melanoma, small cell lung carcinoma, non-small cell lung carcinoma, squamous cell carcinoma, sweat gland carcinoma, synovioma, thyroid cancer, uveal melanoma, and Wilm's tumor.

In certain embodiments, the compositions and methods disclosed herein are useful for preventing or reducing tumor invasion and tumor metastasis.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

List of Abbreviations

NaOH=sodium hydroxide; M=molar; mL=milliliter; h=hour; min.=minute; HCl=hydrogen chloride; $H_2O$=water; MS=mass spectrometry; ES+=electrospray positive ionization; $^1$H-NMR=proton nuclear magnetic resonance; MHz=megahertz; DMSO-$d_6$=dimethyl sulfoxide deuterated-6; H=hydrogen; rt=room temperature; ° C.=Celsius; $Br_2$=bromine; $NaHSO_3$=sodium bisulfite; NMP=N-Methyl-2-pyrrolidone; MW=microwave; KF=potassium fluoride;

Pd(dppf)Cl$_2$=[1,1'-bis(diphenylphosphino)ferrocene]palladium(II) dichloride; PE=petroleum ether; EA=ethyl acetate; CDCl$_3$=deuterated chloroform; MeOH=methanol; D$_2$O=deuterated water; HPLC=high pressure liquid chromatography; DMSO=dimethyl sulfoxide; MeCN=acetonitrile; NIS=N-iodosuccinimide; DMF=dimethylformamide; K$_3$PO$_4$=potassium phosphate, tribasic; N$_2$=nitrogen; TBDMS=TBS=tert-butyldimethylsilyl; TFA=trifluoroacetic acid; DCM=dichloromethane; K$_2$CO$_3$=potassium carbonate; ul=microliter.

Synthetic Intermediates

The following synthetic intermediates can be used to practice the present invention.

Intermediate 101 tert-Butyl methyl(4-methylpiperidin-4-yl)carbamate

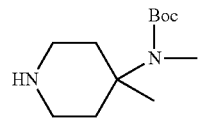

tert-Butyl 1-benzyl-4-methylpiperidin-4-yl carbamate To a solution of tert-butyl 4-methylpiperidin-4-yl carbamate (214 mg, 1.0 mmol) and K$_2$CO$_3$ (276 mg, 2.0 mmol) in DMF (10 mL) was added benzyl bromide (178 mg, 1.05 mmol). The reaction mixture was stirred at 50° C. for overnight. H$_2$O was added and extracted with EtOAc. The organic layer was separated and washed with brine, dried over Na$_2$SO$_4$, filtered, and concentrated under reduced pressure. The residue was purified by silica gel column chromatography (Petroleum ether:EtOAc=2:1) to give tert-butyl 1-benzyl-4-methylpiperidin-4-yl carbamate as a colorless oil (267 mg, 88%).

MS (ES+) C$_{18}$H$_{28}$N$_2$O$_2$ requires: 304, found: 305 [M+H]+.

1-Benzyl-N,4-dimethylpiperidin-4-amine To a solution of the product from the previous step (267 mg, 0.88 mmol) in dry THF (10 mL) was added LiAlH$_4$ (100 mg, 2.64 mmol) slowly. The reaction mixture was heated to reflux for overnight. After cooled to rt, 2-3 drops of H$_2$O was added and filtered. The solid was washed by EtOAc. The combined organics were concentrated to give the title compound as a colorless oil (180 mg, 94%).

MS (ES+) C$_{14}$H$_{22}$N$_2$ requires: 218, found: 219 [M+H]+.

tert-Butyl 1-benzyl-4-methylpiperidin-4-yl(methyl)carbamate To a solution of the product from the previous step (180 mg, 0.82 mmol) and (Boc)$_2$O (268 mg, 1.23 mmol) in CH$_2$Cl$_2$ (10 mL) was added TEA (166 mg, 1.64 mmol). The reaction mixture was stirred at rt for 6 h. The solvent was removed and the residue was purified by silica gel column chromatography (Petroleum ether:EtOAc=2:1) to give the title compound as a colorless oil (190 mg, 73%).

MS (ES+) C$_{19}$H$_{30}$N$_2$O$_2$ requires: 318, found: 319 [M+H]+.

tert-Butyl methyl(4-methylpiperidin-4-yl)carbamate A solution of the product from the previous step (190 mg, 0.6 mmol) in MeOH (10 mL) was hydrogenated using 10% Pd/C (20 mg) as catalyst at 75° C. under atmospheric pressure for overnight. The catalyst was removed by filtration on CELITE™ and the solvent was evaporated under reduced pressure to give the title compound as a colorless oil (120 mg, 88%).

MS (ES+) C$_{12}$H$_{24}$N$_2$O$_2$ requires: 228, found: 229 [M+H]+. $^1$H NMR (500 MHz, CDCl$_3$) δ 2.84-2.8 (m, 5H), 2.23-2.18 (m, 2H), 1.71-1.67 (m, 4H), 1.46 (s, 9H), 1.28 (s, 3H).

Intermediate 102

(R)—N—((R)-1-(4-Methoxyphenyl)ethyl)-8-azaspiro[4.5]decan-1-amine

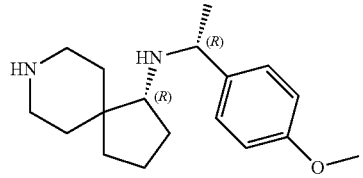

(R)-tert-butyl 1-((R)-1-(4-methoxyphenyl)ethylamino)-8-azaspiro [4.5]decane-8-carboxylate To a solution of tert-butyl 1-oxo-8-azaspiro[4.5]decane-8-carboxylate (2.0 g, 7.9 mmol) in THF (15 mL) was added (R)-1-(4-methoxyphenyl) ethanamine (1.79 g, 11.9 mmol) and Ti(OEt)$_4$ (2 mL) at RT under N$_2$, then stirred at 85° C. for 18 h. The mixture was concentrated in vacuo, then MeOH (10 mL) was added at RT, followed by the slow addition of LiBH$_4$ (0.33 g, 15.8 mmol). The mixture was stirred at RT for 2 h. The reaction was then quenched with H$_2$O (5 mL) and extracted with EtOAc (15 mL×3). The organic layer was separated and washed with brine, dried over Na$_2$SO$_4$, filtered, and concentrated under reduced pressure to give the title compound as a colorless oil (2.0 g, 66%).

MS (ES+) C$_{23}$H$_{36}$N$_2$O$_3$ requires: 388, found: 389 [M+H]$^+$.

(R)—N—((R)-1-(4-methoxyphenyl)ethyl)-8-azaspiro [4.5]decan-1-amine A mixture of the product from the previous step (2.0 g, 5.2 mmol) in HCl/MeOH (3 M, 10 mL) was stirred at RT for 2 h. The mixture was then concentrated in vacuo. An aqueous solution of NaOH was then added to adjust the pH to 10-12. The mixture was extracted with EtOAc (15 mL×3). The combined organic layers were separated and washed with brine, dried over Na$_2$SO$_4$, filtered, and concentrated under reduced pressure to give the crude title product as a colorless oil (1.2 g, 86%), which was used directly without further purification.

MS (ES+) C$_{18}$H$_{28}$N$_2$O requires: 288, found: 289 [M+H]$^+$.

Intermediate 103

(S)—N—((R)-1-(4-Methoxyphenyl)ethyl)-2-oxa-8-azaspiro[4.5]decan-4-amine

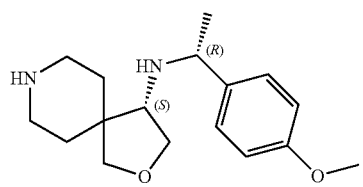

tert-Butyl 4-hydroxy-2-oxa-8-azaspiro[4.5]decane-8-carboxylate To a solution of 2-oxa-8-azaspiro[4.5]decan-4-ol (1.0 g, 6.4 mmol) in $CH_2Cl_2$ (15 mL), was added di-tert-butyl dicarbonate (1.7 g, 7.6 mmol) at RT, then $Et_3N$ (1.2 mL, 12.8 mmol) was added at RT. The reaction mixture was stirred at RT for 2 h, quenched with $H_2O$ (5 mL) and extracted with EtOAc (15 mL×3). The organic layer was separated and washed with brine, dried over $Na_2SO_4$, filtered, and concentrated under reduced pressure to give the title compound as a colorless oil (1.5 g, 90%), which was used directly without further purification.

MS (ES+) $C_{13}H_{23}NO_4$ requires: 257, found: 280 $[M+Na]^+$.

tert-Butyl 4-oxo-2-oxa-8-azaspiro[4.5]decane-8-carboxylate To a solution of the product from the previous step (1.5 g, 5.8 mmol) in $CH_2Cl_2$ (15 mL) was added Dess-Martin reagent (3.7 g, 8.7 mmol) at rt. The resulting mixture was stirred at rt overnight. The reaction mixture was filtered, then quenched with $H_2O$ (5 mL) and extracted with EtOAc (15 mL×3). The organic layer was separated and washed with brine, dried over $Na_2SO_4$, filtered, and concentrated under reduced pressure. The residue was purified by silica gel column chromatography (Petroleum ether:EtOAc=5:1) to give the title compound as a colorless oil (1.2 g, 86%).

MS (ES+) $C_{13}H_{21}NO_4$ requires: 255, found: 200 $[M–55]^+$.

(S)-tert-Butyl 4-((R)-1-(4-methoxyphenyl)ethylamino)-2-oxa-8-azaspiro[4.5]-decane-8-carboxylate To a solution of the product from the previous step in THF (15 mL) was added (R)-1-(4-methoxyphenyl)ethanamine (1.06 g, 7.06 mmol) and $Ti(OEt)_4$ (2 mL) at RT under $N_2$, then stirred at 85° C. for 18 h. The residue was concentrated in vacuo, then MeOH (10 mL) was added. $LiBH_4$ (0.35 g, 14.8 mmol) was added at RT slowly, then the mixture was stirred at RT for 2 h. The reaction was quenched with the addition of $H_2O$ (5 mL). The mixture was extracted with EtOAc (15 mL×3). The organic layer was separated and washed with brine, dried over $Na_2SO_4$, filtered, and concentrated under reduced pressure. The residue was purified by silica gel column chromatography (petroleum ether:EtOAc=4:1) to give the title compound as a colorless oil (1.3 g, 72%).

MS (ES+) $C_{22}H_{34}N_2O_4$ requires: 390, found: 391 $[M+H]^+$.

(S)—N—((R)-1-(4-Methoxyphenyl)ethyl)-2-oxa-8-azaspiro [4.5]decan-4-amine

A mixture of (S)-tert-butyl 4-((R)-1-(4-methoxyphenyl) ethylamino)-2-oxa-8-azaspiro[4.5]decane-8-carboxylate (1.3 g, 3.3 mmol) in HCl/MeOH (3 M, 10 mL) was stirred at RT for 2 h. Concentrated in vacuo and aqueous solution of NaOH was added to adjust the pH to 10-12, extracted with EtOAc (25 mL×3). The organic layer was separated and washed with brine, dried over $Na_2SO_4$, filtered, and concentrated under reduced pressure to give the crude (S)—N—((R)-1-(4-methoxyphenyl) ethyl)-2-oxa-8-azaspiro[4.5] decan-4-amine as a colorless oil (800 mg, yield: 89%) which was used directly without further purification.

MS (ES+) $C_{17}H_{26}N_2O_2$ requires: 290, found: 291 $[M+H]^+$.

Intermediate 104

Benzyl 4-(hydroxymethyl)piperidin-4-yl carbamate hydrochloride

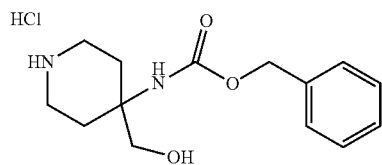 [SMILES: Cl ; O=C(NC1(CO)CCNCC1)OCc1ccccc1]

tert-Butyl 4-(benzyloxycarbonylamino)-4-(hydroxymethyl)piperidine-1-carboxylate To a solution of tert-butyl 4-amino-4-(hydroxymethyl)piperidine-1-carboxylate (355 mg, 1.54 mmol) and benzyl chloroformate (288 mg, 1.69 mmol) in $CH_2Cl_2$ (20 mL) was added DIPEA (596 mg, 4.62 mmol) at 0° C. The reaction mixture was stirred at RT for overnight. The solvent was removed and the residue was purified by silica gel column chromatography (Petroleum ether:EtOAc=2:1) to give the titled compound as a white solid (450 mg, 80%).

MS (ES+) $C_{19}H_{28}N_2O_5$ requires: 364, found: 387.2 $[M+Na]^+$. $^1H$ NMR (500 MHz, DMSO-$d_6$) δ 7.40-7.31 (m, 5H), 6.94 (s, 1H), 4.98 (s, 2H), 4.73 (t, J=6.0 Hz, 1H), 3.65-3.61 (m, 2H), 3.41 (d, J=6.0 Hz, 2H), 2.93-2.89 (m, 2H), 1.95-1.92 (m, 2H), 1.40-1.35 (m, 10H).

Benzyl 4-(hydroxymethyl)piperidin-4-yl carbamate hydrochloride A solution of the product from the previous step (182 mg, 0.5 mmol) in HCl/MeOH (4M, 2 mL) was stirred at RT for 4 h. The solvent was removed under reduced pressure to give the title compound as a colorless oil (150 mg, 100%) which was used directly without further purification.

MS (ES+) $C_{14}H_{21}ClN_2O_3$ requires: 264, found: 265.3 $[M+H]^+$.

Intermediate 105

Benzyl 4-(fluoromethyl)piperidin-4-yl carbamate hydrochloride

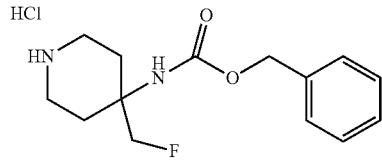 [SMILES: Cl ; O=C(NC1(CF)CCNCC1)OCc1ccccc1]

tert-Butyl 4-(benzyloxycarbonylamino)-4-(fluoromethyl) piperidine-1-carboxylate To a solution of tert-butyl 4-(benzyloxycarbonylamino)-4-(hydroxymethyl)-piperidine-1-carboxylate (255 mg, 0.7 mmol) in $CH_2Cl_2$ (10 mL) was added diethylaminosulfur trifluoride (147 mg, 0.9 mmol) at 0° C. The resulting mixture was stirred at 5° C. for 3 h. The solvent was removed and the residue was purified by silica gel column chromatography (Petroleum ether:EtOAc=4:1) to give the title compound as a white solid (180 mg, 70%).

MS (ES+) $C_{19}H_{27}FN_2O_4$ requires: 366, found: 389.2 $[M+Na]^+$.

Benzyl 4-(fluoromethyl)piperidin-4-yl carbamate hydrochloride A solution of the product from the previous step (92 mg, 0.25 mmol) in HCl/MeOH (4M, 2 mL) was stirred at RT for 4 h. The solvent was removed under reduced pressure to give the title compound as a colorless oil (75 mg, 100%) which was used directly without further purification.

MS (ES+) $C_{14}H_{20}ClFN_2O_2$ requires: 266, found: 267 $[M+H]^+$.

Intermediate 106

(2-Chloropyridin-3-yl)(3,5-dichloropyrazin-2-yl)methanone

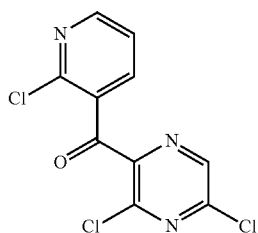 [SMILES: O=C(c1cccnc1Cl)c1ncc(Cl)nc1Cl]

(2-Chloropyridin-3-yl)(3,5-dichloropyrazin-2-yl)methanol To a −78° C. solution of LDA (2.0 M in hexane, 22.0 mmol) in dry THF (40 mL), under argon was slowly added 2,6-dichloropyrazine (1.65 g, 11.1 mmol) in THF (10 mL). After addition was completed, the resulting mixture was stirred at −78° C. for an additional 1 h, then 2-chloronicotinaldehyde (2.34 g, 16.6 mmol) in THF (10 mL) was added dropwise. The reaction mixture was stirred for another hour, then quenched with hydrochloric acid (3.6 mL)/EtOH (15 mL)/THF (18 mL) mixture, and warmed to RT. The reaction mixture was diluted with saturated aqueous NaHCO$_3$ and extracted with EtOAc. The organic layer was separated and washed with brine, dried over Na$_2$SO$_4$, filtered, and concentrated under reduced pressure. The residue was purified by silica gel column chromatography (Petroleum ether:EtOAc=4:1) to give the title compound as a yellow solid (880 mg, 27%).

MS (ES+) $C_{10}H_6Cl_3N_3O$ requires: 289, found: 290 $[M+H]^+$.

(2-Chloropyridin-3-yl)(3,5-dichloropyrazin-2-yl)methanone To a solution of the product from the previous step (0.88 g, 3.0 mmol) in CH$_2$Cl$_2$ (30 mL) was added solid MnO$_2$ (5.28 g, 60.0 mmol) in portions. The resulting mixture was stirred at RT overnight. The reaction mixture was filtered, and the filtrate was concentrated under reduced pressure. The residue was purified by silica gel column chromatography (Petroleum ether:EtOAc=4:1) to give the title compound as a yellow solid (380 mg, 43%).

MS (ES+) $C_{10}H_4Cl_3N_3O$ requires: 287, found: 288 $[M+H]^+$.

Intermediate 107

(3-Chloropyridin-4-yl)(3,5-dichloropyrazin-2-yl)methanone

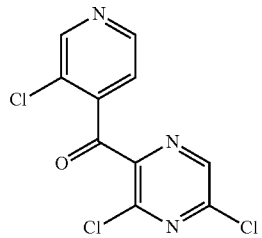 [SMILES: O=C(c1ccncc1Cl)c1ncc(Cl)nc1Cl]

(3-Chloropyridin-4-yl)(3,5-dichloropyrazin-2-yl)methanol To a −78° C. solution of LDA (2.0 M in hexane, 22.0 mmol) in dry THF (40 mL), under argon was slowly added 2,6-dichloropyrazine (1.65 g, 11.1 mmol) in THF (5 mL). After addition was completed, the resulting mixture was stirred at −78° C. for an additional 1 h, then 3-chloroisonicotinaldehyde (2.34 g, 16.6 mmol) in THF (5 mL) was added dropwise. The reaction mixture was stirred for another hour, then quenched with hydrochloric acid (3.6 mL)/EtOH (15 mL)/THF (18 mL) mixture, and warmed to rt. The reaction mixture was diluted with saturated aqueous NaHCO$_3$ and extracted with EtOAc. The organic layer was separated and washed with brine, dried over Na$_2$SO$_4$, filtered, and concentrated under reduced pressure. The residue was purified by silica gel column chromatography (Petroleum ether:EtOAc=2:1) to give the crude title compound as a yellow solid (900 mg) which was used in next step without further purification.

MS (ES+) $C_{10}H_6Cl_3N_3O$ requires: 289, found: 290 $[M+H]^+$.

(3-Chloropyridin-4-yl)(3,5-dichloropyrazin-2-yl)methanone To a solution of the crude product from the previous step (0.9 g, 3.1 mmol) in CH$_2$Cl$_2$ (30 mL) was added solid MnO$_2$ (5.46 g, 62.0 mmol) in portions. The resulting mixture was stirred at rt overnight. The reaction mixture was filtered, and the filtrate was concentrated under reduced pressure. The residue was purified by Prep-HPLC to give the title compound as a yellow solid (118 mg, 4% over 2 steps).

MS (ES+) $C_{10}H_4Cl_3N_3O$ requires: 287, found: 288 $[M+H]^+$.

Intermediate 108

(3-Chloro-2-(4-methoxybenzylamino) pyridin-4-yl)(3,5-dichloropyrazin-2-yl)methanone

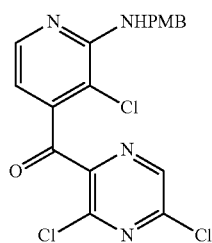

(2,3-Dichloropyridin-4-yl)methanol A mixture of 2,3-dichloroisonicotinic acid (19.2 g, 10 mmol) in BH$_3$/THF (1 M, 300 mL) was stirred at 60° C. for 3 h. After cooling to RT, MeOH (100 mL) was slowly added, then the reaction mixture was concentrated and diluted with H$_2$O (100 mL) and extracted with EtOAc (200 mL×3). The organic layer was separated and washed with brine, dried over Na$_2$SO$_4$, filtered and concentrated under reduced pressure to give the crude title compound (15.4 g, yield 87%) as a yellow solid which was used directly without further purification.

MS (ES+) C$_6$H$_5$Cl$_2$NO requires: 177, found: 178 [M+H]+.

(3-Chloro-2-(4-methoxybenzylamino)pyridin-4-yl) methanol A mixture of the product from the previous step (15.4 g, 86.5 mmol) in (4-methoxyphenyl)methanamine (15 mL) was stirred at 150° C. for 4 h. The mixture was purified by silica gel column chromatography (Petroleum ether: EtOAc=4:1-2:1) to give the title compound as a yellow solid (20 g, yield 83.3%).

MS (ES+) C$_{14}$H$_{15}$ClN$_2$O$_2$ requires: 278, found: 279 [M+H]+.

3-Chloro-2-(4-methoxybenzylamino)isonicotinaldehyde To a solution of the product from the previous step (20 g, 71.9 mmol) in DCM (2 L) was added MnO$_2$ (125 g, 1.38 mol) in portionwise. The mixture was stirred at RT overnight. The reaction was filtered and the filtrate was purified by silica gel column chromatography (Petroleum ether: EtOAc=10:1~5:1) to give the title compound as a yellow solid (15 g, yield 75.7%).

MS (ES+) C$_{14}$H$_{13}$ClN$_2$O$_2$ requires: 276, found: 277 [M+H]+.

(3-Chloro-2-(4-methoxybenzylamino)pyridin-4-yl) (3,5-dichloropyrazin-2-yl)methanol To a −78° C. solution of LDA (2.0 M in hexane, 22.0 mmol) in dry THF (40 mL), under argon was added 2,6-dichloropyrazine (1.648 g, 11.0 mmol) in THF (10 mL) slowly. After addition was complete, the resulting mixture was stirred at −78° C. for an additional 1 h, then the product from the previous step (4.55 g, 16.5 mmol) in THF (30 mL) was added dropwise. The reaction mixture was stirred for another hour, then quenched with HCl (1.8 mL)/EtOH (7.5 mL)/THF (9.0 mL) mixture, and warmed to RT. The reaction mixture was diluted with saturated aqueous NaHCO$_3$ solution and extracted with EtOAc. The organic layer was separated and washed with brine, dried over Na$_2$SO$_4$, filtered and concentrated under reduced pressure. The residue was purified by silica gel column chromatography (Petroleum ether:EtOAc=3:1) to give the title compound as a yellow solid (500 mg, yield 10.7%).

MS (ES+) C$_{18}$H$_{15}$Cl$_3$N$_4$O$_2$ requires: 424, found: 425 [M+H]+.

(3-Chloro-2-(4-methoxybenzylamino)pyridin-4-yl)(3,5-dichloropyrazin-2-yl)methanone To a solution of the product from the previous step (500 mg, 1.18 mmol) in CH$_2$Cl$_2$ (200 mL) was added solid MnO$_2$ (2.05 g, 23.58 mmol) portionwise. The result mixture was stirred at RT overnight. The reaction mixture was filtered off and the filtrate was concentrated to give the titled compound as a yellow solid (480 mg, yield 96%).

MS (ES+) C$_{18}$H$_{13}$Cl$_3$N$_4$O$_2$ requires: 422, found: 423 [M+H]+.

Intermediate 109

(3-Chloro-2-methoxypyridin-4-yl)(3,5-dichloropyrazin-2-yl)methanone

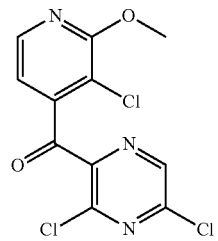 [SMILES: COc1nccc(C(=O)c2ncc(Cl)nc2Cl)c1Cl]

(3-Chloro-2-methoxypyridin-4-yl)methanol Freshly prepared NaOMe in MeOH (from Na (4.12 g) in dry MeOH (45 mL)) was added dropwise to a solution of (2,3-dichloropyridin-4-yl)methanol (15 g, 87.2 mmol) in dry MeOH (20 mL). The reaction mixture was refluxed overnight, allowed to cool to RT and concentrated. The resulting mixture was quenched with H$_2$O (300 mL) and extracted with EtOAc (3×300 mL). The combined organic layers were washed with brine (3×100 mL), dried over Na$_2$SO$_4$ and concentrated in vacuo to afford crude the title compound (13 g, yield 86.6%).

MS (ES+) C$_7$H$_8$ClNO$_2$ requires: 173, found: 174 [M+H]+.

3-Chloro-2-methoxyisonicotinaldehyde To a solution of the product from the previous step (13 g, 75.1 mmol) in DCM (2 L) was added MnO$_2$ (130 g, 1.5 mol) portionwise. The mixture was stirred at RT overnight. The reaction was filtered, and the filtrate was purified by silica gel column chromatography (Petroleum ether:EtOAc=10:1~8:1) to give the title compound as a white solid (10 g, yield 78.1%).

MS (ES+) C$_7$H$_6$ClNO$_2$ requires: 171, found: 172 [M+H]$^+$.

(3-Chloro-2-methoxypyridin-4-yl)(3,5-dichloropyrazin-2-yl)methanol To a −78° C. solution of LDA (2.0 M in hexane, 22.0 mmol) in dry THF (40 mL) under argon was added 2,6-dichloropyrazine (1.648 g, 11.0 mmol) in THF (10 mL) slowly. After addition was complete, the resulting mixture was stirred at −78° C. for an additional 1 h, then the product from the previous step (2.82 g, 16.5 mmol) in THF (10 mL) was added dropwise. The reaction mixture was stirred for another hour, then quenched with HCl (1.8 mL)/EtOH (7.5 mL)/THF (9.0 mL) mixture, and warmed to RT. The reaction mixture was diluted with sat. aq. NaHCO$_3$ solution and extracted with EtOAc. The organic layer was separated and washed with brine, dried over Na$_2$SO$_4$, filtered, and concentrated under reduced pressure. The residue was purified by silica gel column chromatography (Petroleum ether:EtOAc=3:1) to give the title compound as a white solid (500 mg, yield 14.2%).

MS (ES+) C$_{11}$H$_8$Cl$_3$N$_3$O$_2$ requires: 319, found: 320 [M+H]+.

(3-Chloro-2-methoxypyridin-4-yl)(3,5-dichloropyrazin-2-yl)methanone To a solution of the product from the previous step (500 mg, 1.56 mmol) in CH$_2$Cl$_2$ (200 mL) was added solid MnO$_2$ (2.71 g, 31.2 mmol) portionwise. The result mixture was stirred at RT overnight. The reaction mixture was filtered, and the filtrate was concentrated to give the title compound as a white solid (480 mg, yield 96%).

MS (ES+) C$_{11}$H$_6$Cl$_3$N$_3$O$_2$ requires: 317, found: 318 [M+H]+.

Intermediate 110

(4-(4-Methoxybenzylamino)piperidin-4-yl)methanol dihydrochloride

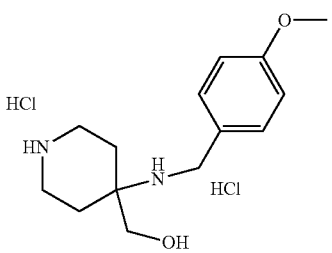 [SMILES: Cl ; COc1ccc(CNC2(CO)CCNCC2)cc1 ; Cl]

tert-Butyl 4-(hydroxymethyl)-4-(4-methoxybenzylamino)piperidine-1-carboxylate To a solution of tert-butyl 4-amino-4-(hydroxymethyl)piperidine-1-carboxylate (100 mg, 0.43 mmol) and $K_2CO_3$ (119 mg, 0.86 mmol) in DMF (5 mL) was added 1-(chloromethyl)-4-methoxybenzene (81 mg, 0.52 mmol). The mixture was stirred at 50° C. overnight. $H_2O$ (20 mL) was added, and the resulting mixture was extracted with ETOAc (20 mL×3), dried and concentrated. The residue was purified by Prep-TLC eluting with PE:EtOAc=2:1 to give the title compound as a colorless oil (85 mg, 57%).

MS (ES+) $C_{19}H_{30}N_2O_4$ requires: 350, found: 351 [M+H]+.

(4-(4-Methoxybenzylamino)piperidin-4-yl)methanol dihydrochloride A solution of the product from the previous step (85 mg, 0.24 mmol) in 4M HCl/MeOH (3 mL) was stirred at RT for 4 h. The solvent was removed to give the title compound as a white solid (78 mg, 100%), which was used directly without further purification.

MS (ES+) $C_{14}H_{24}Cl_2N_2O_2$ requires: 250, found: 251.2 [M+H]+.

Intermediate 111

(5-Chloro-2-(4-methoxybenzylamino)pyridin-4-yl)(3,5-dichloropyrazin-2-yl)methanone

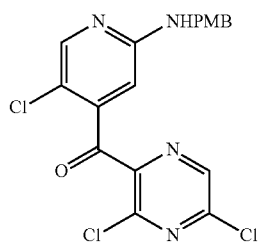

To a solution of (5-chloro-2-(4-methoxybenzylamino)pyridin-4-yl)(3,5-dichloropyrazin-2-yl)methanol (170 mg, 0.4 mmol) in DCM (20 mL) was added Dess-Martin reagent (255 mg, 0.6 mmol) at 0° C. The reaction mixture was stirred at RT for 4 h, then poured into aq. $NaHCO_3$ and extracted with EtOAc (25 mL×3). The organic layers were dried over $Na_2SO_4$, filtered, and concentrated under reduced pressure. The residue was purified by Prep-TLC eluting with PE:EtOAc=3:1 to give the title compound as a yellow solid (137 mg, 80%).

MS (ES+) $C_{18}H_{13}Cl_3N_4O_2$ requires: 422, found: 423.1 [M+H]+.

Intermediate 112

(3-Amino-2-chlorophenyl)(3,5-dichloropyrazin-2-yl)methanone

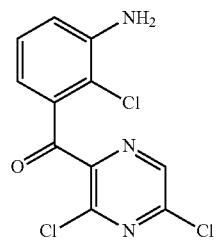

(2-Chloro-3-nitrophenyl)(3,5-dichloropyrazin-2-yl)methanol To a solution of 2,6-dichloropyrazine (1.06 g, 7.2 mmol) in THF (10 mL) was added 2 M LDA in THF (7.2 mL, 14.4 mmol) at −78° C. under $N_2$ slowly. The mixture was then stirred at −78° C. for 1 h. A solution of 2-chloro-3-nitrobenzaldehyde (2.0 g, 10.8 mmol) in THF (5 mL) was added, and the mixture was stirred at −78° C. for another 1 h. The reaction was then quenched with aq. $NH_4Cl$ (10 mL), then the mixture was extracted with EtOAc (20 mL×3). The combined organic layers were washed with brine, dried over $Na_2SO_4$ and concentrated. The residue was purified by column chromatography on silica gel, eluting with PE:EtOAc=3:1 to give the title compound as a yellow solid (1.2 g, 50%).

MS (ES+) $C_{11}H_6Cl_3N_3O_3$ requires: 333, found: 334 [M+H]+.

(2-Chloro-3-nitrophenyl)(3,5-dichloropyrazin-2-yl)methanone To a solution of the product from the previous step in DCM (15 mL) was added $MnO_2$ (3.1 g, 36 mmol) at RT, then the mixture was stirred for 18 h, filtered and concentrated in vacuo. The residue was purified by column chromatography on silica gel, eluting with PE:EtOAc=4:1 to give the title compound as a white solid (0.6 g, 50%).

MS (ES+) $C_{11}H_4Cl_3N_3O_3$ requires: 331, found: 332 [M+H]+.

(3-Amino-2-chlorophenyl)(3,5-dichloropyrazin-2-yl)methanone To a solution of the product from the previous step (0.6 g, 1.8 mmol) in EtOH (10 mL) was added $SnCl_2.2H_2O$ (0.8 g, 3.6 mmol) at RT. The mixture was then stirred at 90° C. for 18 h, then concentrated in vacuo. The residue was purified by column chromatography on silica gel, eluting with PE:EtOAc=1:1 to give the titled compound as a white solid (0.4 g, 74%).

MS (ES+) $C_{11}H_6Cl_3N_3O$ requires: 301, found: 302 [M+H]+.

Intermediate 113

(3-Chloro-2-(methylamino)pyridin-4-yl)(3,5-dichloropyrazin-2-yl)methanone

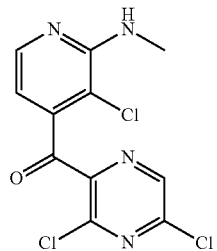 [SMILES: CNc1nccc(C(=O)c2ncc(Cl)nc2Cl)c1Cl]

(3-Chloro-2-(methylamino)pyridin-4-yl)methanol To a solution of (2,3-dichloropyridin-4-yl)methanol (15.4 g, 87 mmol) in CH$_3$NH$_2$ (7 M in H$_2$O, 200 mL) was added MeOH (20 mL). The reaction mixture was stirred at 120° C. for 24 h, allowed to cool to RT and concentrated. The mixture was poured into H$_2$O (100 mL) and extracted with EtOAc (3×300 mL). The combined organic layers were washed with brine (3×100 mL), dried over Na$_2$SO$_4$ and concentrated in vacuo to afford the titled compound crude (13 g, yield 86.6%).

MS (ES+) C$_7$H$_9$ClN$_2$O requires: 172, found: 173 [M+H]+.

3-Chloro-2-(methylamino)isonicotinaldehyde To a solution of the product from the previous step (13 g, 75.5 mmol) in DCM (2 L) was added MnO$_2$ (131 g, 1.5 mol) portionwise. The mixture was stirred at RT overnight. The reaction was filtered, and the filtrate was purified by silica gel column chromatography (Petroleum ether:EtOAc=10:1-4:1) to give the title compound as a yellow solid (11 g, yield 84.6%).

MS (ES+) C$_7$H$_7$ClN$_2$O requires: 170, found: 171 [M+H]+.

(3-Chloro-2-(methylamino)pyridin-4-yl)(3,5-dichloropyrazin-2-yl) methanol To a −78° C. solution of LDA (2.0 M in hexane, 22.0 mmol) in dry THF (40 mL) under argon was added 2,6-dichloropyrazine (1.648 g, 11.0 mmol) in THF (10 mL) slowly. After addition was complete, the resulting mixture was stirred at −78° C. for an additional 1 h, then the product from the previous step (2.8 g, 16.5 mmol) in THF (10 mL) was added dropwise. The reaction mixture was stirred for another hour, then quenched with HCl (1.8 mL)/EtOH (7.5 mL)/THF (9.0 mL) mixture, and warmed to RT. The reaction mixture was diluted with sat. aq. NaHCO$_3$ solution and extracted with EtOAc. The organic layer was separated and washed with brine, dried over Na$_2$SO$_4$, filtered and concentrated under reduced pressure. The residue was purified by silica gel column chromatography (Petroleum ether:EtOAc=3:1) to give the title compound as a yellow solid (500 mg, yield 14.2%).

MS (ES+) C$_{11}$H$_9$Cl$_3$N$_4$O requires: 318, found: 319 [M+H]+.

(3-Chloro-2-(methylamino)pyridin-4-yl)(3,5-dichloropyrazin-2-yl)methanone

To a solution of the product from the previous step (500 mg, 1.56 mmol) in CH$_2$Cl$_2$ (200 mL) was added solid MnO$_2$ (2.71 g, 31.2 mmol) portionwise. The resulting mixture was stirred at RT overnight. The reaction mixture was filtered, and the filtrate was concentrated to give the titled compound as a yellow solid (480 mg, yield 96%).

MS (ES+) C$_{11}$H$_7$Cl$_3$N$_4$O requires: 316, found: 317 [M+H]+.

Intermediate 114

(R)-2-methyl-N-(1-(4-methylpiperidin-4-yl)ethyl)propane-2-sulfinamide

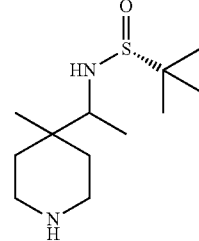

tert-Butyl 4-(methoxy(methyl)carbamoyl)-4-methylpiperidine-1-carboxylate To a solution of 1-(tert-butyloxycarbonyl)-4-methylpiperidine-4-carboxylic acid (15 g, 61.7 mmol), N,O-dimethylhydroxylamine hydrochloride (12 g, 123.4 mmol) and HATU (30.8 g, 80.2 mmol) in DMF (100 mL) was added TEA (25 g). The mixture was stirred at RT overnight. The mixture was diluted with EtOAc (700 mL) and washed with aq. NH$_4$Cl (200 mL×5). The organic phase was dried over Na$_2$SO$_4$ and concentrated to obtain the title compound as a brown oil (15 g, 90%).

MS (ES+) C$_{14}$H$_{26}$N$_2$O$_4$ requires: 286, found: 287 [M+H]+.

tert-Butyl 4-acetyl-4-methylpiperidine-1-carboxylate To a solution of the product from the previous step (5 g, crude) in THF (50 mL) was added MeMgCl (2M in THF, 26 mL, 52 mmol) at 0° C. The mixture was stirred at RT overnight. The mixture was poured into cold aq. NH$_4$Cl slowly then extracted with EtOAc (100 mL×3). The organic phase was washed with brine (100 mL), dried with Na$_2$SO$_4$, and concentrated to obtained the title compound as a brown oil (4 g, 85%).

MS (ES+) C$_{13}$H$_{23}$NO$_3$ requires 241, found: 242 [M+H]+.

(R,E)-tert-Butyl 4-(1-(tert-butylsulfinylimino)ethyl)-4-methylpiperidine-1-carboxylate To a solution of the product from the previous step (2.0 g, 8.3 mmol) in dry THF (20 mL) was added (R)-2-methylpropane-2-sulfinamide (2.0 g, 16.6 mmol) and Ti(OEt)$_4$ (6 mL). The mixture was stirred at 85° C. overnight. The mixture was concentrated and use directly for the next step.

MS (ES+) C$_{17}$H$_{32}$N$_2$O$_3$S requires: 344, found: 345 [M+H]+.

tert-Butyl 4-(1-((R)-1,1-dimethylethylsulfinamido)ethyl)-4-methylpiperidine-1-carboxylate and diasteromer To a mixture of the product from the previous step (2 g, crude) in MeOH (10 mL) was added NaBH$_4$ (631 mg, 16.6 mmol) at 0° C. The resulting mixture was stirred at RT for 4 hours. The mixture was quenched with water (10 mL), then concentrated under vacuum. EtOAc (50 mL) was added and filtered through a short CELITE® column. The aqueous phase was extracted with EtOAc (50 mL×3), then the organic phases were combined and washed with brine (50 mL), dried with MgSO$_4$, concentrated and purified by Pre- HPLC to obtain the title compound as a white solid (isomer 1: 500 mg, isomer 2: 240 mg).

MS (ES+) $C_{17}H_{34}N_2O_3S$ requires: 346, found: 347 [M+H]+.

(R)-2-methyl-N-(1-(4-methylpiperidin-4-yl)ethyl)propane-2-sulfinamide To a solution of tert-butyl 4-(1-((R)-1,1-dimethylethylsulfinamido)ethyl)-4-methylpiperidine-1-carboxylate (isomer 1, 200 mg) in DCM (10 mL) was added TFA (2 mL) slowly at 0° C. and stirred at this temperature for 30 min, concentrated and used directly for the next step.

MS (ES+) $C_{12}H_{26}N_2OS$ requires: 246, found: 247 [M+H]+.

The same method was used to prepare the other diastereomer.

Intermediate 115

(3,5-Dichloropyrazin-2-yl)(2-(4-methoxybenzylamino)-3-methylpyridin-4-yl)methanone

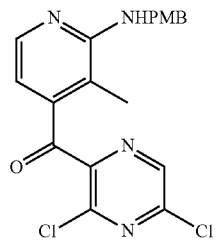

2-Fluoro-4-iodo-3-methylpyridine To a solution of LDA (68 mL, 135 mmol) at −78° C. was added a solution of 2-fluoro-3-iodopyridine (30 g, 135 mmol) in THF (100 mL), and the mixture is stirred for 1 hour at −78° C. under nitrogen. MeI (25 mL, 405 mmol) was then added, and the mixture was stirred for 30 min at −78° C. The mixture was quenched with sat. aq. NaHCO$_3$solution at −78° C. and then extracted with ether. The combined ether extracts were dried with MgSO$_4$ and concentrated in vacuo. The residue was purified by silica gel column chromatography (Petroleum ether:EtOAc=4:1) to give the title compound as a brown solid (22 g, 69%).

MS (ES+) $C_6H_5FIN$ requires: 237, found: 238 [M+H]+.

Methyl 2-fluoro-3-methylisonicotinate A mixture of the product from the previous step (22 g, 93 mmol), Pd(OAc)$_2$ (2.2 g, 9.8 mmol), 1,1'-bisdiphenylphosphino ferrocene (5.1 g, 9.2 mmol), and NaHCO$_3$ (46.7 g, 556 mmol) in MeOH (1 L) was stirred overnight in a CO atmosphere at 80° C. The mixture was cooled to room temperature, then water and sat. aq. NaHCO$_3$solution were added. The mixture was then extracted with EtOAc. The organic layers was washed with saturated brine, and then dried over anhydrous sodium sulfate. The mixture was filtered and concentrated under reduced pressure, and the obtained residue was purified by silica gel column chromatography (Petroleum ether: EtOAc=4:1) to give the title compound as a colorless oil (12 g, 77%).

MS (ES+) $C_8H_8FNO_2$ requires: 169, found: 170 [M+H]+.

(2-Fluoro-3-methylpyridin-4-yl)methanol To a solution of the product from the previous step (12 g, 71 mmol) in MeOH (100 mL) was added NaBH$_4$ (11 g, 290 mmol) portionwise. The resulting mixture was stirred at RT for 0.5 h, concentrated in vacuo. The residue was purified by silica gel column chromatography (Petroleum ether:EtOAc=2:1) to give the title compound as a brown solid (9 g, 90%).

MS (ES+) $C_7H_8FNO$ requires: 141, found: 142 [M+H]+.

(2-(4-Methoxybenzylamino)-3-methylpyridin-4-yl)methanol A solution of the product from the previous step (9.7 g, 69 mmol), methoxybenzylamine (14.1 g, 103 mmol) and K$_2$CO$_3$ (14.1 g, 103 mmol) in DMSO (100 mL) was sealed and stirred at 150° C. for 1 hour. The reaction mixture was cooled to room temperature, then poured into cold water (500 mL) and extracted with EtOAc (500 mL×2). The combined EtOAc solution was washed with brine, dried over Na$_2$SO$_4$ and concentrated. The residue was purified by silica gel column chromatography (DCM:MeOH=100:3) to give the title compound as a brown solid (8 g, 45%).

MS (ES+) $C_{15}H_{18}N_2O_2$ requires: 258, found: 259 [M+H]+.

2-(4-Methoxybenzylamino)-3-methylisonicotinaldehyde To a solution of the product from the previous step (8 g, 31 mmol) in CH$_2$Cl$_2$ (1.5 L) was added MnO$_2$ (54 g, 620 mmol). The mixture was stirred at RT overnight, then filtered. The filtrate was concentrated under reduced pressure, and the obtained residue was purified by silica gel column chromatography (Petroleum ether:EtOAc=4:1) to give the title compound as a brown solid (7.2 g, 91%).

MS (ES+) $C_{15}H_{16}N_2O_2$ requires: 256, found: 257 [M+H]+.

(3,5-Dichloropyrazin-2-yl)(2-(4-methoxybenzylamino)-3-methyl pyridin-4-yl)methanol To a −78° C. solution of LDA (26 mL, 52 mmol) in dry THF (100 mL) under Ar was added 2,6-dichloropyrazine (3.9 g, 26 mmol) in 20 mL THF dropwise. The resulting solution was stirred at −78° C. for 1 h, then the product from the previous step (6.7 g, 26 mmol) in THF (20 mL) was added to the mixture dropwise at −78° C. The resulting solution was stirred at −78° C. for 1 h, then quenched with HCl (1.8 mL)/EtOH (7.5 mL)/THF (9.0 mL) mixture and warmed to rt. The reaction mixture was diluted with sat. aq. NaHCO$_3$solution and extracted with EtOAc. The combined organic layers were separated and washed with brine, dried over Na$_2$SO$_4$, filtered, and concentrated under reduced pressure. The residue was purified by silica gel column chromatography (Petroleum ether:EtOAc=4:1) to give the title compound as a yellow solid (1.1 g, 11%).

MS (ES+) $C_{19}H_{18}Cl_2N_4O_2$ requires: 404, found: 405 [M+H]+.

(3,5-Dichloropyrazin-2-yl)(2-(4-methoxybenzylamino)-3-methyl pyridin-4-yl)methanone To a solution of the product from the previous step (1.1 g, 2.7 mmol) in CH$_2$Cl$_2$ (200 mL) was added MnO$_2$ (4.7 g, 54 mmol). The mixture was stirred at RT overnight, filtered, and concentrated under reduced pressure The obtained residue was purified by silica gel column chromatography (Petroleum ether:EtOAc=2:1) to give the title compound as a brown solid (600 mg, 55%).

MS (ES+) $C_{19}H_{16}Cl_2N_4O_2$ requires: 402, found: 403 [M+H]+.

Intermediate 116

(R)—N-((1R,3S)-3-(tert-butyldimethylsilyloxy)-8-azaspiro[4.5] decan-1-yl)-2-methylpropane-2-sulfinamide

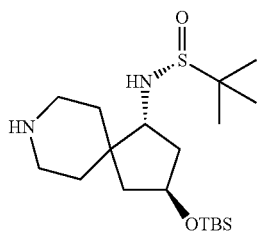 [SMILES: CC(C)(C)[S@@](=O)N[C@@H]1C[C@@H](O[Si](C)(C)C(C)(C)C)CC12CCNCC2]

tert-Butyl 2-oxo-6-oxaspiro[bicyclo[3.1.0]hexane-3,4'-piperidine]-1'-carboxylate A stirred solution of tert-butyl-1-oxo-8-azaspiro[4.5]dec-2-ene-8-carboxylate (500 mg; 1.99 mmoles) in MeOH (10 mL) was added $H_2O_2$ (13.93 mmol, 1.58 mL) followed by NaOH (656 µmol; 131 L) at 0° C. After 45 min, the reaction was quenched by addition of one drop AcOH. The reaction mixture was poured into brine and extracted with EtOAc (3×25 mL). The combined organic layers were washed with $NaHSO_3$, dried and concentrated to obtain the title compound (440 mg, yield 82.7%) as a light brown oil which was used directly in the next step.

MS (ES+): $C_{14}H_{21}NO_4$ requires: 267.1, found: 290.0 [M+Na]$^+$, $^1$H NMR (500 MHz, CDCl$_3$) δ 4.08-3.95 (m, 1H), 3.92 (t, J=2.0 Hz, 1H), 3.88-3.73 (m, 1H), 3.48 (d, J=2.2 Hz, 1H), 2.92 (d, J=11.5 Hz, 2H), 2.44 (d, J=14.6 Hz, 1H), 1.87 (d, J=14.6 Hz, 1H), 1.78 (ddd, J=13.4, 11.4, 4.3 Hz, 1H), 1.70-1.62 (m, 1H), 1.45 (s, 9H), 1.32-1.18 (m, 2H).

tert-Butyl 3-hydroxy-1-oxo-8-azaspiro[4.5]decane-8-carboxylate

A solution of the product from the previous step (979 mg, 3.7 mmol) in acetone (25 mL) was treated with NaI (2.0 g, 13.5 mmol), NaOAc (1.36 mmol, 111 mg) and AcOH (13.55 mmol, 776 µL) at 25° C. for 30 min. The iodine formed from the reaction was reduced by addition of a saturated aqueous $Na_2S_2O_3$ solution (25 mL), and the acetone was removed by evaporation. The remaining aqueous mixture was diluted with EtOAc (75 mL) and washed with water (2×25 mL), sat. aq. $Na_2CO_3$ solution (3×25 mL), and brine (20 mL). The organic layer was dried (MgSO$_4$) and concentrated. The residue was purified on silica gel eluting with EtOAc-DCM 10-50% to obtain the title compound (819 mg, 83% yield) as a white solid.

MS (ES+): $C_{14}H_{23}NO_4$ requires: 269.2, found: 292.1 [M+Na]+; $^1$H NMR (500 MHz, CDCl$_3$) δ 4.67-4.56 (m, 1H), 3.99-3.75 (m, 2H), 3.10-2.90 (m, 2H), 2.65 (dd, J=18.4, 5.9 Hz, 1H), 2.46-2.33 (m, 1H), 2.19-2.04 (m, 2H), 1.97 (s, 1H), 1.85-1.76 (m, 1H), 1.70-1.62 (m, 2H), 1.45 (s, 9H).

tert-Butyl 3-(tert-butyldimethylsilyloxy)-1-oxo-8-azaspiro[4.5] decane-8-carboxylate A mixture of the product from the previous step (819 mg, 3.04 mmol), imidazole (4.56 mmol, 320.12 mg) and TBDMSCl (3.80 mmol, 590.61 mg) in DMF (5 mL) was stirred 16 h at room temperature. The reaction mixture was poured into a separation funnel containing sat. aq NH$_4$Cl:H$_2$O (1:1, 50 mL) and extracted with Et$_2$O (5×20 mL). The combined organic phases were dried over MgSO$_4$ and filtered, and the volatiles were removed under reduced pressure. The resulting residue was purified by silica chromatography (0-30% EtOAc/heptane eluent) to give the title compound (965 mg, 82.7% yield) as a colorless oil.

MS (ES+): $C_{20}H_{37}NO_4Si$ requires: 383.2, found: 406.2 [M+Na]+, $^1$H NMR (500 MHz, CDCl$_3$) δ 4.47-4.42 (m, 1H), 3.92-3.74 (m, 2H), 3.04-2.84 (m, 2H), 2.49 (dd, J=18.2, 5.7 Hz, 1H), 2.29 (d, J=18.1 Hz, 1H), 2.07-1.93 (m, 2H), 1.75-1.67 (m, 1H), 1.64-1.56 (m, 2H), 1.40 (s, 9H), 1.24-1.21 (m, 1H), 0.81 (s, 9H), 0.01 (s, 3H), −0.00 (s, 3H).

(R,E)-tert-butyl 3-(tert-butyldimethylsilyloxy)-1-((R)-tert-butylsulfinylimino)-8-azaspiro[4.5]decane-8-carboxylate and (S,E)-tert-butyl 3-(tert-butyldimethylsilyloxy)-1-((R)-tert-butylsulfinylimino)-8-azaspiro[4.5]decane-8-carboxylate A solution of the product from the previous step (0.21 g, 547 µmol), Ti(OEt)$_4$ (2.19 mmol, 462 µL) and (R)-2-methylpropane-2-sulfinamide (1.09 mmol, 132.7 mg) in THF (3 mL) was heated at 65° C. for 16 hours. The mixture was cooled to RT, quenched with sat. NaHCO$_3$solution, and extracted with EtOAc (15 mL×4). The combined organic layers were washed with brine (20 mL), dried (Na$_2$SO$_4$), filtered and concentrated, and the residue was purified on silica gel eluting with EtOAc-PE 0-45% to obtain first the (R,E)-isomer (R$_f$=0.75, 74 mg, 28% yield) as a white solid:

MS (ES+): $C_{24}H_{46}N_2O_4SSi$ requires: 486.3, found: 509.3 [M+Na]+, $^1$H NMR (500 MHz, CDCl$_3$) δ 4.42-4.34 (m, 1H), 4.05-3.83 (m, 2H), 3.16 (dd, J=19.0, 3.3 Hz, 1H), 3.04-2.73 (m, 3H), 1.88-1.77 (m, 2H), 1.75-1.63 (m, 3H), 1.40 (s, J=3.3 Hz, 9H), 1.31-1.25 (m, 1H), 1.19 (s, 9H), 0.80 (s, 9H), 0.00 (d, J=3.0 Hz, 6H).

followed by the (S,E)-isomer (R$_f$=0.35, 75 mg, 28% yield) as a colorless oil:

MS (ES+): $C_{24}H_{46}N_2O_4SSi$ requires: 486.3, found: 509.3 [M+Na]+, $^1$H NMR (500 MHz, CDCl$_3$) δ 4.47-4.38 (m, 1H), 4.01-3.81 (m, 2H), 3.07 (dd, J=18.8, 5.6 Hz, 1H), 2.96-2.78 (m, 3H), 1.91 (d, J=13.4 Hz, 1H), 1.77 (dd, J=13.5, 5.0 Hz, 2H), 1.73-1.65 (m, 2H), 1.41 (s, 9H), 1.35-1.30 (m, 1H), 1.19 (s, 9H), 0.80 (s, 9H), −0.00 (s, 6H).

(1R,3S)-tert-butyl 3-(tert-butyldimethylsilyloxy)-1-((R)-1,1-dimethyl ethylsulfinamido)-8-azaspiro[4.5]decane-8-carboxylate To a solution of the product from the previous step (0.072 g, 148 µmol) in THF (5 mL) was added MeOH (0.5 mL) at −78° C., followed by LiBH$_4$ (444 µmol, 222 µL). The resulting mixture was stirred for 4 h at −78° C. Sat. NH$_4$Cl solution was then added slowly to quench the excess of borohydride, followed by addition of EtOAc (25 mL). The resulting mixture was vigorously stirred for 15 min and then filtered through a pad of CELITE®. The volatiles were removed under reduced pressure, and the resulting residue was purified by silica chromatography (0 to 50% EtOAc/heptane) to give the title compound (56 mg, 77% yield) as a colorless oil.

MS (ES+): $C_{24}H_{48}N_2O_4SSi$ requires: 488.3, found: 489.3 [M+H]$^+$; $^1$H NMR (500 MHz, CDCl$_3$) δ 4.26 (s, 1H), 4.04-3.78 (m, 2H), 3.27 (s, 1H), 2.95-2.75 (m, 2H), 2.29 (s, 1H), 1.891.51 (m, 7H), 1.41 (s, 9H), 1.26-1.20 (m, 1H), 1.16 (s, 9H), 0.83 (s, 9H), −0.00 (s, 6H).

(R)—N-((1R,3S)-3-(tert-butyldimethylsilyloxy)-8-azaspiro[4.5] decan-1-yl)-2-methylpropane-2-sulfinamide To the product from the previous step (50 mg, 102 µmol) in DCM (5 mL) was added TFA (0.5 mL). The mixture was stirred at RT for 2 hours, then concentrated to obtain the title compound (40 mg, 100% yield) as a pale oil which was used without further purification.

MS (ES+): $C_{19}H_{40}N_2O_2SSi$ requires: 388.3, found: 389.3 [M+H]$^+$.

Intermediate 117

4-Aminopiperidine-4-carboxamide dihydrochloride

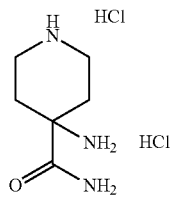

tert-butyl 4-amino-4-carbamoylpiperidine-1-carboxylate To a solution of tert-butyl 4-amino-4-cyanopiperidine-1-carboxylate (50 mg, 0.22 mmol) and $K_2CO_3$ (61 mg, 0.44 mmol) in DMSO (1 mL) was added $H_2O_2$ (30% in water, 25 mg, 0.44 mmol) slowly. The resulting mixture was stirred at RT for 72 h. The reaction mixture was quenched with aqueous $Na_2S_2O_3$ (15 mL), extracted with $CHCl_3$:i-PrOH (4:1, 30 mL×3), washed with brine, dried over $Na_2SO_4$ and concentrated under reduced pressure to give the title compound as a colorless syrup solid (60 mg, crude).

MS (ES+) $C_{11}H_{21}N_3O_3$ requires: 243, found 266 [M+Na]+.

4-Aminopiperidine-4-carboxamide dihydrochloride To a solution of tert-butyl 4-amino-4-carbamoylpiperidine-1-carboxylate (60 mg, 0.25 mmol) in MeOH (0.5 mL) was added HCl/dioxane (4 M, 3 mL, 12 mmol). The resulting mixture was stirred at RT for 2 h. The solid precipitated was filtered to give the title compound as a white solid (60 mg).

MS (ES+) $C_6H_{13}N_3O$ requires: 143, found: 144 [M+H]+.

Intermediate 118

(3,5-Dichloropyrazin-2-yl)(2-(4-methoxybenzylamino)-5-methyl pyridin-4-yl)methanone

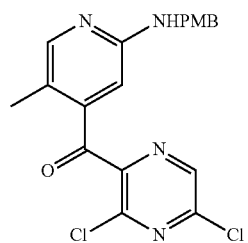

Methyl 2-fluoro-5-methylisonicotinate A mixture of 2-fluoro-4-iodo-5-methyl-pyridine (3.4 g, 14 mmol), Pd(OAc)$_2$ (314 mg, 1.4 mmol), 1,1'-bisdiphenylphosphino ferrocene (776 mg, 1.4 mmol), TEA (7 g, 70 mmol) in MeOH (200 mL) was stirred overnight in a CO atmosphere at 80° C. The mixture was cooled to RT, then concentrated and purified by silica gel column chromatography (Petroleum ether:EtOAc=4:1) to give the title compound as a white solid (1.5 g, 75%).

MS (ES+) $C_8H_8FNO_2$ requires: 169, found: 170 [M+H]+.

(2-Fluoro-5-methylpyridin-4-yl)methanol To a solution of the product from the previous step (1.2 g, 7.1 mmol) in MeOH (20 mL) was added NaBH$_4$ (1.1 g, 29 mmol) portionwise. The resulting mixture was stirred at RT for 0.5 h, the reaction mixture was concentrated in vacuo. The residue was dissolved in EtOAc (50 mL), washed with brine (50 mL×3), and concentrated to give the title compound as a brown solid (970 mg, crude).

MS (ES+) $C_7H_8FNO$ requires: 141, found: 142 [M+H]+.

(2-(4-Methoxybenzylamino)-5-methylpyridin-4-yl) methanol A solution of (2-fluoro-5-methylpyridin-4-yl) methanol (0.97 g, 6.9 mmol) in 4-methoxybenzylamine (5 mL) was sealed and stirred at 135° C. for 72 hours. The reaction mixture was cooled to RT, and then purified by silica gel column chromatography (DCM:MeOH=100:3) to give the title compound as a brown solid (800 mg, crude).

MS (ES+) $C_{15}H_{18}N_2O_2$ requires: 258, found: 259 [M+H]+.

2-(4-Methoxybenzylamino)-5-methylisonicotinaldehyde To a solution of the product from the previous step (0.8 g, 3.1 mmol) in $CH_2Cl_2$ (300 mL) was added $MnO_2$ (5.4 g, 62 mmol), The mixture was stirred at RT overnight, then filtered. The filtrate was concentrated under reduced pressure, and the obtained residue was purified by silica gel column chromatography (Petroleum ether:EtOAc=4:1) to give the title compound as a brown solid (720 mg, 90%).

MS (ES+) $C_{15}H_{16}N_2O_2$ requires: 256, found: 257 [M+H]+.

(3,5-Dichloropyrazin-2-yl)(2-(4-methoxybenzylamino)-5-methyl pyridin-4-yl)methanol To a −78° C. solution of LDA (2.6 mL, 5.2 mmol) in dry THF (10 mL) under argon was added 2,6-dichloropyrazine (390 mg, 26 mmol) in THF (4 mL) dropwise at −78° C. The resulting solution was stirred at −78° C. for 1 h, then the product from the previous step (670 mg, 2.6 mmol) in THF (4 mL) was added to the mixture dropwise at −78° C. The resulting solution was stirred at −78° C. for 1 h, then quenched with HCl (1.8 mL)/EtOH (7.5 mL)/THF (9.0 mL) mixture, and warmed to RT. The reaction mixture was diluted with sat. aq. NaHCO$_3$ solution and extracted with EtOAc. The organic layer was separated and washed with brine, dried over Na$_2$SO$_4$, filtered, and concentrated under reduced pressure. The residue was purified by silica gel column chromatography (Petroleum ether:EtOAc=4:1) and further purified with Pre-HPLC to give the title compound as a yellow solid (80 mg, 6%). MS (ES+) $C_{19}H_{18}Cl_2N_4O_2$ requires: 404, found: 405 [M+H]+.

(3,5-Dichloropyrazin-2-yl)(2-(4-methoxybenzylamino)-5-methyl pyridin-4-yl)methanone To a solution of the product from the previous step (80 mg, 0.20 mmol) in $CH_2Cl_2$ (10 mL) was added Dess-Martin periodinane (127 mg, 0.3 mmol) at 0° C., the mixture was stirred at 0° C. for 1 hour, then another batch of Dess-Martin periodinane (127 mg, 0.3 mmol) was added and the mixture was stirred for another 4 hours at 0° C. The mixture was washed with aq. NaHCO$_3$ dried over MgSO$_4$, and concentrated under reduced pressure, and the residue was purified by silica gel column chromatography (Petroleum ether:EtOAc=2:1) to give the title compound as a brown solid (20 mg, 25%).

MS (ES+) $C_{19}H_{16}Cl_2N_4O_2$ requires: 402, found: 403 [M+H]+.

Synthetic Schemes

The following schemes can be used to practice the present invention.

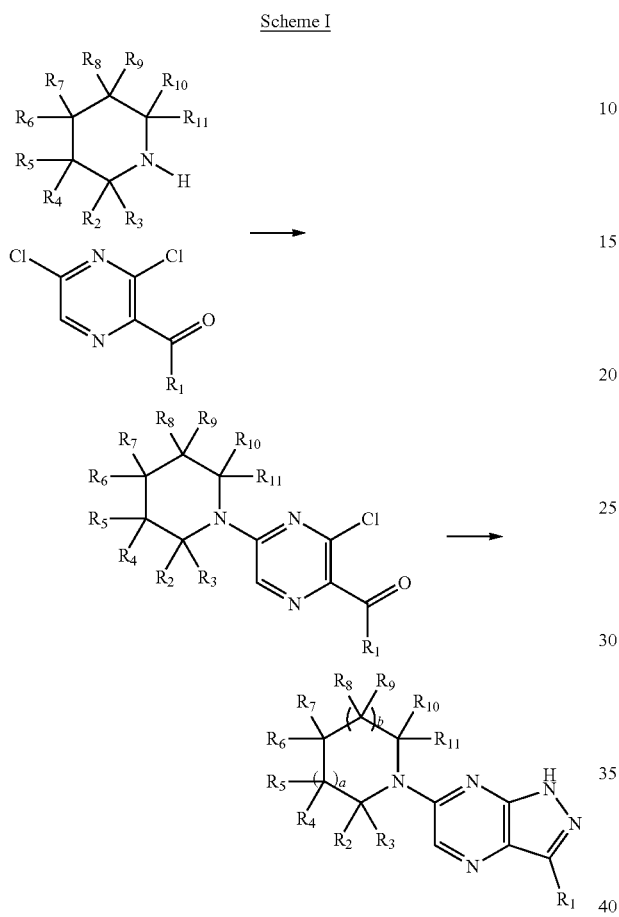

A general, non-limiting synthetic strategy for the disclosed compounds is illustrated in Scheme I, above. An appropriately substituted piperidine is condensed with a chlorinated pyrazine. The pyrazolo[3,4-b]pyrazine core formed on reaction of the intermediate with hydrazine. It will be appreciated that other synthetic routes may be available for practice of the present invention.

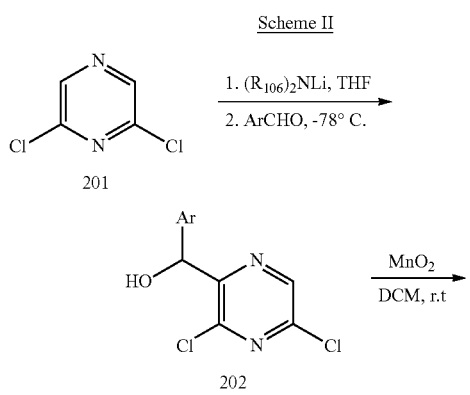

Examples disclosed herein can be synthesized using the general synthetic procedure set forth in Scheme II. Ortho metalation of the pyrazine 201 can be accomplished with a metalated secondary amine $(R_{106})_2NLi$, which can be prepared from $(R_{106})_2NH$ and BuLi (not shown). Without limitation, examples of suitable secondary amines $(R_{106})_2NH$ for this transformation include diiosopropylamine and 2,2,6,6-tetramethylpiperidine. The metalated pyrazine is condensed with a substituted aryl carboxaldehyde to give benzylic alcohol 202. Oxidation to the ketone 203 is followed by substitution of the aryl halide with an appropriately substituted piperidine to give amine 204. Reaction with hydrazine gives the pyrazolo[3,4-b]pyrazine ring of 205.

It will be apparent that Scheme II can be modified to accommodate functionality in the piperidine. A protected amine can be incorporated into the piperidine as an —$NHP_1$ group. In this scheme the group "$P_1$" is an appropriate amino protecting group. Without limitation, $P_1$ can be a carbamate protecting group such as Boc or CBz, or a labile aromatic protecting group, such asp-methoxybenzyl. The protecting group $P_1$ is removed from 205 to afford the product. A carbamate protecting group can be removed under acid conditions to afford the product.

Scheme III

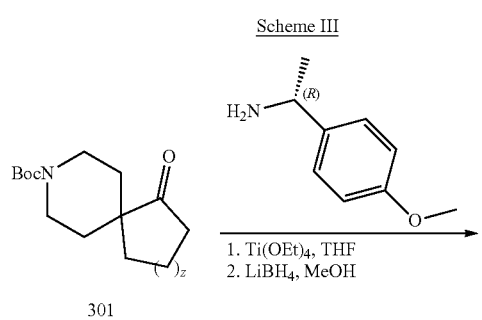

301

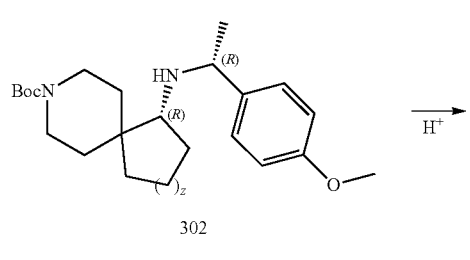

302

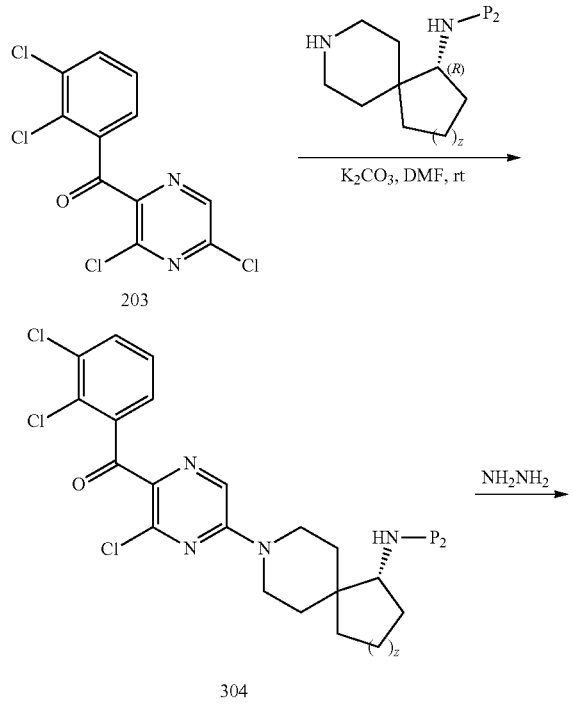

303

204

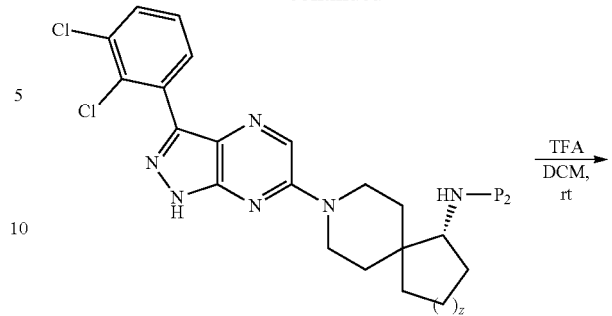

305

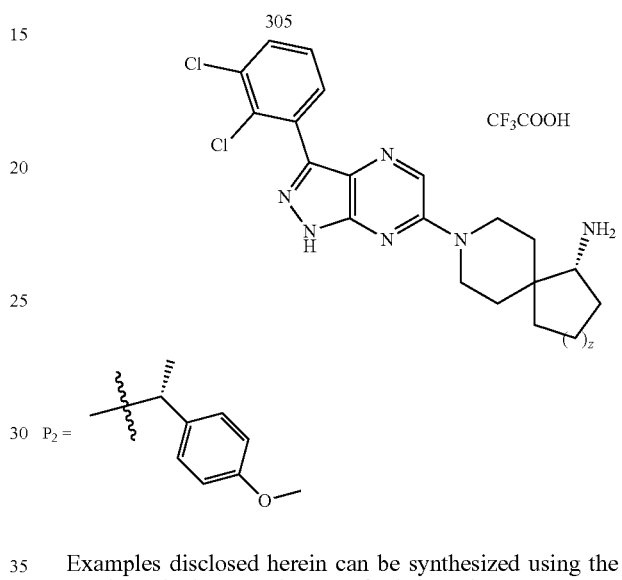

Examples disclosed herein can be synthesized using the general synthetic procedure set forth in Scheme III. Condensation of spiro ketone 301 (z=1) with enantiopure 1-(4-methoxyphenyl)ethylamine), followed by reduction, gives chiral secondary amine 302. The Boc protecting group is removed under acidic conditions, giving amine 303. In this scheme, the symbol P2 is intended to represent the 1-(4-methoxyphenyl)ethyl group. Reaction with a ketone such as 203 (Scheme II) affords amine 304. Reaction with hydrazine gives the pyrazolo[3,4-b]pyrazine ring of 305. Finally, the 1-(4-methoxyphenyl)ethyl group is removed under acid conditions. This procedure can be modified to access spiro compounds of differing ring sizes, i.e., z≠1. The compound may then be isolated as the free base by methods known in the art.

Scheme IV

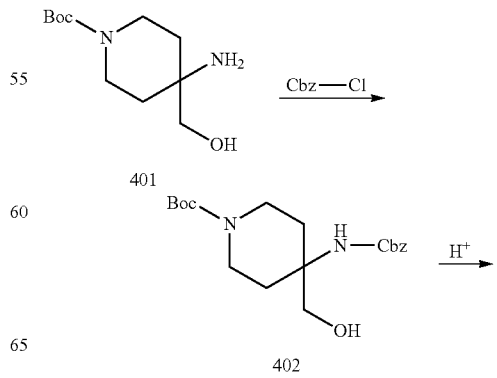

-continued

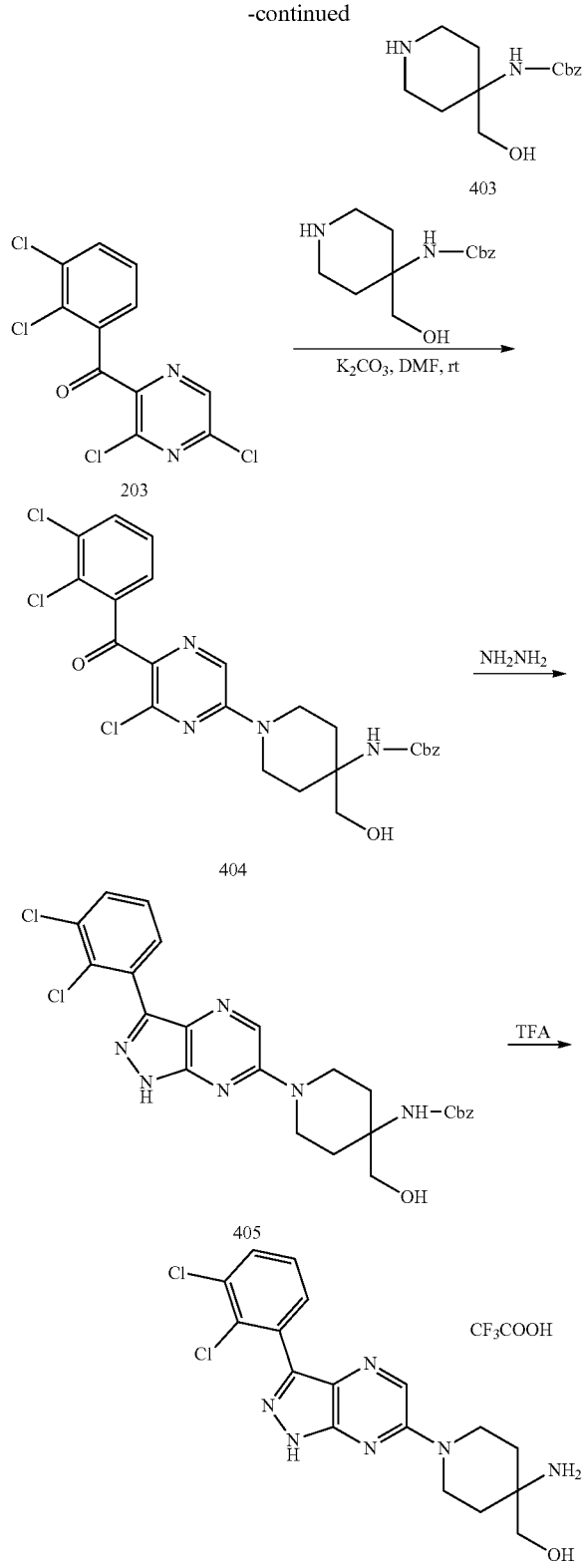

Examples disclosed herein can be synthesized using the general synthetic procedure set forth in Scheme IV. Reaction of primary amine 401 with CBz-Cl gives protected amine 402. The Boc protecting group is removed under acidic conditions, giving amine 403, and leaving the CBz group intact. Reaction with the previously presented ketone 203 affords amine 404. Reaction with hydrazine gives the pyrazolo[3,4-b]pyrazine ring of 405. Finally, the CBz group is removed under more vigorous acid conditions to give the product. The compound may then be isolated as the free base by methods known in the art.

The invention is further illustrated by the following examples, which may be synthesized and isolated as free bases or as TFA salts.

EXAMPLE 1

1-(3-(2,3-dichlorophenyl)-1H-pyrazolo[3,4-b]pyrazin-6-yl)-4-methylpiperidin-4-amine

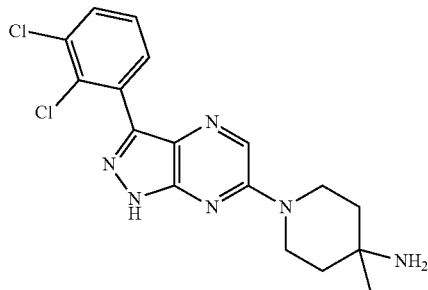 [SMILES: CC1(N)CCN(c2cnc3c(-c4cccc(Cl)c4Cl)n[nH]c3n2)CC1]

(2,3-Dichlorophenyl)(3,5-dichloropyrazin-2-yl)methanol To a −20° C. solution of n-butyllithium (2.5M in hexane, 6.6 mmol) in dry THF (20 mL), under argon, was added 2,2,6,6-tetramethylpiperidine (1.15 mL, 6.6 mmol). The resulting solution was warmed to 0° C. over 0.5 hour period. The solution was then cooled to −78° C., and a solution of 2,6-dichloropyrazine (824 mg, 5.5 mmol) in THF (5 mL) was slowly added. After the addition was complete, the resulting mixture was stirred at −78° C. for an additional 1 hr, then 2,3-dichlorobenzaldehyde (1.44 g, 8.3 mmol) in THF (5 mL) was added dropwise. The reaction mixture was stirred for another hour, then quenched with hydrochloric acid (1.8 mL)/EtOH (7.5 mL)/THF (9.0 mL) mixture, and warmed to rt. The reaction mixture was diluted with saturated aqueous sodium bicarbonate solution and extracted with EtOAc. The organic layer was separated and washed with brine, dried over $Na_2SO_4$, filtered, and concentrated under reduced pressure. The residue was purified by silica gel column chromatography (Petroleum ether:EtOAc=4:1) to give the title compound as a yellow solid (740 mg, 41%).

MS (ES+) $C_{11}H_6Cl_4N_2O$ requires: 322, found: 323 [M+H]+. $^1$H NMR (500 MHz, DMSO-$d_6$) δ 8.73 (s, 1H), 7.76 (dd, J=8.0, 1.0 Hz, 1H), 7.61 (dd, J=8.0, 1.0 Hz, 1H), 7.48 (t, J=8.0 Hz, 1H), 6.77 (d, J=6.0 Hz, 1H), 6.33 (d, J=6.0 Hz, 1H).

(2,3-Dichlorophenyl)(3,5-dichloropyrazin-2-yl)methanone To a solution of the product from the previous step (97 mg, 0.3 mmol) in $CH_2Cl_2$ (10 mL) was added solid $MnO_2$ (522 mg, 6.0 mmol) in portions. The resulting mixture was stirred at rt overnight. The reaction mixture was filtered, and the filtrate was concentrated to give the title compound as a yellow solid (80 mg, 83%).

MS (ES+) $C_{11}H_4Cl_4N_2O$ requires: 320, found: 321 [M+H]+.

tert-Butyl 1-(6-chloro-5-(2,3-dichlorobenzoyl)pyrazin-2-yl)-4-methylpiperidin-4-yl carbamate To a solution of the product from the previous step (80 mg, 0.25 mmol) in 5 mL DMF, under $N_2$, was added tert-butyl 4-methylpiperidin-4-yl carbamate (54 mg, 0.25 mmol) and $K_2CO_3$ (69 mg, 0.5 mmol). The resulting mixture was stirred overnight at rt and then concentrated. The residue was dissolved in EtOAc and washed with $H_2O$ and brine. The organic layer was dried over $Na_2SO_4$, filtered, and concentrated under reduced pressure. The residue was purified by silica gel column chromatography (Petroleum ether:EtOAc=4:1) to give the title compound as a yellow oil (64 mg, 52%).

MS (ES+) $C_{22}H_{25}Cl_3N_4O_3$ requires: 498, found: 499 [M+H]+.

tert-Butyl 1-(3-(2,3-dichlorophenyl)-1H-pyrazolo[3,4-b]pyrazin-6-yl)-4-methylpiperidin-4-yl carbamate To a solution of the product from the previous step (64 mg, 0.13 mmol) in EtOH (10 mL) was added hydrazine hydrate (13 mg, 0.26 mmol). The resulting mixture was refluxed under $N_2$ for 2 h. The solvent was removed to give the crude title compound as a yellow solid (61 mg, 100%), which was used directly without further purification.

MS (ES+) $C_{22}H_{26}Cl_2N_6O_2$ requires: 476, found: 477 [M+H]+.

1-(3-(2, 3-Dichlorophenyl)-1H-pyrazolo[3,4-b]pyrazin-6-yl)-4-methylpiperidin-4-amine TFA salt (1): To a solution of the product from the previous step (61 mg, 0.13 mmol) in $CH_2Cl_2$ (2 mL) was added TFA (2 mL). The mixture was stirred at rt for 4 h, then concentrated under reduced pressure. The residue was purified by Prep-HPLC under acidic condition to give the title compound as a white solid (34.5 mg, 54%). The free base may then be isolated by methods known in the art.

MS (ES+) $C_{19}H_{19}Cl_2F_3N_6O_2$ requires: 376, found: 377 [M+H]+. $^1$H NMR (500 MHz, DMSO-$d_6$) δ 13.49 (s, 1H), 8.49 (s, 1H), 7.94 (s, 3H), 7.76 (dd, J=8.0, 1.0 Hz, 1H), 7.69 (dd, J=8.0, 1.0 Hz, 1H), 7.50 (t, J=8.0 Hz, 1H), 4.20-4.17 (m, 2H), 3.49-3.43 (m, 2H), 1.77-1.76 (m, 4H), 1.40 (s, 3H).

The following Examples were synthesized with synthetic methods that were similar to that used for Example 1, and can generally be made by methods disclosed herein. The Examples may be made as free bases or as TFA salts.

TABLE 1

Examples 2-14.

| Ex. | Name | Structure | Spectral Data |
|---|---|---|---|
| 2 | 8-(3-(2,3-dichlorophenyl)-1H-pyrazolo[3,4-b]-pyrazin-6-yl)-2,8-diazaspiro-[4.5]decane | 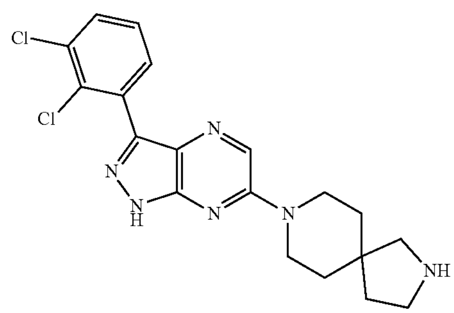 [SMILES: Clc1cccc(-c2n[nH]c3nc(N4CCC5(CCNC5)CC4)cnc23)c1Cl] | MS (ES+) $C_{21}H_{21}Cl_2F_3N_6O_2$ requires: 402, found: 403 [M + H]+. $^1$H NMR (500 MHz, DMSO-$d_6$) δ 13.41 (s, 1H), 8.91 (br, 2H), 8.47 (s, 1H), 7.75 (dd, J = 7.5, 1.5 Hz, 1H), 7.69 (dd, J = 7.5, 1.5 Hz, 1H), 7.49 (t, J = 8.0 Hz, 1H), 3.81-3.70 (m, 4H), 3.31-3.29 (m, 2H), 3.07 (s, 2H), 1.89 (t, J = 7.5 Hz, 2H), 1.68-1.64 (m, 4H). |
| 3 | (1R,5S,6S)-3-(3-(2,3-dichlorophenyl)-1H-pyrazolo[3,4-b]-pyrazin-6-yl)-3-aza-bicyclo[3.1.0]hexan-6-amine | 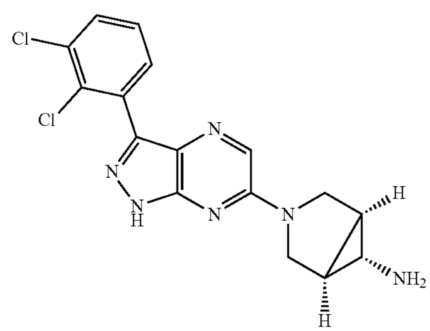 [SMILES: N[C@@H]1[C@H]2CN(c3cnc4c(-c5cccc(Cl)c5Cl)n[nH]c4n3)C[C@@H]12] | MS (ES+) $C_{18}H_{15}Cl_2F_3N_6O_2$ requires: 360, found: 361 [M + H]+. $^1$H NMR (500 MHz, DMSO-$d_6$) δ 13.45 (s, 1H), 8.24 (br, 3H), 8.08 (s, 1H), 7.75 (dd, J = 8.0, 1.0 Hz, 1H), 7.68 (dd, J = 8.0, 1.0 Hz, 1H), 7.49 (t, J = 8.0 Hz, 1H), 3.88 (d, J = 11.0 Hz, 2H), 3.65 (d, J = 11.0 Hz, 2H), 3.32 (m, 1H), 2.16 (s, 2H). |
| 4 | (1-(3-(2,3-dichlorophenyl)-1H-pyrazolo[3,4-b]-pyrazin-6-yl)-4-methylpiperidin-4-yl)methanamine | 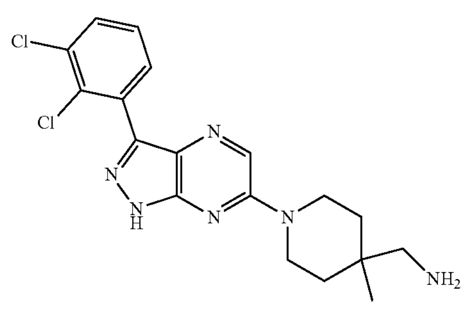 [SMILES: CC1(CN)CCN(c2cnc3c(-c4cccc(Cl)c4Cl)n[nH]c3n2)CC1] | MS (ES+) $C_{20}H_{21}Cl_2F_3N_6O_2$ requires: 390, found: 391 [M + H]+. $^1$H NMR (500 MHz, DMSO-$d_6$) δ 13.40 (s, 1H), 8.46 (s, 1H), 7.76-7.68 (m, 5H), 7.50 (t, J = 8.0 Hz, 1H), 4.04-4.01 (m, 2H), 3.53-3.48 (m, 2H), 2.81-2.79 (m, 2H), 1.56-1.54 (m, 2H), 1.47-1.44 (m, 2H), 1.09 (s, 3H). |

TABLE 1-continued

Examples 2-14.

| Ex. | Name | Structure | Spectral Data |
|---|---|---|---|
| 5 | (S)-8-(3-(2,3-dichlorophenyl)-1H-pyrazolo[3,4-b]pyrazin-6-yl)-8-azaspiro[4.5]decan-1-amine | 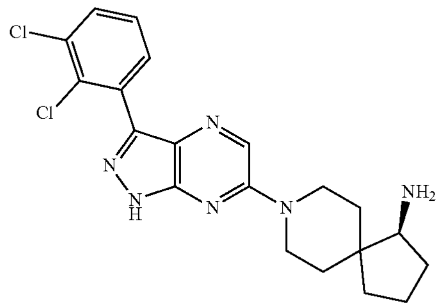 [SMILES: N[C@H]1CCCC12CCN(c1cnc3c(-c4cccc(Cl)c4Cl)n[nH]c3n1)CC2] | MS (ES+) C$_{22}$H$_{23}$Cl$_2$F$_3$N$_6$O$_2$ requires: 416, found: 417 [M + H]+. $^1$H NMR (500 MHz, DMSO-d$_6$) δ 13.42 (s, 1H), 8.48 (s, 1H), 7.76-7.74 (m, 4H), 7.69 (dd, J = 7.5, 1.5 Hz, 1H), 7.50 (t, J = 8.0 Hz, 1H), 4.39-4.29 (m, 2H), 3.23-3.14 (m, 3H), 2.03-2.01 (m, 1H), 1.86-1.42 (m, 9H). |
| 6 | 1-(3-(2,3-Dichlorophenyl)-1H-pyrazolo[3,4-b]-pyrazin-6-yl)-N,4-dimethylpiperidin-4-amine | 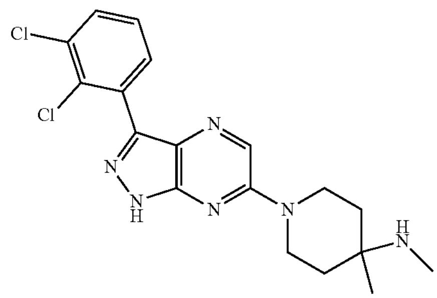 [SMILES: CNC1(C)CCN(c2cnc3c(-c4cccc(Cl)c4Cl)n[nH]c3n2)CC1] | MS (ES+) C$_{20}$H$_{21}$Cl$_2$F$_3$N$_6$O$_2$ requires: 390, found: 391 [M + H]+. $^1$H NMR (500 MHz, DMSO-d$_6$) δ 13.50 (s, 1H), 8.54 (br, 2H), 8.50 (s, 1H), 7.76 (dd, J = 8.0, 1.5 Hz, 1H), 7.69 (dd, J = 7.5, 1.5 Hz, 1H), 7.50 (t, J = 8.0 Hz, 1H), 4.37-4.34 (m, 2H), 3.33-3.28 (m, 2H), 2.55-2.53 (m, 3H), 1.84-1.77 (m, 4H), 1.41 (s, 3H). |
| 7 | 3-(2,3-dichlorophenyl)-6-(1,7-diazaspiro[3.5]nonan-7-yl)-1H-pyrazolo[3,4-b]pyrazine | 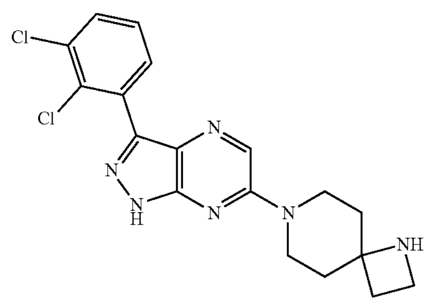 [SMILES: Clc1cccc(-c2n[nH]c3nc(N4CCC5(CCN5)CC4)cnc23)c1Cl] | MS (ES+) C$_{18}$H$_{18}$Cl$_2$N$_6$ requires: 388, found: 389 [M + H]$^+$. $^1$H NMR (500 MHz, DMSO-d$_6$) δ 13.47 (s, 1H), 8.77 (br, 2H), 8.51 (s, 1H), 7.76 (dd, J = 8.0, 1.5 Hz, 1H), 7.69 (dd, J = 8.0, 1.5 Hz, 1H), 7.50 (t, J = 8.0 Hz, 1H), 3.95-3.88 (m, 4H), 3.65-3.60 (m, 2H), 2.37 (t, J = 8.5 Hz, 2H), 2.09 (t, J = 6.0 Hz, 4H). |
| 8 | 4-(aminomethyl)-1-(3-(2,3-dichlorophenyl)-1H-pyrazolo[3,4-b]-pyrazin-6-yl)-piperidin-4-ol | 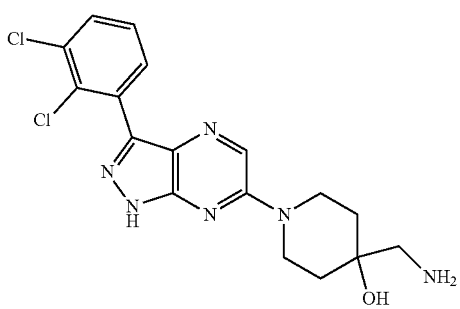 [SMILES: NCC1(O)CCN(c2cnc3c(-c4cccc(Cl)c4Cl)n[nH]c3n2)CC1] | MS (ES+) C$_{17}$H$_{18}$Cl$_2$N$_6$O requires: 392, found: 393 [M + H]$^+$. $^1$H NMR (500 MHz, DMSO-d$_6$) δ 13.42 (s, 1H), 8.48 (s, 1H), 7.79-7.74 (m, 4H), 7.69 (dd, J = 8.0, 1.5 Hz, 1H), 7.50 (t, J = 8.0 Hz, 1H), 5.21 (s, 1H), 4.21-4.18 (m, 2H), 3.48-3.44 (m, 2H), 2.83-2.81 (m, 2H), 1.67-1.59 (m, 4H). |
| 9 | (1-(3-(3-chlorophenyl)-1H-pyrazolo[3,4-b]-pyrazin-6-yl)-4-methylpiperidin-4-yl)methanamine | 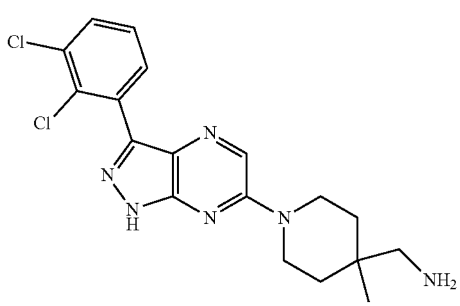 | MS (ES+) C$_{18}$H$_{21}$ClN$_6$ requires: 356, found: 357 [M + H]$^+$. $^1$H NMR (500 MHz, DMSO-d$_6$) δ 13.34 (s, 1H), 8.56 (s, 1H), 8.40 (t, J = 2.0 Hz, 1H), 8.27 (d, J = 7.5 Hz, 1H), 7.74 (br, 3H), 7.53 (t, J = 8.0 Hz, 1H), 7.45 (dd, 8.0, 1.0 Hz, 1H), 4.04-4.01 (m, 2H), 3.53-3.49 (m, 2H), 2.81 (s, 2H), 1.57-1.45 (m, 4H), 1.10 (s, 3H). |

TABLE 1-continued

Examples 2-14.

| Ex. | Name | Structure | Spectral Data |
|---|---|---|---|
| 10 | 1-(3-(3-chloro-phenyl)-1H-pyrazolo[3,4-b]-pyrazin-6-yl)-4-methylpiperidin-4-amine | 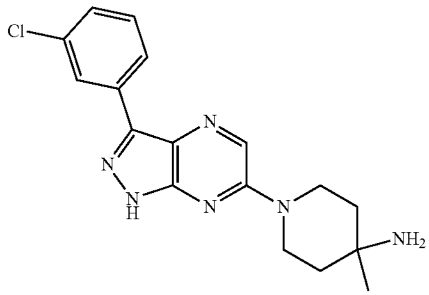 [SMILES: CC1(N)CCN(c2cnc3c(-c4cccc(Cl)c4)n[nH]c3n2)CC1] | MS (ES+) $C_{17}H_{19}ClN_6$ requires: 342, found: 343 [M + H]$^+$. $^1$H NMR (500 MHz, DMSO-d$_6$) δ 13.42 (s, 1H), 8.58 (s, 1H), 8.40 (t, J = 1.5 Hz, 1H), 8.27 (d, J = 8.0 Hz, 1H), 7.99 (br, 3H), 7.54 (t, J = 8.0 Hz, 1H), 7.46 (dd, 8.0, 1.5 Hz, 1H), 4.20-4.17 (m, 2H), 3.49-3.46 (m, 2H), 1.79-1.77 (m, 4H), 1.40 (s, 3H). |
| 11 | (1-(3-(3,5-dichloro-phenyl)-1H-pyrazolo[3,4-b]-pyrazin-6-yl)-4-methylpiperidin-4-yl)methanamine | 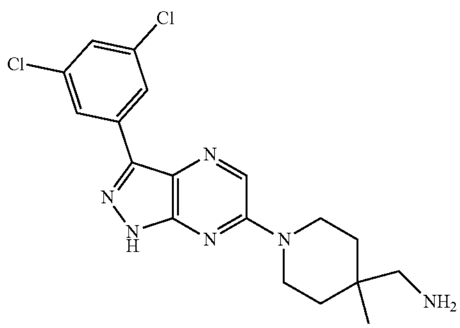 [SMILES: CC1(CN)CCN(c2cnc3c(-c4cc(Cl)cc(Cl)c4)n[nH]c3n2)CC1] | MS (ES+) $C_{18}H_{20}Cl_2N_6$ requires: 390, found: 391 [M + H]$^+$. $^1$H NMR (500 MHz, DMSO-d$_6$) δ 13.48 (s, 1H), 8.59 (s, 1H), 8.32 (d, J = 1.5 Hz, 2H), 7.75 (br, 3H), 7.63 (t, J = 2.0 Hz, 1H), 4.04-4.01 (m, 2H), 3.54-3.51 (m, 2H), 2.81-2.80 (m, 2H), 1.57-1.45 (m, 4H), 1.10 (s, 3H). |
| 12 | 1-(3-(3,5-dichloro-phenyl)-1H-pyrazolo[3,4-b]-pyrazin-6-yl)-4-methylpiperidin-4-amine | 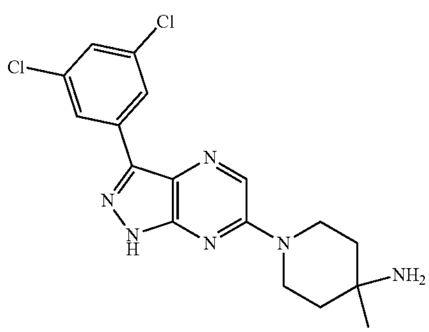 [SMILES: CC1(N)CCN(c2cnc3c(-c4cc(Cl)cc(Cl)c4)n[nH]c3n2)CC1] | MS (ES+) $C_{17}H_{18}Cl_2N_6$ requires: 376, found: 377 [M + H]$^+$. $^1$H NMR (500 MHz, DMSO-d$_6$) δ 13.56 (s, 1H), 8.61 (s, 1H), 8.32 (d, J = 2.0 Hz, 2H), 7.99 (br, 3H), 7.64 (t, J = 2.0 Hz, 1H), 4.20-4.17 (m, 2H), 3.50-3.47 (m, 2H), 1.80-1.78 (m, 4H), 1.40 (s, 3H). |
| 13 | (1-(3-(3,4-dichloro-phenyl)-1H-pyrazolo[3,4-b]-pyrazin-6-yl)-4-methylpiperidin-4-yl)methanamine | 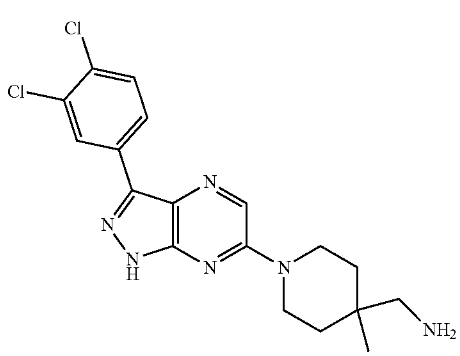 [SMILES: CC1(CN)CCN(c2cnc3c(-c4ccc(Cl)c(Cl)c4)n[nH]c3n2)CC1] | MS (ES+) $C_{19}H_{21}F_3N_6$ requires: 390, found: 391 [M + H]$^+$. $^1$H NMR (500 MHz, DMSO-d$_6$) δ 13.40 (s, 1H), 8.71 (s, 1H), 8.59-8.57 (m, 2H), 7.77-7.74 (m, 5H), 4.04-4.01 (m, 2H), 3.55-3.50 (m, 2H), 2.81 (s, 2H), 1.58-1.45 (m, 4H), 1.10 (s, 3H). |

TABLE 1-continued

Examples 2-14.

| Ex. | Name | Structure | Spectral Data |
|---|---|---|---|
| 14 | (1-(3-(3-Chloro-4-fluorophenyl)-1H-pyrazolo[3,4-b]pyrazin-6-yl)-4-methylpiperidin-4-yl)methanamine | 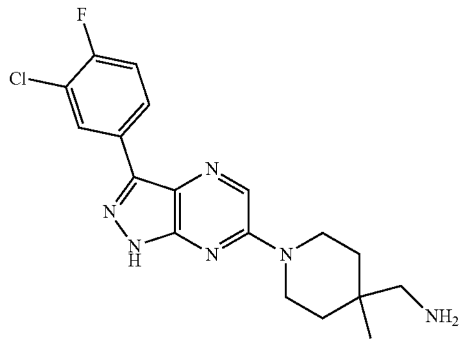 [SMILES: CC1(CN)CCN(c2cnc3c(-c4ccc(F)c(Cl)c4)n[nH]c3n2)CC1] | MS (ES+) $C_{18}H_{20}ClFN_6$ requires: 374, found: 375 [M + H]$^+$. $^1$H NMR (500 MHz, DMSO-d$_6$) δ 13.34 (s, 1H),), 8.55 (s, 1H), 8.50 (dd, J = 7.5, 2.0 Hz, 1H), 8.31-8.28 (m, 1H), 7.77 (br, 3H), 7.56 (t, J = 9.0 Hz, 1H), 4.04-4.00 (m, 2H), 3.54-3.49 (m, 2H), 2.81 (s, 2H), 1.57-1.45 (m, 4H), 1.10 (s, 3H). |

EXAMPLE 15

1-(3-(4-Chlorophenyl)-1H-pyrazolo[3,4-b]pyrazin-6-yl)-4-methylpiperidin-4-amine

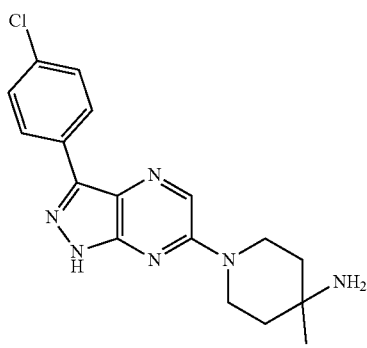 [SMILES: CC1(N)CCN(c2cnc3c(-c4ccc(Cl)cc4)n[nH]c3n2)CC1]

(4-Chlorophenyl)(3,5-dichloropyrazin-2-yl)methanol To a −78° C. solution of LDA (2.0 M in hexane, 22.0 mmol) in dry THF (40 mL), under argon was slowly added 2,6-dichloropyrazine (1.648 g, 11.0 mmol) in THF (10 mL). After addition was complete, the resulting mixture was stirred at −78° C. for an additional 1 h, then 4-chlorobenzaldehyde (2.30 g, 16.5 mmol) in THF (10 mL) was added dropwise. The reaction mixture was stirred for another hour, then quenched with hydrochloric acid (1.8 mL)/EtOH (7.5 mL)/THF (9.0 mL) mixture, and warmed to rt. The reaction mixture was diluted with saturated aqueous NaHCO$_3$ solution and extracted with EtOAc. The organic layer was separated and washed with brine, dried over Na$_2$SO$_4$, filtered, and concentrated under reduced pressure. The residue was purified by silica gel column chromatography (petroleum ether:EtOAc=4:1) to give the title compound as a yellow solid (650 mg, 20%).

MS (ES+) $C_{11}H_7Cl_3N_2O$ requires: 288, found: 289 [M+H]$^+$.

(4-Chlorophenyl)(3,5-dichloropyrazin-2-yl)methanone To a solution of (4-chlorophenyl)(3,5-dichloropyrazin-2-yl)methanol (650 mg, 2.3 mmol) in CH$_2$Cl$_2$ (200 mL) was added solid MnO$_2$ (3.99 g, 46 mmol) in portions. The resulting mixture was stirred at rt overnight. The reaction mixture was filtered, and the filtrate was concentrated to give the title compound as a yellow solid (620 mg, 95%).

MS (ES+) $C_{11}H_5Cl_3N_2O$ requires: 286, found: 287 [M+H]$^+$. $^1$H NMR (500 MHz, DMSO-d$_6$) δ 8.83 (s, 1H), 7.44-7.38 (m, 4H), 6.41 (d, J=5.7 Hz, 1H), 6.12 (d, J=5.6 Hz, 1H).

tert-Butyl 1-(6-chloro-5-(4-chlorobenzoyl)pyrazin-2-yl)-4-methylpiperidin-4-yl carbamate To a solution of (4-chlorophenyl)(3,5-dichloropyrazin-2-yl)methanone in 2 mL DMF, under N$_2$, was added tert-butyl 4-methylpiperidin-4-yl carbamate (53.5 mg, 0.25 mmol) and K$_2$CO$_3$ (69 mg, 0.5 mmol). The resulting mixture was stirred overnight at RT and then poured into H$_2$O (20 mL). The solid was collected and dried to give the crude title compound as a yellow solid (120 mg) which was used directly without further purification.

MS (ES+) $C_{22}H_{26}Cl_2N_4O_3$ requires: 464, found: 465 [M+H]$^+$.

tert-Butyl 1-(3-(4-chlorophenyl)-1H-pyrazolo[3,4-b]pyrazin-6-yl)-4-methylpiperidin-4-yl carbamate To a solution of the crude product from the previous step (120 mg, 0.23 mmol) in EtOH (10 mL) was added hydrazine hydrate (23 mg, 0.46 mmol). The resulting mixture was refluxed under N$_2$ for 2 h. The solvent was removed to give the crude title compound as a yellow solid (100 mg), which was used directly without further purification.

MS (ES+) $C_{22}H_{27}ClN_6O_2$ requires: 442, found: 443 [M+H]$^+$.

1-(3-(4-Chlorophenyl)-1H-pyrazolo[3,4-b]pyrazin-6-yl)-4-methylpiperidin-4-amine trifluoroacetate (M) To a solution of the crude product from the previous step (100 mg) in CH$_2$Cl$_2$ (2 mL) was added TFA (2 mL). The mixture was stirred at RT for 4 h, then concentrated under reduced pressure. The residue was purified by Prep-HPLC under acidic condition to give the title compound as a yellow solid (43.4 mg, 50% over 3 steps).

MS (ES+) $C_{17}H_{19}ClN_6$ requires: 342, found: 343 [M+H]$^+$. $^1$H NMR (400 MHz, DMSO-d6) δ 13.36 (s, 1H), 8.54 (s, 1H), 8.36 (d, J=8.6 Hz, 2H), 7.93 (br, 3H), 7.57 (d, J=8.6 Hz, 2H), 4.17 (d, J=14.1 Hz, 2H), 3.49 (dd, J=13.9, 6.5 Hz, 2H), 1.78 (m, 4H), 1.40 (s, 3H).

The following Examples were synthesized with synthetic methods that were similar to that used for Example 15, and can generally be made by methods disclosed herein. The Examples may be made as free bases or as TFA salts.

TABLE 2

Examples 16-20.

| Ex. | Name | Structure | Spectral Data |
|---|---|---|---|
| 16 | (1-(3-(4-chloro-phenyl)-1H-pyrazolo[3,4-b]-pyrazin-6-yl)-4-methylpiperidin-4-yl)methanamine | 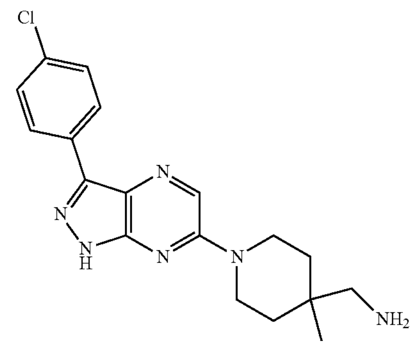 [SMILES: CC1(CN)CCN(c2cnc3c(-c4ccc(Cl)cc4)n[nH]c3n2)CC1] | MS (ES+) $C_{18}H_{21}ClN_6$ requires: 356, found: 357 [M + H]$^+$. $^1$H NMR (500 MHz, DMSO-d=) δ 13.28 (s, 1H), 8.52 (s, 1H), 8.35 (d, J = 8.5 Hz, 2H), 7.75 (br, 3H), 7.57 (d, J = 8.5 Hz, 2H), 4.03-4.00 (m, 2H), 3.53-3.50 (m, 2H), 2.80 (s, 1H), 1.57-1.47 (m, 4H), 1.10 (s, 3H). |
| 17 | (R)-8-(3-(4-chlorophenyl)-1H-pyrazolo[3,4-b]-pyrazin-6-yl)-8-aza-spiro[4.5]decan-1-amine | 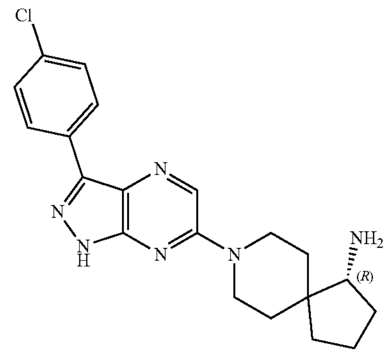 | MS (ES+) $C_{20}H_{23}ClN_6$ requires: 382, found: 383 [M + H]$^+$. $^1$H NMR (500 MHz, DMSO-d$_6$) δ 13.29 (s, 1H), 8.54 (s, 1H), 8.35 (d, J = 8.5 Hz, 2H), 7.76 (br, 3H), 7.57 (d, J = 8.5 Hz, 2H), 4.40-4.31 (m, 2H), 3.23-3.15 (m, 3H), 2.06-1.40 (m, 10H). |
| 18 | 1-(3-(3,4-dichloro-phenyl)-1H-pyrazolo[3,4-b]-pyrazin-6-yl)-4-methylpiperidin-4-amine | 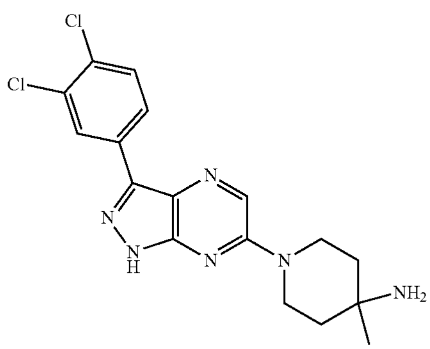 | MS (ES+) $C_{17}H_{18}Cl_2N_6$ requires: 376, found: 377 [M + H]$^+$. $^1$H NMR (500 MHz, DMSO-d$_6$) δ 13.49 (s, 1H), 8.59 (s, 1H), 8.56 (d, J = 2.0 Hz, 1H), 8.28 (dd, J = 8.0, 2.0 Hz, 1H), 7.97 (br, 3H), 7.78 (d, J = 8.5 Hz, 1H), 4.20-4.17 (m, 2H), 3.49-3.46 (m, 2H), 1.79-1.77 (m, 4H), 1.40 (s, 3H). |
| 19 | 1-(3-(3-Chloro-4-fluorophenyl)-1H-pyrazolo[3,4-b]-pyrazin-6-yl)-4-methylpiperidin-4-amine | 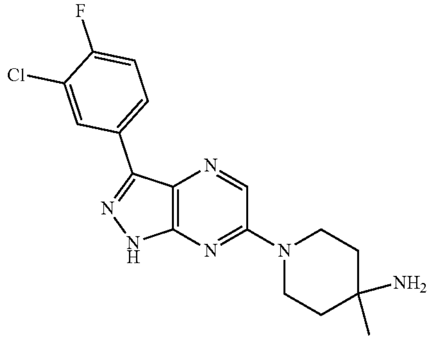 [SMILES: CC1(N)CCN(c2cnc3c(-c4ccc(F)c(Cl)c4)n[nH]c3n2)CC1] | MS (ES+) $C_{17}H_{18}ClFN_6$ requires: 360, found: 361 [M + H]$^+$. $^1$H NMR (500 MHz, DMSO-d$_6$) δ 13.42 (s, 1H), 8.58 (s, 1H), 8.51 (dd, J = 8.0, 2.0 Hz, 1H), 8.32-8.29 (m, 1H), 7.97 (br, 3H), 7.57 (t, J = 9.0 Hz, 1H), 4.20-4.17 (m, 2H), 3.50-3.45 (m, 2H), 1.79-1.77 (m, 4H), 1.40 (s, 3H). |

TABLE 2-continued

Examples 16-20.

| Ex. | Name | Structure | Spectral Data |
|---|---|---|---|
| 20 | 1-(3-(2-Chlorophenyl)-1H-pyrazolo[3,4-b]pyrazin-6-yl)-4-methylpiperidin-4-amine | 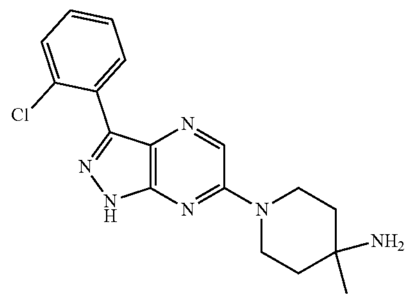 | MS (ES+) $C_{17}H_{19}ClN_6$ requires: 342, found: 343 [M + H]+. 1H NMR (500 MHz, DMSO-$d_6$) δ 13.40 (s, 1H), 8.48 (s, 1H), 7.96 (br, 3H), 7.76-7.74 (m, 1H), 7.62-7.60 (m, 1H), 7.48-7.47 (m, 2H), 4.20-4.17 (m, 2H), 3.48-3.43 (m, 2H), 1.78-1.76 (m, 4H), 1.40 (s, 3H). |

EXAMPLE 21

4-Methyl-1-(3-(3-(trifluoromethyl)phenyl)-1H-pyrazolo [3,4-b] pyrazin-6-yl)piperidin-4-amine

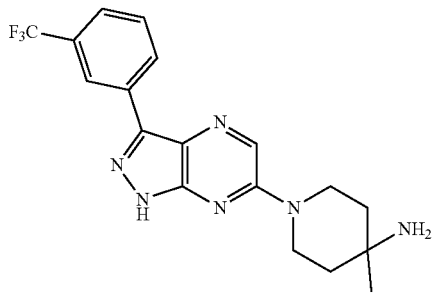 [SMILES: CC1(N)CCN(c2cnc3c(-c4cccc(C(F)(F)F)c4)n[nH]c3n2)CC1]

(3,5-Dichloropyrazin-2-yl)(3-(trifluoromethyl)phenyl) methanol To a −78° C. solution of LDA (2.0 M in hexane, 22.0 mmol) in dry THF (40 mL), under argon was added slowly a solution of 2,6-dichloropyrazine (1.648 g, 11.0 mmol) in THF (10 mL). After addition was complete, the resulting mixture was stirred at −78° C. for an additional 1 h, then 3-(trifluoromethyl)benzaldehyde (2.89 g, 16.5 mmol) in THF (10 mL) was added dropwise. The reaction mixture was stirred for another hour, then quenched with hydrochloric acid (1.8 mL)/EtOH (7.5 mL)/THF (9.0 mL) mixture, and warmed to rt. The reaction mixture was diluted with saturated aqueous sodium bicarbonate solution and extracted with EtOAc. The organic layer was separated and washed with brine, dried over $Na_2SO_4$, filtered, and concentrated under reduced pressure. The residue was purified by silica gel column chromatography (Petroleum ether: EtOAc=4:1) to give the title compound as a yellow solid (720 mg, 20%).

MS (ES+) $C_{12}H_7Cl_2F_3N_2O$ requires: 322, found: 323 [M+H]+. 1H NMR (500 MHz, DMSO-$d_6$) δ 8.82 (d, J=4.6 Hz, 1H), 7.82 (s, 1H), 7.69-7.63 (m, 2H), 7.58 (t, J=7.7 Hz, 1H), 6.58 (d, J=5.7 Hz, 1H), 6.24 (d, J=5.7 Hz, 1H).

(3,5-Dichloropyrazin-2-yl)(3-(trifluoromethyl)phenyl) methanone To a solution of the product from the previous step (720 mg, 2.23 mmol) in $CH_2Cl_2$ (200 mL) was added solid $MnO_2$ (3.88 g, 44.6 mmol) in portions. The resulting mixture was stirred at RT overnight. The reaction mixture was filtered, and the filtrate was concentrated to give the title compound as a yellow solid (650 mg, 90%).

MS (ES+) $C_{12}H_5Cl_2F_3N_2O$ requires: 320, found: 321 [M+H]+.

tert-Butyl 1-(6-chloro-5-(3-(trifluoromethyl)benzoyl) pyrazin-2-yl)-4-methyl-piperidin-4-yl carbamate To a solution of the product from the previous step (80 mg, 0.25 mmol) in 2 mL DMF, under $N_2$, was added tert-butyl 4-methylpiperidin-4-yl carbamate (53.6 mg, 0.25 mmol) and $K_2CO_3$ (69 mg, 0.5 mmol). The resulting mixture was stirred overnight at rt and then poured into $H_2O$ (20 mL). The solid was collected and dried to give the title compound as a yellow solid (120 mg), which was used directly without further purification.

MS (ES+) $C_{23}H_{26}ClF_3N_4O_3$ requires: 498, found: 499 [M+H]+.

tert-Butyl 4-methyl-1-(3-(3-(trifluoromethyl)phenyl)-1H-pyrazolo[3,4-b]pyrazin-6-yl)piperidin-4-yl carbamate To a solution of the crude product from the previous step (120 mg, 0.23 mmol) in EtOH (10 mL) was added hydrazine hydrate (23 mg, 0.46 mmol). The resulting mixture was refluxed under $N_2$ for 2 h. The solvent was removed to give the crude title compound as a yellow solid (100 mg), which was used directly without further purification.

MS (ES+) $C_{23}H_{27}F_3N_6O_2$ requires: 476, found: 477 [M+H]+.

4-Methyl-1-(3-(3-(trifluoromethyl)phenyl)-1H-pyrazolo [3,4-b]pyrazine-6-yl)-piperidin-4-amine trifluoroacetate (1) To a solution of the crude product from the previous step (100 mg) in $CH_2Cl_2$ (2 mL) was added TFA (2 mL). The mixture was stirred at RT for 4 h, then concentrated under reduced pressure. The residue was purified by Prep-HPLC under acidic condition to give the title compound as a light yellow solid (34.6 mg, 36.8% over 3 steps).

MS (ES+) $C_{18}H_{19}F_3N_6$ requires: 376, found: 377 [M+H]+. 1H NMR (500 MHz, DMSO-$d_6$) δ 13.49 (s, 1H), 8.72 (s, 1H), 8.64-8.57 (m, 2H), 8.02 (br, 3H), 7.76 (t, J=6.6 Hz, 2H), 4.19 (dd, J=9.4, 4.6 Hz, 2H), 3.53-3.44 (m, 2H), 1.79 (d, J=4.6 Hz, 4H), 1.41 (s, 3H).

The following Examples were synthesized with synthetic methods that were similar to that used for Example 21, and can generally be made by methods disclosed herein. The Examples may be made as free bases or as TFA salts.

TABLE 3

Examples 22-24.

| Ex. | Name | Structure | Spectral Data |
|---|---|---|---|
| 22 | (4-methyl-1-(3-(3-(trifluoromethyl)-phenyl)-1H-pyrazolo[3,4-b]pyrazin-6-yl)-piperidin-4-yl)-methanamine | 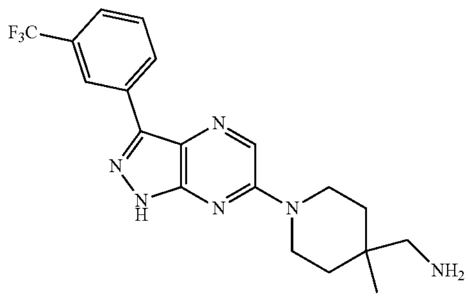 [SMILES: CC1(CN)CCN(c2cnc3c(-c4cccc(C(F)(F)F)c4)n[nH]c3n2)CC1] | MS (ES+) $C_{19}H_{21}F_3N_6$ requires: 390, found: 391 [M + H]$^+$. $^1$H NMR (500 MHz, DMSO-$d_6$) δ 13.40 (s, 1H), 8.71 (s, 1H), 8.59-8.57 (m, 2H), 7.77-7.74 (m, 5H), 4.04-4.01 (m, 2H), 3.55-3.50 (m, 2H), 2.81 (s, 2H), 1.58-1.45 (m, 4H), 1.10 (s, 3H). |
| 23 | 1-(3-(2-chloro-pyridin-3-yl)-1H-pyrazolo[3,4-b]-pyrazin-6-yl)-4-methyl-piperidin-4-amine | 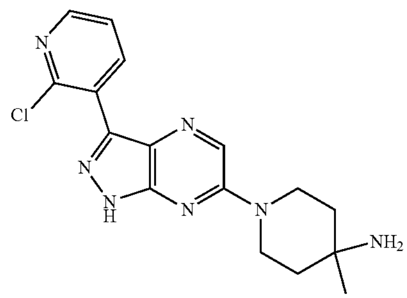 [SMILES: CC1(N)CCN(c2cnc3c(-c4cccnc4Cl)n[nH]c3n2)CC1] | MS (ES+) $C_{16}H_{18}ClN_7$ requires: 343, found: 344 [M + H]$^+$. $^1$H NMR (500 MHz, DMSO-$d_6$) δ 13.54 (s, 1H), 8.52-8.51 (m, 2H), 8.21 (dd, J = 7.5, 2.0 Hz, 1H), 7.96 (br, 3H), 7.58 (dd, J = 8.0, 5.0 Hz, 1H), 4.20-4.17 (m, 2H), 3.48-3.43 (m, 2H), 1.79-1.77 (m, 4H), 1.40 (s, 3H). |
| 24 | 1-(3-(2-chloro-3-fluorophenyl)-1H-pyrazolo[3,4-b]-pyrazin-6-yl)-4-methyl-piperidin-4-amine | 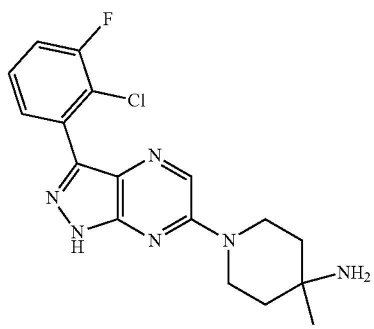 [SMILES: CC1(N)CCN(c2cnc3c(-c4cccc(F)c4Cl)n[nH]c3n2)CC1] | MS (ES+) $C_{17}H_{18}ClFN_6$ requires: 360, found: 361 [M + H]$^+$. $^1$H NMR (400 MHz, DMSO-$d_6$) δ 13.52 (s, 1H), 8.51 (s, 1H), 7.94 (br, 3H), 7.66 (t, J = 4.7 Hz, 1H), 7.52 (dd, J = 6.8, 5.3 Hz, 2H), 4.19 (d, J = 14.1 Hz, 2H), 3.50-3.45 (m, 2H), 1.77 (d, J = 4.7 Hz, 4H), 1.40 (s, 3H). |

EXAMPLE 25

(1-(3-(3-Chloro-2-fluorophenyl)-1H-pyrazolo[3,4-b]pyrazin-6-yl)-4-methylpiperidin-4-yl)methanamine

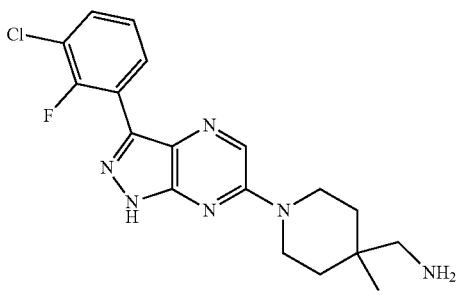 [SMILES: CC1(CN)CCN(c2cnc3c(-c4cccc(Cl)c4F)n[nH]c3n2)CC1]

(3-Chloro-2-fluorophenyl)(3,5-dichloropyrazin-2-yl)methanol To a −78° C. solution of LDA (2.0 M in hexane, 22.0 mmol) in dry THF (40 mL), under argon was added a solution of 2,6-dichloropyrazine (1.648 g, 11.0 mmol) in THF (10 mL). After addition was completed, the resulting mixture was stirred at −78° C. for an additional 1 h, then 3-chloro-2-fluorobenzaldehyde (2.61 g, 16.5 mmol) in THF (10 mL) was added dropwise. The reaction mixture was stirred for another hour, then quenched with hydrochloric acid (1.8 mL)/EtOH (7.5 mL)/THF (9.0 mL) mixture, and warmed to RT The reaction mixture was diluted with saturated aqueous sodium bicarbonate solution and extracted with EtOAc. The organic layer was separated and washed with brine, dried over $Na_2SO_4$, filtered, and concentrated under reduced pressure. The residue was purified by silica gel column chromatography (petroleum ether:EtOAc=4:1) to give the title compound as a yellow solid (700 mg, 20%).

MS (ES+) $C_{11}H_6Cl_3FN_2O$ requires: 306, found: 307 [M+H]$^+$. $^1$H NMR (500 MHz, DMSO-$d_6$) δ 8.80 (s, 1H), 7.61 (t, J=6.6 Hz, 1H), 7.59-7.45 (m, 1H), 7.29 (t, J=7.9 Hz, 1H), 6.66 (d, J=6.0 Hz, 1H), 6.35 (d, J=6.0 Hz, 1H).

(3-Chloro-2-fluorophenyl)(3,5-dichloropyrazin-2-yl)methanone To a solution of the product from the previous step (700 mg, 2.3 mmol) in $CH_2Cl_2$ (200 mL) was added solid $MnO_2$ (3.99 g, 46.0 mmol) in portions. The resulting mixture was stirred at RT overnight. The reaction mixture was filtered, and the filtrate was concentrated to give the title compound as a yellow solid (670 mg, 95%).

MS (ES+) $C_{11}H_4Cl_3FN_2O$ requires: 304, found: 305 [M+H]$^+$.

tert-Butyl (1-(6-chloro-5-(3-chloro-2-fluorobenzoyl)pyrazin-2-yl)-4-methylpiperidin-4-yl)methyl carbamate To a solution of product from the previous step (76 mg, 0.25 mmol) in 2 mL DMF, under $N_2$, was added tert-butyl (4-methylpiperidin-4-yl)-methyl carbamate (57 mg, 0.25 mmol) and $K_2CO_3$ (69 mg, 0.5 mmol). The resulting mixture was stirred overnight at RT and then poured into $H_2O$ (20 mL). The solid was collected and dried to give the crude title compound as a yellow solid (120 mg), which was used directly without further purification.

MS (ES+) $C_{23}H_{27}Cl_2FN_4O_3$ requires: 496, found: 497 [M+H]$^+$.

tert-Butyl (1-(3-(3-chloro-2-fluorophenyl)-1H-pyrazolo[3,4-b]pyrazin-6-yl)-4-methylpiperidin-4-yl)methyl carbamate To a solution of the crude product from the previous step (120 mg, 0.23 mmol) in EtOH (10 mL) was added hydrazine hydrate (23 mg, 0.46 mmol). The resulting mixture was refluxed under $N_2$ for 2 h. The solvent was removed to give the crude title compound as a yellow solid (100 mg) which was used directly without further purification.

MS (ES+) $C_{23}H_{28}ClFN_6O_2$ requires: 474, found: 475 [M+H]$^+$.

(1-(3-(3-Chloro-2-fluorophenyl)-1H-pyrazolo[3,4-b]pyrazin-6-yl)-4-methylpiperidin-4-yl)methanamine trifluoroacetate (2) To a solution of the crude product from the previous step (100 mg) in $CH_2Cl_2$ (2 mL) was added TFA (2 mL). The mixture was stirred at RT for 4 h, then concentrated under reduced pressure. The residue was purified by Prep-HPLC under acidic condition to give the title compound as a light yellow solid (50.6 mg, 54% over 3 steps).

MS (ES+) $C_{18}H_{20}ClFN_6$ requires: 374, found: 375 [M+H]$^+$. $^1$H NMR (500 MHz, DMSO-$d_6$) δ13.47 (s, 1H), 8.51 (s, 1H), 8.14-8.09 (s, 1H), 7.77 (br, 3H), 7.68-7.63 (m, 1H), 7.38 (t, J=7.9 Hz, 1H), 4.03 (dd, J=9.0, 5.1 Hz, 2H), 3.55-3.49 (m, 2H), 2.80 (d, J=4.6 Hz, 2H), 1.61-1.54 (m, 2H), 1.49-1.43 (m, 2H), 1.10 (s, 3H).

The following Examples were synthesized with synthetic methods that were similar to that used for Example 25, and can generally be made by methods disclosed herein. The Examples may be made as free bases or as TFA salts.

TABLE 4

Examples 26-32.

| Ex. | Name | Structure | Spectral Data |
|---|---|---|---|
| 26 | 1-(3-(3-chloro-2-fluorophenyl)-1H-pyrazolo[3,4-b]-pyrazin-6-yl)-4-methylpiperidin-4-amine | 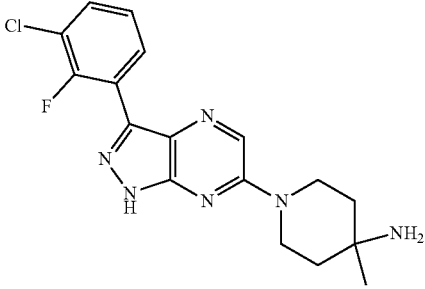 [SMILES: CC1(N)CCN(c2cnc3c(-c4cccc(Cl)c4F)n[nH]c3n2)CC1] | MS (ES+) $C_{17}H_{18}ClFN_6$ requires: 360, found: 361 [M + H]$^+$. $^1$H NMR (400 MHz, DMSO-$d_6$) δ 13.55 (s, 1H), 8.53 (s, 1H), 8.13-8.09 (m, 1H), 7.98 (br, 3H), 7.68-7.64 (m, 1H), 7.38 (t, J = 8.0 Hz, 1H), 4.20-4.17 (m, 2H), 3.51-3.48 (m, 2H), 1.78-1.73 (m, 4H), 1.41 (s, 3H). |
| 27 | (1-(3-(2-chloro-3-methoxyphenyl)-1H-pyrazolo[3,4-b]pyrazin-6-yl)-4-methylpiperidin-4-yl)methanamine | 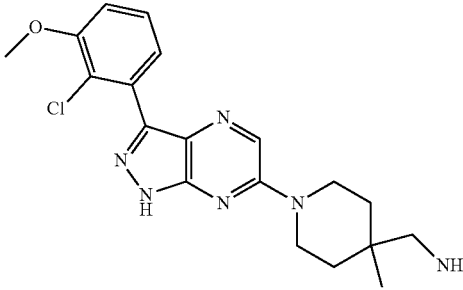 | MS (ES+) $C_{19}H_{23}ClN_6O$ requires: 386, found: 387 [M + H]$^+$. $^1$H NMR (500 MHz, DMSO-$d_6$) δ 13.27 (s, 1H), 8.43 (s, 1H), 7.72 (br, 3H), 7.41 (t, J = 8.0 Hz, 1H), 7.28-7.21 (m, 2H), 4.02 (d, J = 14.2 Hz, 2H), 3.92 (s, 3H), 3.50 (s, 2H), 2.80 (d, J = 5.9 Hz, 2H), 1.56 (t, J = 9.6 Hz, 2H), 1.45 (d, J = 13.9 Hz, 2H), 1.09 (s, 3H). |
| 28 | (1-(3-(3-chloro-2-methylphenyl)-1H-pyrazolo[3,4-b]-pyrazin-6-yl)-4-methylpiperidin-4-yl)methanamine | 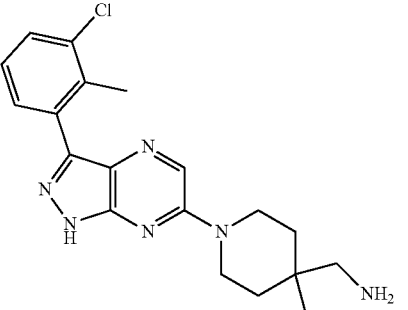 | MS (ES+) $C_{19}H_{23}ClN_6$ requires: 370, found: 371 [M + H]$^+$. $^1$H NMR (500 MHz, DMSO-$d_6$) δ 13.31 (s, 1H), 8.46 (s, 1H), 7.77-7.66 (m, 4H), 7.52 (d, J = 8.0 Hz, 1H), 7.34 (t, J = 7.8 Hz, 1H), 4.02 (d, J = 14.0 Hz, 2H), 3.50 (t, J = 10.1 Hz, 2H), 2.80 (d, J = 5.4 Hz, 2H), 2.47 (s, 3H), 1.57 (t, J = 9.6 Hz, 2H), 1.46 (d, J = 13.6 Hz, 2H), 1.10 (s, 3H). |

TABLE 4-continued

Examples 26-32.

| Ex. | Name | Structure | Spectral Data |
|---|---|---|---|
| 29 | (1-(3-(2-chloro-phenyl)-1H-pyrazolo[3,4-b]-pyrazin-6-yl)-4-methylpiperidin-4-yl)methanamine | 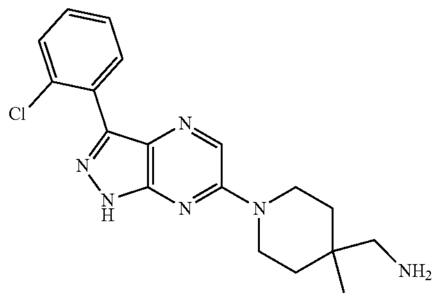 [SMILES: CC1(CN)CCN(c2cnc3c(-c4ccccc4Cl)n[nH]c3n2)CC1] | MS (ES+) $C_{18}H_{21}ClN_6$ requires: 356, found: 357 [M + H]$^+$. $^1$H NMR (500 MHz, DMSO-d$_6$) δ 13.32 (s, 1H), 8.45 (s, 1H), 7.76-7.73 (m, 4H), 7.61-7.59 (m, 1H), 7.48-7.46 (m, 2H), 4.04-4.00 (m, 2H), 3.52-3.48 (m, 2H), 2.81-2.80 (m, 2H), 1.59-1.44 (m, 4H), 1.10 (s, 3H). |
| 30 | (4-methyl-1-(3-(2-methylpyridin-3-yl)-1H-pyrazolo[3,4-b]pyrazin-6-yl)-piperidin-4-yl)methanamine | 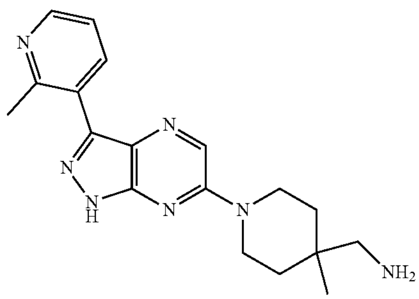 [SMILES: Cc1ncccc1-c1n[nH]c2nc(N3CCC(C)(CN)CC3)cnc12] | MS (ES+) $C_{18}H_{23}N_7$ requires: 337, found: 338 [M + H]$^+$. $^1$H NMR (500 MHz, DMSO-d$_6$) δ 13.55 (s, 1H), 8.72-8.65 (m, 2H), 8.53 (s, 1H), 7.78 (br, 3H), 7.68 (t, J = 5.0 Hz, 1H), 4.06-4.01 (m, 2H), 3.56-3.51 (m, 2H), 2.85-2.81 (m, 5H), 1.60-1.46 (m, 4H), 1.10 (s, 3H). |
| 31 | (1-(3-(3-chloro-pyridin-4-yl)-1H-pyrazolo[3,4-b]-pyrazin-6-yl)-4-methylpiperidin-4-yl)methanamine | 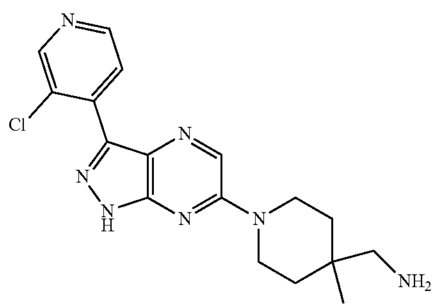 [SMILES: CC1(CN)CCN(c2cnc3c(-c4ccncc4Cl)n[nH]c3n2)CC1] | MS (ES+) $C_{17}H_{20}ClN_7$ requires: 357, found: 358 [M + H]$^+$. $^1$H NMR (500 MHz, DMSO-d$_6$) δ 13.66 (s, 1H), 8.78 (s, 1H), 8.64 (d, J = 5.0 Hz, 1H), 8.53 (s, 1H), 8.03 (d, J = 5.0 Hz, 1H), 7.75 (br, 3H), 4.06-4.01 (m, 2H), 3.55-3.50 (m, 2H), 2.81-2.79 (m, 2H), 1.57-1.45 (m, 4H), 1.10 (s, 3H). |
| 32 | 1-(3-(2-chloro-6-fluorophenyl)-1H-pyrazolo[3,4-b]-pyrazin-6-yl)-4-methylpiperidin-4-amine | 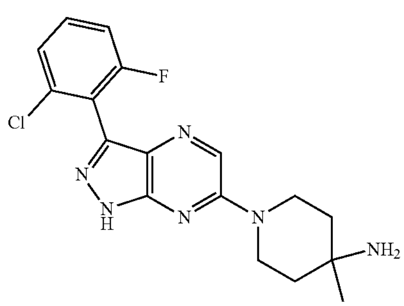 [SMILES: CC1(N)CCN(c2cnc3c(-c4c(F)cccc4Cl)n[nH]c3n2)CC1] | MS (ES+) $C_{17}H_{18}ClFN$ requires: 360, found: 361 [M + H]$^+$. $^1$H NMR (500 MHz, DMSO-d$_6$) δ 13.53 (s, 1H), 8.45 (s, 1H), 7.95 (br, 3H), 7.59-7.39 (m, 3H), 4.20-4.17 (m, 2H), 3.48-3.43 (m, 2H), 1.78-1.76 (m, 4H), 1.40 (s, 3H). |

EXAMPLE 33

(1-(3-(4-Chloro-3-methoyphenyl)-1H-pyrazolo[3,4-b]pyrazin-6-yl)-4-methylpiperidin-4-yl)methanamine

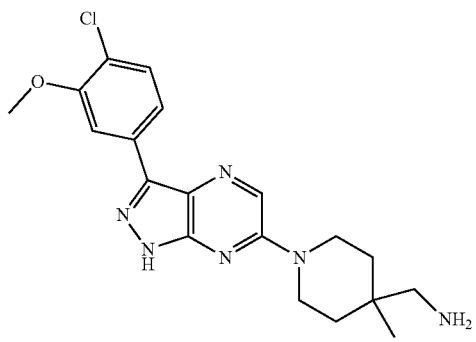 [SMILES: COc1cc(-c2n[nH]c3nc(N4CCC(C)(CN)CC4)cnc23)ccc1Cl]

(4-Chloro-3-methoxyphenyl)(3,5-dichloropyrazin-2-yl)methanol To a −78° C. solution of LDA (2.0 M in hexane, 22.0 mmol) in dry THF (40 mL), under argon was added a solution of 2,6-dichloropyrazine (1.648 g, 11.0 mmol) in THF (10 mL). After addition was completed, the resulting mixture was stirred at −78° C. for an additional 1 h, then 4-chloro-3-methoxybenzaldehyde (2.81 g, 16.5 mmol) in THF (10 mL) was added dropwise. The reaction mixture was stirred for another hour, then quenched with hydrochloric acid (1.8 mL)/EtOH (7.5 mL)/THF (9.0 mL) mixture, and warmed to RT. The reaction mixture was diluted with saturated aqueous sodium bicarbonate solution and extracted with EtOAc. The organic layer was separated and washed with brine, dried over $Na_2SO_4$, filtered, and concentrated under reduced pressure. The residue was purified by silica gel column chromatography (petroleum ether: EtOAc=4:1) to give the title compound (600 mg, 17%).

MS (ES+) $C_{12}H_9Cl_3N_2O_2$ requires: 318, found: 319 $[M+H]^+$.

(4-Chloro-3-methoxyphenyl)(3,5-dichloropyrazin-2-yl)methanone To a solution of the product from the previous step (600 mg, 1.875 mmol) in $CH_2Cl_2$ (200 mL) was added solid $MnO_2$ (3.26 g, 37.5 mmol) in portions. The resulting mixture was stirred at RT overnight. The reaction mixture was filtered, and the filtrate was concentrated to give the title compound as a yellow solid (495 mg, 83%).

MS (ES+) $C_{12}H_7Cl_3N_2O_2$ requires: 316, found: 317 $[M+H]^+$.

tert-Butyl (1-(6-chloro-5-(4-chloro-3-methoxybenzoyl)pyrazin-2-yl)-4-methylpiperidin-4-yl)methyl carbamate To a solution of the product from the previous step (80 mg, 0.25 mmol) in 2 mL DMF, under $N_2$, was added tert-butyl (4-methylpiperidin-4-yl)methyl carbamate (57 mg, 0.25 mmol) and $K_2CO_3$ (69 mg, 0.5 mmol). The resulting mixture was stirred overnight at RT and then poured into $H_2O$ (20 mL). The solid was collected and dried to give the crude title compound as a yellow solid (120 mg) which was used directly without further purification.

MS (ES+) $C_{24}H_{30}Cl_2N_4O_4$ requires: 508, found: 509 $[M+H]^+$.

tert-Butyl (1-(3-(4-chloro-3-methoxyphenyl)-1H-pyrazolo[3,4-b]pyrazin-6-yl)-4-methylpiperidin-4-yl)methyl carbamate To a solution of the crude product from the previous step (120 mg, 0.23 mmol) in EtOH (10 mL) was added hydrazine hydrate (23 mg, 0.46 mmol). The resulting mixture was refluxed under $N_2$ for 2 h. The solvent was removed to give the crude title compound as a yellow solid (100 mg), which was used directly without further purification.

MS (ES+) $C_{24}H_{31}ClN_6O_3$ requires: 486, found: 487 $[M+H]^+$.

(1-(3-(4-Chloro-3-methoxyphenyl)-1H-pyrazolo[3,4-b]pyrazin-6-yl)-4-methylpiperidin-4-yl)methanamine trifluoroacetate (33) To a solution of the crude product from the previous step (100 mg) in $CH_2Cl_2$ (2 mL) was added TFA (2 mL). The mixture was stirred at RT for 4 h, then concentrated under reduced pressure. The residue was purified by Prep-HPLC under acidic condition to give the title compound as a yellow solid (15.3 mg, 15% over 3 steps).

MS (ES+) $C_{19}H_{23}ClN_6O$ requires: 386, found: 387 $[M+H]^+$. $^1$H NMR (500 MHz, DMSO-$d_6$) δ 13.28 (s, 1H), 8.54 (s, 1H), 8.05 (d, J=1.7 Hz, 1H), 7.99 (dd, J=8.2, 1.7 Hz, 1H), 7.71 (br, 3H), 7.55 (d, J=8.2 Hz, 1H), 4.03 (d, J=14.0 Hz, 2H), 3.95 (s, 3H), 3.51 (d, J=10.0 Hz, 2H), 2.80 (d, J=5.7 Hz, 2H), 1.57 (t, J=9.6 Hz, 2H), 1.46 (d, J=14.4 Hz, 2H), 1.10 (s, 3H).

The following Examples were synthesized with synthetic methods that were similar to that used for Example 33, and can generally be made by methods disclosed herein. The Examples may be made as free bases or as TFA salts.

TABLE 5

Examples 34-36.

| Ex. | Name | Structure | Spectral Data |
|---|---|---|---|
| 34 | (R)-8-(3-(4-chloro-3-methoxyphenyl)-1H-pyrazolo[3,4-b]-pyrazin-6-yl)-8-azaspiro[4.5]decan-1-amine | 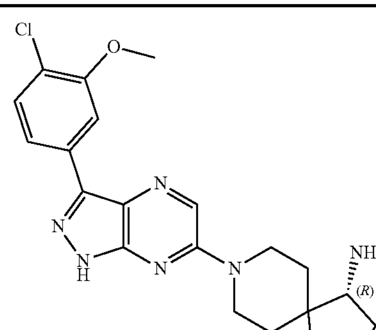 | MS (ES+) $C_{21}H_{25}ClN_6O$ requires: 412, found: 413 $[M + H]^+$. $^1$H NMR (500 MHz, DMSO-$d_6$) δ 13.31 (s, 1H), 8.56 (s, 1H), 8.05 (d, J = 1.5 Hz, 1H), 7.99 (dd, J = 8.0, 1.5 Hz, 1H), 7.80 (br, 3H), 7.55 (d, J = 8.0 Hz, 1H), 4.40-4.28 (m, 2H), 4.00 (s, 3H), 3.23-3.14 (m, 3H), 2.10-1.43 (m, 10H). |

TABLE 5-continued

Examples 34-36.

| Ex. | Name | Structure | Spectral Data |
|---|---|---|---|
| 35 | (1-(3-(3-chloro-5-methoxyphenyl)-1H-pyrazolo[3,4-b]-pyrazin-6-yl)-4-methylpiperidin-4-yl)methanamine | 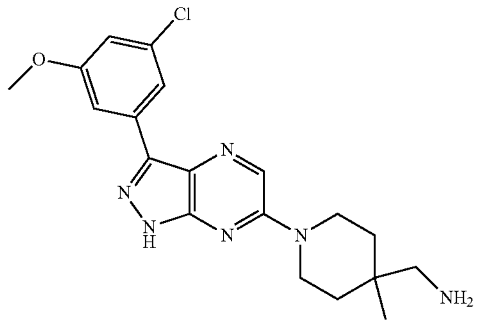 [SMILES: COc1cc(Cl)cc(-c2n[nH]c3nc(N4CCC(C)(CN)CC4)cnc23)c1] | MS (ES+) $C_{19}H_{23}ClN_6O$ requires: 386, found: 387 [M + H]⁺. ¹H NMR (500 MHz, DMSO-d₆) δ 13.33 (s, 1H), 8.56 (s, 1H), 7.99 (t, J = 1.5 Hz, 1H), 7.84 (q, J = 1.5 Hz, 1H), 7.72 (br, 3H), 7.05 (t, J = 2.0 Hz, 1H), 4.07-4.00 (m, 2H), 3.85 (s, 3H), 3.54-3.49 (m, 2H), 2.81-2.79 (m, 2H), 1.60-1.45 (m, 4H), 1.10 (s, 3H). |
| 36 | (1-(3-(2-chloro-pyridin-3-yl)-1H-pyrazolo[3,4-b]-pyrazin-6-yl)-4-methylpiperidin-4-yl)methanamine | 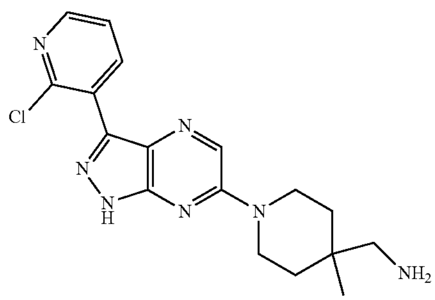 [SMILES: CC1(CN)CCN(c2cnc3c(-c4cccnc4Cl)n[nH]c3n2)CC1] | MS (ES+) $C_{17}H_{20}ClN_7$ requires: 357, found: 358 [M + H]⁺. ¹H NMR (500 MHz, DMSO-d₆) δ 13.47 (s, 1H), 8.51-8.48 (m, 2H), 8.22 (dd, J = 8.0, 2.0 Hz, 1H), 7.77 (br, 3H), 7.58 (dd, J = 8.0, 5.0 Hz, 1H), 4.05-4.00 (m, 2H), 3.54.3.49 (m, 2H), 2.81 (s, 2H), 1.59-1.46 (m, 4H), 1.10 (s, 3H). |

EXAMPLE 37

4-(Aminomethyl)-1-(3-(2cloro-3-fluorophenyl)-1H-pyrazolol[3,4-b]pyrazin-6-yl)-piperidin 4-ol

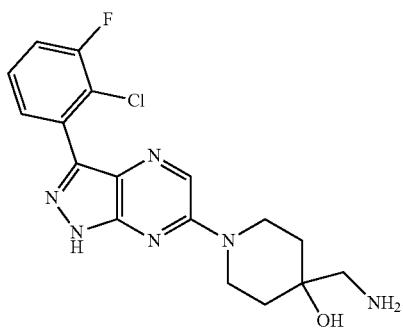 [SMILES: NCC1(O)CCN(c2cnc3c(-c4cccc(F)c4Cl)n[nH]c3n2)CC1]

(2-Chloro-3-fluorophenyl)(3,5-dichloropyrazin-2-yl)methanol To a −78° C. solution of LDA (2.0 M in hexane, 22.0 mmol) in dry THF (40 mL), under argon was added a solution of 2,6-dichloropyrazine (1.648 g, 11.0 mmol) in THF (10 mL). After addition was completed, the resulting mixture was stirred at −78° C. for an additional 1 h, then 2-chloro-3-fluorobenzaldehyde (2.61 g, 16.5 mmol) in THF (10 mL) was added dropwise. The reaction mixture was stirred for another hour, then quenched with hydrochloric acid (1.8 mL)/EtOH (7.5 mL)/THF (9.0 mL) mixture, and warmed to rt. The reaction mixture was diluted with saturated aqueous NaHCO₃ solution and extracted with EtOAc. The organic layer was separated and washed with brine, dried over Na₂SO₄, filtered, and concentrated under reduced pressure. The residue was purified by silica gel column chromatography (petroleum ether:EtOAc=4:1) to give the title compound as a yellow solid (700 mg, 20%).

MS (ES+) $C_{11}H_6Cl_3FN_2O$ requires: 306, found: 307 [M+H]⁺.

(2-Chloro-3-fluorophenyl)(3,5-dichloropyrazin-2-yl)methanone To a solution of the product from the previous step (700 mg, 2.3 mmol) in CH₂Cl₂ (200 mL) was added solid MnO₂ (3.99 g, 46.0 mmol) in portions. The resulting mixture was stirred at RT overnight. The reaction mixture was filtered, and the filtrate was concentrated to give the title compound as a yellow solid (650 mg, 93%).

MS (ES+) $C_{11}H_4Cl_3FN_2O$ requires: 304, found: 305 [M+H]⁺. ¹H NMR (500 MHz, DMSO-d6) δ 8.93 (s, 1H), 7.78-7.67 (m, 1H), 7.61-7.50 (m, 2H).

tert-Butyl (1-(6-chloro-5-(2-chloro-3-fluorobenzoyl)pyrazin-2-yl)-4-hydroxypiperidin-4-yl)methyl carbamate To a solution of the product from the previous step in DMF (2 mL), under N₂, was added tert-butyl (4-hydroxypiperidin-4-yl)methyl carbamate (57.5 mg, 0.25 mmol) and K₂CO₃ (69 mg, 0.5 mmol). The resulting mixture was stirred overnight at RT and then poured into H₂O (20 mL). The solid was collected and dried to give the crude title compound as a yellow solid (120 mg), which was used directly without further purification.

MS (ES+) $C_{22}H_{25}Cl_2FN_4O_4$ requires: 498, found: 499 [M+H]+.

tert-Butyl (1-(3-(2-chloro-3-fluorophenyl)-1H-pyrazolo[3,4-b]pyrazin-6-yl)-4-hydroxypiperidin-4-yl)methyl carbamate To a solution of the product from the previous step (120 mg, 0.23 mmol) in EtOH (10 mL) was added hydrazine hydrate (23 mg, 0.46 mmol). The resulting mixture was refluxed under $N_2$ for 2 h. The solvent was removed to give the crude title compound as a yellow solid (100 mg) which was used directly without further purification MS (ES+) $C_{22}H_{26}ClFN_6O_3$ requires: 476, found: 477 [M+H]+.

4-(Aminomethyl)-1-(3-(2-chloro-3-fluorophenyl)-1H-pyrazolo[3,4-b]pyrazin-6-yl)piperidin-4-ol trifluoroacetate (37) 'To a solution of the crude product from the previous step (100 mg) in $CH_2Cl_2$ (2 mL) was added TFA (2 mL). The mixture was stirred at rt for 4 h, then concentrated under reduced pressure. The residue was purified by Prep-HPLC under acidic condition to give the title compound as a yellow solid (69.8 mg, 74% over 3 steps).

MS (ES+) $C_{17}H_{18}ClFN_6O$ requires: 376, found: 377 [M+H]+. 1H NMR (400 MHz, DMSO-d6) δ 13.45 (s, 1H), 8.50 (s, 1H), 7.77 (br, 3H), 7.66-7.64 (m, 1H), 7.53-7.50 (m, 2H), 5.20 (s, 1H), 4.21-4.18 (m, 2H), 3.47-3.43 (m, 2H), 2.83-2.81 (m, 2H), 1.64-1.62 (m, 4H).

EXAMPLE 38

(S)-8-(3-(2,3-Dichlorophenyl)-1H-pyrazolo[3,4-b]pyrazin-6-yl)-2-oxa-8-azaspiro[4.5]-decan-4-amine

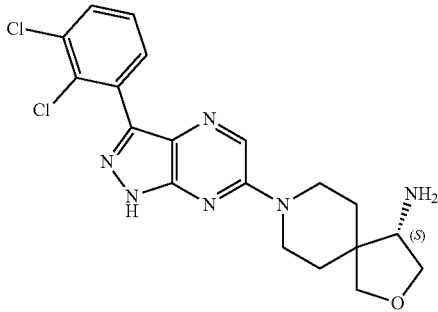

(3-Chloro-5-((S)-4-((R)-1-(4-methoxyphenyl)ethylamino)-2-oxa-8-azaspiro-[4.5]decan-8-yl)pyrazin-2-yl)(2,3-dichlorophenyl)methanone To a solution of (2,3-dichlorophenyl)(3,5-dichloropyrazin-2-yl)methanone (80 mg, 0.25 mmol) in DMF (2 mL), under $N_2$, was added Intermediate 103 (72 mg, 0.25 mmol) and $K_2CO_3$ (69 mg, 0.5 mmol). The resulting mixture was stirred overnight at RT and then poured into $H_2O$ (20 mL). The solid was that formed was collected and dried to give the crude title compound as a yellow solid (120 mg), which was used directly without further purification.

MS (ES+) $C_{28}H_{29}Cl_3N_4O_3$ requires: 574, found: 575 [M+H]+.

(S)-8-(3-(2,3-dichlorophenyl)-1H-pyrazolo[3,4-b]pyrazin-6-yl)-N—((R)-1-(4-methoxyphenyl)ethyl)-2-oxa-8-azaspiro[4.5]decan-4-amine To a solution of the crude product from the previous step (120 mg, 0.23 mmol) in EtOH (10 mL) was added hydrazine hydrate (23 mg, 0.46 mmol). The resulting mixture was refluxed under $N_2$ for 2 h. The solvent was removed to give the crude title compound as a yellow solid (100 mg) which was used directly without further purification.

MS (ES+) $C_{28}H_{30}Cl_2N_6O_2$ requires: 552, found: 553 [M+H]+.

(S)-8-(3-(2,3-dichlorophenyl)-1H-pyrazolo[3,4-b]pyrazin-6-yl)-2-oxa-8-aza-spiro[4.5]decan-4-amine 2,2,2-trifluoroacetate (3) A mixture of the crude product from the previous step (100 mg) in TFA (2 mL) was stirred under microwave at 130° C. for 15 min. The mixture was concentrated under reduced pressure. The residue was purified by Prep-HPLC under acidic condition to give the title compound as a light yellow solid (28 mg, 24% over 3 steps).

MS (ES+) $C_{19}H_{20}Cl_2N_6O$ requires: 418, found: 419 [M+H]+. 1H NMR (500 MHz, DMSO-d6) δ 13.44 (s, 1H), 8.49 (s, 1H), 8.04 (br, 3H), 7.76-7.68 (m, 2H), 7.50 (t, J=8.0 Hz, 1H), 4.31-4.21 (m, 2H), 4.11-4.07 (m, 1H), 3.88-3.80 (m, 2H), 3.71-3.25 (m, 4H), 1.76-1.62 (m, 4H).

The following Examples were synthesized with synthetic methods that were similar to that used for Example 38, and can generally be made by methods disclosed herein. The Examples may be made as free bases or as TFA salts.

TABLE 6

| | Examples 39-42. | | |
|---|---|---|---|
| Ex. | Name | Structure | Spectral Data |
| 39 | (S)-8-(3-(2-chlorophenyl)-1H-pyrazolo[3,4b]-pyrazin-6-yl)-2-oxa-8-azaspiro[4.5]-decan-4-amine | | MS (ES+) $C_{19}H_{21}ClN_6O$ requires: 384, found: 385 [M + H]+. 1H NMR (500 MHz, DMSO-d6) δ 13.35 (s, 1H), 8.48 (s, 1H), 8.04 (br, 3H), 7.76-7.74 (m, 1H), 7.62-7.60 (m, 1H), 7.48-7.46 (m, 2H), 4.31-4.21 (m, 2H), 4.11-4.07 (m, 1H), 3.88-3.80 (m, 2H), 3.71-3.25 (m, 4H), 1.73-1.62 (m, 4H). |

TABLE 6-continued

Examples 39-42.

| Ex. | Name | Structure | Spectral Data |
|---|---|---|---|
| 40 | (4S)-8-(3-(2-Chloro-6-fluorophenyl)-1H-pyrazolo[3,4-b]-pyrazin-6-yl)-2-oxa-8-azaspiro[4.5]-decan-4-amine | 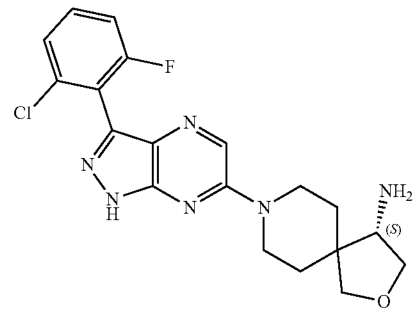 | MS (ES+) $C_{19}H_{20}ClFN_6O$ requires: 402, found: 403 [M + H]+. 1H NMR (500 MHz, DMSO-$d_6$) δ 13.48 (s, 1H), 8.45 (s, 1H), 8.01 (br, 3H), 7.59-7.49 (m, 2H), 7.39 (t, J = 8.0 Hz, 1H), 4.31-4.21 (m, 2H), 4.11-4.07 (m, 1H), 3.88-3.80 (m, 2H), 3.71-3.25 (m, 4H), 1.73-1.62 (m, 4H). |
| 41 | (S)-8-(3-(2-chloro-pyridin-3-yl)-1H-pyrazolo[3,4-b]-pyrazin-6-yl)-2-oxa-8-azaspiro[4.5]-decan-4-amine trifluoroacetate | 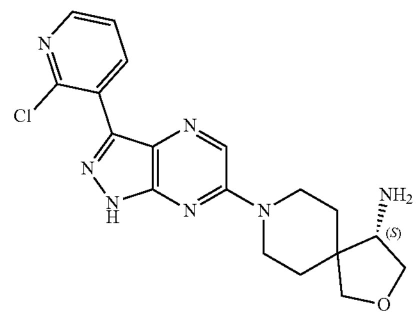 | MS (ES+) $C_{18}H_{20}ClN_7O$ requires: 385, found: 386 [M + H]+. 1H NMR (500 MHz, DMSO-$d_6$) δ 13.52 (s, 1H), 8.52-8.51 (m, 2H), 8.21 (dd, J = 9.5, 2.5 Hz, 1H), 8.02 (br, 3H), 7.59 (dd, J = 9.5, 2.5 Hz, 1H), 4.28-4.21 (m, 2H), 4.11-4.07 (m, 1H), 3.89-3.79 (m, 2H), 3.71-3.26 (m, 4H), 1.73-1.61 (m, 4H). |
| 42 | (S)-8-(3-(2-chloro-3-fluorophenyl)-1H-pyrazolo[3,4-b]-pyrazin-6-yl)-2-oxa-8-azaspiro[4.5]-decan-4-amine | 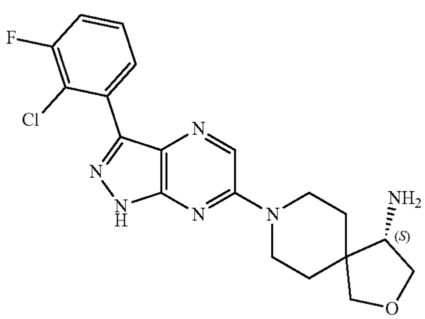 | MS (ES+) $C_{19}H_{20}ClFN_6O$ requires: 402, found: 403 [M + H]+. 1H NMR (500 MHz, DMSO-$d_6$) δ 13.48 (s, 1H), 8.51 (s, 1H), 8.04 (br, 3H), 7.66 (t, J = 5.0 Hz, 1H), 7.53-7.49 (m, 2H), 4.31-4.21 (m, 2H), 4.11-4.07 (m, 1H), 3.88-3.80 (m, 2H), 3.71-3.25 (m, 4H), 1.73-1.62 (m, 4H). |

EXAMPLE 43

(R)-8-(3-(2,3-Dichlorophenyl)-1H-pyrazolo[3,4-b] pyrazin-6-yl)-8-azaspiro[4.5]decan-1-amine

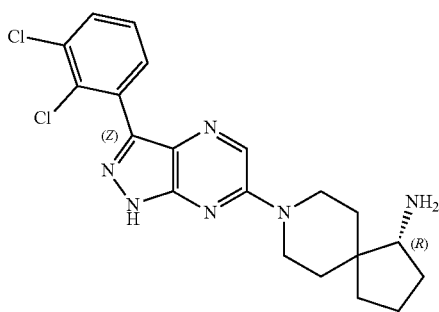

(R)-tert-butyl 1-((R)-1-(4-methoxyphenyl)ethylamino)-8-azaspiro [4.5]decane-8-carboxylate To a solution of tert-butyl 1-oxo-8-azaspiro[4.5]decane-8-carboxylate (2.0 g, 7.9 mmol) in THF (15 mL) was added (R)-1-(4-methoxyphenyl) ethanamine (1.79 g, 11.9 mmol) and Ti(OEt)$_4$ (2 mL) at RT under N$_2$, then stirred at 85° C. for 18 h. Concentrated in vacuo and added MeOH (10 mL) at RT, LiBH$_4$ (0.33 g, 15.8 mmol) was added at RT slowly, then stirred at RT for 2 h. Quenched with H$_2$O (5 mL) and extracted with EtOAc (15 mL×3). The organic layer was separated and washed with brine, dried over Na$_2$SO$_4$, filtered, and concentrated under reduced pressure to give (R)-tert-butyl 1-((R)-1-(4-methoxyphenyl)ethylamino)-8-azaspiro [4.5]decane-8-carboxylate as a colorless oil (2.0 g, 66%).

MS (ES+) $C_{23}H_{36}N_2O_3$ requires: 388, found: 389 [M+H]+.

(R)—N—((R)-1-(4-methoxyphenyl)ethyl)-8-azaspiro[4.5]decan-1-amine

A mixture of (R)-tert-butyl 1-((R)-1-(4-methoxyphenyl) ethylamino)-8-azaspiro [4.5]decane-8-carboxylate (2.0 g, 5.2 mmol) in HCl/MeOH (3 M, 10 mL) was stirred at RT for 2 h. Concentrated in vacuo and aqueous solution of NaOH was added to adjust the pH to 10~12, extracted with EtOAc (15 mL×3). The organic layer was separated and washed with brine, dried over Na₂SO₄, filtered, and concentrated under reduced pressure to give the crude (R)—N—((R)-1-(4-methoxyphenyl)ethyl)-8-aza spiro[4.5] decan-1-amine as a colorless oil (1.2 g, 86%), which was used directly without further purification.

MS (ES+) $C_{18}H_{28}N_2O$ requires: 288, found: 289 [M+H]⁺.

(3-Chloro-5-((R)-1-((R)-1-(4-methoxyphenyl)ethyl-amino)-8-azaspiro [4.5]decan-8-yl)pyrazin-2-yl)(2,3-dichlorophenyl)methanone To a solution of (2,3-dichlorophenyl)(3,5-dichloropyrazin-2-yl)methanone (80 mg, 0.25 mmol) in 2 mL DMF, under N₂, was added the product from the previous step (72 mg, 0.25 mmol) and K₂CO₃ (69 mg, 0.5 mmol). The resulting mixture was stirred overnight at RT and then poured into H₂O (20 mL). The solid was collected and dried to give the title compound as a yellow solid (114 mg) which was used directly without further purification.

MS (ES+) $C_{29}H_{31}Cl_3N_4O_2$ requires: 572, found: 573 [M+H]+.

(R)-8-(3-(2,3-dichlorophenyl)-1H-pyrazolo[3,4-b]pyrazin-6-yl)-N—((R)-1-(4-methoxyphenyl)ethyl)-8-azaspiro[4.5]decan-1-amine To a solution of the crude product from the previous step (114 mg, 0.2 mmol) in EtOH (10 mL) was added hydrazine hydrate (20 mg, 0.4 mmol). The resulting mixture was refluxed under N₂ for 2 h. The solvent was removed to give the crude the title compound as a yellow solid (100 mg), which was used directly without further purification.

MS (ES+) $C_{29}H_{32}Cl_2N_6O$ requires: 550, found: 551 [M+H]⁺.

(R)-8-(3-(2,3-dichlorophenyl)-1H-pyrazolo[3,4-b]pyrazin-6-yl)-8-azaspiro[4.5]decan-1-amine trifluoroacetate salt (43) A mixture of the crude product from the previous step (100 mg) in TFA (2 mL) was stirred under microwave at 130° C. for 15 min. The mixture was concentrated under reduced pressure. The residue was purified by Prep-HPLC under acidic condition to give the titled compound as a light yellow solid (46.9 mg, 35% over 3 steps).

MS (ES+) $C_{20}H_{22}Cl_2N_6$ requires: 416, found: 417 [M+H]⁺. ¹H NMR (500 MHz, DMSO-d₆) δ 13.42 (s, 1H), 8.48 (s, 1H), 7.76-7.74 (m, 4H), 7.69 (dd, J=7.5, 1.5 Hz, 1H), 7.50 (t, J=8.0 Hz, 1H), 4.39-4.29 (m, 2H), 3.23-3.14 (m, 3H), 2.03-2.01 (m, 1H), 1.86-1.42 (m, 9H).

The following Examples were synthesized with synthetic methods that were similar to that used for Example 43, and can generally be made by methods disclosed herein. The Examples may be made as free bases or as TFA salts.

TABLE 7

Examples 44-56.

| Ex. | Name | Structure | Spectral Data |
| --- | --- | --- | --- |
| 44 | (R)-8-(3-(3-chlorophenyl)-1H-pyrazolo[3,4-b]-pyrazin-6-yl)-8-azaspiro[4.5]-decan-1-amine | 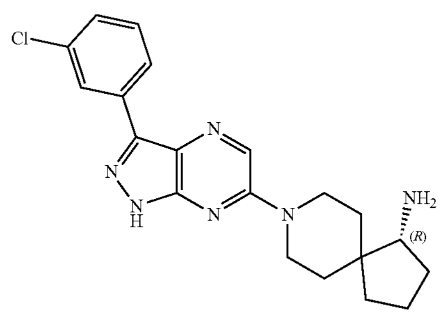 | MS (ES+) $C_{20}H_{23}ClN_6$ requires: 382, found: 383 [M + H]⁺. ¹H NMR (500 MHz, DMSO-d₆) δ 13.35 (s, 1H), 8.58 (s, 1H), 8.40 (t, J = 2.0 Hz, 1H), 8.27 (d, J = 8.0 Hz, 1H), 7.78 (br, 3H), 7.54 (t, J = 8.0 Hz, 1H), 7.46-7.44 (m, 1H), 4.40-4.31 (m, 2H), 3.24-3.15 (m, 3H), 2.07-1.41 (m, 10H). |
| 45 | (R)-8-(3-(3,5-dichlorophenyl)-1H-pyrazolo[3,4-b]-pyrazin-6-yl)-8-azaspiro[4.5]decan-1-amine | 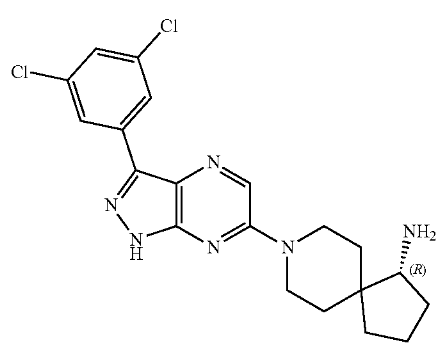 | MS (ES+) $C_{20}H_{22}Cl_2N_6$ requires: 416, found: 417 [M + H]⁺. ¹H NMR (500 MHz, DMSO-d₆) δ 13.50 (s, 1H), 8.61 (s, 1H), 8.33 (d, J = 1.5 Hz, 2H), 7.78 (br, 3H), 7.63 (t, J = 2.0 Hz, 1H), 4.41-4.31 (m, 2H), 3.24-3.14 (m, 3H), 2.07-1.38 (m, 10H). |

TABLE 7-continued

Examples 44-56.

| Ex. | Name | Spectral Data |
|---|---|---|
| 46 | (R)-8-(3-(3,4-dichlorophenyl)-1H-pyrazolo[3,4-b]pyrazin-6-yl)-8-azaspiro[4.5]decan-1-amine | MS (ES+) $C_{20}H_{22}Cl_2N_6$ requires: 416, found: 417 [M + H]$^+$. $^1$H NMR (500 MHz, DMSO-d$_6$) δ 13.43 (s, 1H), 8.58 (s, 1H), 8.56 (d, J = 2.0 Hz, 1H), 8.28 (dd, J = 8.0, 2.0 Hz, 1H), 7.82 (br, 3H), 7.78 (d, J = 8.5 Hz, 1H), 4.43-4.28 (m, 2H), 3.24-3.15 (m, 3H), 2.10-1.37 (m, 10H). |
| 47 | (R)-8-(3-(3-chloro-4-fluorophenyl)-1H-pyrazolo[3,4-b]pyrazin-6-yl)-8-azaspiro[4.5]decan-1-amine | MS (ES+) $C_{20}H_{22}ClFN_6$ requires: 400, found: 401 [M + H]$^+$. $^1$H NMR (500 MHz, DMSO-d$_6$) δ 13.35 (s, 1H), 8.57 (s, 1H), 8.50 (dd, J = 7.5, 2.0 Hz, 1H), 8.32-8.28 (m, 1H), 7.78 (br, 3H), 7.57 (t, J = 8.5 Hz, 1H), 4.39-4.31 (m, 2H), 3.24-3.15 (m, 3H), 2.07-1.41 (m, 10H). |
| 48 | (R)-8-(3-(3-(trifluoromethyl)phenyl)-1H-pyrazolo[3,4-b]pyrazin-6-yl)-8-azaspiro[4.5]decan-1-amine | MS (ES+) $C_{21}H_{23}F_3N_6$ requires: 416, found: 417 [M + H]$^+$. $^1$H NMR (500 MHz, DMSO-d$_6$) δ 13.41 (s, 1H), 8.72 (s, 1H), 8.62-8.57 (m, 2H), 7.76-7.74 (m, 5H), 4.41-4.33 (m, 2H), 3.24-3.15 (m, 3H), 2.07-1.41 (m, 10H). |
| 49 | (R)-8-(3-(3-chloro-2-fluorophenyl)-1H-pyrazolo[3,4-b]pyrazin-6-yl)-8-azaspiro[4.5]decan-1-amine | MS (ES+) $C_{20}H_{22}ClFN_6$ requires: 400, found: 401 [M + H]$^+$. $^1$H NMR (500 MHz, DMSO-d$_6$) δ 13.48 (s, 1H), 8.53 (s, 1H), 8.11 (t, J = 6.5Hz, 1H), 7.77 (br, 3H), 7.65 (dd, J = 8.5, 1.5 Hz, 1H), 7.38 (t, J = 8.0 Hz, 1H), 4.40-4.28 (m, 2H), 3.24-3.14 (m, 3H), 2.07-1.43 (m, 10H). |

TABLE 7-continued

Examples 44-56.

| Ex. | Name | Structure | Spectral Data |
|---|---|---|---|
| 50 | (R)-8-(3-(2-chloro-3-methoxyphenyl)-1H-pyrazolo[3,4-b]pyrazin-6-yl)-8-azaspiro[4.5]decan-1-amine | 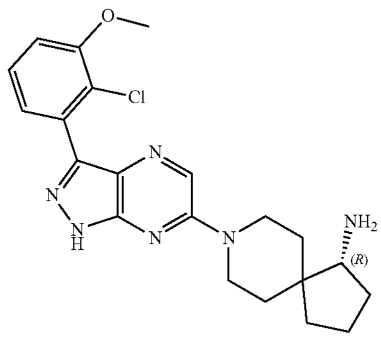 | MS (ES+) $C_{21}H_{25}ClN_6O$ requires: 412, found: 413 [M + H]$^+$. $^1$H NMR (500 MHz, DMSO-d$_6$) δ 13.29 (s, 1H), 8.45 (s, 1H), 7.73 (br, 3H), 7.41 (d, J = 8.0 Hz, 1H), 7.26-7.24 (m, 2H), 4.40-4.28 (m, 2H), 3.92 (s, 3H), 3.22-3.13 (m, 3H), 2.06-1.42 (m, 10H). |
| 51 | (R)-8-(3-(3-chloro-2-methylphenyl)-1H-pyrazolo[3,4-b]pyrazin-6-yl)-8-azaspiro[4.5]decan-1-amine | 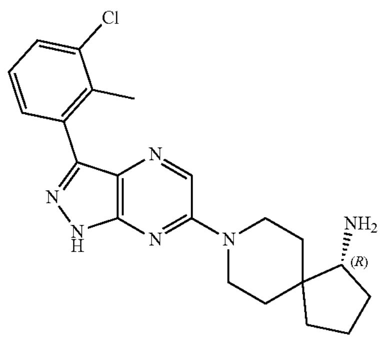 | MS (ES+) $C_{21}H_{25}ClN_6$ requires: 396, found: 397 [M + H]$^+$. $^1$H NMR (500 MHz, DMSO-d$_6$) δ 13.34 (s, 1H), 8.49 (s, 1H), 7.79 (br, 3H), 7.69 (d, J = 9.0 Hz, 1H), 7.52 (dd, J = 10.0, 1.0 Hz, 1H), 7.35 (t, J = 9.5 Hz, 1H), 4.40-4.31 (m, 2H), 3.23-3.12 (m, 3H), 2.47 (s, 3H), 2.07-1.39 (m, 10H). |
| 52 | (R)-8-(3-(3-chloro-5-methoxyphenyl)-1H-pyrazolo[3,4-b]pyrazin-6-yl)-8-azaspiro[4.5]decan-1-amine | 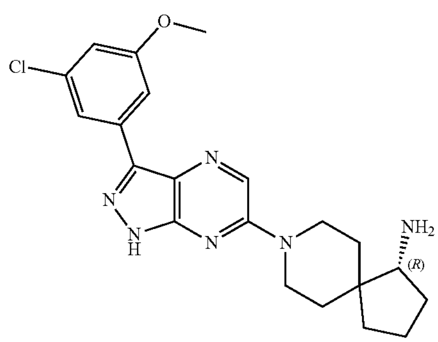 | MS (ES+) $C_{21}H_{25}ClN_6O$ requires: 412, found: 413 [M + H]$^+$. $^1$H NMR (500 MHz, DMSO-d6) δ 13.35 (s, 1H), 8.58 (s, 1H), 7.99 (t, J = 1.5 Hz, 1H), 7.84 (t, J = 1.5 Hz, 1H), 7.76 (br, 3H), 7.05 (t, J = 2.0 Hz, 1H), 4.40-4.30 (m, 2H), 3.85 (s, 3H), 3.24-3.14 (m, 3H), 2.09-1.43 (m, 10H). |
| 53 | (R)-8-(3-(2-chloropyridin-3-yl)-1H-pyrazolo[3,4-b]pyrazin-6-yl)-8-azaspiro[4.5]decan-1-amine | 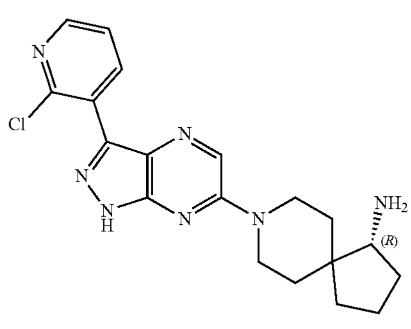 | MS (ES+) $C_{19}H_{22}ClN_7$ requires: 383, found: 384 [M + H]$^+$. $^1$H NMR (500 MHz, DMSO-d$_6$) δ 13.48 (s, 1H), 8.52-8.50 (m, 2H), 8.21 (dd, J = 7.5, 2.0 Hz, 1H), 7.75 (br, 3H), 7.58 (dd, J = 8.0, 4.5 Hz, 1H), 4.40-4.32 (m, 2H), 3.26-3.13 (m, 3H), 2.06-1.40 (m, 10H). |

TABLE 7-continued

Examples 44-56.

| Ex. | Name | Structure | Spectral Data |
|---|---|---|---|
| 54 | (R)-8-(3-(2-chlorophenyl)-1H-pyrazolo[3,4-b]pyrazin-6-yl)-8-azaspiro[4.5]decan-1-amine | 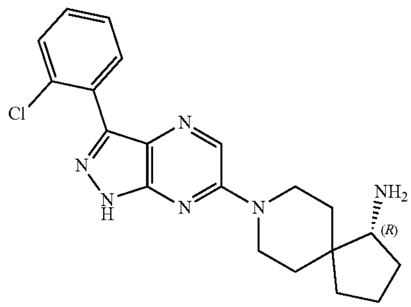 | MS (ES+) C$_{20}$H$_{23}$ClN$_6$ requires: 382, found: 383 [M + H]$^+$. $^1$H NMR (500 MHz, DMSO-d$_6$) δ 13.33 (s, 1H), 8.47 (s, 1H), 7.76-7.74 (m, 4H), 7.61-7.59 (m, 1H), 7.48-7.46 (m, 2H), 4.40-4.31 (m, 2H), 3.22-3.14 (m, 3H), 2.06-1.40 (m, 10H). |
| 55 | (R)-8-(3-(2-methyl-pyridin-3-yl)-1H-pyrazolo[3,4-b]-pyrazin-6-yl)-8-azaspiro[4.5]decan-1-amine | 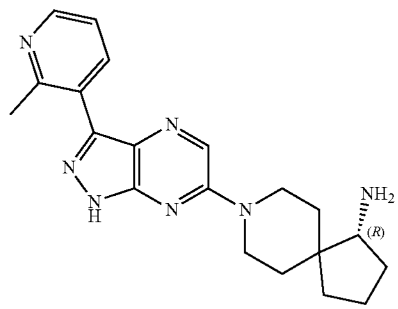 | MS (ES+) C$_{20}$H$_{25}$N$_7$ requires: 363, found: 364 [M + H]$^+$. $^1$H NMR (500 MHz, DMSO-d$_6$) δ 13.57 (s, 1H), 8.72-8.65 (m, 2H), 8.54 (s, 1H), 7.81 (br, 3H), 7.68 (t, J = 5.0 Hz, 1H), 4.40-4.32 (m, 2H), 3.25-3.15 (m, 3H), 2.85 (s, 3H), 2.04-1.41 (m, 10H). |
| 56 | (R)-8-(3-(3-chloro-pyridin-4-yl)-1H-pyrazolo[3,4-b]-pyrazin-6-yl)-8-azaspiro[4.5]decan-1-amine | 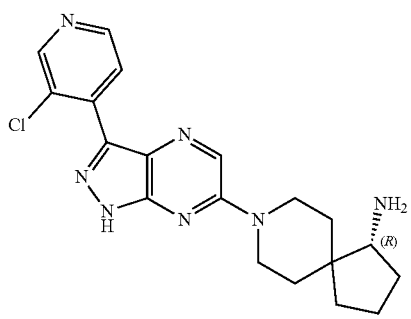 | MS (ES+) C$_{19}$H$_{22}$ClN$_7$ requires: 383, found: 384 [M + H]$^+$. $^1$H NMR (500 MHz, DMSO-d$_6$) δ 13.66 (s, 1H), 8.78 (s, 1H), 8.65 (d, J = 5.0 Hz, 1H), 8.56 (s, 1H), 8.03 (d, J = 5.0 Hz, 1H), 7.76 (br, 3H), 4.40-4.32 (m, 2H), 3.24-3.14 (m, 3H), 2.08-1.43 (m, 10H). |

EXAMPLE 57

(4-Amino-1-(3-(2,3-dichlorophenyl)-1H-pyrazolo[3,4-b]pyrazin-6-yl)piperidin-4-yl)-methanol

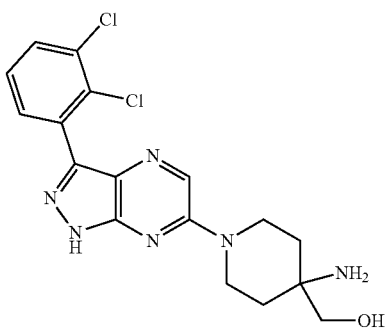 [SMILES: NC1(CO)CCN(c2cnc3c(-c4cccc(Cl)c4Cl)n[nH]c3n2)CC1]

Benzyl 1-(6-chloro-5-(2,3-dichlorobenzoyl)pyrazin-2-yl)-4-(hydroxymethyl)-piperidin-4-yl carbamate To a solution of (2,3-dichlorophenyl)(3,5-dichloropyrazin-2-yl)methanone (80 mg, 0.25 mmol) in 2 mL DMF, under N$_2$, was added Intermediate 104 (75 mg, 0.25 mmol) and K$_2$CO$_3$ (69 mg, 0.5 mmol). The resulting mixture was stirred overnight at RT and then poured into H$_2$O (20 mL). The solid was collected and dried to give the crude title compound as a yellow solid (126 mg) which was used directly without further purification.

MS (ES+) C$_{25}$H$_{23}$Cl$_3$N$_4$O$_4$ requires: 548, found: 549 [M+H]$^+$.

Benzyl 1-(3-(2,3-dichlorophenyl)-1H-pyrazolo[3,4-b]pyrazin-6-yl)-4-(hydroxymethyl)piperidin-4-yl carbamate To a solution of the crude product from the previous step (126 mg, 0.23 mmol) in EtOH (10 mL) was added hydrazine hydrate (23 mg, 0.46 mmol). The resulting mixture was refluxed under N$_2$ for 2 h. The solvent was removed to give the crude title product as a yellow solid (100 mg), which was used directly without further purification.

MS (ES+) C$_{25}$H$_{24}$Cl$_2$N$_6$O$_3$ requires: 526, found: 527 [M+H]$^+$.

(4-Amino-1-(3-(2,3-dichlorophenyl)-1H-pyrazolo[3,4-b]pyrazin-6-yl)piperidin-4-yl)methanol trifluoroacetate (57) A mixture of the crude product from the previous step (100 mg) in TFA (2 mL) was stirred under microwave at 130° C.

for 15 min. The mixture was concentrated under reduced pressure. The residue was purified by Prep-HPLC under acidic condition to give the title compound as a light yellow solid (21.6 mg, 17% over 3 steps).

MS (ES+) $C_{17}H_{18}Cl_2N_6O$ requires: 392, found: 393 [M+H]$^+$. $^1$H NMR (500 MHz, DMSO-d$_6$) δ 13.47 (s, 1H), 8.48 (s, 1H), 7.88 (br, 3H), 7.76 (dd, J=8.0, 1.5 Hz, 1H), 7.69 (dd, J=8.0, 1.5 Hz, 1H), 7.50 (t, J=8.0 Hz, 1H), 5.59 (s, 1H), 4.10-4.04 (m, 2H), 3.63-3.55 (m, 4H), 1.88-1.72 (m, 4H).

The following Examples were synthesized with synthetic methods that were similar to that used for Example 57, and can generally be made by methods disclosed herein. The Examples may be made as free bases or as TFA salts.

TABLE 8

Examples 58-63.

| # | Name | Structure | Spectral Data |
|---|------|-----------|---------------|
| 58 | 1-(3-(2,3-dichlorophenyl)-1H-pyrazolo[3,4-b]-pyrazin-6-yl)-4-(fluoromethyl)-piperidin-4-amine | 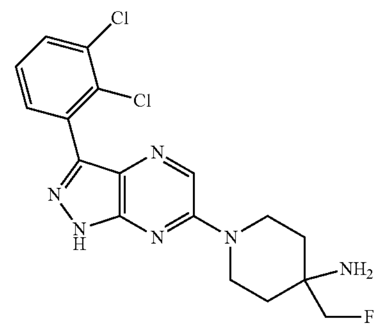 [SMILES: NC1(CF)CCN(c2cnc3c(-c4cccc(Cl)c4Cl)n[nH]c3n2)CC1] | MS (ES+) $C_{17}H_{17}Cl_2N_6$ requires: 394, found: 395 [M + H]$^+$. $^1$H NMR (500 MHz, DMSO-d$_6$) δ 13.48 (s, 1H), 8.52 (s, 1H), 8.07 (br, 3H), 7.76 (dd, J = 8.0, 1.5 Hz, 1H), 7.69 (dd, J = 8.0, 1.5 Hz, 1H), 7.50 (t, J = 8.0 Hz, 1H), 4.40-4.37 (m, 2H), 3.36-3.13 (m, 4H), 1.99-1.79 (m, 4H). |
| 59 | (4-amino-1-(3-(2-chloropyridin-3-yl)-1H-pyrazolo[3,4-b]pyrazin-6-yl)-piperidin-4-yl)-methanol | 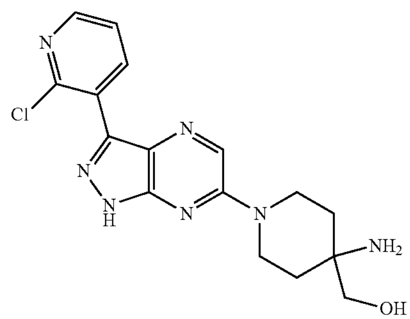 [SMILES: NC1(CO)CCN(c2cnc3c(-c4cccnc4Cl)n[nH]c3n2)CC1] | MS (ES+) $C_{16}H_{18}ClN_7O$ requires: 359, found: 360 [M + H]$^+$. $^1$H NMR (500 MHz, DMSO-d$_6$) δ 13.55 (s, 1H), 8.52-8.51 (m, 2H), 8.21 (dd, J = 7.5, 2.0 Hz, 1H), 7.89 (br, 3H), 7.58 (dd, J = 7.5, 4.5 Hz, 1H), 5.60 (s, 1H), 4.08-4.04 (m, 2H), 3.64-3.56 (m, 4H), 1.88-1.70 (m, 4H). |
| 60 | 4-(aminomethyl)-1-(3-(2-chlorophenyl)-1H-pyrazolo[3,4-b]-pyrazin-6-yl)-piperidin-4-ol | 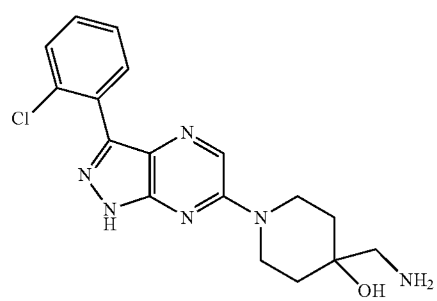 [SMILES: NCC1(O)CCN(c2cnc3c(-c4ccccc4Cl)n[nH]c3n2)CC1] | MS (ES+) $C_{17}H_{19}ClN_6O$ requires: 358, found: 359 [M + H]$^+$. $^1$H NMR (500 MHz, DMSO-d$_6$) δ 13.33 (s, 1H), 8.47 (s, 1H), 7.80-7.74 (m, 4H), 7.61-7.59 (m, 1H), 7.48-7.46 (m, 2H), 5.20 (s, 1H), 4.20-4.17 (m, 2H), 3.48-3.43 (m, 2H), 2.83-2.81 (m, 2H), 1.65-1.62 (m, 4H). |
| 61 | (4-amino-1-(3-(2-chlorophenyl)-1H-pyrazolo[3,4-b]-pyrazin-6-yl)-piperidin-4-yl)-methanol | 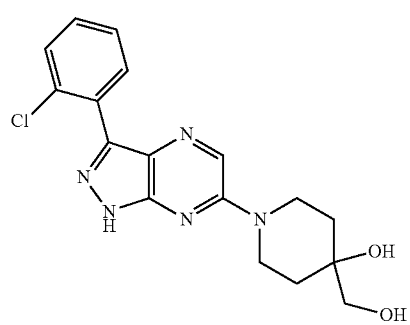 [SMILES: OCC1(O)CCN(c2cnc3c(-c4ccccc4Cl)n[nH]c3n2)CC1] | MS (ES+) $C_{17}H_{18}ClN_6O$ requires: 358, found: 359 [M + H]$^+$. $^1$H NMR (500 MHz, DMSO-d$_6$) δ 13.41 (s, 1H), 8.48 (s, 1H), 7.89 (br, 3H), 7.76-7.73 (m, 1H), 7.62-7.60 (m, 1H), 7.49-7.47 (m, 2H), 5.61 (s, 1H), 4.07-4.03 (m, 2H), 3.63-3.54 (m, 4H), 1.88-1.70 (m, 4H). |

TABLE 8-continued

Examples 58-63.

| | Name | Structure | Spectral Data |
|---|---|---|---|
| 62 | (4-amino-1-(3-(2-chloro-3-fluoro-phenyl)-1H-pyrazolo[3,4-b]-pyrazin-6-yl)-piperidin-4-yl)-methanol | 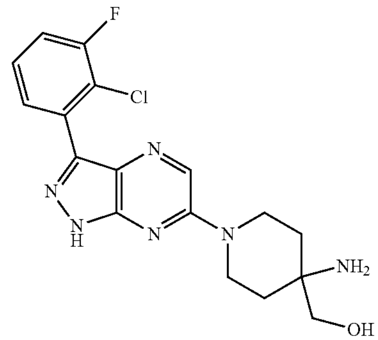 [SMILES: NC1(CO)CCN(c2cnc3c(-c4cccc(F)c4Cl)n[nH]c3n2)CC1] | MS (ES+) $C_{17}H_{18}ClFN_6O$ requires: 376, found: 377 [M + H]$^+$. $^1$H NMR (500 MHz, DMSO-d$_6$) δ 13.51 (s, 1H), 8.50 (s, 1H), 7.88 (br, 3H), 7.67-7.65 (m, 1H), 7.53-7.51 (m, 2H), 5.60 (t, 1H), 4.07-4.04 (m, 2H), 3.64-3.58 (m, 4H), 1.88-1.72 (m, 4H). |
| 63 | 4-(aminomethyl)-1-(3-(2-chloro-6-fluorophenyl)-1H-pyrazolo[3,4-b]-pyrazin-6-yl)-piperidin-4-ol | 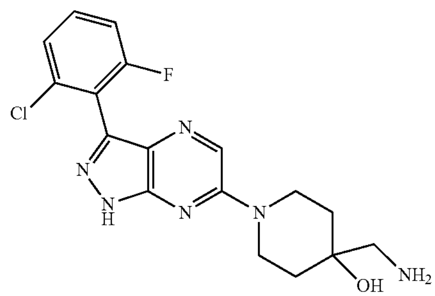 [SMILES: NCC1(O)CCN(c2cnc3c(-c4c(F)cccc4Cl)n[nH]c3n2)CC1] | MS (ES+) $C_{17}H_{18}ClFN_6O$ requires: 376, found: 377 [M + H]$^+$. $^1$H NMR (500 MHz, DMSO-d$_6$) δ 13.46 (s, 1H), 8.44 (s, 1H), 7.76 (br, 3H), 7.58-7.49 (m, 2H), 7.38 (t, J = 8.5 Hz, 1H), 5.19 (s, 1H), 4.20-4.17 (m, 2H), 3.48-3.43 (m, 2H), 2.82 (d, J = 5.5 Hz, 2H), 1.65-1.62 (m, 4H). |

EXAMPLE 64A/B 8-(3-(2,3-Dichlorophenyl)-1H-pyrazolo[3,4-b]pyrazin-6-yl)-2-fluoro-8-azaspiro[4.5]decan-1-amine Diastereomers A and B

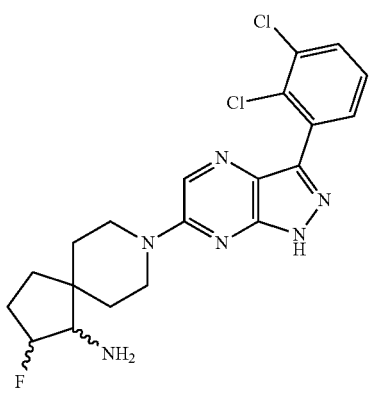 [SMILES: NC1C(F)CCC12CCN(c1cnc3c(-c4cccc(Cl)c4Cl)n[nH]c3n1)CC2]

Benzyl 1-oxo-8-azaspiro[4.5]decane-8-carboxylate To a mixture of 8-azaspiro[4.5]decan-1-one (1 g, crude) in CH$_2$Cl$_2$ (10 mL) was added TEA (1.6 g, 15.8 mmol) and CbzOSu (1.18 g, 4.3 mmol) at 0° C. The mixture was stirred at room temperature for 2 hours. The mixture was diluted with CH$_2$Cl$_2$ (10 mL). The organic layers were washed with NH$_4$Cl (10 mL×2) and brine (10 mL), dried with MgSO$_4$, concentrated and purified by column silica gel (petroleum ether:EtOAc=10:1-1:1) to obtain the title compound as a white solid (940 mg, 83%).

MS (ES+) $C_{17}H_{21}NO_3$ requires: 287, found: 288 [M+H]$^+$.

Benzyl 2-fluoro-1-oxo-8-azaspiro[4.5]decane-8-carboxylate In 15 mL H$_2$O was combined the product from the previous step (940 mg, 3.3 mmol), SELECTFLUOR™ (1.3 g, 3.63 mmol), and sodium dodecyl sulfate (0.8 g). The mixture was purged with N$_2$ and stirred at 80° C. for 48 hours. The mixture was extracted with EtOAc (20 mL×3). The organic phase was dried with Na$_2$SO$_4$, concentrated and purified by column silica gel (petroleum ether:EtOAc=20:1-4:1) to obtain the title compound as a white solid (500 mg).

MS (ES+) $C_{17}H_{20}FNO_3$ requires: 305, found: 306 [M+H]$^+$.

(Z)-Benzyl-1-(tert-butylsulfinylimino)-2-fluoro-8-azaspiro[4.5]decane-8-carboxylate To a solution of the product from the previous step (500 mg, 1.6 mmol) in THF (8 mL, dry) was added 2-methylpropane-2-sulfinamide (581 mg, 4.8 mmol) and Ti(OEt)$_4$ (2 mL). The mixture was stirred at 80° C. overnight. The mixture was concentrated and used directly for the next step.

MS (ES+) $C_{21}H_{29}FN_2O_3S$ requires: 408, found: 409 [M+H]$^+$.

Benzyl 1-(1,1-dimethylethylsulfinamido)-2-fluoro-8-azaspiro[4.5] decane-8-carboxylate To a mixture of the crude product from the previous step (2 g, crude) in MeOH (10 mL) was added LiBH$_4$ (105 mg, 4.8 mmol) at 0° C. The mixture was stirred at RT for 2 hours, then quenched with H$_2$O (10 mL) and concentrated. EtOAc (20 mL) was added, and the residue was filtered through a short CELITE™ column. The water phase was extracted with EtOAc (20 mL×3). The organic phases were combined and washed with brine (20 mL), dried with MgSO$_4$, concentrated and purified by Pre-HPLC to obtain the title compound as a white solid (isomer A: 200 mg, isomer B: 120 mg).

MS (ES+) $C_{21}H_{31}FN_2O_3S$ requires: 410, found: 411 [M+H]$^+$.

N-(2-fluoro-8-azaspiro[4.5]decan-1-yl)-2-methylpropane-2-sulfinamide, isomer A To a solution of isomer A of the compound from the previous step (150 mg) in MeOH (5 mL) was added Pd/C (10%, 30 mg), and Boc$_2$O (0.4 mL). The mixture was filled with H$_2$ and stirred at RT under H$_2$ for 1 hour. The solids were removed by filtration. The resulting solution was concentrated. The residue was dissolved in CH$_2$Cl$_2$ (10 mL), TFA (2 mL) was added slowly at 0° C., and the resulting mixture was stirred at this temperature for 30 min. The reaction was monitored with LCMS until all of the starting material was consumed. At this point, the residue was concentrated and used directly for the next step.

MS (ES+) C$_{13}$H$_{25}$FN$_2$OS requires: 276, found: 277 [M+H]$^+$.

A similar procedure was used for isomer B.

N-(8-(6-chloro-5-(2,3-dichlorobenzoyl)pyrazin-2-yl)-2-fluoro-8-azaspiro-[4.5]decan-1-yl)-2-methylpropane-2-sulfinamide, isomer A To a mixture of the product from the previous step (300 mg, crude) in DMF (5 mL) was added (2,3-dichlorophenyl)(3,5-dichloropyrazin-2-yl)methanone (120 mg) and K$_2$CO$_3$ (300 mg). The mixture was stirred at RT for 2 hours. H$_2$O (20 mL) was added, and the mixture was extracted with EtOAc (20 mL×3). The organic phases were combined and washed with brine (20 mL) and concentrated to obtain the title compound as brown oil (500 mg).

MS (ES+) C$_{24}$H$_{28}$Cl$_3$FN$_4$O$_2$S requires 562, found 563 [M+H]$^+$.

A similar procedure was used for isomer B.

N-(8-(3-(2,3-dichlorophenyl)-1H-pyrazolo[3,4-b]pyrazin-6-yl)-2-fluoro-8-azaspiro[4.5]decan-1-yl)-2-methylpropane-2-sulfinamide, isomer A To a solution of the product from the previous step (500 mg, crude) in EtOH (10 mL) was added NH$_2$NH$_2$ (98%, 0.5 mL). The mixture was stirred at 80° C. for 2 hours, then concentrated to obtain the title compound as a brown solid (600 mg, crude).

MS (ES+) C$_{24}$H$_{29}$Cl$_2$FN$_6$OS requires 538, found 539 [M+H]$^+$.

A similar procedure was used for isomer B.

8-(3-(2,3-Dichlorophenyl)-1H-pyrazolo[3,4-b]pyrazin-6-yl)-2-fluoro-8-azaspiro[4.5]decan-1-amine, isomer A (64) A solution of the product from the previous step (600 mg, crude) in 4 M HCl/dioxane (10 mL) was stirred at 50° C. for 1 hour. The mixture was concentrated and dissolved in DMF, purified by Pre-HPLC to obtain the title compound as a light yellow solid (isomer 1: 42 mg).

Isomer A: MS (ES+) C$_{20}$H$_{21}$Cl$_2$FN$_6$ requires: 435, found: 436 [M+H]$^+$; $^1$H NMR (400 MHz, DMSO-d$_6$) δ 13.39 (s, 1H), 8.44 (s, 1H), 7.75 (dd, J=8.0, 1.5 Hz, 1H), 7.70 (dd, J=7.7, 1.5 Hz, 1H), 7.49 (t, J=7.9 Hz, 1H), 4.84 (dd, J=59.9, 4.0 Hz, 1H), 4.41 (d, J=13.5 Hz, 2H), 3.11 (dt, J=23.3, 15.0 Hz, 2H), 2.58 (dd, J=32.0, 4.0 Hz, 1H), 2.24-0.87 (m, 10H). $^{19}$F NMR (376 MHz, DMSO-d$_6$) δ −184.34 (s).

A similar procedure was used for isomer B.

Isomer B: (33 mg): MS (ES+) C$_{20}$H$_{21}$Cl$_2$FN$_6$ requires: 435, found: 436 [M+H]$^+$; $^1$H NMR (400 MHz, DMSO-d$_6$) δ 13.39 (s, 1H), 8.44 (s, 1H), 7.75 (dd, J=8.0, 1.5 Hz, 1H), 7.70 (dd, J=7.7, 1.5 Hz, 1H), 7.49 (t, J=7.9 Hz, 1H), 4.84 (dd, J=59.9, 4.0 Hz, 1H), 4.41 (d, J=13.0 Hz, 2H), 3.24-2.94 (m, 2H), 2.58 (dd, J=32.4, 3.5 Hz, 1H), 2.20-0.87 (m, 10H). $^{19}$F NMR (376 MHz, DMSO-d$_6$) δ −184.34 (s).

EXAMPLE 65A/B 8-(3-(2,3-Dichlorophenyl)-1H-pyrazolo[3,4-b]pyrazin-6-yl)-2,2-difluoro-8-aza-spiro[4.5]decan-1-amine, Enantiomers A and B

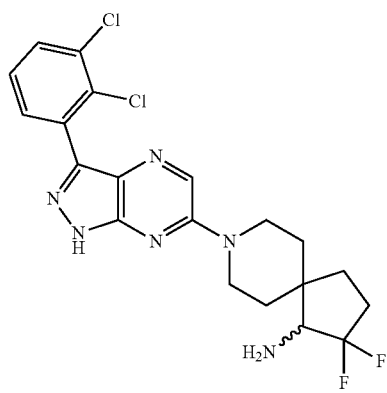 [SMILES: NC1C(F)(F)CCC12CCN(c1cnc3c(-c4cccc(Cl)c4Cl)n[nH]c3n1)CC2]

tert-Butyl 2,2-difluoro-1-oxo-8-azaspiro[4.5]decane-8-carboxylate To a solution of NaHMDS (2 M in THF, 21.7 mL, 43.4 mmol) was added a solution of tert-butyl 1-oxo-8-azaspiro[4.5]decane-8-carboxylate (10.0 g, 39.5 mmol) in THF (25 mL) at −78° C. After stirring for 30 min at this temperature, a solution of N-fluorobenzenesulfonamide (12.5 g, 39.5 mmol) in THF (50 mL) was added. After 3 hours stirring at −78° C., the solution was diluted with sat. aq NaHCO$_3$ (200 mL) and extracted with CH$_2$Cl$_2$ (3×200 mL). The combined organic phases was washed with brine, dried over MgSO$_4$, filtered, and concentrated under reduced pressure. The resulting residue was purified by silica chromatography (0 to 5 percent gradient of MeOH/CH$_2$Cl$_2$) to obtain the title compound as a white solid (800 mg, 7.3%).

MS (ES+) C$_{14}$H$_{21}$F$_2$NO$_3$ requires: 289, found: 234 [M+H−56]$^+$.

(R,Z)-tert-butyl 1-(tert-butylsulfinylimino)-2,2-difluoro-8-azaspiro[4.5]decane-8-carboxylate To a solution of the product from the previous step (800 mg, 2.7 mmol) in THF (10 mL, dry) was added 2-methylpropane-2-sulfinamide (1.0 g, 8.3 mmol) and Ti(OEt)$_4$ (2 mL). The mixture was stirred at 80° C. overnight. The mixture was concentrated and used directly for the next step.

MS (ES+) C$_{18}$H$_{30}$F$_2$N$_2$O$_3$S requires: 392, found: 293 [M+H−100]$^+$.

(S)-tert-butyl 1-((R)-1,1-dimethylethylsulfinamido)-2,2-difluoro-8-azaspiro-[4.5]decane-8-carboxylate To a mixture of the product from the previous step (2 g, crude) in MeOH (10 mL) was added LiBH$_4$ (180 mg, 8.1 mmol) at 0° C. The resulting mixture was stirred at RT for 2 hours. The mixture was quenched with H$_2$O (10 mL), and concentrated. EtOAc (20 mL) was added, and the resulting solution was filtered through a short CELITE™ column. The aqueous phase was extracted with EtOAc (20 mL×3). The combined organic phases were washed with brine (20 mL), dried with MgSO$_4$, concentrated and purified by Pre-HPLC to obtain the title compound as a white solid (isomer A: 450 mg, isomer B: 330 mg).

MS (ES+) $C_{18}H_{32}F_2N_2O_3S$ requires: 394, found: 295 [M+H−100]$^+$.

(R)—N-(2,2-difluoro-8-azaspiro[4.5]decan-1-yl)-2-methylpropane-2 sulfinamide, isomer A To a solution of isomer A of the crude product from the previous step (isomer 1:150 mg) in CH$_2$Cl$_2$ (10 mL) was added TFA (2 mL) slowly at 0° C. The mixture was stirred at this temperature for 30 min, then concentrated and used directly for the next step.

MS (ES+) $C_{13}H_{24}F_2N_2OS$ requires: 294, found: 295 [M+H]+.

A similar procedure was used for isomer B.

(R)—N-(8-(6-chloro-5-(2,3-dichlorobenzoyl)pyrazin-2-yl)-2,2-difluoro-8-azaspiro[4.5]decan-1-yl)-2-methylpropane-2-sulfinamide, isomer A To a mixture of the product from the previous step (300 mg, crude) in DMF (5 mL) was added (2,3-dichlorophenyl)(3,5-dichloropyrazin-2-yl)methanone (120 mg) and K$_2$CO$_3$ (300 mg). The mixture was stirred at RT for 2 hours. H$_2$O (20 mL) was added, and the mixture was extracted with EA (20 mL×3). The combined organic phases was washed with brine (20 mL) and concentrated to obtain the title compound as brown oil (500 mg, crude).

MS (ES+) $C_{24}H_{27}Cl_3F_2N_4O_2S$ requires: 578, found: 579 [M+H]$^+$.

A similar procedure was used for isomer B.

(R)—N-(8-(3-(2,3-dichlorophenyl)-1H-pyrazolo[3,4-b]pyrazin-6-yl)-2,2-difluoro-8-azaspiro[4.5]decan-1-yl)-2-methylpropane-2-sulfinamide, Isomer A To a solution of the product from the previous step (isomer 1: 500 mg, crude) in EtOH (10 mL) was added NH$_2$NH$_2$ (98%, 0.5 mL). The mixture was stirred at 80° C. for 2 hours, then concentrated to obtain the title compound as a brown solid (600 mg, crude).

MS (ES+) $C_{24}H_{28}Cl_2F_2N_6OS$ requires: 556, found: 557 [M+H]$^+$.

A similar procedure was used for isomer B.

8-(3-(2,3-Dichlorophenyl)-1H-pyrazolo[3,4-b]pyrazin-6-yl)-2,2-difluoro-8-azaspiro[4.5]decan-1-amine, isomer A (65A) A solution of the product from the previous step (600 mg, crude) in 4 M HCl/dioxane (10 mL) was stirred at 50° C. for 1 hour. The mixture was concentrated and dissolved in DMF purified by Pre-HPLC to obtain the title compound as a light yellow solid (isomer 1: 70 mg; isomer 2: 49 mg).

Isomer A: MS (ES+) $C_{20}H_{20}Cl_2F_2N_6$ requires: 453, found: 454 [M+H]$^+$; $^1$H NMR (400 MHz, DMSO-d$_6$) δ 13.40 (s, 1H), 8.45 (s, 1H), 7.75 (dd, J=8.0, 1.5 Hz, 1H), 7.70 (dd, J=7.7, 1.5 Hz, 1H), 7.49 (t, J=7.9 Hz, 1H), 4.37 (d, J=10.5 Hz, 2H), 3.24-2.99 (m, 2H), 2.83 (dd, J=18.0, 13.0 Hz, 1H), 2.27-1.08 (m, 10H). $^{19}$F NMR (376 MHz, DMSO-d$_6$) δ −97.16 (d, J=226.1 Hz), −99.39 (d, J=226.0 Hz).

A similar procedure was used for isomer B.

Isomer B: MS (ES+) $C_{20}H_{20}Cl_2F_2N_6$ requires: 453, found: 454 [M+H]$^+$; $^1$H NMR (400 MHz, DMSO-d$_6$) δ 13.40 (s, 1H), 8.44 (s, 1H), 7.74 (d, J=8.0 Hz, 1H), 7.70 (d, J=7.7 Hz, 1H), 7.49 (t, J=7.9 Hz, 1H), 4.37 (d, J=12.6 Hz, 2H), 3.14 (dt, J=23.5, 11.8 Hz, 2H), 2.95-2.70 (m, 1H), 2.30-0.99 (m, 10H). $^{19}$F NMR (376 MHz, DMSO-d$_6$) δ −97.20 (d, J=226.1 Hz), −99.44 (d, J=226.0 Hz).

EXAMPLE 101

4-Methyl-1-(3-(5-(trifluoromethyl)-1H-pyrazol-4-yl)-1H-pyrazolo[3,4-b]pyrazin-6-yl)-piperidin-4-amine

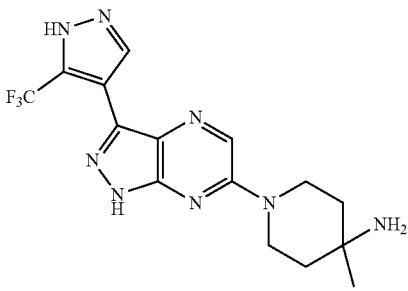 [SMILES: CC1(N)CCN(c2cnc3c(-c4cn[nH]c4C(F)(F)F)n[nH]c3n2)CC1]

tert-Butyl 1-(6-chloro-5-(5-(trifluoromethyl)-1H-pyrazole-4-carbonyl) pyrazin-2-yl)-4-methylpiperidin-4-yl carbamate To a solution of (3,5-dichloropyrazin-2-yl)(5-(trifluoromethyl)-1H-pyrazol-4-yl)methanone (62.2 mg, 0.2 mmol) in DMF (2 mL) under N$_2$ was added tert-butyl 4-methylpiperidin-4-yl carbamate (42.8 mg, 0.2 mmol) and K$_2$CO$_3$ (55.3 mg, 0.4 mmol). The result mixture was stirred overnight at RT and poured into H$_2$O (20 mL). The solid that formed was removed by filtration and dried to give the crude title compound as a yellow solid (120 mg) which was used directly without further purification.

MS (ES+) $C_{20}H_{24}ClF_3N_6O_3$ requires: 488, found: 489 [M+H]+.

tert-Butyl 4-methyl-1-(3-(5-(trifluoromethyl)-1H-pyrazol-4-yl)-1H-pyrazolo [3,4-b]pyrazin-6-yl)piperidin-4-yl carbamate To a solution of the crude product from the previous step (120 mg, 0.24 mmol) in EtOH (10 mL) was added hydrazine hydrate (23 mg, 0.46 mmol). The resulting mixture was refluxed under N$_2$ for 2 h. The solvent was removed to give the crude title compound as a yellow solid (100 mg) which was used directly without further purification.

MS (ES+) $C_{20}H_{25}F_3N_8O_2$ requires: 466, found: 467[M+H]+.

4-Methyl-1-(3-(5-(trifluoromethyl)-1H-pyrazol-4-yl)-1H-pyrazolo [3,4-b]pyrazin-6-yl)piperidin-4-amine A solution of the product from the previous step (100 mg, 0.21 mmol) in TFA (5 mL) was stirred at RT for 5 h, then concentrated under reduced pressure. The residue was purified by Prep-HPLC to give the title compound as a yellow solid (31.2 mg, yield 42%).

MS (ES+) $C_{15}H_{17}F_3N_8$ requires: 366, found: 367 [M+H]+. 1H NMR (500 MHz, DMSO) δ 13.86 (s, 1H), 13.24 (s, 1H), 8.57 (s, 1H), 8.49 (s, 1H), 7.94 (s, 3H), 4.16 (s, 2H), 3.46 (s, 2H), 1.77 (s, 4H), 1.40 (s, 3H).

EXAMPLE 102

(R)-8-(3-(5-(Trifluoromethyl)-1H-pyrazol-4-yl)-1H-pyrazolo[3,4-b]pyrazin-6-yl)-8-azaspiro[4.5]decan-1-amine

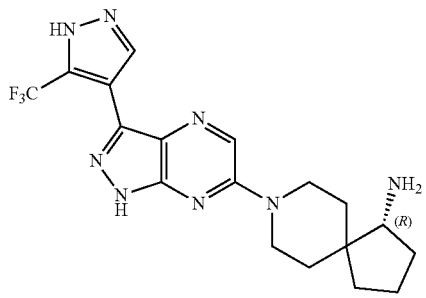

(3-Chloro-5-((1R)-1-(1-(4-methoxyphenyl)ethylamino)-8-azaspiro [4.5]decan-8-yl)pyrazin-2-yl)(5-(trifluoromethyl)-1H-pyrazol-4-yl)methanone To a solution of (3,5-dichloropyrazin-2-yl)(5-(trifluoromethyl)-1H-pyrazol-4-yl) methanone (62.2 mg, 0.2 mmol) in DMF (2 mL) under $N_2$ was added (1R)—N-(1-(4-methoxyphenyl)ethyl)-8-azaspiro [4.5]decan-1-amine (57.6 mg, 0.2 mmol) and $K_2CO_3$ (55.3 mg, 0.4 mmol). The result mixture was stirred overnight at RT, then poured into $H_2O$ (20 mL). The solid that formed was removed by filtration and dried to give the crude title compound as a yellow solid (120 mg) which was used directly without further purification.

MS (ES+) $C_{27}H_{30}ClF_3N_6O_2$ requires: 562, found: 563 [M+H]+.

(1R)—N-(1-(4-methoxyphenyl)ethyl)-8-(3-(5-(trifluoromethyl)-1H-pyrazol-4-yl)-1H-pyrazolo[3,4-b]pyrazin-6-yl)-8-azaspiro[4.5]decan-1-amine To a solution of the crude product from the previous step (120 mg, 0.21 mmol) in EtOH (10 mL) was added hydrazine hydrate (23 mg, 0.46 mmol). The result mixture was refluxed under $N_2$ for 2 h. The solvent was removed to give the crude title compound as a yellow solid (100 mg) which was used directly without further purification.

MS (ES+) $C_{27}H_{31}F_3N_8O$ requires: 540, found: 541[M+H]+.

(R)-8-(3-(5-(Trifluoromethyl)-1H-pyrazol-4-yl)-1H-pyrazolo[3,4-b]pyrazin-6-yl)-8-azaspiro[4.5]decan-1-amine A solution of the product from the previous step (100 mg, 0.18 mmol) in TFA (5 mL) was stirred at 120° C. for 0.5 h under microwave irradiation, then concentrated under reduced pressure. The residue was purified by Prep-HPLC to give the titled compound as yellow solid (13.4 mg, yield 16%).

MS (ES+) $C_{18}H_{21}F_3N_8$ requires: 406, found: 407 [M+H]+. 1H NMR (500 MHz, DMSO) δ 13.85 (s, 1H), 13.17 (s, 1H), 8.56 (s, 1H), 8.48 (s, 1H), 7.77 (s, 3H), 4.35 (dd, J=28.1, 13.5 Hz, 2H), 3.16 (dd, J=18.2, 10.1 Hz, 3H), 2.06 (s, 1H), 1.85-1.42 (m, 9H).

EXAMPLE 103

(R)-8-(3-(5-(Trifluoromethyl)-1H-pyrazol-4-yl)-1H-pyrazolo[3,4-b]pyrazin-6-yl)-8-azaspiro[4.5]decan-1-amine

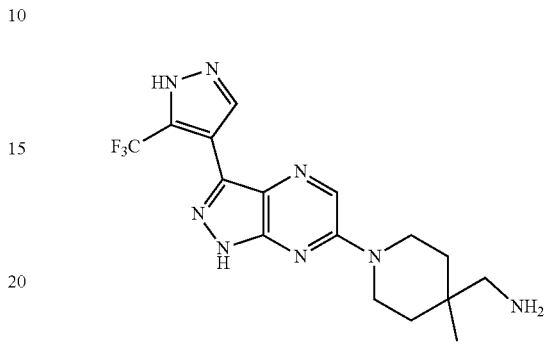

tert-Butyl (1-(6-chloro-5(5-(trifluoromethyl)-1H-pyrazole-4-carbonyl)pyrazine-2-yl)-4-methylpiperidin-4-yl) methyl carbamate To a solution of (3,5-dichloropyrazin-2-yl)(5-(trifluoromethyl)-1H-pyrazol-4-yl)methanone (62.2 mg, 0.2 mmol) in 2 mL DMF under $N_2$ was added tert-butyl (4-methylpiperidin-4-yl)methyl carbamate (45.6 mg, 0.2 mmol) and $K_2CO_3$ (55.3 mg, 0.4 mmol). The resulting mixture was stirred overnight at RT and poured into $H_2O$ (20 mL). The solid that formed was removed by filtration and dried to give the crude title compound crude as a yellow solid (120 mg) which was used directly without further purification.

MS (ES+) $C_{21}H_{26}ClF_3N_6O_3$ requires: 502, found: 503 [M+H]+.

tert-Butyl (4-methyl-1-(3-(5-(trifluoromethyl)-1H-pyrazol-4-yl)-1H-pyrazolo [3,4-b]pyrazin-6-yl)piperidin-4-yl) methyl carbamate To a solution of the crude product from the previous step (120 mg, 0.24 mmol) in EtOH (10 mL) was added hydrazine hydrate (23 mg, 0.46 mmol). The resulting mixture was refluxed under $N_2$ for 2 h. The solvent was removed to give the crude title compound as a yellow solid (100 mg) which was used directly without further purification.

MS (ES+) $C_{21}H_{27}F_3N_8O_2$ requires: 480, found: 481[M+H]+.

(4-Methyl-1-(3-(5-(trifluoromethyl)-1H-pyrazol-4-yl)-1H-pyrazolo[3,4-b]-pyrazine-6-yl)piperidin-4-yl)methanamine A solution of the product from the previous step (100 mg, 0.2 mmol) in TFA (5 mL) was stirred at RT for 4 h, then concentrated under reduced pressure. The residue was purified by Prep-HPLC to give the title compound as yellow solid (25.3 mg, yield 32%).

MS (ES+) $C_{16}H_{19}F_3N_8$ requires: 380, found: 381 [M+H]+. 1H NMR (500 MHz, DMSO) δ 13.83 (s, 1H), 13.14 (s, 1H), 8.55 (s, 1H), 8.46 (s, 1H), 7.70 (s, 3H), 4.02 (d, J=15.0 Hz, 2H), 3.49 (d, J=9.9 Hz, 2H), 2.80 (d, J=5.6 Hz, 2H), 1.55 (d, J=9.7 Hz, 2H), 1.46 (s, 2H), 1.09 (s, 3H).

EXAMPLE 104

4-(6-(4-(Aminomethyl)-4-methylpiperidin-1-yl)-1H-pyrazolo[3,4-b]pyrazin-3-yl)-3-chloro-N-methylpyridin-2-amine

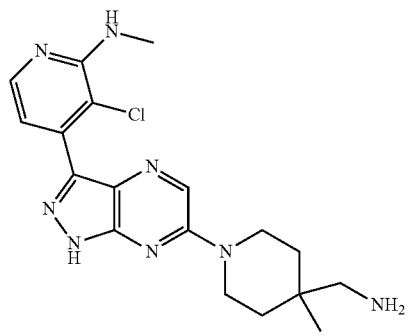 [SMILES: CNc1nccc(-c2n[nH]c3nc(N4CCC(C)(CN)CC4)cnc23)c1Cl]

tert-Butyl (1-(6-chloro-5(3-chloro-2-(methylamino)isonicotinoyl)pyrazine-2-yl)-4-methylpiperidin-4-yl)methyl carbamate To a solution of Intermediate 113 (63.2 mg, 0.2 mmol) in DMF (2 mL) under $N_2$ was added tert-butyl (4-methylpiperidin-4-yl)methyl carbamate (45.6 mg, 0.2 mmol) and $K_2CO_3$ (55.3 mg, 0.4 mmol). The resulting mixture was stirred overnight at RT and poured into $H_2O$ (20 mL). The solid that formed was removed by filtration and dried to give the title compound as a yellow solid (120 mg) which was used directly without further purification.

MS (ES+) $C_{23}H_{30}C_{12}N_6O_3$ requires: 508, found: 509 [M+H]+.

tert-Butyl (1-(3-(3-chloro-2-(methylamino)pyridin-4-yl)-1H-pyrazolo [3,4-b]-pyrazin-6-yl)-4-methylpiperidin-4-yl) methyl carbamate To a solution of the crude product from the previous step (120 mg, 0.24 mmol) in EtOH (10 mL) was added hydrazine hydrate (23 mg, 0.46 mmol). The resulting mixture was refluxed under $N_2$ for 2 h. The solvent was removed to give the crude title compound crude as a yellow solid (100 mg) which was used directly without further purification.

MS (ES+) $C_{23}H_{31}ClN_8O_2$ requires: 486, found: 487[M+H]+.

4-(6-(4-(Aminomethyl)-4-methylpiperidin-1-yl)-1H-pyrazolo[3,4-b]pyrazin-3-yl)-3-chloro-N-methylpyridin-2-amine A solution of the product from the previous step (100 mg, 0.21 mmol) in TFA (5 mL) was stirred at RT for 2 h, then concentrated under reduced pressure. The residue was purified by Prep-HPLC to give the title compound as yellow solid (50 mg, yield 65%).

MS (ES+) $C_{18}H_{23}ClN_8$ requires: 386, found: 387 [M+H]+. 1H NMR (500 MHz, DMSO) δ 13.49 (s, 1H), 8.49 (s, 1H), 8.08 (d, J=5.2 Hz, 1H), 7.74 (s, 3H), 7.02 (d, J=5.1 Hz, 1H), 6.87 (s, 1H), 4.04-4.00 (m, 2H), 3.51 (t, J=10.1 Hz, 2H), 2.93 (s, 3H), 2.80 (d, J=6.0 Hz, 1H), 1.56 (dd, J=16.2, 6.6 Hz, 2H), 1.46 (d, J=13.8 Hz, 2H), 1.09 (s, 3H).

EXAMPLE 105

1-(3-(3-amino-2-chlorophenyl)-1H-pyrazolo[3,4-b]pyrazin-6-yl)-4-methylpiperidin-4-amine

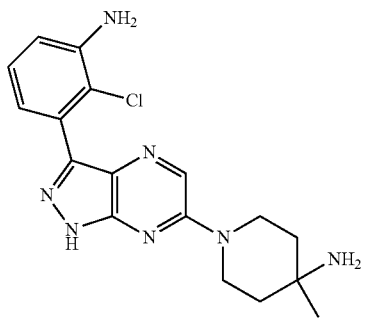 [SMILES: CC1(N)CCN(c2cnc3c(-c4cccc(N)c4Cl)n[nH]c3n2)CC1]

tert-Butyl 1-(5-(3-amino-2-chlorobenzoyl)-6-chloropyrazin-2-yl)-4-methyl-piperidin-4-yl carbamate To a solution of Intermediate 112 (30 mg, 0.1 mmol) in DMF (3 mL) under $N_2$, was added tert-butyl 4-methylpiperidin-4-yl carbamate (21 mg, 0.1 mmol) and $K_2CO_3$ (27 mg, 0.2 mmol). The resulting mixture was stirred at RT for 4 h and then poured into $H_2O$ (20 mL). The mixture was extracted with EtOAc (20 mL×3). The combined organic layers were washed with brine, dried over $Na_2SO_4$ and concentrated to give the crude title compound (43 mg), which was used directly without further purification.

MS (ES+) $C_{22}H_{27}Cl_2N_5O_3$ requires: 479, found: 480.2 [M+H]+.

tert-Butyl 1-(3-(3-amino-2-chlorophenyl)-1H-pyrazolo[3,4-b]pyrazin-6-yl)-4-methylpiperidin-4-yl carbamate To a solution of the crude product from the previous step (43 mg, 0.09 mmol) in EtOH (10 mL) was added hydrazine hydrate (9 mg, 0.18 mmol). The resulting mixture was refluxed under $N_2$ overnight. The solvent was removed to give the title compound as a yellow solid (35 mg) which was used directly without further purification.

MS (ES+) $C_{22}H_{28}ClN_7O_2$ requires: 457, found: 458.2 [M+H]+.

1-(3-(3-Amino-2-chlorophenyl)-1H-pyrazolo[3,4-b]pyrazin-6-yl)-4-methyl-piperidin-4-amine trifluoroacetate A mixture of the crude product from the previous step (35 mg) in TFA (2 mL) and DCM (2 mL) was stirred at RT for 4 h. The mixture was concentrated under reduced pressure. The residue was purified by Prep-HPLC under acidic conditions to give the title compound as a light yellow solid (15.4 mg, 33% over 3 steps).

MS (ES+) $C_{19}H_{21}ClF_3N_7O_2$ requires: 357, found: 358.2 [M+H]+. $^1$H NMR (500 MHz, DMSO-$d_6$) δ 13.29 (s, 1H), 8.44 (s, 1H), 7.98 (br, 3H), 7.11 (t, J=10.0 Hz, 1H), 6.89 (dd, J=2.0, 10.0 Hz, 1H), 6.82 (dd, J=2.0, 10.0 Hz, 1H), 4.19-4.16 (m, 2H), 3.48-3.41 (m, 2H), 1.78-1.76 (m, 4H), 1.40 (s, 3H).

EXAMPLE 106

4-(6-(4-Amino-4-methylpiperidin-1-yl)-1H-pyrazolo[3,4-b]pyrazine-3-yl)-3-chloropyridin-2-amine

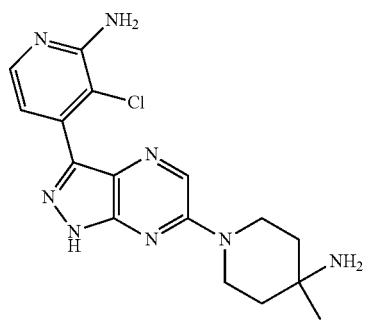 [SMILES: CC1(N)CCN(c2cnc3c(-c4ccnc(N)c4Cl)n[nH]c3n2)CC1]

tert-Butyl 1-(6-chloro-5-(3-chloro-2-(4-methoxybenzylamino)isonicotinoyl)-pyrazin-2-yl)-4-methylpiperidin-4-yl carbamate To a solution of Intermediate 108 (84 mg, 0.2 mmol) in DMF (5 mL), under $N_2$, was added tert-butyl 4-methylpiperidin-4-yl carbamate (43 mg, 0.2 mmol) and $K_2CO_3$ (55 mg, 0.4 mmol). The resulting mixture was stirred at RT for 4 h and then poured into $H_2O$ (20 mL). The mixture was extracted with EtOAc (20 mL×3). The combined organic layers were washed with brine, dried over $Na_2SO_4$ and concentrated to give the crude title compound (108 mg), which was used directly without further purification.

MS (ES+) $C_{29}H_{34}Cl_2N_6O_4$ requires: 600, found: 601.2 [M+H]+.

tert-Butyl 1-(3-(3-chloro-2-(4-methoxybenzylamino)pyridin-4-yl)-1H-pyrazolo[3,4-b]pyrazin-6-yl)-4-methylpiperidin-4-yl carbamate To a solution of the crude product from the previous step (108 mg, 0.18 mmol) in EtOH (10 mL) was added hydrazine hydrate (18 mg, 0.36 mmol). The resulting mixture was refluxed under $N_2$ overnight. The solvent was removed to give the title compound as a yellow solid (90 mg) which was used directly without further purification.

MS (ES+) $C_{29}H_{35}ClN_8O_3$ requires: 578, found: 579.2 [M+H]+.

4-(6-(4-Amino-4-methylpiperidin-1-yl)-1H-pyrazolo[3,4-b]pyrazin-3-yl)-3-chloropyridin-2-amine trifluoroacetate A mixture of the crude product from the previous step (90 mg) in TFA (2 mL) was stirred under microwave at 120° C. for 30 min. The mixture was concentrated under reduced pressure. The residue was purified by Prep-HPLC under acidic condition to give the title compound as a light yellow solid (55 mg, 56% over 3 steps).

MS (ES+) $C_{18}H_{20}ClF_3NO_2$ requires: 358, found: 359 [M+H]+. $^1$H NMR (500 MHz, DMSO-d6) δ 13.65 (s, 1H), 8.52 (s, 1H), 8.02 (d, J=5.5 Hz, 1H), 7.97 (br, 3H), 7.12 (s, 1H), 6.87 (br, 2H), 4.20-4.17 (m, 2H), 3.50-3.44 (m, 2H), 1.78-1.76 (m, 4H), 1.40 (s, 3H).

EXAMPLE 107

4-(6-(4-(Aminomethyl)-4-methylpiperidin-1-yl)-1H-pyrazolo[3,4-b]pyrazin-3-yl)-3-chloropyridin-2-amine

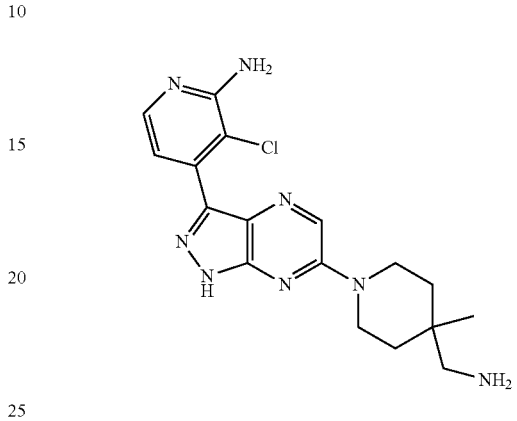

tert-Butyl (1-(6-chloro-5-(3-chloro-2-(4-methoxybenzylamino) isonicotinoyl)-pyrazin-2-yl)-4-methylpiperidin-4-yl)methyl carbamate To a solution of Intermediate 108 (84.4 mg, 0.2 mmol) in DMF (2 mL) under $N_2$ was added tert-butyl (4-methylpiperidin-4-yl)-methyl carbamate (45.6 mg, 0.2 mmol) and $K_2CO_3$ (55.3 mg, 0.4 mmol). The resulting mixture was stirred overnight at RT, then poured into $H_2O$ (20 mL). The solid that formed was removed by filtration and dried to give the title compound crude as a yellow solid (120 mg) which was used directly without further purification.

MS (ES+) $C_{30}H_{36}Cl_2N_6O_4$ requires: 614, found: 615 [M+H]+.

tert-Butyl (1-(3-(3-chloro-2-(4-methoxybenzylamino)pyridin-4-yl)-1H-pyrazolo[3,4-b]pyrazin-6-yl)-4-methylpiperidin-4-yl)methyl carbamate To a solution of the crude product from the previous step (120 mg, 0.19 mmol) in EtOH (10 mL) was added hydrazine hydrate (23 mg, 0.46 mmol). The resulting mixture was refluxed under $N_2$ for 2 h. The solvent was removed to give the title compound crude as a yellow solid (100 mg) which was used directly without further purification.

MS (ES+) $C_{30}H_{37}ClN_8O_3$ requires: 592, found: 593 [M+H]+. 4-(6-(4-(Aminomethyl)-4-methylpiperidin-1-yl)-1H-pyrazolo [3,4-b]pyrazin-3-yl)-3-chloropyridin-2-amine A mixture of the product from the previous step (100 mg, 0.16 mmol) and TFA (3 mL) was stirred at 120° C. for 20 mins with microwave irradiation, then concentrated in vacuo and purified by HPLC to give the title compound as a yellow solid (19.2 mg, yield 24%).

MS (ES+) $C_{17}H_{21}ClN_8$ requires: 372, found: 373 [M+H]+.

1H NMR (500 MHz, DMSO) δ 13.50 (s, 1H), 8.49 (s, 1H), 8.00 (d, J=5.2 Hz, 1H), 7.71 (s, 3H), 7.08 (s, 1H), 6.71-6.54 (m, 2H), 4.01 (s, 2H), 2.80 (d, J=5.8 Hz, 2H), 2.36 (s, 2H), 1.56 (s, 2H), 1.47 (s, 2H), 1.09 (s, 3H).

EXAMPLE 108

4-(6-(4-Amino-4-methylpiperidin-1-yl)-1H-pyrazolo[3,4-b]pyrazin-3-yl)-3-chloropyridin-2-amine

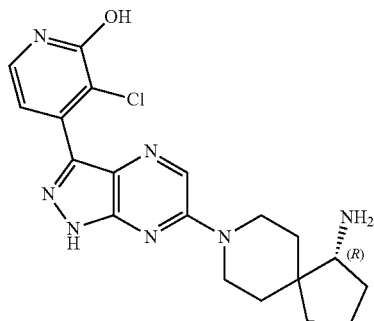

(3-Chloro-2-methoxypyridin-4-yl)(3-chloro-5-((R)-1-((R)-1-(4-methoxy-phenyl)ethylamino)-8-azaspiro[4.5]decan-8-yl)pyrazin-2-yl)methanone To a solution of Intermediate 109 (84 mg, 0.26 mmol) in DMF (5 mL), under $N_2$, was added (R)—N—((R)-1-(4-methoxyphenyl)ethyl)-8-azaspiro[4.5]decan-1-amine (76 mg, 0.26 mmol) and $K_2CO_3$ (72 mg, 0.52 mmol). The resulting mixture was stirred at RT for 4 h and then poured into $H_2O$ (20 mL). The mixture was extracted with EtOAc (20 mL×3). The combined organic layers were washed with brine, dried over $Na_2SO_4$ and concentrated to give the title compound crude as a yellow solid (130 mg) which was used directly without further purification.

MS (ES+) $C_{29}H_{33}Cl_2N_5O_3$ requires: 569, found: 570.3 [M+H]+.

(R)-8-(3-(3-Chloro-2-methoxypyridin-4-yl)-1H-pyrazolo[3,4-b]pyrazin-6-yl)-N—((R)-1-(4-methoxyphenyl)ethyl)-8-azaspiro[4.5]decan-1-amine To a solution of the crude product from the previous step (130 mg, 0.23 mmol) in EtOH (10 mL) was added hydrazine hydrate (23 mg, 0.46 mmol). The resulting mixture was refluxed under $N_2$ overnight. The solvent was removed to give the crude title compound as a yellow solid (100 mg), which was used directly without further purification.

MS (ES+) $C_{29}H_{34}ClN_7O_2$ requires: 547, found: 548.3 [M+H]+.

(R)-4-(6-(1-Amino-8-azaspiro[4.5]decan-8-yl)-1H-pyrazolo[3,4-b]pyrazin-3-yl)-3-chloropyridin-2-ol trifluoroacetate A mixture of the crude product from the previous step (100 mg) in HBr/AcOH (5 mL) was stirred at 50° C. overnight. The solvent was removed and the residue was dissolved in TFA (2 mL). The mixture was stirred under microwave at 120° C. for 30 min. The mixture was concentrated under reduced pressure. and the residue was purified by Prep-HPLC under acidic condition to give the title compound as a light yellow solid (11 mg, 8% over 3 steps).

MS (ES+) $C_{21}H_{23}ClF_3N_7O_3$ requires: 399, found: 400.2 [M+H]+. 1H NMR (500 MHz, DMSO-d6) δ 13.60 (s, 1H), 12.24 (br, 1H), 8.53 (s, 1H), 7.75 (br, 3H), 7.49 (s, 1H), 6.69 (d, J=8.0 Hz, 1H), 4.42-4.32 (m, 2H), 3.23-3.14 (m, 3H), 2.05-1.42 (m, 10H).

EXAMPLE 109

(S)-4-(6-(4-Amino-2-oxa-8-azaspiro[4.5]decan-8-yl)-1H-pyrazolo[3,4-b]pyrazin-3-yl)-3-chloropyridin-2-ol

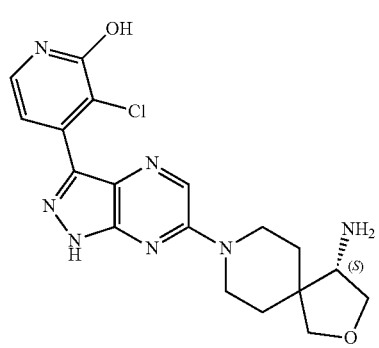

(3-Chloro-2-methoxypyridin-4-yl)(3-chloro-5-((S)-4-((R)-1-(4-methoxy-phenyl)ethylamino)-2-oxa-8-azaspiro[4.5]decan-8-yl)pyrazin-2-yl)methanone A mixture of Intermediate 109 (61 mg, 0.2 mmol), Intermediate 103 (58 mg, 0.2 mmol), $K_2CO_3$ (55 mg, 0.4 mmol) and DMF (5 mL) was stirred at RT for 1 h. The reaction was quenched with $H_2O$ (10 mL). The solid that formed was removed by filtration and dried in vacuo to give the title compound as a light solid (100 mg, yield 88%).

MS (ES+) $C_{28}H_{31}Cl_2N_5O_4$ requires: 571, found: 572 [M+H]+.

(S)-8-(3-(3-chloro-2-methoxypyridin-4-yl)-1H-pyrazolo[3,4-b]pyrazin-6-yl)-N—((R)-1-(4-methoxyphenyl)ethyl)-2-oxa-8-azaspiro[4.5]decan-4-amine A mixture of the product from the previous step (100 mg, 0.18 mmol), $N_2H_4·H_2O$ (0.5 mL) and EtOH (5 mL) was stirred at 80° C. for 2 h, concentrated in vacuo to give the titled compound as a gray solid (80 mg, yield 81%).

MS (ES+) $C_{28}H_{32}ClN_7O_3$ requires: 549, found: 550 [M+H]+.

(S)-4-(6-(4-Amino-2-oxa-8-azaspiro[4.5]decan-8-yl)-1H-pyrazolo [3,4-b]pyrazine-3-yl)-3-chloropyridin-2-ol A mixture of the product from the previous step (80 mg, 0.15 mmol) and HBr in $CH_3COOH$ (5 mL) was stirred at 80° C. for 1 h, concentrated in vacuo and purified by HPC to give the title compound as a yellow solid (20 mg, yield 42%). MS (ES+) $C_{18}H_{20}ClN_7O_2$ requires: 401, found: 402[M+H]+.

1H NMR (500 MHz, MeOD-d4) δ 8.42 (s, 1H), 7.52 (d, J=8.5 Hz, 1H), 6.80 (d, J=8.5 Hz, 1H), 4.49-4.42 (m, 2H), 4.39 (m, 1H), 4.04 (d, 1H), 3.96 (d, 1H), 3.86 (d, 1H), 3.61 (t, 1H), 3.59 (m, 1H), 1.86-1.80 (m, 4H).

EXAMPLE 110

4-(6-(4-Amino-4-(hydroxymethyl)piperidin-1-yl)-1H-pyrazolo[3,4-b]pyrazin-3-yl)-3-chloropyridin-2-ol

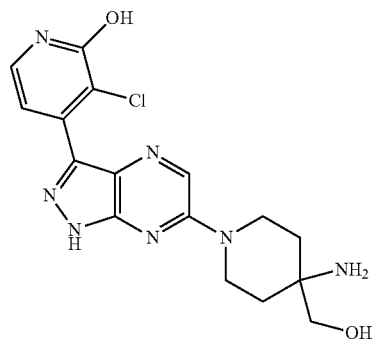 [SMILES: NC1(CO)CCN(c2cnc3c(-c4ccnc(O)c4Cl)n[nH]c3n2)CC1]

Benzyl 1-(6-chloro-5-(3-chloro-2-methoxyisonicotinoyl)pyrazin-2-yl)-4-(hydroxymethyl)piperidin-4-yl carbamate A mixture of Intermediate 109 (61 mg, 0.2 mmol), benzyl 4-(hydroxymethyl)piperidin-4-yl carbamate (52 mg, 0.2 mmol), $K_2CO_3$ (55 mg, 0.4 mmol) and DMF (5 mL) was stirred at RT for 1 h. The reaction was quenched with $H_2O$ (10 mL). The solid that formed was removed by filtration and dried in vacuo to give the title compound as a light solid (100 mg, yield 91%).

MS (ES+) $C_{25}H_{25}Cl_2N_5O_5$ requires: 545, found: 546 [M+H]+.

Benzyl 1-(3-(3-chloro-2-methoxypyridin-4-yl)-1H-pyrazolo[3,4-b]pyrazine-6-yl)-4-(hydroxymethyl)piperidin-4-yl carbamate A mixture of the product from the previous step (100 mg, 0.18 mmol), $N_2H_4 \cdot H_2O$ (0.5 mL) and EtOH (5 mL) was stirred at 80° C. for 2 h, then concentrated in vacuo to give the titled compound as a gray solid (80 mg, yield 83%).

MS (ES+) $C_{25}H_{26}ClN_7O_4$ requires: 523, found: 524 [M+H]+.

(4-Amino-1-(3-(3-chloro-2-methoxypyridin-4-yl)-1H-pyrazolo[3,4-b]pyrazin-6-yl)piperidin-4-yl)methanol A mixture of the product from the previous step (80 mg, 0.15 mmol) and TFA (5 mL) was stirred at 120° C. for 20 mins with microwave irradiation, then concentrated in vacuo to give the titled compound as a yellow oil (50 mg, yield 86%).

MS (ES+) $C_{17}H_{20}ClN_7O_2$ requires: 389, found: 390[M+H]+.

4-(6-(4-Amino-4-(hydroxymethyl)piperidin-1-yl)-1H-pyrazolo [3,4-b]pyrazin-3-yl)-3-chloropyridin-2-ol A mixture of the product from the previous step (50 mg, 0.12 mmol) and HBr in $CH_3COOH$ (2 mL) was stirred at 80° C. for 1 h, then concentrated in vacuo and purified by HPLC to give the titled compound as a yellow solid (25 mg, yield 56%).

MS (ES+) $C_{16}H_{18}ClN_7O_2$ requires: 375, found: 376[M+H]+. 1H NMR (500 MHz, MeOD-d4) δ 8.44 (s, 1H), 7.52 (d, J=8.5 Hz, 1H), 6.81 (d, J=8.5 Hz, 1H), 4.24-4.20 (m, 2H), 3.81 (s, 2H), 3.68-3.62 (m, 2H), 2.71 (s, 1H), 2.09 (m, 2H), 1.92 (m, 2H).

EXAMPLE 111

(R)-8-(3-3Chloro-2-(methylamino)pyridin-4-yl)-1H-pyrazolo[3,4-b]pyrazin-6-yl)-8-azaspiro[4.5]decan-1-amine

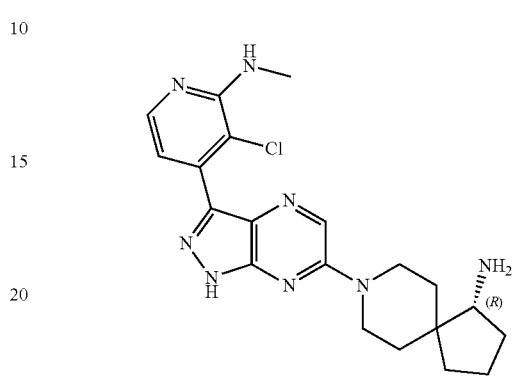

(3-Chloro-2-(methylamino)pyridin-4-yl)(3-chloro-5-((1R)-1-(1-(4-methoxy-phenyl)ethylamino)-8-azaspiro[4.5]decan-8-yl)pyrazin-2-yl)methanone To a solution of (3-chloro-2-(methylamino)pyridin-4-yl)(3,5-dichloropyrazin-2-yl)methanone (63.2 mg, 0.2 mmol) in DMF (2 mL) under nitrogen was added (1R)—N-(1-(4-methoxyphenyl)ethyl)-8-azaspiro[4.5]decan-1-amine (57.6 mg, 0.2 mmol) and $K_2CO_3$ (55.3 mg, 0.4 mmol). The resulting mixture was stirred overnight at r.t. for 1 h and then poured into water (20 mL). The solid was collected and dried to give the title compound as a yellow solid (120 mg) which was used directly without further purification.

MS (ES+) $C_{29}H_{34}Cl_2N_6O_2$ requires: 568, found: 569 [M+H]+.

(1R)-8-(3-(3-Chloro-2-(methylamino)pyridin-4-yl)-1H-pyrazolo[3,4-b]pyrazin-6-yl)-N-(1-(4-methoxyphenyl)ethyl)-8-azaspiro[4.5]decan-1-amine To a solution of the crude product from the previous step (120 mg, 0.21 mmol) in EtOH (10 mL) was added hydrazine hydrate (23 mg, 0.46 mmol). The resulting mixture was refluxed under nitrogen for 2 h. The solvent was removed to give the crude title compound as a yellow solid (100 mg) which was used directly without further purification.

MS (ES+) $C_{29}H_{35}ClN_8O$ requires: 546, found: 547[M+H]+.

(R)-8-(3-(3-Chloro-2-(methylamino)pyridin-4-yl)-1H-pyrazolo[3,4-b]pyrazin-6-yl)-8-azaspiro[4.5]decan-1-amine A solution of the product from the previous step (100 mg, 0.21 mmol) in TFA (5 mL) was stirred at RT for 2 h, then concentrated under reduced pressure. The residue was purified by Prep-HPLC to give the title compound as a yellow solid (33.3 mg, yield 65%).

MS (ES+) $C_{20}H_{25}ClN_8$ requires: 412, found: 413 [M+H]+. 1H NMR (500 MHz, DMSO) δ 13.50 (s, 1H), 8.50 (s, 1H), 8.08 (d, J=5.2 Hz, 1H), 7.78 (s, 3H), 7.00 (d, J=5.1 Hz, 1H), 6.82 (s, 1H), 4.38-4.31 (m, 2H), 3.17 (dd, J=23.7, 9.1 Hz, 3H), 2.93 (s, 3H), 2.06 (d, J=7.0 Hz, 1H), 1.85-1.40 (m, 9H).

EXAMPLE 112

4-(6-(4-Amino-4-methylpiperidin-1-yl)-1H-pyrazolo[3,4-b]pyrazin-3-yl)-3-chloro-N-methylpyridin-2-amine

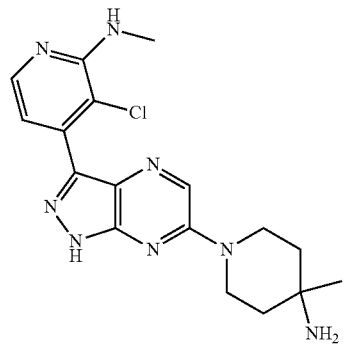 [SMILES: CNc1nccc(-c2n[nH]c3nc(N4CCC(C)(N)CC4)cnc23)c1Cl]

tert-Butyl 1-(6-chloro-5-(3-chloro-2-(methylamino)isonicotinoyl) pyrazin-2-yl)-4-methylpiperidin-4-yl carbamate To a solution of (3-chloro-2-(methylamino)pyridin-4-yl)(3,5-dichloropyrazin-2-yl)methanone (63.2 mg, 0.2 mmol) in DMF (2 mL) under $N_2$ was added tert-butyl 4-methylpiperidin-4-yl carbamate (42.8 mg, 0.2 mmol) and $K_2CO_3$ (55.3 mg, 0.4 mmol). The resulting mixture was stirred overnight at RT for 1 h and then poured into water (20 mL). The solid was collected and dried to give the title compound as a yellow solid (120 mg) which was used directly without further purification.

MS (ES+) $C_{22}H_{28}Cl_2N_6O_3$ requires: 494, found: 495 [M+H]+.

tert-Butyl 1-(3-(3-chloro-2-(methylamino)pyridin-4-yl)-1H-pyrazolo [3,4-b]pyrazin-6-yl)-4-methylpiperidin-4-yl carbamate To a solution of the crude product from the previous step (120 mg, 0.24 mmol) in EtOH (10 mL) was added hydrazine hydrate (23 mg, 0.46 mmol). The resulting mixture was refluxed under nitrogen for 2 h. The solvent was removed to give the crude title compound as a yellow solid (100 mg) which was used directly without further purification.

MS (ES+) $C_{22}H_{29}ClN_8O_2$ requires: 472, found: 473[M+H]+.

4-(6-(4-Amino-4-methylpiperidin-1-yl)-1H-pyrazolo[3,4-b]pyrazin-3-yl)-3-chloro-N-methylpyridin-2-amine A solution of the product from the previous step (100 mg, 0.21 mmol) in TFA (5 mL) was stirred at RT for 2 h, then concentrated under reduced pressure. The residue was purified by Prep-HPLC to give the title compound as a yellow solid. (15 mg, yield 20%).

MS (ES+) $C_{17}H_{21}ClN_8$ requires: 372, found: 373 [M+H]+. 1H NMR (500 MHz, DMSO) δ 13.57 (s, 1H), 8.51 (s, 1H), 8.08 (d, J=5.2 Hz, 1H), 7.97 (s, 3H), 7.00 (d, J=5.2 Hz, 1H), 6.87 (s, 1H), 4.18 (d, J=14.0 Hz, 2H), 3.49-3.37 (m, 2H), 2.93 (s, 3H), 1.77 (d, J=4.6 Hz, 4H), 1.40 (s, 3H).

EXAMPLE 113 A/B 4-(6-(4-(1-Aminoethyl)-4-methylpiperidin-1-yl)-1H-pyrazolo[3,4-b]pyrazin-3-yl)-3-chloropyridin-2-amine

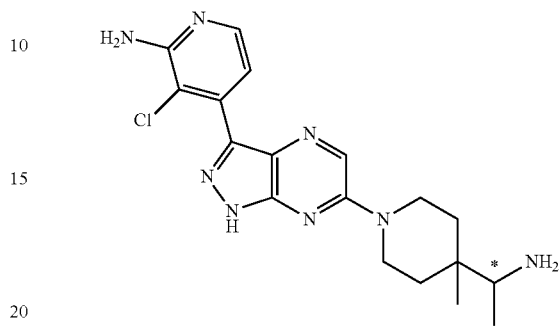

(R)—N-(1-(1-(6-chloro-5-(3-chloro-2-(4-methoxybenzylamino)isonicotinoyl)-pyrazin-2-yl)-4-methylpiperidin-4-ylethyl)-2-methylpropane-2-sulfinamide To a mixture of (R)-2-methyl-N-(1-(4-methylpiperidin-4-yl)ethyl)propane-2-sulfinamide (isomer 1: 300 mg, crude) in DMF (5 mL) was added (3-chloro-2-(4-methoxybenzylamino)pyridin-4-yl)(3,5-dichloropyrazin-2-yl)methanone (200 mg) and $K_2CO_3$ (300 mg). The mixture was stirred at RT for 2 hours. Water (20 mL) was added and the mixture was extracted with EtOAc (20 mL×3). The combined organic phases were washed with brine (20 mL) and concentrated to obtain the title compound as brown oil (500 mg, crude).

MS (ES+) $C_{30}H_{38}Cl_2N_6O_3S$ requires: 632, found: 633 [M+H]+.

The same method for isomer 2.

(R)—N-(1-(1-(3-(3-chloro-2-(4-methoxybenzylamino)pyridin-4-yl)-1H-pyrazolo[3,4-b]-pyrazin-6-yl)-4-methylpiperidin-4-yl)ethyl)-2-methylpropane-2-sulfinamide To a solution of the product from the previous step (isomer 1: 500 mg, crude) in EtOH (10 mL) was added $NH_2NH_2$ (98%, 0.5 mL). The mixture was stirred at 80° C. for 2 hours and then concentrated to obtain the title compound as a brown solid (600 mg, crude).

MS (ES+) $C_{30}H_{39}ClN_8O_2S$ requires: 611, found: 612 [M+H]+.

The same method was used for isomer 2.

4-(6-(4-(1-Aminoethyl)-4-methylpiperidin-1-yl)-1H-pyrazolo[3,4-b]pyrazin-3-yl)-3-chloropyridin-2-amine A solution of the product from the previous step (isomer 1: 600 mg, crude) in TFA (2 mL) was stirred under microwave irradiation at 120° C. for 20 min. The mixture was concentrated and dissolved in DMF purified by Pre-HPLC to obtain the title compound as a white solid (isomer 1: 40 mg; isomer 2: 42 mg).

Isomer 1 (Example 114a): MS (ES+) $C_{18}H_{23}ClN_8$ requires: 386, found: 387 [M+H]+; 1H NMR (500 MHz, DMSO) δ 8.43 (s, 1H), 7.98 (d, J=5.0 Hz, 1H), 6.99 (d, J=5.0 Hz, 1H), 6.36 (s, 2H), 4.16 (m, 2H), 3.30-3.05 (m, 3H), 2.54 (m, 1H), 1.49 (m, 3H), 1.35 (m, 1H), 1.06-0.79 (m, 6H).

Isomer 2 (Example 114b): MS (ES+) $C_{18}H_{23}ClN_8$ requires: 386, found: 387 [M+H]+; 1H NMR (500 MHz, DMSO) δ 8.43 (s, 1H), 7.98 (d, J=5.0 Hz, 1H), 6.99 (d, J=5.0 Hz, 1H), 6.37 (s, 2H), 4.18 (d, J=14.0 Hz, 2H), 3.26 (m, 2H), 2.54 (m, 1H), 1.47 (m, 3H), 1.34 (m, 1H), 1.06-0.73 (m, 6H).

EXAMPLE 114

1-(3-(2-Amino-3-chloropyridin-4-yl)-1H-pyrazolo[3,4-b]pyrazin-6-yl)-4-(aminomethyl)piperidin-4-ol

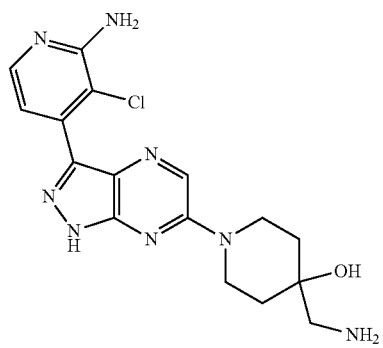 [SMILES: NCC1(O)CCN(c2cnc3c(-c4ccnc(N)c4Cl)n[nH]c3n2)CC1]

tert-Butyl (1-(6-chloro-5-(3-chloro-2-(4-methoxybenzylamino)isonicotinoyl)-pyrazin-2-yl)-4-hydroxypiperidin-4-yl)methyl carbamate To a solution of Intermediate 108 (84.4 mg, 0.2 mmol) in DMF (2 mL) under $N_2$ was added tert-butyl (4-hydroxypiperidin-4-yl)methyl carbamate (46 mg, 0.2 mmol) and $K_2CO_3$ (55.3 mg, 0.4 mmol). The result mixture was stirred overnight at RT then poured into $H_2O$ (20 mL). The solid that formed was removed via filtration and dried to give the crude title compound as a yellow solid (120 mg) which was used directly without further purification.

MS (ES+) $C_{29}H_{34}Cl_2N_6O_5$ requires: 616, found: 617 [M+H]+.

tert-Butyl (1-(3-(3-chloro-2-(4-methoxybenzylamino)pyridin-4-yl)-1H-pyrazolo [3,4-b]pyrazin-6-yl)-4-hydroxypiperidin-4-yl)methyl carbamate To a solution of the crude product from the previous step (120 mg, 0.19 mmol) in EtOH (10 mL) was added hydrazine hydrate (23 mg, 0.46 mmol). The resulting mixture was refluxed under $N_2$ for 2 h. The solvent was removed to give the crude title compound (100 mg), which was used directly without further purification.

MS (ES+) $C_{29}H_{35}ClN_8O_4$ requires: 594, found: 595 [M+H]+.

1-(3-(2-Amino-3-chloropyridin-4-yl)-1H-pyrazolo[3,4-b]pyrazin-6-yl)-4-aminomethyl)piperidin-4-ol A mixture of the product from the previous step (100 mg, 0.16 mmol) and TFA (3 mL) was stirred at 120° C. for 20 mins with microwave irradiation, then concentrated in vacuo and purified by HPLC to give the titled compound as a yellow solid (36 mg, yield 48%).

MS (ES+) $C_{16}H_{19}ClN_8O$ requires: 374, found: 375 [M+H]+. 1H NMR (500 MHz, DMSO) δ 13.55 (s, 1H), 8.52 (s, 1H), 8.00 (d, J=5.2 Hz, 1H), 7.76 (s, 3H), 7.10 (s, 1H), 6.74 (s, 2H), 5.23-5.15 (m, 1H), 4.20 (d, J=14.0 Hz, 2H), 3.45 (d, J=9.4 Hz, 2H), 2.82 (d, J=5.9 Hz, 2H), 1.64 (s, 4H).

EXAMPLE 115

7-(3-(2-Amino-3-chloropyridin-4-yl)-1H-pyrazolo[3,4-b]pyrazin-6-yl)-7-azaspiro[3.5]nonan-1-amine

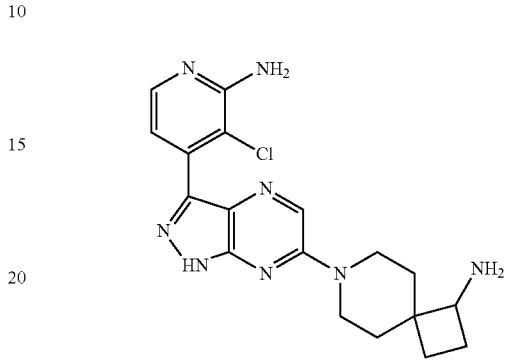

Benzyl 7-(6-chloro-5-(3-chloro-2-(4-methoxybenzylamino) isonicotinoyl)pyrazine-2-yl)-7-azaspiro[3.5]nonan-1-yl carbamate A mixture of Intermediate 108 (150 mg, 0.35 mmol), benzyl 7-azaspiro[3.5] nonan-1-yl carbamate (97 mg, 0.35 mmol), $K_2CO_3$ (193 mg, 1.4 mmol) and DMF (5 mL) was stirred at RT for 1 h. The reaction was quenched with $H_2O$ (10 mL). The solid that formed was removed by filtration and dried in vacuo to give the title compound as a light solid (200 mg, yield 87%).

MS (ES+) $C_{34}H_{34}Cl_2N_6O_4$ requires: 660, found: 661 [M+H]+.

Benzyl 7-(3-(3-chloro-2-(4-methoxybenzylamino)pyridin-4-yl)-1H-pyrazolo[3,4-b]pyrazin-6-yl)-7-azaspiro[3.5] nonan-1-yl carbamate A mixture of the product from the previous step (200 mg, 0.30 mmol), $N_2H_4·H_2O$ (1 mL) and EtOH (5 mL) was stirred at 80° C. for 2 h, then concentrated in vacuo to give the title compound (160 mg, yield 84%).

MS (ES+) $C_{34}H_{35}ClN_8O_3$ requires: 638, found: 639 [M+H]+.

7-(3-(2-amino-3-chloropyridin-4-yl)-1H-pyrazolo[3,4-b]pyrazin-6-yl)-7-azaspiro [3.5]nonan-1-amine A mixture of the product from the previous step (160 mg, 0.25 mmol) and TFA (5 mL) was stirred at 120° C. for 20 mins under microwave irradiation, then concentrated in vacuo, and purified by HPLC to give the title compound as a yellow solid (50 mg, yield 52%).

MS (ES+) $C_{18}H_{21}ClN_8$ requires: 384, found: 385[M+H]+. 1H NMR (500 MHz, MeOD-d4) δ 8.44 (s, 1H), 7.99 (d, J=6 Hz, 1H), 7.44 (d, 1H), 4.59 (d, 1H), 4.45 (d, 1H), 3.53 (m, 1H), 3.28-3.25 (m, 2H), 3.12 (m, 1H), 2.43 (m, 1H), 2.17 (m, 2H), 1.97-1.86 (m, 4H), 1.82 (m, 1H).

Chiral HPLC gave two isomers with retention times 12.13 and 14.24 mins [Column:IC (4.6*250 mm Sum), Mobile phase: n-Hexane (0.1% DEA): EtOH (0.1% DEA)=50:50, Flowrate: 1.0 mL/min, Temp. 40° C.].

EXAMPLE 116

(S)-8-(3-(2-Amino-3-chloropyridin-4-yl)-1H-pyrazolo[3,4-b]pyrazin-6-yl)-2-oxa-8-azaspiro[4.5]decan-4-amine

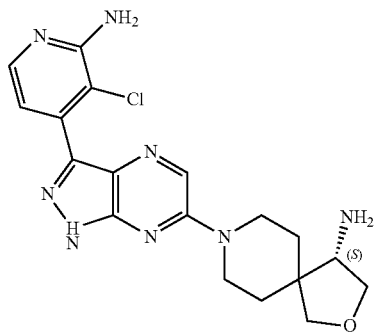

(3-Chloro-2-(4-methoxybenzylamino)pyridin-4-yl)(3-chloro-5-((S)-4-((R)-1-(4-methoxyphenyl)ethylamino)-2-oxa-8-azaspiro[4.5]decan-8-yl)pyrazin-2-yl)methanone A mixture of Intermediate 108 (84 mg, 0.2 mmol), Intermediate 103 (58 mg, 0.2 mmol), K$_2$CO$_3$ (55 mg, 0.4 mmol) and DMF (5 mL) was stirred at r.t for 1 h. The reaction was quenched with H$_2$O (10 mL), and the solid that formed was removed by filtration and dried in vacuo to give the title compound as a light solid (100 mg, yield 74%).

MS (ES+) C$_{35}$H$_{38}$Cl$_2$N$_6$O$_4$ requires: 676, found: 677 [M+H]+.

(S)-8-(3-(3-Chloro-2-(4-methoxybenzylamino)pyridin-4-yl)-1H-pyrazolo[3,4-b]pyrazin-8-yl)-N—((R)-1-(4-methoxyphenyl)ethyl)-2-oxa-8-azaspiro[4.5]decan-4-amine A mixture of (3-chloro-2-(4-methoxybenzylamino)pyridin-4-yl) (3-chloro-5-((S)-4-((R)-1-(4-methoxyphenyl)ethylamino)-2-oxa-8-azaspiro[4.5]decan-8-yl)pyrazin-2-yl)methanone (100 mg, 0.15 mmol), N$_2$H$_4$·H$_2$O (0.5 mL) and EtOH (5 mL) was stirred at 80° C. for 2 h, then concentrated in vacuo to give the titled compound as a gray solid (80 mg, yield 81%). MS (ES+) C$_{35}$H$_{39}$ClN$_8$O$_3$ requires: 654, found: 655 [M+H]+.

(S)-8-(3-(2-Amino-3-chloropyridin-4-yl)-1H-pyrazolo[3,4-b]pyrazin-6-yl)-2-oxa-8-azaspiro[4.5]decan-4-amine A mixture of (S)-8-(3-(3-chloro-2-(4-methoxybenzyl-amino)pyridin-4-yl)-1H-pyrazolo[3,4-b]pyrazin-6-yl)-N—((R)-1-(4-methoxyphenyl)ethyl)-2-oxa-8-azaspiro[4.5]decan-4-amine (80 mg, 0.12 mmol) and TFA (5 mL) was stirred at 120° C. for 20 mins under microwave irradiation, concentrated in vacuo, purified by HPLC to give the titled compound as a yellow solid (20 mg, yield 42%).

MS (ES+) C$_{18}$H$_{21}$ClN$_8$O requires: 400, found: 401[M+H]+. 1H NMR (500 MHz, MeOD-d4) δ 8.46 (s, 1H), 7.99 (d, J=9 Hz, 1H), 7.47 (d, J=9 Hz, 1H), 4.24-4.20 (m, 2H), 4.04 (m, 1H), 3.95 (t, 1H), 3.87 (t, 1H), 3.84 (t, 1H), 3.62 (t, 1H), 3.33 (m, 1H), 3.20 (m, 1H), 1.88-1.80 (m, 4H).

EXAMPLE 117

4-(6-(4-Amino-4-methylpiperidin-1-yl)-1H-pyrazolo[3,4-b]pyrazin-3-yl)-3-chloropyridin-2-ol

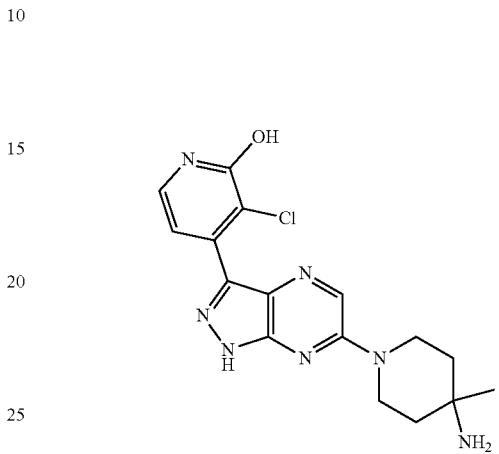

tert-Butyl 1-(6-chloro-5-(3-chloro-2-methoxyisonicotinoyl) pyrazin-2-yl)-4-methylpiperidin-4-yl carbamate To a solution of Intermediate 109 (63.7 mg, 0.2 mmol) in DMF (2 mL) under N$_2$ was added tert-butyl 4-methylpiperidin-4-yl carbamate (42.8 mg, 0.2 mmol) and K$_2$CO$_3$ (55.3 mg, 0.4 mmol). The resulting mixture was stirred overnight at RT and poured into H$_2$O (20 mL). The solid that formed was removed by filtration and dried to give the crude title compound as a yellow solid (120 mg) which was used directly without further purification.

MS (ES+) C$_{22}$H$_{27}$Cl$_2$N$_5$O$_4$ requires: 495, found: 496 [M+H]+.

tert-Butyl 1-(3-(3-chloro-2-methoxypyridin-4-yl)-1H-pyrazolo[3,4-b]pyrazine-6-yl)-4-methylpiperidin-4-yl carbamate To a solution of the crude product from the previous step (120 mg, 0.23 mmol) in EtOH (10 mL) was added hydrazine hydrate (23 mg, 0.46 mmol). The resulting mixture was refluxed under N$_2$ for 2 h. The solvent was removed to give the crude title compound as a yellow solid (100 mg) which was used directly without further purification.

MS (ES+) C$_{22}$H$_{28}$ClN$_7$O$_3$ requires: 473, found: 474[M+H]+.

4-(6-(4-Amino-4-methylpiperidin-1-yl)-1H-pyrazolo[3,4-b]pyrazin-3-yl)-3-chloropyridin-2-ol A solution of the product from the previous step (100 mg, 0.21 mmol) in HBr/CH$_3$COOH (45%, 10 mL) was stirred at 40° C. for 5 h, then concentrated under reduced pressure. The residue was purified by Prep-HPLC to give the titled compound as a yellow solid (43.2 mg, yield 60%).

MS (ES+) C$_{16}$H$_{18}$ClN$_7$O requires: 359, found: 360 [M+H]+. 1H NMR (500 MHz, DMSO) δ 13.66 (s, 1H), 12.23 (s, 1H), 8.53 (s, 1H), 7.95 (s, 3H), 6.69 (d, J=6.7 Hz, 1H), 4.19 (d, J=13.9 Hz, 2H), 3.46 (d, J=6.9 Hz, 2H), 1.77 (d, J=4.9 Hz, 4H), 1.40 (s, 3H).

EXAMPLE 118

1-(3-(2-Amino-3-chloropyridin-4-yl)-1H-pyrazolo[3,4-b]pyrazin-6-yl)-4(aminomethyl)piperidin-4-ol

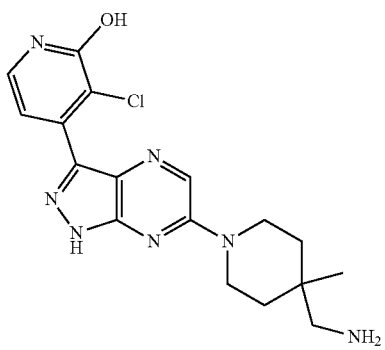 [SMILES: CC1(CN)CCN(c2cnc3c(-c4ccnc(O)c4Cl)n[nH]c3n2)CC1]

tert-Butyl (1-(6-chloro-5-(3-chloro-2-methoxyisonicotinoyl) pyrazin-2-yl)-4-methylpiperidin-4-yl)methyl carbamate To a solution of Intermediate 109 (63.7 mg, 0.2 mmol) in DMF (2 mL) under $N_2$ was added tert-butyl (4-methylpiperidin-4-yl)methyl carbamate (45.6 mg, 0.2 mmol) and $K_2CO_3$ (55.3 mg, 0.4 mmol). The resulting mixture was stirred overnight at RT and then poured into $H_2O$ (20 mL). The solid that formed was removed by filtration and dried to give the title compound crude as a yellow solid (120 mg) which was used directly without further purification.

MS (ES+) $C_{23}H_{29}Cl_2N_5O_4$ requires: 509, found: 510 [M+H]+.

tert-Butyl (1-(3-(3-chloro-2-methoxypyridin-4-yl)-1H-pyrazolo [3,4-b]pyrazine-6-yl)-4-methylpiperidin-4-yl) methyl carbamate To a solution of the crude product from the previous step (120 mg, 0.23 mmol) in EtOH (10 mL) was added hydrazine hydrate (23 mg, 0.46 mmol). The resulting mixture was refluxed under $N_2$ for 2 h. The solvent was removed to give the title compound crude as a yellow solid (100 mg), which was used directly without further purification.

MS (ES+) $C_{23}H_{30}ClN_7O_3$ requires: 487, found: 488[M+H]+.

4-(6-(4-(Aminomethyl)-4-methylpiperidin-1-yl)-1H-pyrazolo[3,4-b]pyrazin-3-yl)-3-chloropyridin-2-ol A solution of the product from the previous step (100 mg, 0.20 mmol) in HBr/$CH_3COOH$ (45%, 10 mL) was stirred at 40° C. for 5 h, then concentrated under reduced pressure. The residue was purified by Prep-HPLC to give the title compound as a yellow solid (42.3 mg, yield 56%).

MS (ES+) $C_{17}H_{20}ClN_7O$ requires: 373, found: 374 [M+H]+. 1H NMR (500 MHz, DMSO) δ 13.57 (s, 1H), 12.22 (s, 1H), 8.51 (s, 1H), 7.71 (s, 3H), 7.49 (d, J=6.8 Hz, 1H), 6.70 (d, J=6.7 Hz, 1H), 4.03 (d, J=14.1 Hz, 2H), 3.51 (t, J=10.1 Hz, 2H), 2.80 (d, J=5.8 Hz, 2H), 1.56 (t, J=9.8 Hz, 2H), 1.45 (d, J=14.3 Hz, 2H), 1.09 (s, 3H).

EXAMPLE 119

(4-Amino-1-(3-(2-amino-3-chloropyridin-4-yl)-1H-pyrazolo[3,4-b]pyrazin-6-yl)-piperidin-4-yl)methanol

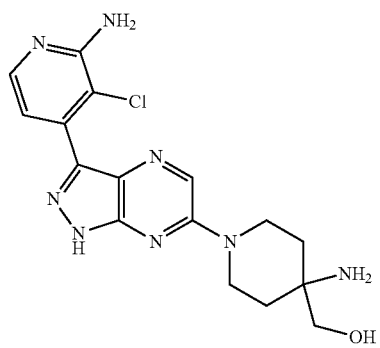 [SMILES: Nc1nccc(-c2n[nH]c3nc(N4CCC(N)(CO)CC4)cnc23)c1Cl]

Benzyl 1-(6-chloro-5-(3-chloro-2-(4-methoxybenzylamino) isonicotinoyl)-pyrazine-2-yl)-4-(hydroxymethyl)piperidin-4-yl carbamate A mixture of Intermediate 108 (84 mg, 0.2 mmol), benzyl 4-(hydroxymethyl)piperidin-4-yl carbamate (52 mg, 0.2 mmol), $K_2CO_3$ (55 mg, 0.4 mmol) and DMF (5 mL) was stirred at rt for 1 h. The reaction was quenched with $H_2O$ (10 mL). The solid that formed was removed by filtration and dried in vacuo to give the title compound as a light solid (100 mg, yield 77%).

MS (ES+) $C_{32}H_{32}Cl_2N_6O_5$ requires: 650, found: 651 [M+H]+.

Benzyl 1-(3-(3-chloro-2-(4-methoxybenzylamino)pyridin-4-yl)-1H-pyrazolo [3,4-b]pyrazin-6-yl)-4-(hydroxymethyl)piperidin-4-yl carbamate A mixture of the product from the previous step (100 mg, 0.15 mmol), $N_2H_4 \cdot H_2O$ (0.5 mL) and EtOH (5 mL) was stirred at 80° C. for 2 h. The mixture was concentrated in vacuo to give the title compound as a gray solid (90 mg, yield 96%).

MS (ES+) $C_{32}H_{33}ClN_8O_4$ requires: 628, found: 629 [M+H]+.

(4-Amino-1-(3-(2-amino-3-chloropyridin-4-yl)-1H-pyrazolo [3,4-b]pyrazin-6-yl)piperidin-4-yl)methanol A mixture of the product from the previous step and TFA (5 mL) was stirred at 120° C. for 20 min with microwave irradiation, concentrated in vacuo and purified by HPLC to give the titled compound as a yellow solid (30 mg, yield 58%).

MS (ES+) $C_{16}H_{19}ClN_8O$ requires: 374, found: 375 [M+H]+. 1H NMR (500 MHz, MeOD-d4) δ 8.48 (s, 1H), 7.99 (d, J=6 Hz, 1H), 7.46 (d, J=6 Hz, 1H), 4.24 (dd, J=14.5 Hz, 1H), 3.81 (s, 2H), 3.69 (dd, J=14.5 Hz, 2H), 2.09 (d, J=18 Hz, 1H), 1.91 (d, J=18 Hz, 2H).

EXAMPLE 120

4-(6-(4-(Aminomethyl)-4-hydroxypiperidin-1-yl)-1H-pyrazolo[3,4-b]pyrazin-3-yl)-3-chloropyridin-2-ol

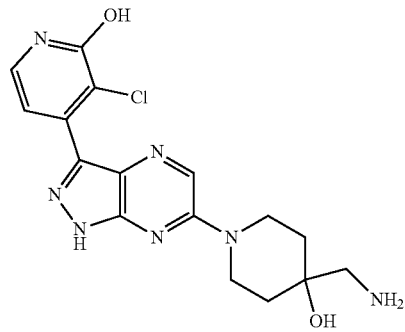 [SMILES: NCC1(O)CCN(c2cnc3c(-c4ccnc(O)c4Cl)n[nH]c3n2)CC1]

tert-Butyl (1-(6-chloro-5-(3-chloro-2-methoxyisonicotinoyl) pyrazin-2-yl)-4-hydroxypiperidin-4-yl)methyl carbamate To a solution of Intermediate 109 (63.7 mg, 0.2 mmol) in DMF (2 mL) under $N_2$ was added tert-butyl (4-hydroxypiperidin-4-yl)methyl carbamate (46 mg, 0.2 mmol) and $K_2CO_3$ (55.3 mg, 0.4 mmol). The resulting mixture was stirred overnight at RT and poured into $H_2O$ (20 mL). The solid that formed was removed by filtration and dried to give the crude title compound as a yellow solid (120 mg) which was used directly without further purification.

MS (ES+) $C_{22}H_{27}Cl_2N_5O_5$ requires: 511, found: 512 [M+H]+.

tert-Butyl (1-(3-(3-chloro-2-methoxypyridin-4-yl)-1H-pyrazolo[3,4-b]pyrazine-6-yl)-4-hydroxypiperidin-4-yl) methyl carbamate To a solution of the crude product from the previous step (120 mg, 0.19 mmol) in EtOH (10 mL) was added hydrazine hydrate (23 mg, 0.46 mmol). The result mixture was refluxed under $N_2$ for 2 h. The solvent was removed to give the crude title compound as a yellow solid (100 mg) which was used directly without further purification.

MS (ES+) $C_{22}H_{28}ClN_7O_4$ requires: 489, found: 490[M+H]+.

4-(6-(4-(Aminomethyl)-4-hydroxypiperidin-1-yl)-1H-pyrazolo[3,4-b]pyrazine-3-yl)-3-chloropyridin-2-ol A solution of the product from the previous step (100 mg, 0.21 mmol) in HBr/CH₃COOH (45%, 10 mL) was stirred at 40° C. for 5 h, then concentrated under reduced pressure. The residue was purified by Prep-HPLC to give the title compound as a yellow solid (11 mg, yield 15%).

MS (ES+) $C_{16}H_{18}ClN_7O_2$ requires: 375, found: 376 [M+H]+. 1H NMR (500 MHz, MeOD) δ 8.41 (s, 1H), 7.51 (d, J=6.7 Hz, 1H), 6.81 (d, J=6.7 Hz, 1H), 4.37 (d, J=13.6 Hz, 2H), 3.62-3.49 (m, 2H), 2.96 (s, 2H), 1.90-1.67 (m, 4H).

EXAMPLE 121

(4-Amino-1-(3-(2-chloro-6-fluorophenyl)-1H-pyrazolo[3,4-b]pyrazin-6-yl)-piperidin-4-yl)methanol

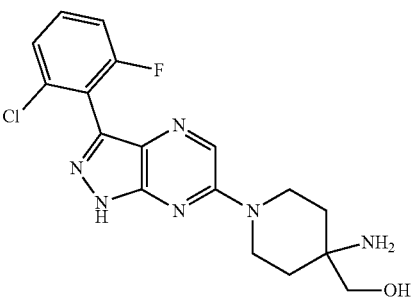 [SMILES: NC1(CO)CCN(c2cnc3c(-c4c(F)cccc4Cl)n[nH]c3n2)CC1]

(3-Chloro-5-(4-(hydroxymethyl)-4-(4-methoxybenzylamino)piperidin-1-yl)pyrazin-2-yl)(2-chloro-6-fluorophenyl)methanone To a solution of (2-chloro-6-fluorophenyl)(3,5-dichloropyrazin-2-yl)methanone (73 mg, 0.24 mmol) in DMF (5 mL) under $N_2$ was added (4-(4-methoxy benzylamino)piperidin-4-yl)methanol dihydrochloride (78 mg, 0.24 mmol) and $K_2CO_3$ (136 mg, 0.96 mmol). The resulting mixture was stirred at RT for 4 h and then poured into $H_2O$ (20 mL). The mixture was extracted with EtOAc (20 mL×3). The combined organic layers were washed with brine, dried over $Na_2SO_4$ and concentrated to give the title compound crude as a yellow solid (103 mg), which was used directly without further purification.

MS (ES+) $C_{25}H_{25}Cl_2FN_4O_3$ requires: 518, found: 519 [M+H]+.

(1-(3-(2-Chloro-6-fluorophenyl)-1H-pyrazolo[3,4-b] pyrazin-6-yl)-4-(4-methoxybenzylamino)piperidin-4-yl) methanol To a solution of the crude product from the previous step (103 mg, 0.2 mmol) in EtOH (10 mL) was added hydrazine hydrate (20 mg, 0.4 mmol). The resulting mixture was refluxed under $N_2$ for 3 days. The solvent was removed to give the title compound crude as a yellow solid (90 mg), which was used directly without further purification.

MS (ES+) $C_{25}H_{26}ClFN_6O_2$ requires: 496, found: 497.2 [M+H]+.

(4-Amino-1-(3-(2-chloro-6-fluorophenyl)-1H-pyrazolo[3,4-b]pyrazin-6-yl)-piperidin-4-yl)methanol trifluoroacetate A mixture of the crude product from the previous step (90 mg) in TFA (2 mL) was stirred under microwave at 120° C. for 30 min. The mixture was concentrated under reduced pressure. The residue was purified by Prep-HPLC under acidic conditions to give the title compound as a light yellow solid (16 mg, 14% over 3 steps).

MS (ES+) $C_{19}H_{19}ClF_4N_6O_3$ requires: 376, found: 377.1 [M+H]+. ¹H NMR (500 MHz, CD₃OD) δ 8.26 (s, 1H), 7.43-7.41 (m, 1H), 7.33 (d, J=8.5 Hz, 1H), 7.15 (t, J=8.5 Hz, 1H), 4.12-4.09 (m, 2H), 3.69 (s, 2H), 3.55-3.50 (m, 2H), 1.97-1.93 (m, 2H), 1.75-1.73 (s, 2H).

EXAMPLE 122

3-(2,3-Dichlorophenyl)-6-(2,8-diazaspiro[4.5]decan-8-yl)-1H-pyrazolo[3,4-b]pyrazine

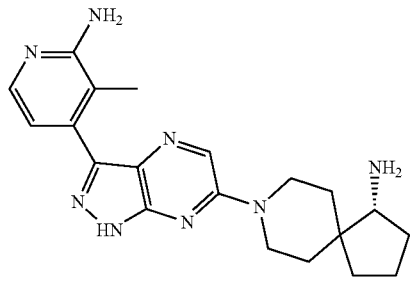 [SMILES: Cc1c(-c2n[nH]c3nc(N4CCC5(CCC[C@H]5N)CC4)cnc23)ccnc1N]

(3-Chloro-5-((R)-1-((R)-1-(4-methoxyphenyl)ethylamino)-8-azaspiro[4.5]decan-8-yl)pyrazin-2-yl)(2-(4-methoxybenzylamino)-3-methylpyridin-4-yl)methanone To a solution of (3,5-dichloropyrazin-2-yl)(2-(4-methoxybenzylamino)-3-methyl pyridin-4-yl)methanone (180 mg, 0.45 mmol) in DMF (2 mL) was added (R)—N—((R)-1-(4-methoxyphenyl)ethyl)-8-azaspiro[4.5]decan-1-amine (161 mg, 0.45 mmol) and K$_2$CO$_3$ (247 mg, 1.8 mmol). The resulting mixture was stirred at RT for 2 h. The solvent was removed to give the crude title compound as a yellow solid (220 mg) which was used directly without further purification.

MS (ES+) C$_{37}$H$_{43}$ClN$_6$O$_3$ requires: 654, found: 655[M+H]+.

(R)-8-(3-(2-(4-Methoxybenzylamino)-3-methylpyridin-4-yl)-1H-pyrazolo[3,4-b]pyrazin-6-yl)-N—((R)-1-(4-methoxyphenyl)ethyl)-8-azaspiro[4.5]decan-1-amine To a solution of the crude product from the previous step (220 mg, 0.33 mmol) in EtOH (10 mL) was added hydrazine hydrate (23 mg, 0.46 mmol). The resulting mixture was refluxed under N$_2$ for 2 h. The solvent was removed to give the title compound crude as a yellow solid (180 mg) which was used directly without further purification.

MS (ES+) C$_{37}$H$_{44}$N$_8$O$_2$ requires: 632, found: 633 [M+H]+.

(R)-8-(3-(2-amino-3-methylpyridin-4-yl)-1H-pyrazolo[3,4-b]pyrazin-6-yl)-8-azaspiro[4.5]decan-1-amine The solution of the crude product from the previous step (180 mg, 0.28 mmol) in TFA (5 mL) was stirred at 120° C. with microwave irradiation under Ar for 20 min, then concentrated under reduced pressure. The residue was purified by Prep-HPLC under acidic condition to give the title compound as a light yellow solid (80 mg, 37% over 3 steps).

MS (ES+) C$_{22}$H$_{27}$F$_3$N$_8$O$_2$ requires: 378, found: 379 [M+H]+. $^1$H NMR (500 MHz, DMSO-d6) δ 13.77 (s, 1H), 8.57 (s, 1H), 7.97 (d, J=6.5 Hz, 1H), 7.82 (s, 5H), 7.46 (d, J=6.5 Hz, 1H), 4.36 (dd, J=8.5, 14 Hz, 1H), 3.21 (m, 4H), 2.40 (s, 3H), 2.07 (t, J=8.0 Hz, 2H), 1.3 (m, 9H).

EXAMPLE 123

4-(6-(4-amino-4-methylpiperidin-1-yl)-1H-pyrazolo[3,4-b]pyrazin-3-yl)-3-methylpyridin-2-amine

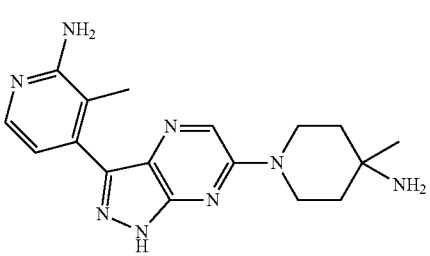 [SMILES: Cc1c(-c2n[nH]c3nc(N4CCC(C)(N)CC4)cnc23)ccnc1N]

tert-Butyl 1-(6-chloro-5-(2-(4-methoxybenzylamino)-3-methylisonicotinoyl)-pyrazin-2-yl)-4-methylpiperidin-4-ylcarbamate To a solution of (3,5-dichloropyrazin-2-yl)(2-(4-methoxybenzylamino)-3-methyl pyridin-4-yl)methanone (180 mg, 0.45 mmol) in DMF (2 mL) under N$_2$ was added tert-butyl 4-methylpiperidin-4-ylcarbamate (96 mg, 0.45 mmol) and K$_2$CO$_3$ (185 mg, 1.3 mmol). The resulting mixture was stirred at RT for 2 h, and then poured into water (20 mL). The solid was collected and dried to give the title compound crude (220 mg) which was used directly without further purification.

MS (ES+) C$_{30}$H$_{37}$ClN$_6$O$_4$ requires: 580, found: 581 [M+H]+.

tert-Butyl 1-(3-(2-(4-methoxybenzylamino)-3-methyl pyridin-4-yl)-1H-pyrazolo[3,4-b]pyrazin-6-yl)-4-methylpiperidin-4-ylcarbamate To a solution of the crude product from the previous step (220 mg, 0.38 mmol) in EtOH (10 mL) was added hydrazine hydrate (38 mg, 0.76 mmol). The resulting mixture was refluxed under nitrogen for 2 h. The solvent was removed to give the title compound crude as a yellow solid (200 mg) which was used directly without further purification.

MS (ES+) C$_{30}$H$_{38}$N$_8$O$_3$ requires: 558, found: 559 [M+H]+.

4-(6-(4-Amino-4-methylpiperidin-1-yl)-1H-pyrazolo[3,4-b]pyrazin-3-yl)-3-methylpyridin-2-amine The solution of the crude product from the previous step (200 mg, 0.36 mmol) in TFA (5 mL) was stirred at 120° C. with microwave irradiation under Ar for 20 min, then concentrated under reduced pressure. The residue was purified by Prep-HPLC under acidic condition to give the title compound as a light yellow solid (83 mg, 41% over 3 steps).

MS (ES+) C$_{19}$H$_{23}$F$_3$N$_8$O$_2$ requires: 338, found: 339 [M+H]$^+$. $^1$H NMR (500 MHz, DMSO-d6) δ 13.83 (s, 1H), 8.57 (s, 1H), 8.02 (s, 3H), 7.82-7.87 (m, 2H), 7.46 (t, 1H), 4.18 (d, J=14.0 Hz, 2H), 3.47-3.52 (m, 2H), 2.40 (s, 3H), 1.78 (d, J=5.1 Hz, 4H), 1.39 (d, J=7.9 Hz, 3H).

EXAMPLE 124

4-(6-(4-(Aminomethyl)-4-methylpiperidin-1-yl)-1H-pyrazolo[3,4-b]pyrazin-3-yl)-3-methylpyridin-2-amine

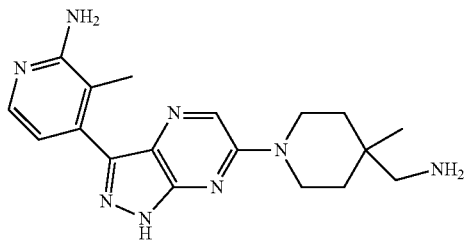 [SMILES: Cc1c(-c2n[nH]c3nc(N4CCC(C)(CN)CC4)cnc23)ccnc1N]

tert-Butyl (1-(6-chloro-5-(2-(4-methoxybenzylamino)-3-methylisonicotinoyl)-pyrazin-2-yl)-4-methylpiperidin-4-yl)methylcarbamate To a solution of (3,5-dichloro-pyrazin-2-yl)(2-(4-methoxybenzylamino)-3-methylpyridin-4-yl)methanone (180 mg, 0.45 mmol) in DMF (2 mL), under nitrogen was added tert-butyl (4-methylpiperidin-4-yl)methylcarbamate (102 mg, 0.45 mmol) and $K_2CO_3$ (185 mg, 1.3 mmol). The resulting mixture was stirred at RT for 2 h, and then poured into water (20 mL). The solid was collected and dried to give the title compound crude (220 mg) which was used directly without further purification.

MS (ES+) $C_{31}H_{39}ClN_6O_4$ requires: 594, found: 595 [M+H]+.

tert-Butyl (1-(3-(2-(4-methoxybenzylamino)-3-methylpyridin-4-yl)-1H-pyrazolo[3,4-b]pyrazin-6-yl)-4-methylpiperidin-4-yl)methylcarbamate To a solution of the crude product from the previous step (220 mg, 0.37 mmol) in EtOH (10 mL) was added hydrazine hydrate (38 mg, 0.76 mmol). The resulting mixture was refluxed under nitrogen for 2 h. The solvent was removed to give the title compound crude as a yellow solid (200 mg) which was used directly without further purification.

MS (ES+) $C_{31}H_{40}N_8O_3$ requires: 572, found: 573 [M+H]+.

4-(6-(4-(Aminomethyl)-4-methylpiperidin-1-yl)-1H-pyrazolo[3,4-b] pyrazin-3-yl)-3-methylpyridin-2-amine A solution of the crude product from the previous step (200 mg, 0.35 mmol) in TFA (5 mL) was stirred at 120° C. with microwave irradiation under Ar for 20 min, then concentrated under reduced pressure. The residue was purified by Prep-HPLC under acidic condition to give the title compound as a light yellow solid (85 mg, 41% over 3 steps).

MS (ES+) $C_{20}H_{25}F_3N_8O_2$ requires: 352, found: 353 [M+H]+. $^1$H NMR (500 MHz, DMSO-d6) δ 13.76 (s, 1H), 8.55 (s, 1H), 7.96 (d, J=8.5 Hz, 1H), 7.75-7.77 (d, J=10.0 Hz, 5H), 7.46-7.47 (d, J=7.0 Hz, 1H), 4.02 (d, J=14.1 Hz, 2H), 3.51-3.55 (m, 2H), 2.81 (d, J=5.5 Hz, 2H), 2.40 (s, 3H), 1.54 (dd, J=30.2, 20.9 Hz, 4H), 1.08 (s, 3H).

EXAMPLE 125

(R)-8-(3-(2-amino-5-chloropyridin-4-yl)-1H-pyrazolo[3,4-b]pyrazin-6-yl)-8-azaspiro[4.5]decan-1-amine

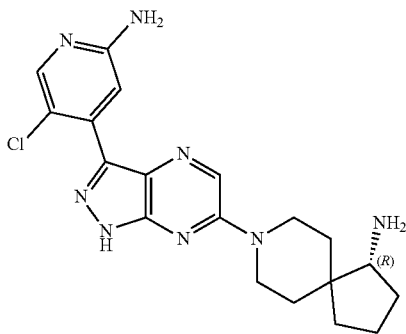

(5-Chloro-2-(4-methoxybenzylamino)pyridin-4-yl)(3-chloro-5-((R)-1-((R)-1-(4-methoxyphenyl)ethylamino)-8-azaspiro[4.5]decan-8-yl)pyrazin-2-yl)methanone To a solution of Intermediate 111 (78 mg, 0.18 mmol) in DMF (5 mL), under $N_2$, was added (R)—N—((R)-1-(4-methoxyphenyl)ethyl)-8-azaspiro[4.5]decan-1-amine (53 mg, 0.18 mmol) and $K_2CO_3$ (50 mg, 0.36 mmol). The resulting mixture was stirred at RT for 4 h and then poured into $H_2O$ (20 mL). The mixture was extracted with EtOAc (20 mL×3). The combined organic layers were washed with brine, dried over $Na_2SO_4$ and concentrated to give the title compound crude as a yellow solid (108 mg) which was used directly without further purification.

MS (ES+) $C_{36}H_{40}Cl_2N_6O_3$ requires: 674, found: 675.3 [M+H]+.

(R)-8-(3-(5-Chloro-2-(4-methoxybenzylamino)pyridin-4-yl)-1H-pyrazolo[3,4-b]pyrazin-6-yl)-N—((R)-1-(4-methoxyphenyl)ethyl)-8-azaspiro[4.5]decan-1-amine To a solution of the crude product from the previous step (108 mg, 0.16 mmol) in EtOH (10 mL) was added hydrazine hydrate (16 mg, 0.32 mmol). The resulting mixture was refluxed under $N_2$ overnight. The solvent was removed to give the title compound crude as a yellow solid (100 mg), which was used directly without further purification.

MS (ES+) $C_{36}H_{41}ClN_8O_2$ requires: 652, found: 653.1 [M+H]+.

(R)-8-(3-(2-Amino-5-chloropyridin-4-yl)-1H-pyrazolo[3,4-b]pyrazin-6-yl)-8-azaspiro[4.5]decan-1-amine trifluoroacetate A mixture of the crude product from the previous step (100 mg) in TFA (2 mL) was stirred under microwave at 120° C. for 30 min. The mixture was concentrated under reduced pressure. The residue was purified by Prep-HPLC under acidic condition to give the titled compound as a light yellow solid (27.2 mg, 30% over 3 steps).

MS (ES+) $C_{21}H_{24}ClF_3N_8O_2$ requires: 398, found: 399.1 [M+H]+. $^1$H NMR (500 MHz, DMSO-d6) δ 13.55 (s, 1H), 8.51 (s, 1H), 8.10 (s, 1H), 7.78 (br, 3H), 7.09 (s, 1H), 6.68 (br, 2H), 4.40-4.32 (m, 2H), 3.23-3.14 (m, 3H), 2.07-1.40 (m, 10H).

EXAMPLE 126

(2S,4R)-4-Amino-8-(3-(2-amino-3-chloropyridin-4-yl)-1H-pyrazolo [3,4-b]pyrazin-6-yl)-8-azaspiro[4.5]decan-2-ol

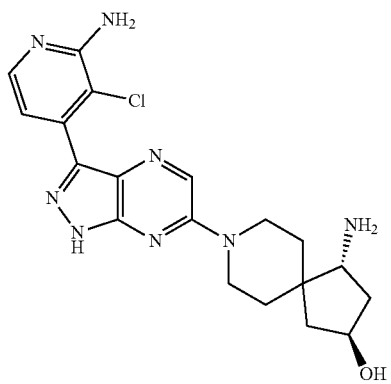 [SMILES: Nc1nccc(-c2n[nH]c3nc(N4CCC5(CC4)C[C@H](O)C[C@H]5N)cnc23)c1Cl]

(R)—N-((1R,3S)-8-(6-Chloro-5-(3-chloro-2-(4-methoxybenzylamino) isonicotinoyl)pyrazin-2-yl)-3-hydroxy-8-azaspiro[4.5]decan-1-yl)-2-methylpropane-2-sulfinamide To a solution of (R)—N-((1R,3S)-3-(tert-butyldimethylsilyloxy)-8-azaspiro-[4.5]decan-1-yl)-2-methylpropane-2-sulfinamide (40 mg, 102 µmol) and (3-chloro-2-(4-methoxy benzylamino)pyridin-4-yl)(3,5-dichloropyrazin-2-yl)methanone (43.6 mg, 102 umol) in DMF (1 mL) was added $K_2CO_3$ (44 mg, 309 µmol). The resulting mixture was stirred at RT overnight. The mixture was then diluted with water, and extracted with EtOAc (10 mL×3). The combined organic layers were washed with brine (10 mL×1), dried ($Na_2SO_4$), filtered and concentrated to obtain the title compound (40 mg, 59% yield) as a yellow solid which was used directly in the next step.

MS (ES+): $C_{31}H_{38}Cl_2N_6O_4S$ requires: 660.2, found: 661.3 [M+H]+.

N-((1R,3S)-8-(3-(3-Chloro-2-(4-methoxybenzylamino)pyridin-4-yl)-1H-pyrazolo[3,4-b]pyrazin-6-yl)-3-hydroxy-8-azaspiro[4.5]decan-1-yl)-2-methylpropane-2-sulfinamide To a solution of the product from the previous step (40 mg, 60.45 µmol) in EtOH (3 mL) was added hydrazine hydrate (302 µmol, 15 µL). The mixture was refluxed for 4 hours, then concentrated to obtain the crude title compound (32 mg, 82% yield) as a yellow solid which was used directly in the next step.

MS (ES+): $C_{31}H_{39}ClN_8O_3S$ requires: 638.3, found: 639.3 [M+H]+.

(2S,4R)-4-Amino-8-(3-(2-amino-3-chloropyridin-4-yl)-1H-pyrazolo [3,4-b]-pyrazin-6-yl)-8-azaspiro[4.5]decan-2-ol A solution of the product from the previous step (32 mg; 50.06 µmol) in TFA (1 mL) was heated at 120° C. with microwave irradiation for 20 min, cooled to RT, then concentrated. The residue was purified by Pre-HPLC to obtain the title compound (1.6 mg; 6% yield) as yellow solids.

MS (ES+): $C_{19}H_{23}ClN_8O$, requires: 414.2, found: 415.1 [M+H]+; 1H NMR (500 MHz, MeOD) δ 8.46 (s, 1H), 7.98 (s, 1H), 7.48 (d, J=6.2 Hz, 1H), 4.71-4.54 (m, 1H), 4.54-4.35 (m, 2H), 3.31-3.20 (m, 3H), 2.49-2.35 (m, 1H), 2.21-2.10 (m, 1H), 2.07-1.97 (m, 1H), 1.95-1.85 (m, 2H), 1.79 (s, 2H), 1.66-1.58 (m, 1H).

EXAMPLE 127

(1R)-(3-(3,5-dimethyl-H-pyrazol-4-yl)-1H-pyrazolo [3,4-b] pyrazin-6-yl)-8-azaspiro[4.5]decan-1-amine

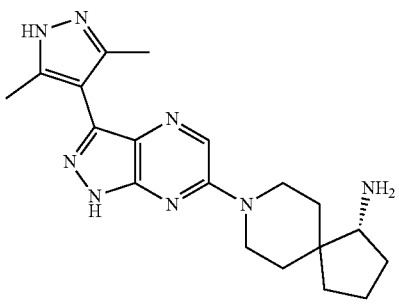 [SMILES: Cc1n[nH]c(C)c1-c1n[nH]c2nc(N3CCC4(CCC[C@H]4N)CC3)cnc12]

6-Chloro-3-iodo-1-(4-methoxybenzyl)-1H-pyrazolo[3,4-b]pyrazine A solution of 6-chloro-3-iodo-1H-pyrazolo[3,4-b]pyrazine (90 mg, 0.3 mmol) in DMF (2 mL) was added $Cs_2CO_3$ (260 mg, 0.8 mmol) and 4-methoxybenzyl chloride (75 mg, 0.5 mmol). The reaction mixture was stirred at RT overnight. The reaction mixture was diluted with EtOAc (50 mL) and washed with brine (50 ml×3). The organic layer was dried ($MgSO_4$) and concentrated in vacuo. The residue was purified by silica gel column chromatography (Petroleum ether:EtOAc=2:1) to give the title compound as a white solid (70 mg, 55%).

MS (ES+) $C_6H_5FIN$ requires: 400, found: 401 [M+H]+. 1H NMR (500 MHz, CDCl3) δ 8.45 (s, 1H), 7.30 (d, J=9.0 Hz, 2H), 6.78 (d, J=9.0 Hz, 2H), 5.50 (s, 2H), 3.71 (s, 3H).

6-Chloro-3-(3,5-dimethyl-H-pyrazol-4-yl)-1-(4-methoxybenzyl)-1H-pyrazolo[3,4-b]pyrazine A solution of the product from the previous step (60 mg, 0.15 mmol) in dioxane/$H_2O$ (6/2 mL) was treated with 3,5-dimethyl-4-(4,4,5,5-tetramethyl-1,3,2-dioxaborolan-2-yl)-1H-pyrazole (39 mg, 0.18 mmol), $PdCl_2dppf$ (20 mg, 0.03 mmol) and KOAc (36 mg, 0.36 mmol). The resulting mixture was refluxed under $N_2$ overnight, then filtered. The filtrate was concentrated under reduced pressure, and the obtained residue was purified by silica gel column chromatography (Petroleum ether:EtOAc=1:1) to give the title compound as a white solid (25 mg, 45%).

MS (ES+) $C_{18}H_{17}ClN_6O$ requires: 368, found: 369 [M+H]+.

(1R)-8-(3-(3,5-dimethyl-H-pyrazol-4-yl)-1-(4-methoxybenzyl)-1H-pyrazolo[3,4-b]pyrazin-6-yl)-N—((R)-1-(4-methoxyphenyl)ethyl)-8-azaspiro[4.5]decan-1-amine To a solution of the product from the previous step (25 mg, 0.07 mmol) in DMF (2 mL) was added (R)—N—((R)-1-(4-methoxyphenyl)ethyl)-8-azaspiro[4.5]decan-1-amine (20 mg, 0.07 mmol) and $K_2CO_3$ (28 mg, 0.2 mmol). The resulting mixture was stirred at RT overnight, then filtered. The solvent was removed to give the crude title compound as a yellow solid (18 mg) which was used directly without further purification.

MS (ES+) $C_{36}H_{44}N_8O_2$ requires: 620, found: 621 [M+H]+.

(1R)-8-(3-(3,5-dimethyl-1H-pyrazol-4-yl)-1H-pyrazolo[3,4-b]pyrazin-6-yl)-8-azaspiro[4.5]decan-1-amine A mixture of the crude product from the previous step (18 mg, 0.03 mmol) and TFA (2 mL) was stirred at 120° C. with microwave irradiation under Ar for 20 min, then concentrated under reduced pressure. The residue was purified by Prep- HPLC under acidic conditions to give the title compound as a white solid (7 mg, 28% over 2 steps).

MS (ES+) $C_{19}H_{26}N_8$ requires: 366, found: 367 [M+H]+. 1H NMR (500 MHz, CD30D-d4) δ 8.36 (s, 1H), 4.52 (d, J=13.5 Hz, 1H), 4.45 (d, J=13 Hz, 1H), 3.25-3.30 (m, 4H), 2.40 (s, 6H), 2.23-2.30 (m, 1H), 1.17-1.98 (m, 10H).

EXAMPLE 128

4-amino-1-(3-(2-amino-3-chloropyridin-4-yl)-1H-pyrazolo[3,4-b] pyrazin-6-yl)-piperidine-4-carboxamide

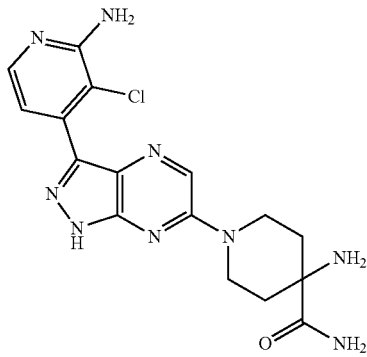 [SMILES: NC(=O)C1(N)CCN(c2cnc3c(-c4ccnc(N)c4Cl)n[nH]c3n2)CC1]

4-Amino-1-(6-chloro-5-(3-chloro-2-(4-methoxybenzylamino)isonicotinoyl)-pyrazin-2-yl)piperidine-4-carboxamide To a solution of (3-chloro-2-(4-methoxy-benzylamino)pyridin-4-yl)(3,5-dichloro pyrazin-2-yl)methanone (30 mg, 0.07 mmol) in DMF (1.5 mL) under nitrogen was added 4-aminopiperidine-4-carboxamide dihydrochloride (15 mg, 0.07 mmol) and $K_2CO_3$ (48 mg, 0.35 mmol). The resulting mixture was stirred at RT for 12 h and then poured into water (20 mL). The mixture was then extracted with EtOAc (30 mL×2). The combined organic layers were washed with brine (20 mL), dried over anhydrous $Na_2SO_4$, and concentrated, and the crude product was purified by flash chromatography (DCM:MeOH=10:1) to give the title compound as a yellow solid (13 mg).

MS (ES+) $C_{24}H_{25}Cl_2N_7O_3$ requires: 529, found: 530[M+H]+.

4-Amino-1-(3-(3-chloro-2-(4-methoxybenzylamino)pyridin-4-yl)-1H-pyrazolo[3,4-b]pyrazin-6-yl)piperidine-4-carboxamide To a solution of the crude product from the previous step (12 mg, 0.022 mmol) in EtOH (1.7 mL) was added hydrazine hydrate (98%, 2.4 mg, 0.044 mmol). The resulting mixture was refluxed under $N_2$ for 2 h. The solvent was removed to give the title compound crude as a yellow solid (7 mg, yield 63%) which was used directly without further purification.

MS (ES+) $C_{24}H_{26}ClN_9O_2$ requires: 507, found: 508 [M+H]+.

4-Amino-1-(3-(2-amino-3-chloropyridin-4-yl)-1H-pyrazolo[3,4-b] pyrazin-6-yl)piperidine-4-carboxamide A mixture of the product from the previous step (6 mg, 0.012 mmol) in TFA (1.5 mL) was stirred at 120° C. for 30 min under microwave irradiation, then concentrated in vacuo and purified by HPLC to give the title compound as a white solid. (2 mg, yield 43%).

MS (ES+) $C_{16}H_{18}ClN_9O$ requires: 387, found: 388[M+H]+. 1H NMR (500 MHz, MeOD) δ 8.39 (s, 1H), 7.99 (d, J=5.1 Hz, 1H), 7.00 (d, J=5.2 Hz, 1H), 4.29 (d, J=13.6 Hz, 2H), 3.63 (t, J=10.8 Hz, 2H), 2.20 (d, J=10.1 Hz, 2H), 1.65 (d, J=13.5 Hz, 2H).

EXAMPLE 129

(R)-8-(3-(2-amino-5-methylpyridin-4-yl)-1H-pyrazolo[3,4-b] pyrazin-6-yl)-8-azaspiro[4.5]decan-1-amine

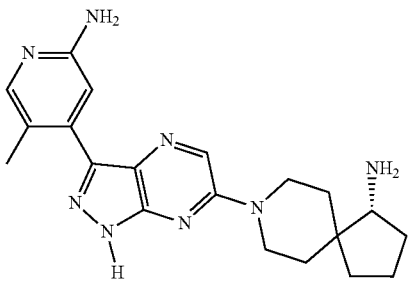 [SMILES: Cc1cnc(N)cc1-c1n[nH]c2nc(N3CCC4(CCC[C@H]4N)CC3)cnc12]

(3-Chloro-5-((R)-1-((R)-1-(4-methoxyphenyl)ethylamino)-8-azaspiro [4.5]decan-8-yl)pyrazin-2-yl)(2-(4-methoxybenzylamino)-5-methylpyridin-4-yl)methanone To a solution of (3,5-dichloropyrazin-2-yl)(2-(4-methoxybenzylamino)-5-methyl pyridin-4-yl)methanone (20 mg, 0.05 mmol) in DMF (2 mL) was added (R)—N—((R)-1-(4-methoxyphenyl)ethyl)-8-azaspiro[4.5]decan-1-amine (19 mg, 0.05 mmol) and $K_2CO_3$ (30 mg, 0.2 mmol), and the resulting mixture was stirred at RT for 2 h. The solvent was removed to give the title compound crude as a brown oil (100 mg) which was used directly without further purification.

MS (ES+) $C_{37}H_{43}ClN_6O_3$ requires: 654, found: 655[M+H]+.

(R)-8-(3-(2-(4-Methoxybenzylamino)-5-methylpyridin-4-yl)-1H-pyrazolo[3,4-b]pyrazin-6-yl)-N—((R)-1-(4-methoxyphenyl)ethyl)-8-azaspiro[4.5]decan-1-amine To a solution of the crude product from the previous step (100 mg) in EtOH (5 mL) was added hydrazine hydrate (0.5 ml). The resulting mixture was refluxed under $N_2$ for 2 h. The solvent was removed to give the title compound as a brown oil (100 mg, crude) which was used directly without further purification.

MS (ES+) $C_{37}H_{44}N_8O_2$ requires: 632, found: 633 [M+H]+.

(R)-8-(3-(2-Amino-5-methylpyridin-4-yl)-1H-pyrazolo[3,4-b]pyrazin-6-yl)-8-azaspiro[4.5]decan-1-amine A mixture of the crude product (100 mg) and TFA (2 mL) was stirred at 120° C. with microwave irradiation under Ar for 20 min, then concentrated under reduced pressure. The residue was purified by Prep-HPLC to give the title compound as a white solid (1 mg).

MS (ES+) $C_{22}H_{27}F_3N_8O_2$ requires: 378, found: 379 [M+H]+. 1H NMR (500 MHz, MeOD) δ 8.36 (s, 1H), 7.87 (s, 1H), 7.11 (s, 1H), 4.56-4.29 (m, 2H), 3.26 (t, J=7.9 Hz, 2H), 2.90 (t, J=7.3 Hz, 1H), 2.32 (s, 3H), 2.21-1.28 (m, 10H).

TABLE 9

Examples 130-138. The following compounds were synthesized using methods as set forth previously.

| | Name | Structure | Spectral data |
|---|---|---|---|
| 130 | (1R)-8-[3-(2-amino-3-chloropyridin-4-yl)-1H-pyrazolo[3,4-b]pyrazin-6-yl]-8-azaspiro[4.5]decan-1-amine | 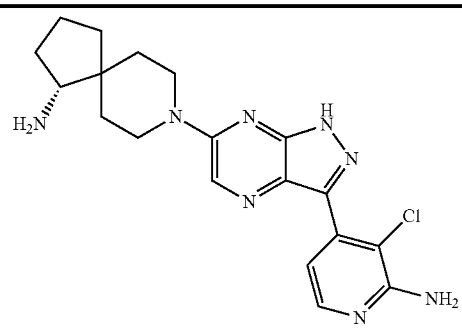 | MS (ES+) $C_{21}H_{24}ClF_3N_8O_2$ requires: 398, found: 399.3 [M + H]+. $^1$H NMR (400 MHz, DMSO-d6) δ 13.61 (s, 1H), 8.53 (s, 1H), 8.01 (d, J = 5.6 Hz, 1H), 7.78 (br, 3H), 7.13 (d, J = 5.2 Hz, 1H), 6.88 (br, 2H), 4.40-4.32 (m, 2H), 3.24-3.14 (m, 3H), 2.05-1.40 (m, 10H). |
| 131 | (1R)-8-[3-(3-amino-2-chlorophenyl)-1H-pyrazolo[3,4-b]-pyrazin-6-yl]-8-aza-spiro[4.5]decan-1-amine | 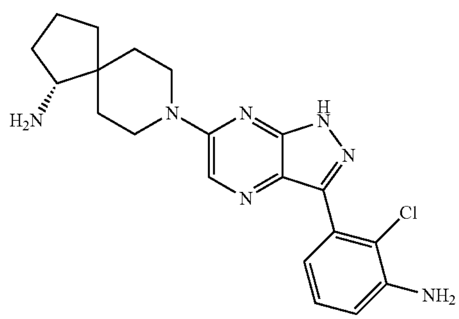 [SMILES: Nc1cccc(-c2n[nH]c3nc(N4CCC5(CCC[C@H]5N)CC4)cnc23)c1Cl] | MS (ES+) $C_{22}H_{25}ClF_3N_7O_2$ requires: 397, found: 398.2 [M + H]+. $^1$H NMR (500 MHz, DMSO-d$_6$) δ 13.20 (s, 1H), 8.43 (s, 1H), 7.75 (br, 3H), 7.11 (t, J = 8.0 Hz, 1H), 6.88 (dd, J = 1.5, 8.0 Hz, 1H), 6.82 (dd, J = 1.5, 8.0 Hz, 1H), 5.50 (br, 2H), 4.41-4.30 (m, 2H), 3.22-3.11 (m, 3H), 2.05-1.39 (m, 10H). |
| 132 | 3-{6-[4-(amino-methyl)-4-methyl-piperidin-1-yl]-1H-pyrazolo[3,4-b]-pyrazin-3-yl}-2-chloroaniline | 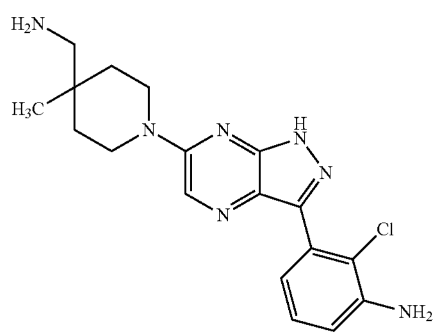 [SMILES: CC1(CN)CCN(c2cnc3c(-c4cccc(N)c4Cl)n[nH]c3n2)CC1] | MS (ES+) $C_{20}H_{23}ClF_3N_7O_2$ requires: 371, found: 372.2 [M + H]+. $^1$H NMR (500 MHz, DMSO-d$_6$) δ 13.21 (s, 1H), 8.41 (s, 1H), 7.77 (br, 3H), 7.11 (t, J = 8.0 Hz, 1H), 6.88 (dd, J = 1.5, 8.0 Hz, 1H), 6.82 (dd, J = 1.5, 8.0 Hz, 1H), 5.11 (br, 2H), 4.02-3.99 (m, 2H), 3.51-3.47 (m, 2H), 2.81-2.79 (m, 2H), 1.56-1.46 (m, 4H), 1.09 (s, 1H). |
| 133 | 4-{6-[4-(amino-methyl)-4-methyl-piperidin-1-yl]-1H-pyrazolo[3,4-b]-pyrazin-3-yl}-5-chloropyridin-2-amine | 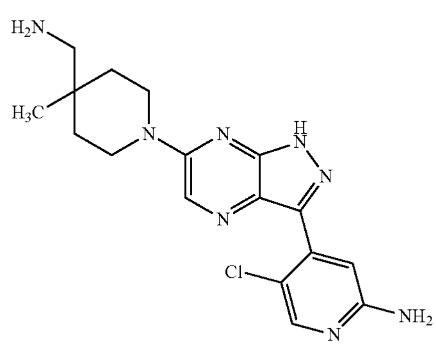 [SMILES: CC1(CN)CCN(c2cnc3c(-c4cc(N)ncc4Cl)n[nH]c3n2)CC1] | MS (ES+) $C_{19}H_{22}ClF_3N_8O_2$ requires: 372, found: 373.1 [M + H]+. $^1$H NMR (500 MHz, DMSO-d$_6$) δ 13.53 (s, 1H), 8.49 (s, 1H), 8.10 (s, 1H), 7.73 (br, 1H), 7.09 (s, 1H), 6.72 (br, 2H), 4.04-4.01 (m, 2H), 3.54-3.49 (m, 2H), 2.81-2.79 (m, 2H), 1.59-1.44 (m, 4H), 1.09 (s, 3H). |

TABLE 9-continued

Examples 130-138. The following compounds were synthesized using methods as set forth previously.

| Name | Structure | Spectral data |
| --- | --- | --- |
| 134 | 1-[3-(2-amino-5-chloropyridin-4-yl)-1H-pyrazolo[3,4-b]pyrazin-6-yl]-4-(aminomethyl)-piperidin-4-ol | | MS (ES+) $C_{18}H_{20}ClF_3N_8O_3$ requires: 374, found: 375.1 [M + H]+. $^1$H NMR (500 MHz, DMSO-d$_6$) δ 13.54 (s, 1H), 8.51 (s, 1H), 8.09 (s, 1H), 7.77 (br, 1H), 7.07 (s, 1H), 6.65 (br, 2H), 5.20 (br, 1H), 4.21-4.18 (m, 2H), 3.49-3.43 (m, 2H), 2.82-2.81 (m, 2H), 1.64-1.60 (m, 4H). |
| 135 | 4-[6-(4-amino-4-ethylpiperidin-1-yl)-1H-pyrazolo[3,4-b]pyrazin-3-yl]-3-chloropyridin-2-amine | | MS (ES+) $C_{19}H_{22}ClF_3N_8O_2$ requires: 372, found: 373.1 [M + H]+. 1H NMR (500 MHz, DMSO-d6) δ 13.66 (s, 1H), 8.52 (s, 1H), 8.02 (d, J = 5.5 Hz, 1H), 7.94 (br, 3H), 7.13 (d, J = 5.5 Hz, 1H), 6.92 (br, 2H), 4.03-3.99 (m, 2H), 3.66-3.61 (m, 2H), 1.85-1.73 (m, 6H), 0.94 (t, J = 7.5 Hz, 3H). |
| 136 a | 7-[3-(2-amino-3-chloropyridine-4-yl)-1H-pyrazolo[3,4-b]pyrazin-6-yl]-7-azaspiro[3.5]nonan-1-amine, enantiomer 1 | | Exact mass 384 |
| 136 b | 7-[3-(2-amino-3-chloropyridin-4-yl)-1H-pyrazolo[3,4-b]pyrazin-6-yl]-7-azaspiro[3.5]nonan-1-amine, enantiomer 2 | | Exact mass 384 |

TABLE 9-continued

Examples 130-138. The following compounds were synthesized using methods as set forth previously.

| # | Name | Structure | Spectral data |
|---|------|-----------|---------------|
| 137 | (4S)-8-[3-(2-amino-5-chloropyridin-4-yl)-1H-pyrazolo[3,4-b]pyrazin-6-yl]-2-oxa-8-azaspiro[4.5]-decan-4-amine | 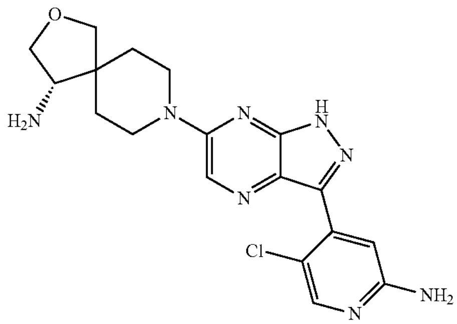 [SMILES: Nc1cc(-c2n[nH]c3nc(N4CCC5(CC4)COC[C@H]5N)cnc23)c(Cl)cn1] | MS (ES+) $C_{20}H_{22}ClF_3N_8O_3$ requires: 400, found: 401.1 [M + H]+. $^1$H NMR (500 MHz, CD$_3$OD) δ 8.34 (s, 1H), 8.01 (s, 1H), 7.45 (s, 1H), 4.37-4.27 (m, 2H), 4.12-4.09 (m, 1H), 3.91 (d, J = 9.0 Hz, 1H), 3.83 (d, J = 9.0 Hz, 1H), 3.74 (dd, J = 10.5, 2.5 Hz), 3.50-3.49 (m, 1H), 3.32-3.17 (m, 2H), 1.79-1.67 (m, 4H). |
| 138 | 4-[6-(4-amino-4-methylpiperidin-1-yl)-1H-pyrazolo[3,4-b]pyrazin-3-yl]-5-chloropyridin-2-amine | 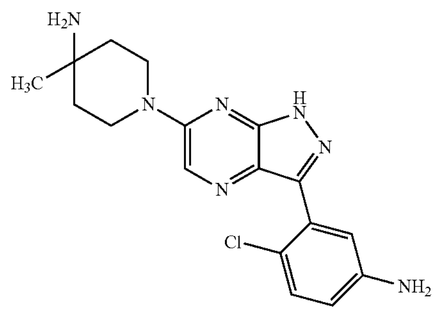 [SMILES: CC1(N)CCN(c2cnc3c(-c4cc(N)ccc4Cl)n[nH]c3n2)CC1] | MS (ES+) $C_{18}H_{20}ClF_3N_8O_2$ requires: 358, found: 359.1 [M + H]+. $^1$HNMR (500 MHz, CD$_3$OD) δ 8.49 (s, 1H), 8.13 (s, 1H), 7.52 (s, 1H), 4.35-4.35 (m, 2H), 3.58-3.54 (m, 2H), 1.95-1.92 (m, 4H), 1.55 (s, 3H). |

The following compounds can generally be made using the methods described above. It is expected that these compounds when made will have activity similar to those that have been prepared. The Examples may be made as free bases or as TFA salts.

| Name | Structure |
|------|-----------|
| 1-amino-8-(3-(2-amino-3-chloro-pyridin-4-yl)-1H-pyrazolo[3,4-b]pyrazin-6-yl)-8-azaspiro-[4.5]decan-2-ol | 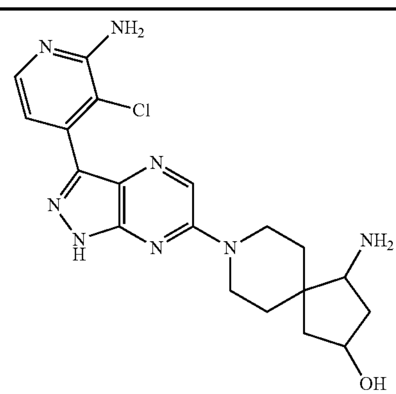 |

-continued
| Name | Structure |
|---|---|
| (4-methyl-1-(3-(2-amino-6-chloropyridin-4-yl)-1H-pyrazolo-[3,4-b]pyrazin-6-yl)piperidin-4-yl)methanamine | 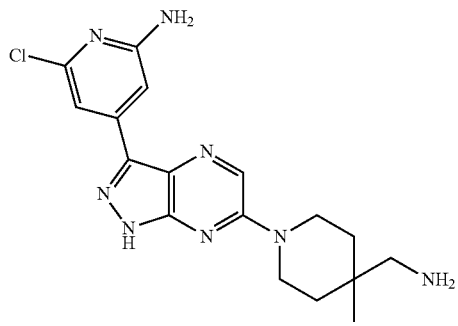 [SMILES: CC1(CN)CCN(c2cnc3c(-c4cc(N)nc(Cl)c4)n[nH]c3n2)CC1] |
| (4-amino-1-(3-(2-amino-6-chloropyridin-4-yl)-1H-pyrazolo[3,4-b]pyrazin-6-yl)piperidin-4-yl)-methanol trifluoroacetate | 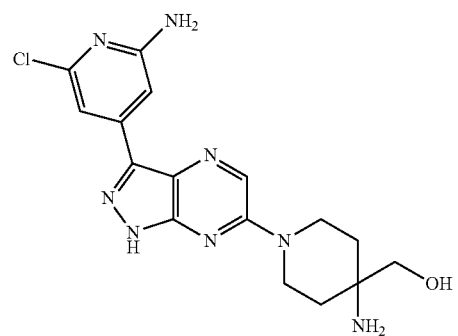 [SMILES: Nc1cc(-c2n[nH]c3nc(N4CCC(N)(CO)CC4)cnc23)cc(Cl)n1] |
| 4-(aminomethyl)-1-(3-(2-amino-6-chloropyridin-4-yl)-1H-pyrazolo[3,4-b]pyrazin-6-yl)-piperidin-4-ol | 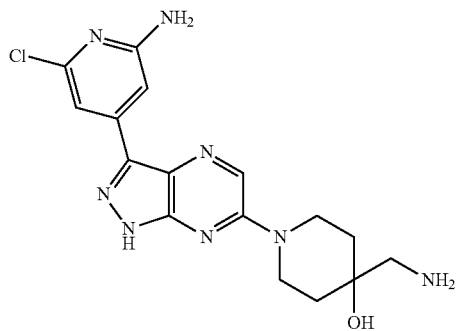 [SMILES: NCC1(O)CCN(c2cnc3c(-c4cc(N)nc(Cl)c4)n[nH]c3n2)CC1] |
| 1-(3-(2-amino-6-chloropyridin-4-yl)-1H-pyrazolo[3,4-b]pyrazin-6-yl)-4-methylpiperidin-4-amine | 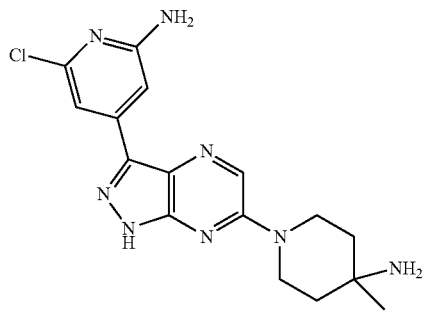 [SMILES: CC1(N)CCN(c2cnc3c(-c4cc(N)nc(Cl)c4)n[nH]c3n2)CC1] |

| Name | Structure |
|---|---|
| (S)-8-(3-(2-amino-6-chloro-pyridin-4-yl)-1H-pyrazolo[3,4-b]pyrazin-6-yl)-2-oxa-8-aza-spiro[4.5]decan-4-amine | 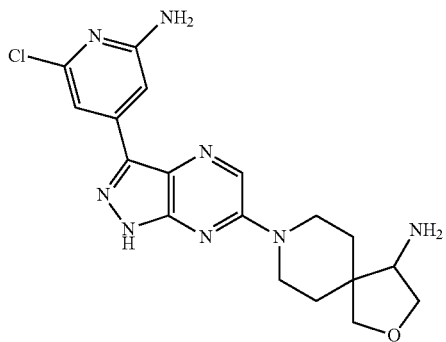 [SMILES: Nc1cc(-c2n[nH]c3nc(N4CCC5(CC4)COCC5N)cnc23)cc(Cl)n1] |
| 8-(3-(2-amino-6-chloropyridin-4-yl)-1H-pyrazolo[3,4-b]pyrazin-6-yl)-8-azaspiro[4.5]decan-1-amine | 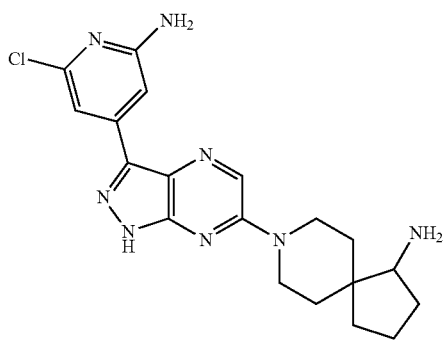 [SMILES: Nc1cc(-c2n[nH]c3nc(N4CCC5(CCCC5N)CC4)cnc23)cc(Cl)n1] |
| 1-amino-8-(3-(2-amino-6-chloro-pyridin-4-yl)-1H-pyrazolo[3,4-b]pyrazin-6-yl)-8-azaspiro-[4.5]decan-3-ol | 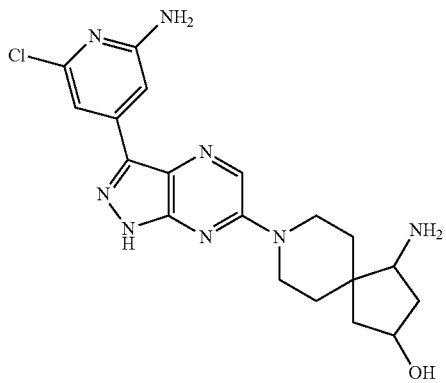 [SMILES: Nc1cc(-c2n[nH]c3nc(N4CCC5(CC4)CC(O)CC5N)cnc23)cc(Cl)n1] |
| 1-amino-8-(3-(3-chloro-2-hydroxypyridin-4-yl)-1H-pyrazolo[3,4-b]pyrazin-6-yl)-8-azaspiro[4.5]decan-1-ol | 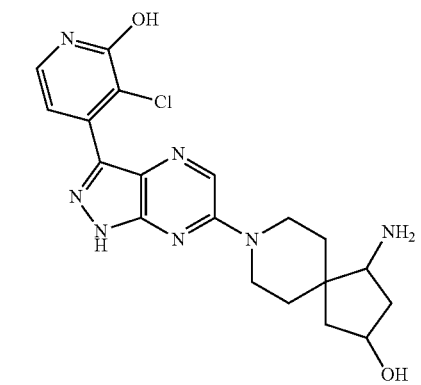 [SMILES: NC1CC(O)CC12CCN(c1cnc3c(-c4ccnc(O)c4Cl)n[nH]c3n1)CC2] |

-continued

| Name | Structure |
|---|---|
| (4-methyl-1-(3-(3-chloropyridazin-4-yl)-1H-pyrazolo[3,4-b]pyrazin-6-yl)piperidin-4-yl)-methanamine | 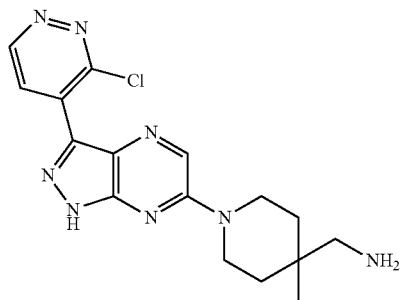 [SMILES: CC1(CN)CCN(c2cnc3c(-c4ccnnc4Cl)n[nH]c3n2)CC1] |
| (4-amino-1-(3-(3-chloropyridazin-4-yl)-1H-pyrazolo[3,4-b]pyrazin-6-yl)piperidin-4-yl)-methanol trifluoroacetate | 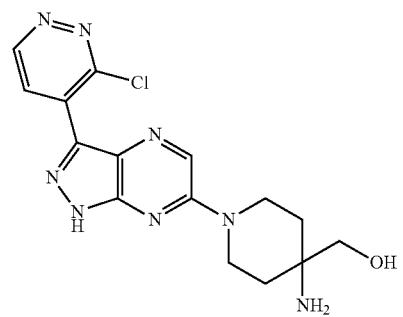 [SMILES: NC1(CO)CCN(c2cnc3c(-c4ccnnc4Cl)n[nH]c3n2)CC1] |
| 4-(aminomethyl)-1-(3-(3-chloropyridazin-4-yl)-1H-pyrazolo[3,4-b]pyrazin-6-yl)-piperidin-4-ol | 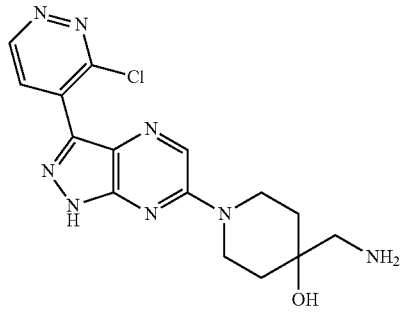 [SMILES: NCC1(O)CCN(c2cnc3c(-c4ccnnc4Cl)n[nH]c3n2)CC1] |
| 1-(3-(3-(3-chloropyridazin-4-yl)-1H-pyrazolo[3,4-b]pyrazin-6-yl)-4-methylpiperidin-4-amine | 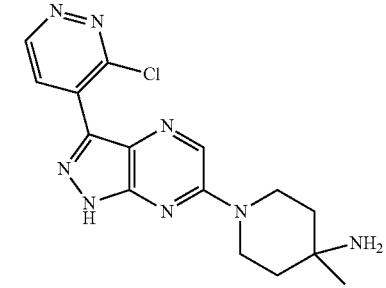 [SMILES: CC1(N)CCN(c2cnc3c(-c4ccnnc4Cl)n[nH]c3n2)CC1] |
| (S)-8-(3-(3-(3-chloropyridazin-4-yl)-1H-pyrazolo[3,4-b]pyrazin-6-yl)-2-oxa-8-azaspiro[4.5]decan-4-amine | 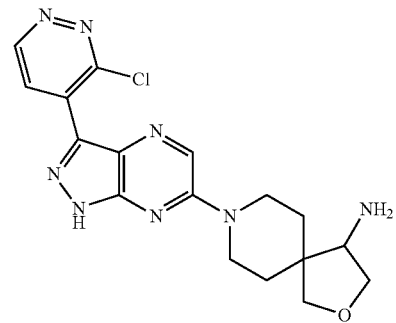 [SMILES: NC1COCC12CCN(c1cnc3c(-c4ccnnc4Cl)n[nH]c3n1)CC2] |

-continued
| Name | Structure |
|---|---|
| 8-(3-(3-chloropyridazin-4-yl)-1H-pyrazolo[3,4-b]pyrazin-6-yl)-8-azaspiro[4.5]decan-1-amine | 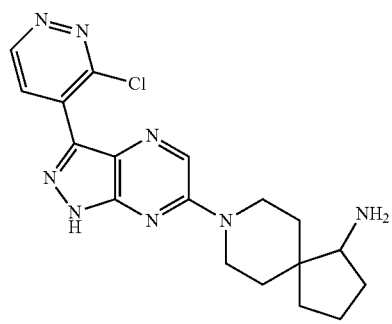 [SMILES: NC1CCCC12CCN(c1cnc3c(-c4ccnnc4Cl)n[nH]c3n1)CC2] |
| 1-amino-8-(3-(3-chloropyridazin-4-yl)-1H-pyrazolo[3,4-b]-pyrazin-6-yl)-8-azaspiro-[4.5]decan-2-ol | 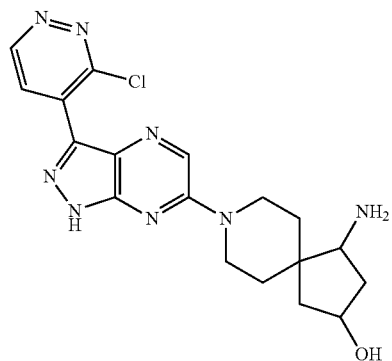 [SMILES: NC1CC(O)CC12CCN(c1cnc3c(-c4ccnnc4Cl)n[nH]c3n1)CC2] |
| 4-(aminomethyl)-1-(3-(2-amino-3,6-dichloropyridin-4-yl)-1H-pyrazolo[3,4-b]pyrazin-6-yl)-4-methylpiperidine | 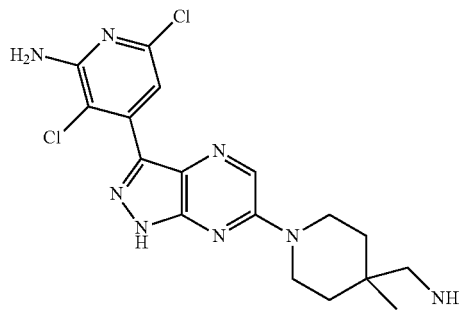 [SMILES: CC1(CN)CCN(c2cnc3c(-c4cc(Cl)nc(N)c4Cl)n[nH]c3n2)CC1] |
| 1-(3-(3-(2-amino-3,6-dichloropyridin-4-yl)-1H-pyrazolo[3,4-b]pyrazin-6-yl)-4-methylpiperidin-4-amine | 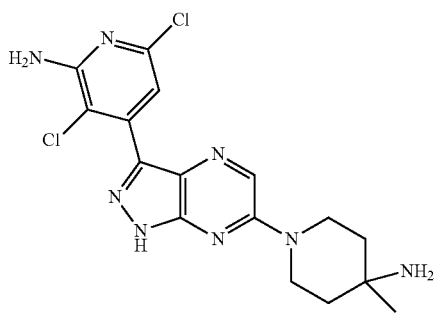 [SMILES: CC1(N)CCN(c2cnc3c(-c4cc(Cl)nc(N)c4Cl)n[nH]c3n2)CC1] |

-continued
| Name | Structure |
|---|---|
| (R)-8-(3-(3-(3-(2-amino-3,6-dichloropyridin-4-yl)-1H-pyrazolo[3,4-b]pyrazin-6-yl)-8-azaspiro[4.5]decan-1-amine | 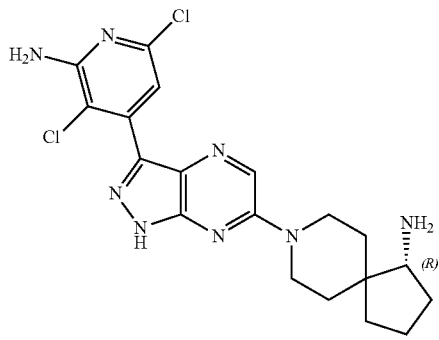 |
| 4-(aminomethyl)-1-(3-(2,3-dihydro-7-azaindol-4-yl)-1H-pyrazolo[3,4-b]pyrazin-6-yl)4-methylpiperidine | 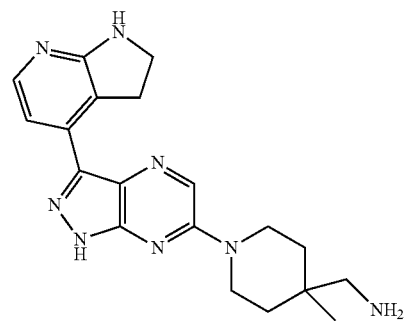 [SMILES: CC1(CN)CCN(c2cnc3c(-c4ccnc5c4CCN5)n[nH]c3n2)CC1] |
| 1-(3-(3-(2,3-dihydro-7-azaindol-4-yl)-1H-pyrazolo[3,4-b]pyrazin-6-yl)-4-methylpiperidin-4-amine | 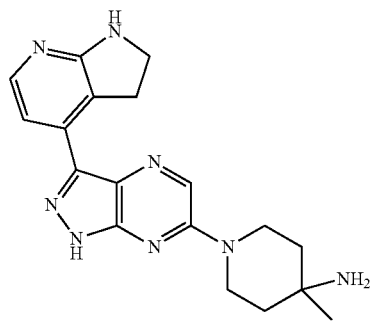 [SMILES: CC1(N)CCN(c2cnc3c(-c4ccnc5c4CCN5)n[nH]c3n2)CC1] |
| (R)-8-(3-(3-(3-(2,3-dihydro-7-azaindol-4-yl)-1H-pyrazolo[3,4-b]pyrazin-6-yl)-8-azaspiro-[4.5]decan-1-amine | 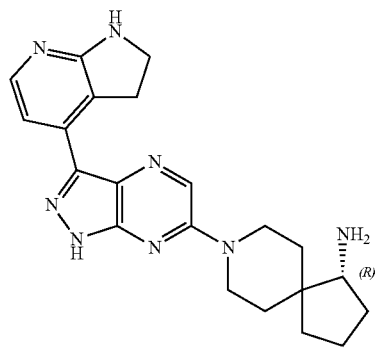 |

-continued
| Name | Structure |
|---|---|
| 4-(aminomethyl)-1-(3-(1,2,3,4-tetrahydro-1,8-naphthyridin-5-yl)-1H-pyrazolo[3,4-b]pyrazin-6-yl)-4-methylpiperidine | 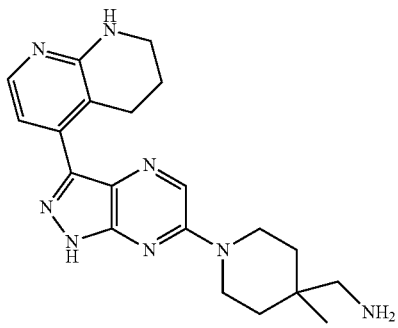 [SMILES: CC1(CN)CCN(c2cnc3c(-c4ccnc5c4CCCN5)n[nH]c3n2)CC1] |
| 1-(3-(3-(1,2,3,4-tetrahydro-1,8-naphthyridin-5-yl)-1H-pyrazolo-[3,4-b]pyrazin-6-yl)-4-methylpiperidin-4-amine | 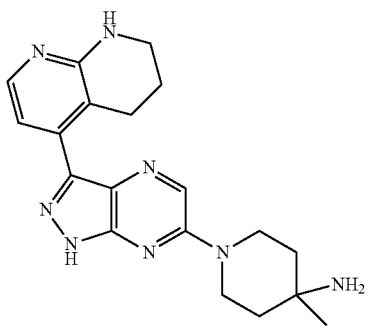 [SMILES: CC1(N)CCN(c2cnc3c(-c4ccnc5c4CCCN5)n[nH]c3n2)CC1] |
| (R)-8-(3-(3-(1,2,3,4-tetra-hydro-1,8-naphthyridin-5-yl)-1H-pyrazolo[3,4-b]pyrazin-6-yl)-8-azaspiro[4.5]decan-1-amine | 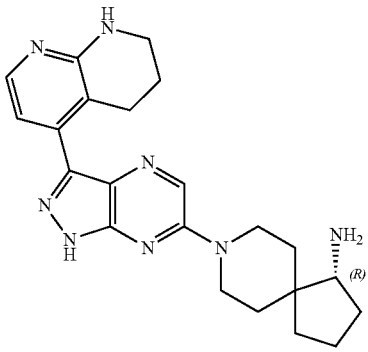 |
| 4-(aminomethyl)-1-(3-(2-amino-5-methylpyridin-4-yl)-1H-pyrazolo[3,4-b]pyrazin-6-yl)-4-methylpiperidine | 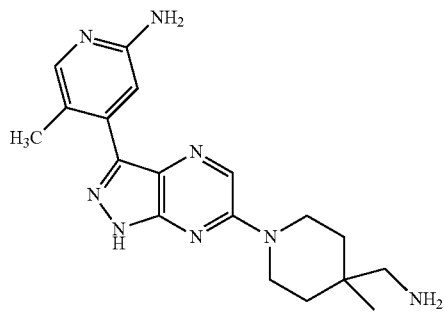 [SMILES: Cc1cnc(N)cc1-c1n[nH]c2nc(N3CCC(C)(CN)CC3)cnc12] |

-continued

| Name | Structure |
|---|---|
| 1-(3-(3-(2-amino-5-methyl-pyridin-4-yl)-1H-pyrazolo[3,4-b]pyrazin-6-yl)-4-methylpiperidin-4-amine | 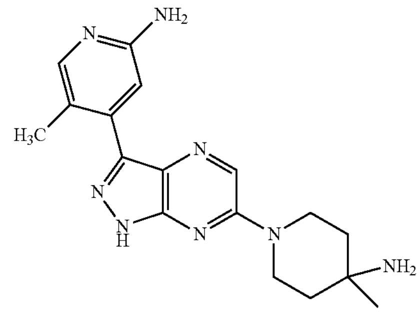 [SMILES: Cc1cnc(N)cc1-c1n[nH]c2nc(N3CCC(C)(N)CC3)cnc12] |
| (R)-8-(3-(3-(2-amino-5-methylpyridin-4-yl)-1H-pyrazolo[3,4-b]pyrazin-6-yl)-8-azaspiro[4.5]decan-1-amine | |
| 4-(aminomethyl)-1-(3-(3,5-dimethylpyrazol-4-yl)-1H-pyrazolo[3,4-b]pyrazin-6-yl)-4-methylpiperidine | 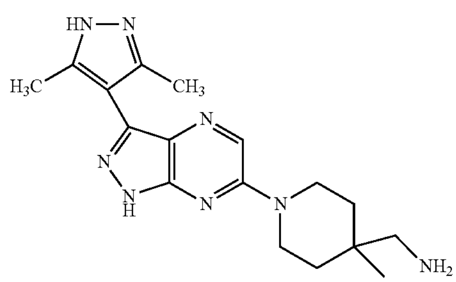 [SMILES: Cc1n[nH]c(C)c1-c1n[nH]c2nc(N3CCC(C)(CN)CC3)cnc12] |
| 1-(3-(3-(3,5-dimethylpyrazol-4-yl)-1H-pyrazolo[3,4-b]pyrazin-6-yl)-4-methylpiperidin-4-amine | 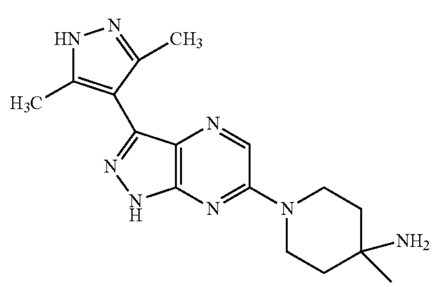 [SMILES: Cc1n[nH]c(C)c1-c1n[nH]c2nc(N3CCC(C)(N)CC3)cnc12] |
| (R)-8-(3-(3-(3,5-dimethyl-pyrazol-4-yl)-1H-pyrazolo[3,4-b]pyrazin-6-yl)-8-azaspiro-[4.5]decan-1-amine | |

| Name | Structure |
|---|---|
| 4-(aminomethyl)-1-(3-(2-amino-5-cyanopyridin-4-yl)-1H-pyrazolo[3,4-b]pyrazin-6-yl)-4-methylpiperidine | 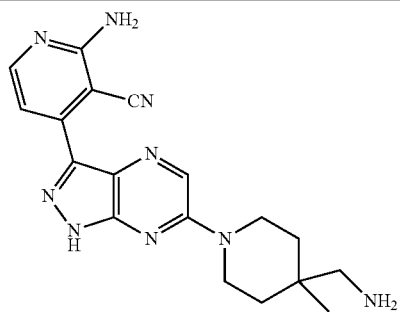 [SMILES: CC1(CN)CCN(c2cnc3c(-c4ccnc(N)c4C#N)n[nH]c3n2)CC1] |
| 1-(3-(3-(2-amino-3-cyano-pyridin-4-yl)-1H-pyrazolo[3,4-b]pyrazin-6-yl)-4-methylpiperidin-4-amine | 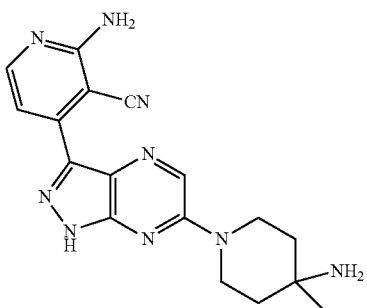 |
| (R)-8-(3-(3-(2-amino-3-cyano-pyridin-4-yl)-1H-pyrazolo[3,4-b]pyrazin-6-yl)-8-azaspiro-[4.5]decan-1-amine | 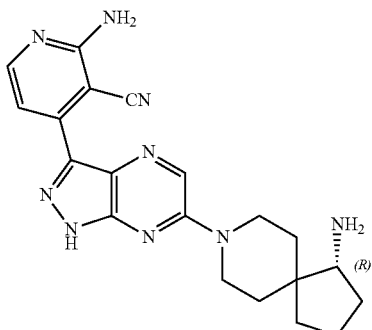 |
| 4-(aminomethyl)-1-(3-(2-amino-3-cyanopyridin-4-yl)-1H-pyrazolo[3,4-b]pyrazin-6-yl)4-methylpiperidine | 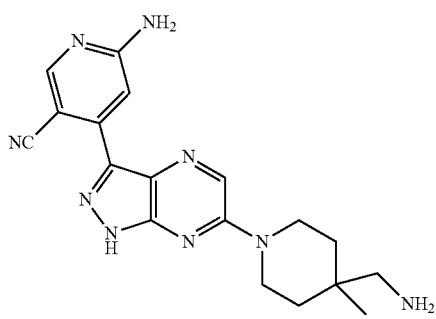 [SMILES: CC1(CN)CCN(c2cnc3c(-c4cc(N)ncc4C#N)n[nH]c3n2)CC1] |
| 1-(3-(3-(2-amino-5-cyano-pyridin-4-yl)-1H-pyrazolo[3,4-b]pyrazin-6-yl)-4-methylpiperidin-4-amine | 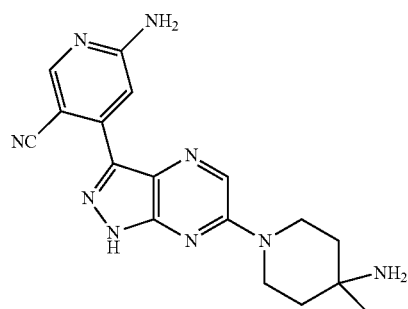 |

-continued
| Name | Structure |
|---|---|
| (R)-8-(3-(3-(3-(2-amino-5-cyano-pyridin-4-yl)-1H-pyrazolo[3,4-b]pyrazin-6-yl)-8-azaspiro-[4.5]decan-1-amine | 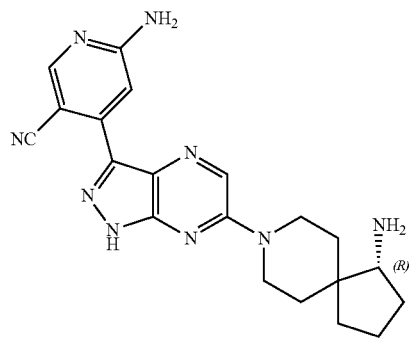 |
| 4-(aminomethyl)-1-(3-(2-chloro-3-(methylamino)-phenyl)-1H-pyrazolo[3,4-b]pyrazin-6-yl)4-methylpiperidine | 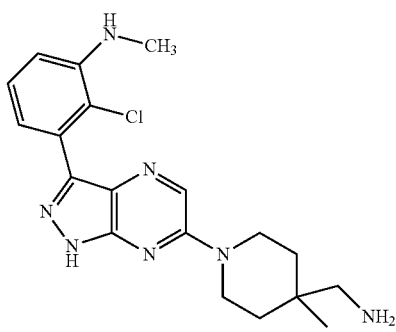 [SMILES: CNc1cccc(-c2n[nH]c3nc(N4CCC(C)(CN)CC4)cnc23)c1Cl] |
| 1-(3-(3-(2-chloro-3-(methyl-amino)-phenyl)-1H-pyrazolo-[3,4-b]pyrazin-6-yl)-4-methylpiperidin-4-amine | 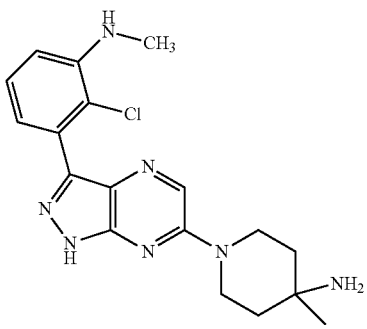 [SMILES: CNc1cccc(-c2n[nH]c3nc(N4CCC(C)(N)CC4)cnc23)c1Cl] |
| (R)-8-(3-(3-(2-chloro-3-(methylamino)-phenyl)-1H-pyrazolo[3,4-b]pyrazin-6-yl)-8-azaspiro[4.5]decan-1-amine | 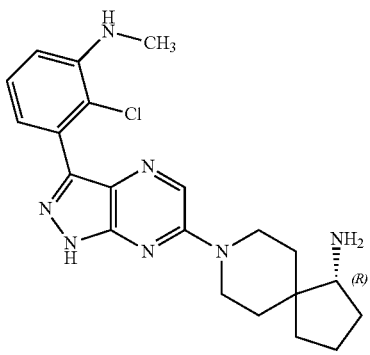 |

| Name | Structure |
|---|---|
| 4-(aminomethyl)-1-(3-(2-chloro-3-(dimethylamino)-phenyl)-1H-pyrazolo[3,4-b]pyrazin-6-yl)-4-methylpiperidine | 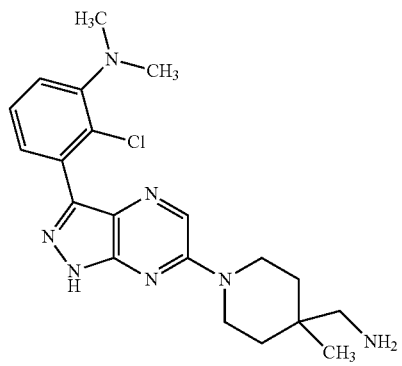 [SMILES: CN(C)c1cccc(-c2n[nH]c3nc(N4CCC(C)(CN)CC4)cnc23)c1Cl] |
| 1-(3-(3-(2-chloro-3-(dimethyl-amino)-phenyl)-1H-pyrazolo-[3,4-b]pyrazin-6-yl)-4-methylpiperidin-4-amine | 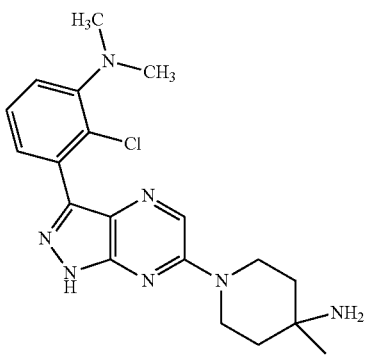 [SMILES: CN(C)c1cccc(-c2n[nH]c3nc(N4CCC(C)(N)CC4)cnc23)c1Cl] |
| (R)-8-(3-(3-(2-chloro-3-(dimethylamino)-phenyl)-1H-pyrazolo[3,4-b]pyrazin-6-yl)-8-azaspiro[4.5]decan-1-amine | 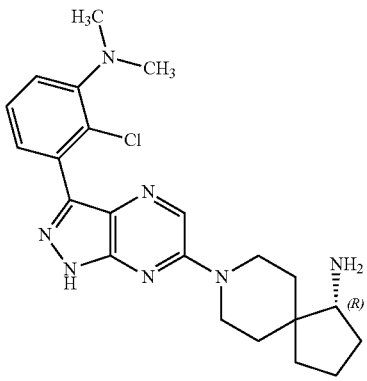 |
| 1-(3-(3-(2-chloro-3-amino)-phenyl)-1H-pyrazolo[3,4-b]pyrazin-6-yl)-4-(2-propyl)-piperidin-4-amine | 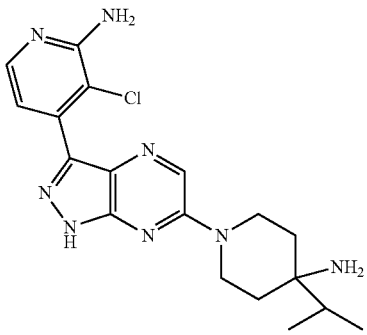 [SMILES: CC(C)C1(N)CCN(c2cnc3c(-c4ccnc(N)c4Cl)n[nH]c3n2)CC1] |

| Name | Structure |
|---|---|
| 1-(3-(3-(2-chloro-3-amino)-phenyl)-1H-pyrazolo[3,4-b]pyrazin-6-yl)-4-cyano-piperidin-4-amine | 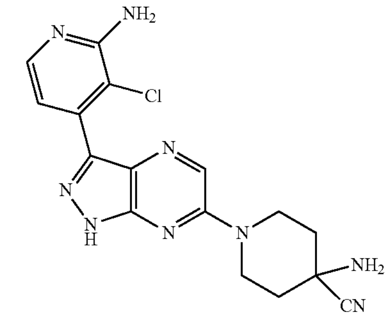 [SMILES: N#CC1(N)CCN(c2cnc3c(-c4ccnc(N)c4Cl)n[nH]c3n2)CC1] |
| 1-(3-(3-(2-chloro-3-amino)-phenyl)-1H-pyrazolo[3,4-b]pyrazin-6-yl)-4-(amino-methyl)-4-cyanopiperidine | 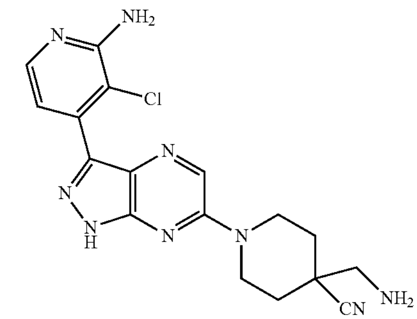 [SMILES: N#CC1(CN)CCN(c2cnc3c(-c4ccnc(N)c4Cl)n[nH]c3n2)CC1] |

Biological Activity Assay

The activity of the compounds in the Examples disclosed herein as PTPN11 inhibitors is illustrated in the following assays. Other compounds listed herein, which have not yet been made and/or tested, are predicted to have activity in these assays as well.

PTPN11 Enzymatic Assay

Recombinant full-length wild-type and E76K mutant human PTPN11 proteins were cloned, expressed (*E. coli* system), and isolated via a two-step purification of Ni affinity followed by S75 size exclusion chromatography. Phosphatase activity of full length wild-type PTPN11 (PTPN11-WT) or PTPN11-E76K mutant enzyme was measured using the fluorogenic 6,8-difluoro-4-methylumbelliferyl phosphate (DiFMUP; Molecular Probes) as the substrate. Enzyme (250 pM) was incubated with or without increasing concentrations of compounds in assay buffer (62.5 mM HEPES, 125 mM NaCl, 1 mM EDTA, 1.25 mM TECP, 0.1% BSA) for 30 min at room temperature. Reaction was initiated by addition of DiFMUP (50 μM) at room temperature in 384-well black plate with a final reaction volume of 20 uL in assay buffer. After 1 hour, DiFMUP fluorescence signal was measured (Ex:340/Em:460) using Envision plate reader. Dose-response curves were analyzed using $IC_{50}$ regression curve fitting (GeneData Screener). Curves were normalized to a high controls without inhibitor, and low controls without enzyme. Results are given below in Table 1. Other compounds disclosed herein are expected to have activity similar to the results below, showing activity as PTPN11 inhibitors.

pERK AlphaScreen Protocol

KYSE-520 cells (10 k cells/well) were grown in 384-well plate in 20 uL of medium (RPMI-1640, without phenol red, containing 10% FBS) at 37° C. with 5% $CO_2$ overnight. DMSO (control) or increasing concentrations of compounds were diluted in medium, added to the 384-well plate (5 uL/well, final DMSO concentration of 1%), and cells were then incubated with compounds for 2 hr. Phospho-ERK levels were measured using phospho-ERK1/2 AlphaScreen SureFire (PerkinElmer, TGRESB10K) following manufacturer's recommendations. Dose-response curves were analyzed using $IC_{50}$ regression curve fitting (GeneData Screener). Curves were normalized to a high control without inhibitor (DMSO only), and low control (1 μM selumetinib).

TABLE 10

Biological Activity for inhibition of PTPN11-E76K mutant enzyme and pERK AlphaScreen

| Ex. | PTPN11-E76K Avg $IC_{50}$ (nM) | PERK Avg $IC_{50}$ (nm) |
|---|---|---|
| 1 | 109.88 | |
| 2 | 787 | |
| 3 | 1072.5 | |
| 4 | N.A. | |
| 5 | N.A. | |
| 6 | 2 | |
| 7 | 196 | 79 |
| 8 | 204 | 86 |
| 9 | 367 | 482 |
| 10 | 333 | 172 |
| 11 | 632 | 1173 |
| 12 | 404 | 623 |
| 13 | 158 | 562 |
| 14 | 521 | 569 |
| 15 | 140 | 103 |
| 16 | 169 | 309 |
| 17 | 118 | 82 |
| 18 | 141 | 667 |
| 19 | 510 | 534 |
| 20 | 326 | 158 |

TABLE 10-continued

Biological Activity for inhibition of PTPN11-E76K mutant enzyme and pERK AlphaScreen

| Ex. | PTPN11-E76K Avg IC$_{50}$ (nM) | PERK Avg IC$_{50}$ (nm) |
|---|---|---|
| 21 | 956 | 620 |
| 22 | 1747 | 976 |
| 23 | 1824 | 428 |
| 24 | 204 | 142 |
| 25 | 101 | 47 |
| 26 | 213 | N.A. |
| 27 | 80 | 55 |
| 28 | 142 | 190 |
| 29 | 178 | 87 |
| 30 | 2509 | 1597 |
| 31 | 929 | 710 |
| 32 | N.A. | 284 |
| 33 | 72 | 96 |
| 34 | 102 | N.A. |
| 35 | 304 | 704 |
| 36 | 967 | 320 |
| 37 | 623 | 223 |
| 38 | 75 | 40 |
| 39 | 158 | 103 |
| 40 | 203 | 186 |
| 41 | 966 | 394 |
| 42 | N.A. | 63 |
| 43 | N.A. | N.A. |
| 44 | 429 | 304 |
| 45 | 355 | 1416 |
| 46 | 193 | 666 |
| 47 | 493 | 343 |
| 48 | 1756 | 586 |
| 49 | 143 | 62 |
| 50 | 39 | 34 |
| 51 | 153 | N.A. |
| 52 | 313 | N.A. |
| 53 | 641 | 224 |
| 54 | 119 | 64 |
| 55 | 1143 | 712 |
| 56 | 552 | 200 |
| 57 | 104 | 53 |
| 58 | 338 | 109 |
| 59 | N.A. | 1040 |
| 60 | 918 | 317 |
| 61 | 401 | 221 |
| 62 | N.A. | 310 |
| 63 | N.A. | 687 |
| 64A | 98 | 34 |
| 64B | 221 | 70 |
| 65A | 235 | 93 |
| 65B | 471 | 165 |
| 101 | 1894 | 638 |
| 102 | 2154 | 1182 |
| 103 | 2603 | 1629 |
| 104 | 99 | 47 |
| 105 | 191 | 120 |
| 106 | 253 | 174 |
| 107 | 162 | 246 |
| 108 | 726 | 6801 |
| 109 | 1095 | 10000 |
| 110 | 3679 | 7848 |
| 111 | 43 | 20 |
| 112 | 128 | 58 |
| 113a | 180 | 100 |
| 113b | N.A. | N.A. |
| 114 | 779 | 2492 |
| 115 | 701 | 427 |
| 116 | 132 | 483 |
| 117 | 1941 | 4779 |
| 118 | 1128 | 8284 |
| 119 | 422 | 1727 |
| 120 | 5372 | 9698 |
| 121 | 1083 | 1649 |
| 122 | 205 | N.A. |
| 123 | 670 | N.A. |
| 124 | 377 | N.A. |
| 125 | 509 | 429 |
| 126 | 75 | N.A. |
| 127 | N.A. | N.A. |
| 128 | N.A. | N.A. |
| 129 | N.A. | N.A. |
| 130 | 83 | 65 |
| 131 | 84 | 35 |
| 132 | 119 | 63 |
| 133 | 840 | 533 |
| 134 | 1532 | 2009 |
| 135 | 529 | 122 |
| 136a | 15155 | 2269 |
| 136b | 4318 | 1956 |
| 137 | 504 | 1033 |
| 138 | 587 | 406 |

N.A. = Not Available

ERK Phosphorylation (Phospho-ERK) Target Engagement Assay

KYSE-520 cells (10 k cells/well) are plated onto 384-well plate in 20 uL of medium (RPMI-1640, without phenol red, containing 10% FBS) and incubated at 37° C., 5% CO$_2$ 16 h. DMSO (control) or increasing concentrations of compounds are diluted in medium, added to the 384-well plate (10 uL/well, final DMSO concentration of 0.5-1%), and cells are then incubated with compounds for 2 hr. Phospho-ERK levels are measured using a TR-FRET based phospho-ERK1/2 HTRF kit (CisBio, 64ERKPEH) following manufacturer's recommendations, and fluorescence signal was measured at 665 nm and 620 nm using Synergy Neo plate reader. Dose-response curves were analyzed using IC$_{50}$ regression curve fitting (GeneData Screener). Curves were normalized to a high controls without inhibitor, and low controls with 1 µM of selumetinib. Some compounds of this invention showed IC$_{50}$<1 µM.

TABLE 11 pERK target engagement assay

| Ex. | Avg IC$_{50}$ (nM) |
|---|---|
| 1 | 49 |
| 2 | 169 |
| 3 | 322 |
| 4 | 73 |
| 5 | N.A. |
| 6 | 124 |

Colony Formation Assay

KYSE-520 cells (2000 cells/well) are plated in 6-well plate containing 2 mL of medium (RPMI-1640, containing 10% FBS), in the presence of DMSO (control; 1% final concentration) or increasing compound concentration. After 14 days of culture at 37° C. in a humidified 5% CO$_2$ incubator, colonies are fixed and stained with 0.1% crystal violet and 15% ethanol solution. Plates are imaged and colony area quantified and normalized to DMSO with ImageJ, Colony Area plugin. (Guzmán, Camilo, PloS one 2014). Compounds disclosed herein are expected to have activity in inhibiting cellular proliferation and/or colony formation in the foregoing assay.

In Vivo Tumor Models

Xenografts were initiated with BT474 human breast carcinomas cell line and maintained by serial subcutaneous transplantation in CB-17/SCID mice (Charles River). On the day of tumor implant, each test mouse received a 1 mm³ BT474 fragment implanted subcutaneously in the right flank, and tumor growth was monitored as the average size approached the target range of 100 to 150 mm³. About three weeks post-implantation, the animals were randomized and grouped based on tumor volume and mouse body weight. The animals were then dosed with Example 1 at 100 mg/kg once per day through oral gavage on a 5 days on/2 days off schedule for 4 weeks, where the first day of dosing was designated as study day 1. Tumors were measured in two dimensions using calipers, and volume was calculated using the formula: Tumor Volume (mm³)=w²×l/2.

Figure 2:
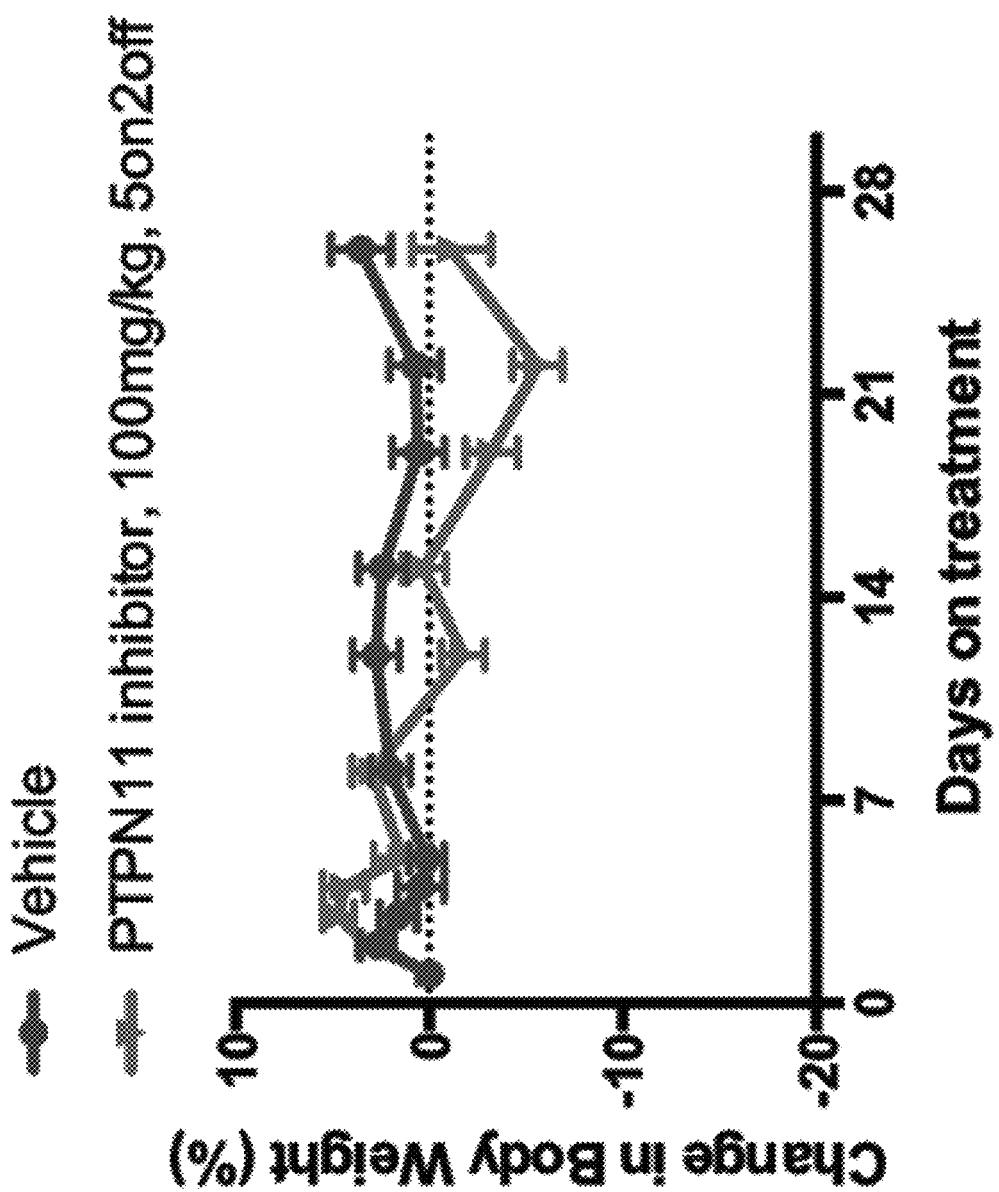
FIG. 2 shows the effect of the compound Example 1 on body weight, as compared to carrier alone.

Results are found in FIGS. 1 and 2. The inhibition of PTPN11 induced significant suppression of tumor growth at tolerated dose in BT474 (HER2+) xenograft model in mouse.

All references, patents or applications, U.S. or foreign, cited in the application are hereby incorporated by reference as if written herein in their entireties. Where any inconsistencies arise, material literally disclosed herein controls.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of structural Formula I:

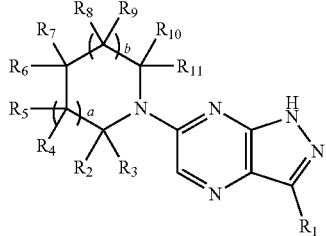

(I)

or a pharmaceutically acceptable salt or tautomer thereof, wherein:
a is 1;
b is 1;
$R_1$ is phenyl or 5- to 6-membered heteroaryl group containing 1 to 4 heteroatoms or groups independently selected from N, C(O), O, and S;
said phenyl or heteroaryl of $R_1$ is substituted with 1 to 5 $R_{12}$ groups independently selected from halo, hydroxy, amino, $C_{1-4}$alkylamino, $C_{1-4}$dialkylamino, cyano, $C_{1-4}$alkyl, $C_{1-4}$alkoxy, $C_{1-4}$hydroxyalkyl, $C_{1-4}$haloalkyl, and $C_{1-4}$aminoalkyl;
$R_2$, $R_3$, $R_{10}$, and $R_{11}$ are independently selected from hydrogen, $C_{1-4}$alkyl, and $C_{3-8}$cycloalkyl;
$R_4$, $R_5$, $R_8$, and $R_9$ are independently selected from hydrogen, cyano, $C_{1-4}$alkyl, $C_{1-4}$alkoxy, amino, hydroxy, $C_{3-8}$cycloalkyl, halo, and $C_{1-4}$alkylamino;
$R_6$ and $R_7$ together with the carbon atom to which they are both attached form a 3- to 7-membered saturated or unsaturated ring that contains 1 to 3 heteroatoms or groups independently selected from N, C(O), O, and S(O)$_m$, and said 3- to 7-membered saturated ring is optionally substituted with one $R_{17}$ group, and is optionally substituted with one or more $R_{18}$ groups;
m is selected from 0, 1, and 2;
any two groups selected from $R_2$, $R_3$, $R_4$, $R_5$, $R_8$, $R_9$, $R_{10}$ and $R_{11}$ can form a 5- to 6-membered ring, optionally containing a N, O or S heteroatom;
any two groups selected from $R_2$, $R_4$, $R_8$ and $R_{10}$ can form a direct bond, or a 1 or 2 atom carbon bridge; and
each $R_{17}$ and $R_{18}$ is independently selected from amino, halo, hydroxy, cyano, trifluoromethyl, trifluoromethoxy, $C_{1-4}$alkyl, and $C_{1-4}$alkoxy.

2. The compound as recited in claim 1, wherein $R_2$, $R_3$, $R_4$, $R_5$, $R_8$, $R_9$, $R_{10}$ and $R_{11}$ are each hydrogen.

3. The compound as recited in claim 1, wherein $R_6$ and $R_7$ together with the carbon atom to which they are both attached forms a 3- to 7-membered saturated ring that contains 1 to 3 heteroatoms or groups independently selected from N, C(O), O, and S(O)$_m$, and said 3- to 7-membered saturated ring is optionally substituted with one $R_{17}$ group, and is optionally substituted with one or more $R_{18}$ groups.

4. The compound as recited in claim 1, wherein $R_6$ and $R_7$ together with the carbon atom to which they are both attached form a 3- to 6-membered saturated ring that contains a heteroatom of N or O, and said 3- to 6-membered saturated ring is substituted with one $R_{17}$ group and one or more $R_{18}$ groups.

5. The compound as recited in claim 1, wherein $R_6$ and $R_7$ together with the carbon atom to which they are both attached form a 3- to 6-membered saturated ring that contains a heteroatom of O, and said 3- to 6-membered saturated ring is substituted with one $R_{17}$ group and one or more $R_{18}$ groups.

6. The compound as recited in claim 1, wherein
$R_1$ is phenyl or 5- to 6-membered heteroaryl group containing 1 to 4 heteroatoms or groups independently selected from N, C(O), O, and S; and
said phenyl or heteroaryl of $R_1$ is optionally substituted with 1 to 5 $R_{12}$ groups independently selected from halo, hydroxy, alkoxy, amino, $C_{1-4}$alkylamino, $C_{1-4}$dialkylamino, cyano, and $C_{1-4}$alkyl.

7. The compound as recited in claim 1, wherein $R_1$ is selected from:

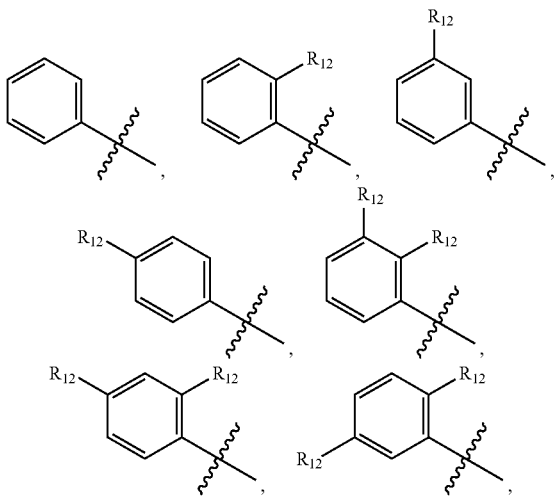

-continued
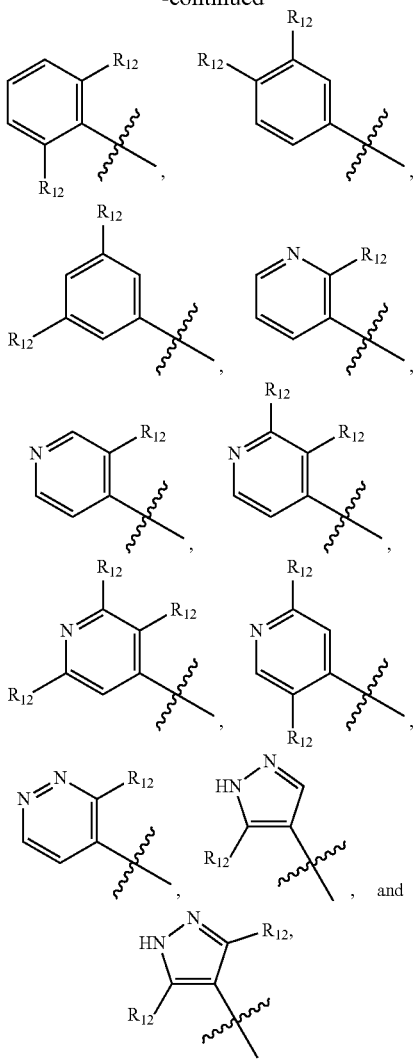
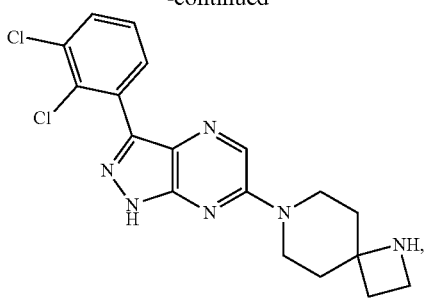
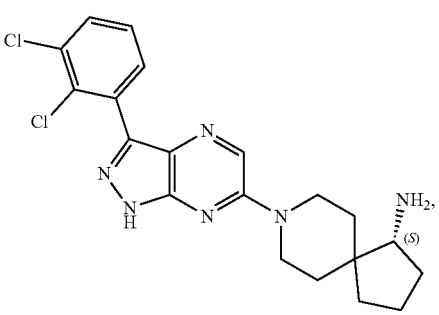
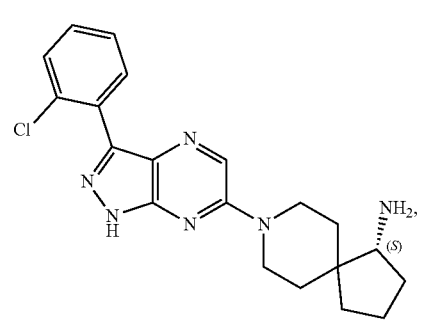
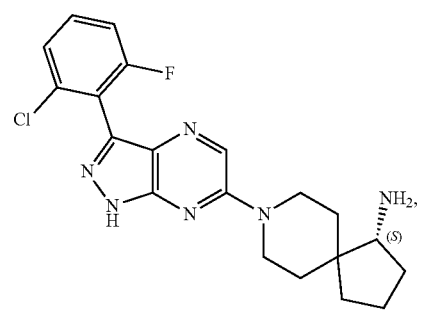
and
each R$_{12}$ is independently selected from halo, hydroxy, amino, methylamino, dimethylamino, cyano, C$_{1-4}$alkyl, and C$_{1-4}$alkoxy.
8. The compound as recited in claim 1, wherein R$_1$ is pyridyl.
9. The compound as recited in claim 1, wherein R$_1$ is phenyl.
10. The compound as recited in claim 1, wherein the structure is selected from:
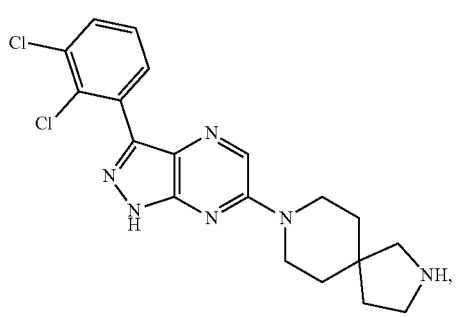
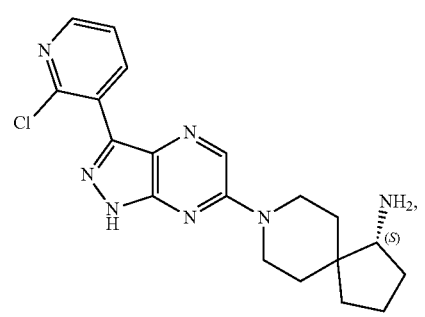

-continued

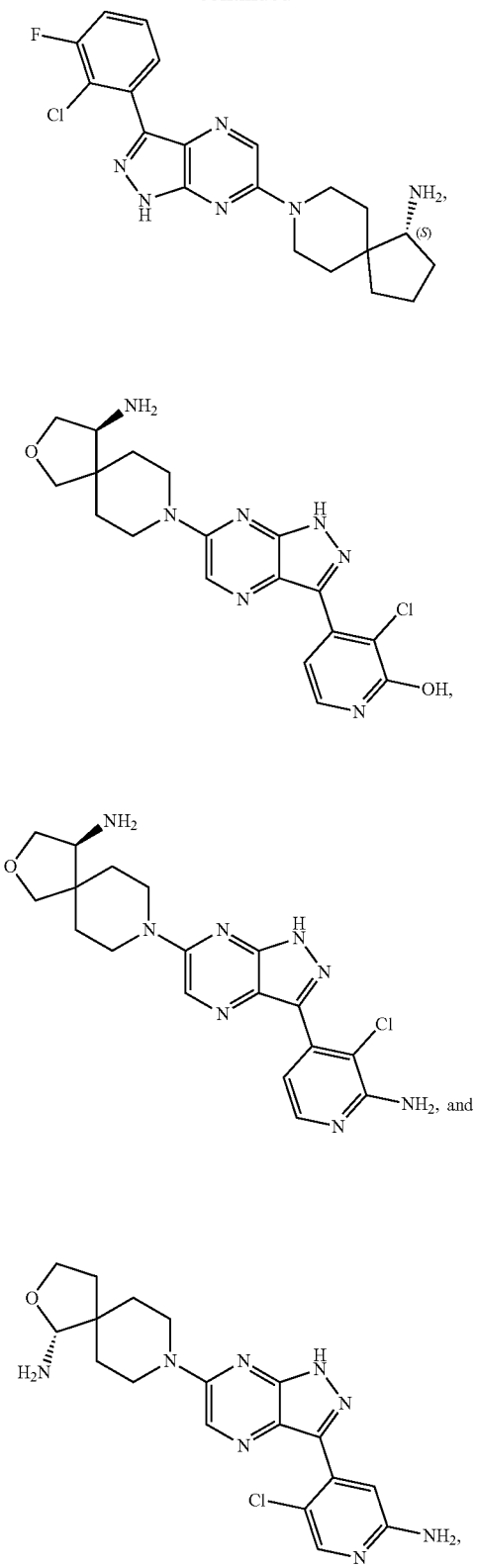

or a pharmaceutically acceptable salt or tautomer thereof.

11. The compound as recited in claim 1, wherein the structure is selected from:

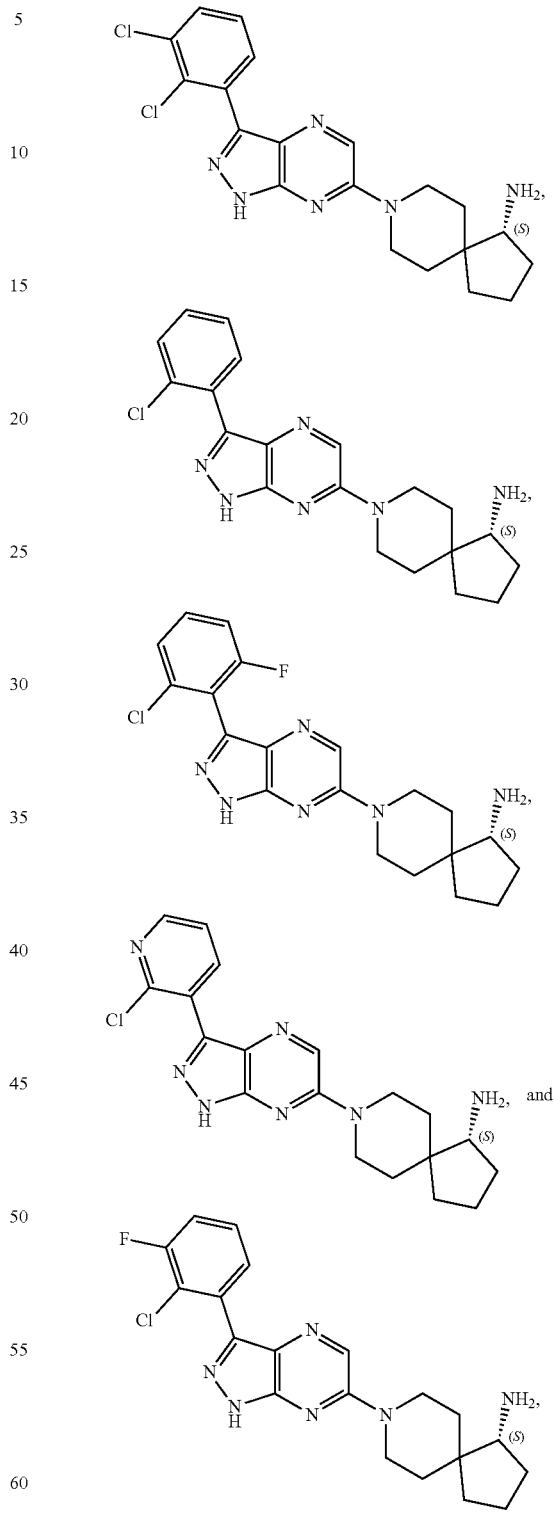

or an enantiomer of any one of the above structures,
or a pharmaceutically acceptable salt or tautomer of any one of the above structures,
or a pharmaceutically acceptable salt or tautomer of the enantiomer of any one of the above structures.

12. A pharmaceutical composition comprising a compound as recited in claim 1 together with a pharmaceutically acceptable carrier.

13. A method of inhibition of PTPN11 comprising contacting PTPN11 with a compound as recited in claim 1.

14. A method of treatment of a PTPN11-mediated disease comprising the administration of a therapeutically effective amount of a compound of Formula I as recited in claim 1 to a patient in need thereof, wherein the patient has the PTPN11-mediated disease; and the PTPN11-mediated disease is a Noonan Syndrome, LEOPARD Syndrome, or cancer selected from the group consisting of breast cancer, colon cancer, lung cancer, leukemia, and melanoma.

15. The method as recited in claim 14, wherein the PTPN11-mediated disease is cancer selected from the group consisting of breast cancer, colon cancer, lung cancer, leukemia, and melanoma.

16. The method as recited in claim 14, wherein the PTPN11-mediated disease is Noonan Syndrome or LEOPARD Syndrome.

17. The method of claim 14 further comprising a second therapeutic agent.

18. The method of claim 14, wherein the compound is selected from:

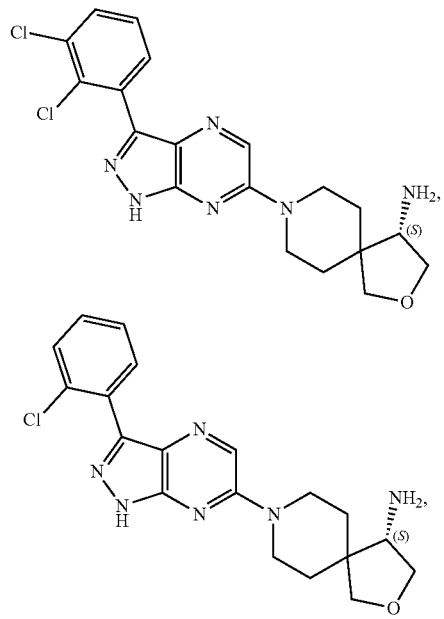

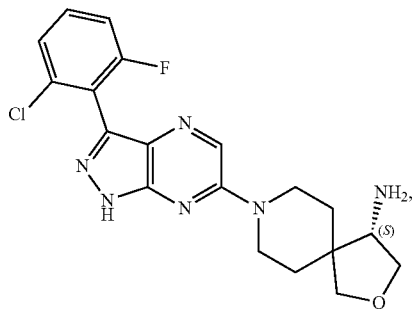

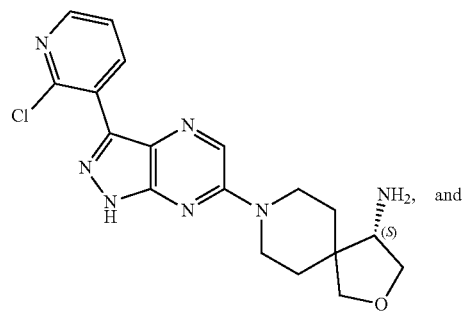

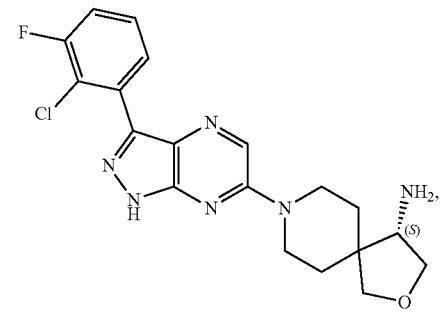

or a pharmaceutically acceptable salt or tautomer thereof.

* * * * *